US011014917B2

(12) United States Patent
Xu et al.

(10) Patent No.: US 11,014,917 B2
(45) Date of Patent: May 25, 2021

(54) 5-FLUORO-C-(ARYL OR HETEROCYCLYL)-GLYCOSIDE DERIVATIVES USEFUL AS DUAL SGLT1 / SGLT2 MODULATORS

(71) Applicant: Janssen Pharmaceutica NV, Beerse (BE)

(72) Inventors: Guozhang Xu, Chesterbrook, PA (US); Gee-Hong Kuo, Scotch Plains, NJ (US); Micheal Gaul, Yardley, PA (US)

(73) Assignee: Janssen Pharmaceutica NV, Beerse (BE)

( * ) Notice: Subject to any disclaimer, the term of this patent is extended or adjusted under 35 U.S.C. 154(b) by 0 days.

(21) Appl. No.: 16/890,331

(22) Filed: Jun. 2, 2020

(65) Prior Publication Data
US 2020/0291004 A1 Sep. 17, 2020

Related U.S. Application Data

(62) Division of application No. 16/106,104, filed on Aug. 21, 2018, now Pat. No. 10,696,662.

(60) Provisional application No. 62/547,911, filed on Aug. 21, 2017.

(51) Int. Cl.
C07D 409/10 (2006.01)
C07D 513/04 (2006.01)
C07D 405/14 (2006.01)
C07D 411/14 (2006.01)
C07D 407/14 (2006.01)

(52) U.S. Cl.
CPC ......... *C07D 409/10* (2013.01); *C07D 405/14* (2013.01); *C07D 407/14* (2013.01); *C07D 411/14* (2013.01); *C07D 513/04* (2013.01)

(58) Field of Classification Search
CPC .. C07D 409/10; C07D 407/14; C07D 513/04; C07D 405/14; C07D 411/14
See application file for complete search history.

(56) References Cited

U.S. PATENT DOCUMENTS

| 7,419,959 | B2 | 9/2008 | Eckhardt et al. |
| 9,328,100 | B2 * | 5/2016 | Henschke ............ C07D 409/10 |
| 9,695,159 | B2 * | 7/2017 | Bhirud ................. C07D 333/16 |
| 2008/0027014 | A1 | 1/2008 | Nomura et al. |
| 2011/0059910 | A1 | 3/2011 | Frick et al. |
| 2014/0271474 | A1 | 9/2014 | Wright et al. |
| 2016/0222047 | A1 | 8/2016 | Zhong et al. |

FOREIGN PATENT DOCUMENTS

| CN | 104327027 A | 2/2015 |
| WO | WO 2008/116195 A3 | 11/2008 |
| WO | WO 2011/048112 A1 | 4/2011 |
| WO | WO 2012/165914 A3 | 3/2013 |

OTHER PUBLICATIONS

Xu, Bioorg & Med Chem Lett, vol. 28, 3446-3453, 2018. (Year: 2018).*
Chen et al., "Quantitative PCR Tissue Expression Profiling of the Human SGLT2 Gene and Related Family Members", *Diabetes Ther.*, Dec. 2010, pp. 57-92, vol. 1(2).
Derdau et al., "Synthesis of isotopically labelled SGLT inhibitors and their metabolites", *Tetrahedron*, Feb. 13, 2010, pp. 1472-1482, vol. 66(7), XP026874135.
Georgescu, E.F., "Angiotensin Receptor Blockers in the Treatment of NASH/NAFLD: Could They Be a First-Class Option?", *Advances in Therapy*, 2008, pp. 1141-1174, vol. 25, Issue 11.
Hediger et al., "Expression cloning and cDNA sequencing of the Na+/glucose co-transporter.". *Nature*, Nov. 26-Dec. 2, 1987, pp. 37-381, vol. 330(6146).
Imamura et al., "Discovery of Ipragliflozin (ASP1941): A novel-glucoside with benzothiophene structure as a potent and selective sodium glucose co-transporter 2 (SGLT2) inhibitor for the treatment of type 2 diabetes mellitus" *Bioorganic & Medicinal Chemistry*, Mar. 22, 2012, pp. 3263-3279, vol. 20, (10), XP028422762.
Lee et al., "The High Affinity Na+/Glucose Cotransporter. Re-evaluation of Function and Distribution of Expression", *J. Biol. Chem.*, Apr. 22, 1994, pp. 12032-12039, vol. 269(16).
Marsenic, O., "Glucose Control by the Kidney: An Emerging Target in Diabetes", Am. J. Kidney Dis., May 2009, pp. 875-883, vol. 53(5).
Scafoglio et al., "Functional expression of sodium-glucose transporters in cancer", PNAS, 2015, pp. E41111-E4119, vol. 112(3).
Wright, E.M., "Renal Na(+)-glucose cotransporters", *Am J Physiol, Renal Physiol*, Jan. 2001, pp. F10-F18, vol. 280(1).
Wright, E.M., et al., "Biology of Human Sodium Glucose Transporters", *Physiol. Rev.*, Apr. 2011, pp. 733-794, vol. 91(2).
You et al., "Molecular Characteristic of Na(+)-coupled Glucose Transporters in Adult and Embryonic Rat Kidney", *J. Biol. Chem.*, Dec. 8, 1995, pp. 29365-29371, vol. 270(49).

* cited by examiner

*Primary Examiner* — D Margaret M Seaman

(57) ABSTRACT

The present invention is directed to 5-fluoro-C-(aryl or heterocyclyl)-glycoside derivatives, pharmaceutical compositions containing them and their use in the treatment of disorders and conditions modulated by SGLT activity, more particularly dual SGLT1/2 activity.

7 Claims, No Drawings

5-FLUORO-C-(ARYL OR HETEROCYCLYL)-GLYCOSIDE DERIVATIVES USEFUL AS DUAL SGLT1 / SGLT2 MODULATORS

CROSS REFERENCE TO RELATED APPLICATIONS

This Application is a divisional of U.S. patent application Ser. No. 16/106,104, filed on Aug. 21, 2018, granted as U.S. Pat. No. 10,696,662, on Jun. 20, 2020, which claims priority to U.S. Provisional Patent Application No. 62/547,911, filed Aug. 21, 2017, the disclosures of which are hereby incorporated by reference in their entireties.

FIELD OF THE INVENTION

The present invention is directed to 5-fluoro-C-(aryl or heterocyclyl)-glycoside derivatives, pharmaceutical compositions containing them and their use in the treatment of disorders and conditions modulated by SGLT activity, more particularly dual SGLT1/2 activity. More particularly, the compounds of the present invention are useful in the treatment of for example, Type II diabetes mellitus, Syndrome X, and complications and symptoms associated with said disorders.

BACKGROUND OF THE INVENTION

Diabetes is a chronic disorder affecting carbohydrate, fat and protein metabolism in animals.

Type I diabetes mellitus, which comprises approximately 10% of all diabetes cases, was previously referred to as insulin-dependent diabetes mellitus (IDDM) or juvenile onset diabetes. This disease is characterized by a progressive loss of insulin secretory function by beta cells of the pancreas. This characteristic is also shared by non-idiopathic, or "secondary", diabetes having its origins in pancreatic disease. Type I diabetes mellitus is associated with the following clinical signs or symptoms: persistently elevated plasma glucose concentration or hyperglycemia; polyuria; polydipsia and/or hyperphagia; chronic microvascular complications such as retinopathy, nephropathy and neuropathy; and macrovascular complications such as hyperlipidemia and hypertension which can lead to blindness, end-stage renal disease, limb amputation and myocardial infarction. Therapy for IDDM patients has consistently focused on administration of exogenous insulin, which may be derived from various sources (e.g., human, bovine, porcine insulin). The use of heterologous species material gives rise to formation of anti-insulin antibodies which have activity limiting effects and result in progressive requirements for larger doses in order to achieve desired hypoglycemic effects.

Type II diabetes mellitus (non-insulin-dependent diabetes mellitus or NIDDM) is a metabolic disorder involving the dysregulation of glucose metabolism and impaired insulin sensitivity. Type II diabetes mellitus usually develops in adulthood and is associated with the body's inability to utilize or make sufficient insulin. In addition to the insulin resistance observed in the target tissues, patients suffering from type II diabetes mellitus have a relative insulin deficiency—that is, patients have lower than predicted insulin levels for a given plasma glucose concentration. Type II diabetes mellitus is characterized by the following clinical signs or symptoms: persistently elevated plasma glucose concentration or hyperglycemia; polyuria; polydipsia and/or hyperphagia; chronic microvascular complications such as retinopathy, nephropathy and neuropathy; and macrovascular complications such as hyperlipidemia and hypertension which can lead to blindness, end-stage renal disease, limb amputation and myocardial infarction. Typical treatment of Type II diabetes mellitus focuses on maintaining the blood glucose level as near to normal as possible with lifestyle modification relating to diet and exercise, and when necessary, the treatment with antidiabetic agents, insulin or a combination thereof. NIDDM that cannot be controlled by dietary management is treated with oral antidiabetic agents.

Syndrome X, also termed Insulin Resistance Syndrome (IRS), Metabolic Syndrome, or Metabolic Syndrome X, is recognized in some 2% of diagnostic coronary catheterizations. Often disabling, it presents symptoms or risk factors for the development of Type II diabetes mellitus and cardiovascular disease, including impaired glucose tolerance (IGT), impaired fasting glucose (IFG), hyperinsulinemia, insulin resistance, dyslipidemia (e.g., high triglycerides, low HDL), hypertension and obesity. Although insulin resistance is not always treated in all Syndrome X patients, those who exhibit a prediabetic state (e.g., IGT, IFG), where fasting glucose levels may be higher than normal but not at the diabetes diagnostic criterion, is treated in some countries (e.g., Germany) with metformin to prevent diabetes. The anti-diabetic agents may be combined with pharmacological agents for the treatment of the concomitant co-morbidities (e.g., antihypertensives for hypertension, hypolipidemic agents for lipidemia).

Hyperglycemia is one common characteristic of these diabetic disorders. Treatments of hyperglycemia are focused on excretion of excessive glucose directly into urine, which involves sodium-glucose cotransporters (SGLTs), primarily found in the chorionic membrane of the intestine and kidney. In particular, renal reabsorption of glucose is mediated by SGLT1 and SGLT2 (MARSENIC, O., "Glucose Control by the Kidney: An Emerging Target in Diabetes", *AM. J. Kidney Dis.*, 2009 May, pp 875-883, Vol. 53(5); WRIGHT, E. M., et al., "Biology of Human Sodium Glucose Transporters", *Physiol. Rev.*, 2011 April, pp 733-794, Vol. 91(2)). SGLT1, a high-affinity low-capacity transporter with a $Na^+$: glucose transport ratio of 2:1, is present in intestinal and renal epithelial cells (LEE, W. S., et al., "The High Affinity $Na_+$/Glucose Cotransporter. Re-evaluation of Function and Distribution of Expression", *J. Biol. Chem.*, 1994 April 22, pp 12032-12039, Vol. 269(16)). On the other hand, SGLT2, also known as SAAT1, a low-affinity high-capacity transporter with a $Na^+$:glucose transport ratio of 1:1, is found in the epithelium of the kidney (YOU, G., et al., "Molecular Characteristic of Na(+)-coupled Glucose Transporters in Adult and Embryonic Rat Kidney", *J. Biol. Chem.*, 1995 Dec. 8, pp 29365-29371, Vol. 270(49); CHEN, J., et al., "Quantitative PCR Tissue Expression Profiling of the Human SGLT2 Gene and Related Family Members", *Diabetes Ther.*, 2010 December, pp 57-92, Vol. 1(2)). In addition, glucose absorption in the intestine is primarily mediated by SGLT1 and SGLT2. Thus, inhibition of SGLT1 and SGLT2 reduces plasma glucose through suppression of glucose reabsorption in the kidney, which was demonstrated in rodent models of IDDM and NIDDM by increasing the excretion of glucose in urine and lowering blood glucose levels.

Non-alcoholic fatty liver disease (NAFLD) is one cause of a fatty liver, occurring when fat is deposited (steatosis) in the liver. NAFLD is considered to cover a spectrum of disease activity. This spectrum begins as fatty accumulation in the liver (hepatic steatosis). A liver can remain fatty without disturbing liver function, but by varying mechanisms and possible insults to the liver may also progress to become NASH, a state in which steatosis is combined with inflammation and fibrosis. Non-alcoholic steatohepatitis (NASH) is a progressive, severe form of NAFLD. Over a 10-year period, up to 20% of patients with NASH will develop cirrhosis of the liver, and 10% will suffer death related to liver disease. The exact cause of NAFLD is still unknown, however, both obesity and insulin resistance are thought to play a strong role in the disease process. The exact reasons and mechanisms by which the disease progresses from one stage to the next are not known.

NAFLD has been linked to insulin resistance (IR) and the metabolic syndrome (MS). As the renin-angiotensin system (RAS) plays a central role in insulin resistance, and subsequently in NAFLD and NASH, an attempt to block the deleterious effects of RAS overexpression has been proposed a target for treatment. While many potential therapies tested in NASH target only the consequences of this condition, or try to "get rid" of excessive fat, angiotensin receptor blockers (ARBs) may act as a tool for correction of the various imbalances that act in harmony in NASH/NAFLD. Indeed, by inhibiting RAS the intracellular insulin signaling pathway may be improved, resulting in better control of adipose tissue proliferation and adipokine production, as well as more balanced local and systemic levels of various cytokines. At the same time, by controlling the local RAS in the liver fibrosis may be prevented and the cycle that links steatosis to necroinflammation slowed down. (GEORGESCU, E. F., in *Advances in Therapy*, 2008, pp 1141-1174, Vol. 25, Issue 11)

SCAFOGLIO, C., et al., in "Functional expression of sodium-glucose transporters in cancer", *PNAS*, 2015, pp E4111-E4119, Vol 112(3), describe the role of sodium-dependent glucose transporters (SGLTs) in pancreatic and prostate adenocarcinomas, and their role in cancer cell survival. SGLT2 was found to be functionally expressed in pancreatic and prostate adenocarcinomas and further found to block glucose uptake and reduce tumor growth and survival in a xenograft model of pancreatic cancer, suggesting that SGLT2 inhibitors could be useful in treating certain types of cancers.

There remains a need for SGLT inhibitor compounds that have pharmacokinetic and pharmacodynamic properties suitable for use as human pharmaceuticals.

SUMMARY OF THE INVENTION

The present invention is directed to compounds of formula (I)

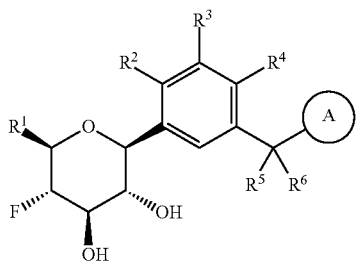

(I)

wherein $R^1$ is selected from the group consisting of —$C_{1-4}$alkyl, hydroxy substituted $C_{1-4}$alkyl, —$CH_2$—$R^{10}$, $C_{3-6}$cycloalkyl, hydroxy substituted $C_{3-6}$cycloalkyl, —C(O)OH and —C(O)O—($C_{1-4}$alkyl);

wherein $R^{10}$ is selected from the group consisting of fluoro, $C_{1-2}$alkoxy, cyano and $NR^A R^B$; wherein $R^A$ and $R^B$ are each independently selected from the group consisting of hydrogen and $C_{1-2}$alkyl;

$R^2$ is selected from the group consisting of hydrogen, halogen, hydroxy, $C_{1-4}$alkyl, —($C_{1-4}$alkyl)-OH, $C_{1-4}$alkoxy, cyano substituted $C_{1-4}$alkoxy, $C_{2-4}$alkenyl, $C_{2-4}$alkenyl-oxy, benzyloxy and carboxy;

$R^3$ is selected from the group consisting of hydrogen, halogen, $C_{1-4}$alkyl and $C_{2-4}$alkenyl;

$R^4$ is selected from the group consisting of hydrogen, halogen, hydroxy, cyano, $C_{1-4}$alkyl, fluorinated $C_{1-2}$alkyl, $C_{1-4}$alkoxy, fluorinated $C_{1-2}$alkoxy, cyano substituted $C_{1-4}$alkoxy and $C_{3-6}$cycloalkyl;

alternatively, $R^2$ and $R^3$ or $R^3$ and $R^4$ are taken together with the carbon atoms to which they are bound to form a ring structure selected from the group consisting of 2,3-dihydrofuranyl and 3,4-dihydro-2H-pyranyl;

wherein —$R^2$-$R^3$— is selected from the group consisting of —O—$CH_2$—$CH_2$—, —$CH_2$—$CH_2$—O—, —$CH_2$—O—$CH_2$—$CH_2$— and $CH_2$—$CH_2$—O—$CH_2$—; and wherein —$R^3$-$R^4$— is selected from the group consisting of —O—$CH_2$—$CH_2$—, —$CH_2$—$CH_2$—O—, —$CH_2$—O—$CH_2$—$CH_2$— and $CH_2$—$CH_2$—O—$CH_2$—;

wherein the 2,3-dihydrofuranyl or 3,4-dihydro-2H-pyranyl is optionally substituted with one or more substituents independently selected from the group consisting of hydroxy, methyl, ethyl, hydroxy-methyl- and hydroxyethyl-;

$R^5$ and $R^6$ are the same and are hydrogen;

Ⓐ is selected from the group consisting of $C_{5-12}$cycloalkyl, $C_{5-12}$cycloalkenyl, phenyl, heteroaryl and heterocyclyl;

wherein the phenyl, heteroaryl or heterocyclyl is optionally substituted with one or more substituents independently selected from the group consisting of halogen, hydroxy, oxo (i.e. =O), $C_{1-4}$alkyl, $C_{1-4}$alkoxy, fluorinated $C_{1-2}$alkyl, fluorinated $C_{1-2}$alkoxy, cyano, 2,5-dimethyl-thien-3-yl, 5-methyl-thiazol-2-yl and —C(O)—$R^{11}$;

wherein $R^{11}$ is selected from the group consisting of $C_{1-4}$alkyl, $C_{1-4}$alkoxy, $C_{3-6}$cycloalkyl, azetidin-1-yl, pyrrolidin-1-yl, piperidin-1-yl, piperazin-1-yl, morpholin-4-yl, thiomorpholin-4-yl and thiazol-2-yl;

provided that when Ⓐ is bicyclo[4.2.0]octa-1 (6),2,4-trien-3-yl (i.e. benzocyclobut-4-yl) or bicyclo[4.2.0]octan-3-yl, then $R^2$ and $R^3$ or $R^3$ and $R^4$ are taken together with the carbon atoms to which they are bound to form a ring structure selected from the group consisting of 2,3-dihydrofuranyl and 3,4-dihydro-2H-pyranyl;

wherein 2,3-dihydrofuranyl or 3,4-dihydro-2H-pyranyl is optionally substituted with one or more substituents independently selected from the group consisting of hydroxy, methyl, ethyl, hydroxy-methyl- and hydroxyethyl-;

provided further that when Ⓐ is phenyl, wherein the phenyl is optionally substituted, then $R^2$ and $R^3$ or $R^3$ and $R^4$ are taken together with the carbon atoms to which they are bound to form a ring structure selected from the group consisting of 2,3-dihydrofuranyl and 3,4-dihydro-2H-pyranyl;

provided further that when Ⓐ is thienyl or pyridyl, then $R^2$ and $R^3$ or $R^3$ and $R^4$ are taken together with the carbon atoms to which they are bound to form a ring structure selected from the group consisting of 2,3-dihydrofuranyl and 3,4-dihydro-2H-pyranyl;

provided further that when R¹ is —CH₂OH, R² is H, R³ is H, R⁴ is H or Cl, R⁵ is H and R⁶ is H, then Ⓐ is other than benzothien-2-yl;

and isotopologues and pharmaceutically acceptable salts thereof.

The present invention is further directed to compounds of formula (V-S)

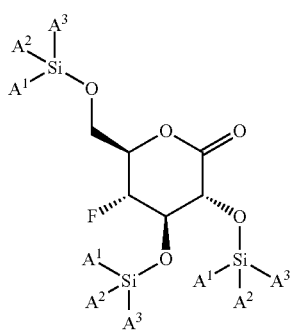

(V-S)

wherein A¹, A² and A³ are each an independently selected from the group consisting of C₁₋₈alkyl, C₃₋₆cycloalkyl, bicyclo[2.2.1]heptan-2-yl

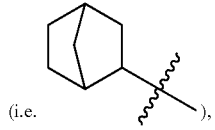

(i.e. ), phenyl and 3,5-di(trifluoromethyl)phenyl. The compounds of formula (V-S) are useful as intermediates in the synthesis of pharmaceutical agents.

The present invention is further directed to a process for the preparation of the compound of formula (V-S)

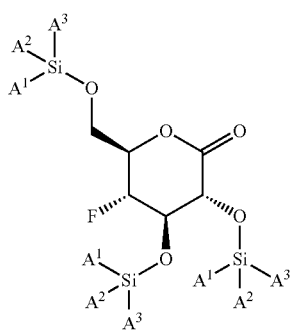

(V-S)

wherein A¹, A² and A³ are each an independently selected from the group consisting of C₁₋₈alkyl, C₃₋₆cycloalkyl, bicyclo[2.2.1]heptan-2-yl, phenyl and 3,5-di(trifluoromethyl)phenyl;

comprising

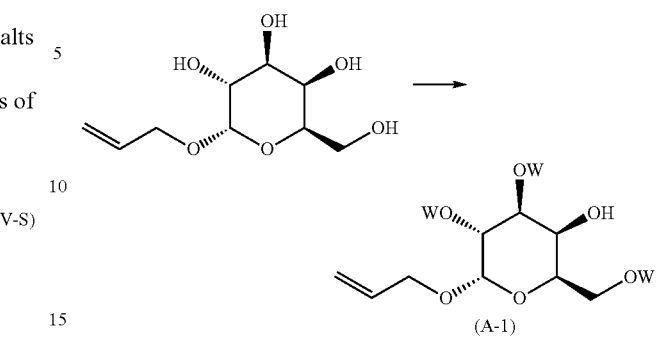

reacting (2S,3R,4S,5R,6R)-2-(allyloxy)-6-(hydroxymethyl)tetrahydro-2H-pyran-3,4,5-triol, with an acylating agent; in the presence of an inorganic or organic base; neat, when in the presence of an organic base or when in the presence of an inorganic base, in an organic solvent; at a temperature in the range of from about −50° C. to about room temperature; to yield the corresponding compound of formula (A-1), wherein W is the corresponding acyl group, preferably —C(O)-methyl, —C(O)-ethyl, —C(O)-benzyl, more preferably —C(O)-benzyl (benzoyl);

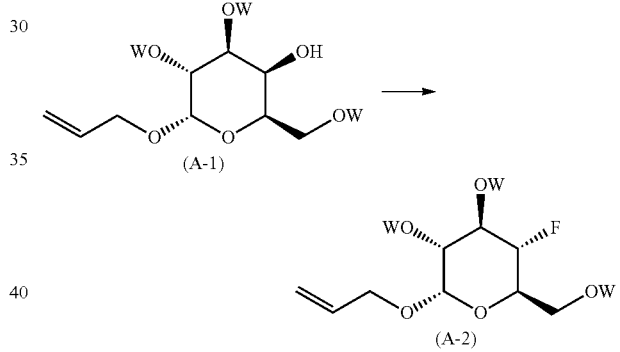

reacting the compound of formula (A-1) with a fluorinating agent; in an organic solvent or mixture of organic solvents; at a temperature in the range of from about −50° C. to about room temperature; to yield the corresponding compound of formula (A-2);

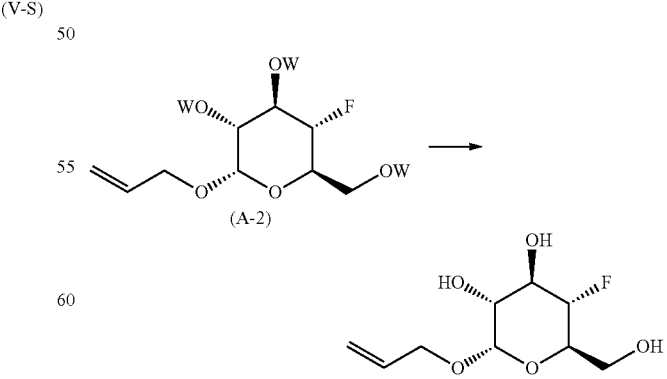

de-protecting the compound of formula (A-2) to yield (2S,3R,4R,5S,6R)-2-(allyloxy)-5-fluoro-6-(hydroxymethyl)tetrahydro-2H-pyran-3,4-diol;

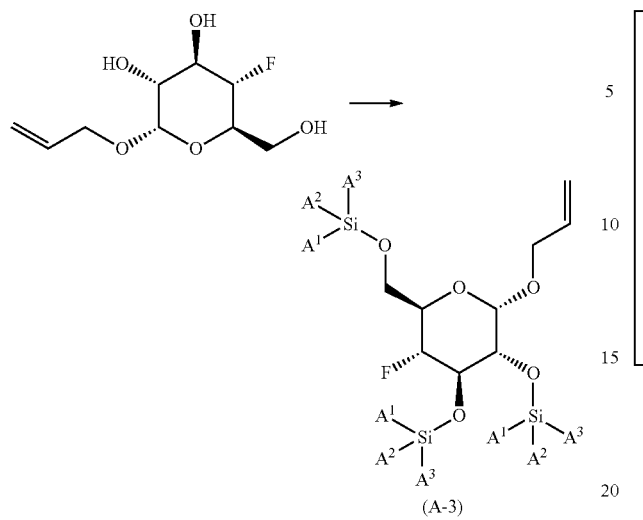

reacting (2S,3R,4R,5S,6R)-2-(allyloxy)-5-fluoro-6-(hydroxymethyl)tetrahydro-2H-pyran-3,4-diol with a trialkyl silyl reagent; in the presence of an organic base; in an organic solvent or mixture of organic solvents; at a temperature in the range of from about 0° C. to about 50° C.; to yield the corresponding compound of formula (A-3) wherein $A^1$, $A^2$ and $A^3$ are the corresponding alkyl groups;

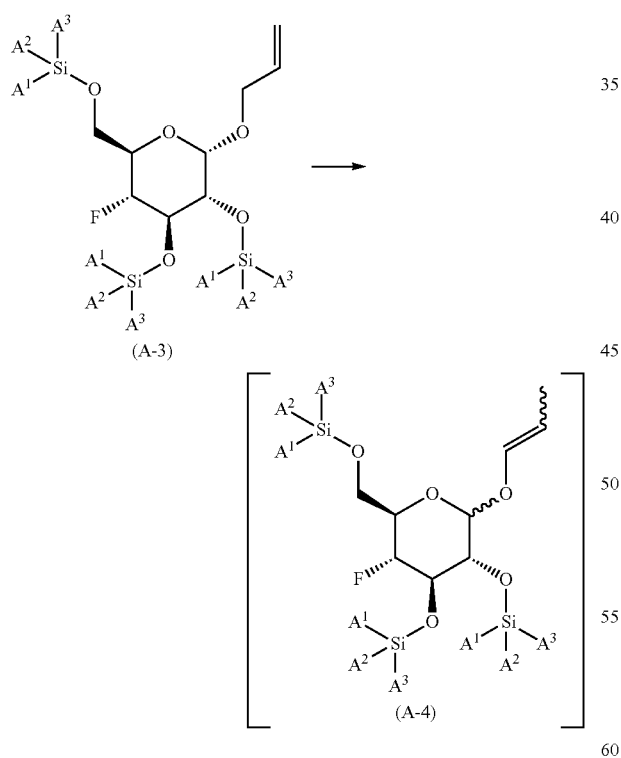

reacting the compound of formula (A-3) with allyl isomerization catalyst in an organic solvent or mixture of water and a water miscible organic solvent; at a temperature of in the range of from about 75° C. to about 105° C.; to yield the corresponding compound of formula (A-4), wherein the compound of formula (A-4) is not isolated;

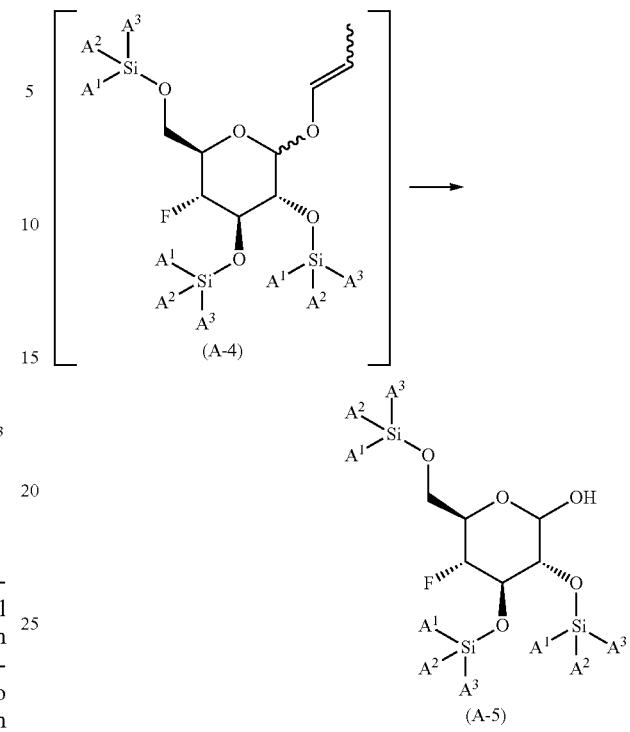

reacting the compound of formula (A-4) with an co-oxidant; in the presence of an oxidizing reagent; in an organic solvent or mixture of water and a water miscible organic solvent; at a temperature in the range of from about 0° C. to about 50° C.; to yield the corresponding compound of formula (A-5);

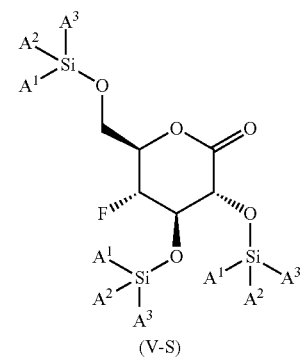

reacting the compound of formula (A-5) under SWERN oxidation conditions; to yield the corresponding compound of formula (V-S)

The present invention is further directed to processes for the preparation of the compounds of formula (I). The present invention is further directed to a product prepared according to any of the process(es) described herein.

Illustrative of the invention are pharmaceutical compositions comprising a pharmaceutically acceptable carrier and a compound of formula (I) as described herein. An illustration of the invention is a pharmaceutical composition made by mixing a compound of formula (I) as described herein and a pharmaceutically acceptable carrier. Illustrating the invention is a process for making a pharmaceutical composition comprising mixing a compound of formula (I) as described herein and a pharmaceutically acceptable carrier.

Exemplifying the invention are methods of treating a disease, disorder, or condition mediated by SGLT activity (preferably, dual SGLT1 and SGLT2 activity) selected from the group consisting of impaired glucose tolerance (IGT), impaired fasting glucose (IFT), gestational diabetes, Type II diabetes mellitus, Syndrome X (also known as Metabolic Syndrome), obesity, nephropathy, neuropathy, retinopathy, hypertension, angina, atherosclerosis, heart disease, heart attack, ischemia, stroke, nerve damage or poor blood flow in the feet, non-alcoholic steatohepatitis (NASH), non-alcoholic fatty liver disease (NAFLD), liver fibrosis, cataracts, polycystic ovarian syndrome, irritable bowel syndrome, inflammation and cancer (preferably prostate cancer or pancreatic cancer), comprising administering to a subject in need thereof a therapeutically effective amount of any of the compounds or pharmaceutical compositions described above.

In an embodiment, the present invention is directed to a compound of formula (I) for use as a medicament. In another embodiment, the present invention is directed to a compound of formula (I) for use in the treatment of a disorder mediated SGLT activity (preferably dual SGLT1 and SGLT2 activity) selected from the group consisting impaired glucose tolerance (IGT), impaired fasting glucose (IFT), gestational diabetes, Type II diabetes mellitus, Syndrome X (also known as Metabolic Syndrome), obesity, nephropathy, neuropathy, retinopathy, hypertension, angina, atherosclerosis, heart disease, heart attack, ischemia, stroke, nerve damage or poor blood flow in the feet, non-alcoholic steatohepatitis (NASH), non-alcoholic fatty liver disease (NAFLD), liver fibrosis, cataracts, polycystic ovarian syndrome, irritable bowel syndrome, inflammation and cancer (preferably prostate cancer or pancreatic cancer). In another embodiment, the present invention is directed to a composition comprising a compound of formula (I) for the treatment of a disorder mediated by SGLT activity (preferably dual SGLT1 and SGLT2 activity) selected from the group consisting impaired glucose tolerance (IGT), impaired fasting glucose (IFT), gestational diabetes, Type II diabetes mellitus, Syndrome X (also known as Metabolic Syndrome), obesity, nephropathy, neuropathy, retinopathy, hypertension, angina, atherosclerosis, heart disease, heart attack, ischemia, stroke, nerve damage or poor blood flow in the feet, non-alcoholic steatohepatitis (NASH), non-alcoholic fatty liver disease (NAFLD), liver fibrosis, cataracts, polycystic ovarian syndrome, irritable bowel syndrome, inflammation and cancer (preferably prostate cancer or pancreatic cancer).

Another example of the invention is the use of any of the compounds described herein in the preparation of a medicament for treating: (a) impaired glucose tolerance (IGT), (b) impaired fasting glucose (IFT), (c) gestational diabetes, (d) Type II diabetes mellitus, (e) Syndrome X (also known as Metabolic Syndrome), (f) obesity, (g) nephropathy, (h) neuropathy, (i) retinopathy, (j) hypertension, (k) angina, (l) atherosclerosis, (m) heart disease, (n) heart attack, (o) ischemia, (p) stroke, (q) nerve damage or poor blood flow in the feet, (r) non-alcoholic steatohepatitis (NASH), (s) non-alcoholic fatty liver disease (NAFLD), (t) liver fibrosis, (u) cataracts, (v) polycystic ovarian syndrome, (w) irritable bowel syndrome, (x) inflammation and (y) cancer (preferably prostate cancer or pancreatic cancer), in a subject in need thereof. In another example, the present invention is directed to a compound as described herein for use in a methods for treating a disorder selected from the group consisting of impaired glucose tolerance (IGT), impaired fasting glucose (IFT), gestational diabetes, Type II diabetes mellitus, Syndrome X (also known as Metabolic Syndrome), obesity, nephropathy, neuropathy, retinopathy, hypertension, angina, atherosclerosis, heart disease, heart attack, ischemia, stroke, nerve damage or poor blood flow in the feet, non-alcoholic steatohepatitis (NASH), non-alcoholic fatty liver disease (NAFLD), liver fibrosis, cataracts, polycystic ovarian syndrome, irritable bowel syndrome, inflammation and cancer (preferably prostate cancer or pancreatic cancer), in a subject in need thereof.

DETAILED DESCRIPTION OF THE INVENTION

The present invention is directed to compounds of formula (I)

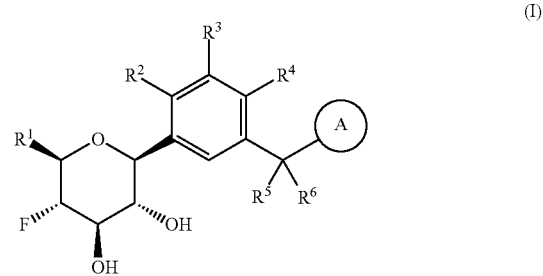

(I)

wherein $R^1$, $R^2$, $R^3$, $R^4$, $R^5$, $R^6$ and Ⓐ are as herein defined; and isotopologues and pharmaceutically acceptable salts thereof. The compounds of the present invention are useful in the treatment of diseases, disorders and complications associated with SGLT activity (preferably dual SGLT1 and SGLT2 activity) selected from the group of impaired glucose tolerance (IGT), impaired fasting glucose (IFT), gestational diabetes, Type II diabetes mellitus, Syndrome X (also known as Metabolic Syndrome), obesity, nephropathy, neuropathy, retinopathy, hypertension, angina, atherosclerosis, heart disease, heart attack, ischemia, stroke, nerve damage or poor blood flow in the feet, non-alcoholic steatohepatitis (NASH), non-alcoholic fatty liver disease (NAFLD), liver fibrosis, cataracts, polycystic ovarian syndrome, irritable bowel syndrome, inflammation and cancer (preferably prostate cancer or pancreatic cancer).

In an embodiment, the present invention is directed to compounds of formula (I) wherein $R^1$ is selected from the group consisting of —$C_{1-4}$alkyl, hydroxy substituted $C_{1-4}$alkyl, —$CH_2$—$R^{10}$, $C_{3-6}$cycloalkyl, hydroxy substituted $C_{3-6}$cycloalkyl and —C(O)OH; wherein $R^{10}$ is selected from the group consisting of fluoro, $C_{1-2}$alkoxy, cyano and $NR^AR^B$; wherein $R^A$ and $R^B$ are each independently selected from the group consisting of hydrogen and $C_{1-2}$alkyl. In another embodiment, the present invention is directed to compounds of formula (I) wherein $R^1$ is selected from the group consisting of —$C_{1-2}$alkyl, hydroxy substituted $C_{1-2}$alkyl, —$CH_2$—$R^{10}$, hydroxy substituted $C_{3-6}$cycloalkyl and —C(O)OH; wherein $R^{10}$ is selected from the group consisting of fluoro, $C_{1-2}$alkoxy, cyano and amino.

In another embodiment, the present invention is directed to compounds of formula (I) wherein $R^1$ is selected from the group consisting of methyl-, fluoro-methyl-, cyano-methyl-, amino-methyl-, hydroxy-methyl-, methoxy-methyl-, 1R-hydroxy-ethyl-, 1 S-hydroxy-ethyl-, 1-hydroxy-isopropyl, 1-hydroxy-cyclopro-1-yl and carboxy. In another embodiment, the present invention is directed to compounds of formula (I) wherein $R^1$ is selected from the group consisting of methyl-, fluoro-methyl-, cyano-methyl-, hydroxy-methyl-, 1R-hydroxy-ethyl- and 1S-hydroxy-ethyl-. In another embodiment, the present invention is directed to compounds of formula (I) wherein $R^1$ is selected from the group consisting of hydroxy-methyl- and 1R-hydroxy-ethyl-. In another embodiment, the present invention is directed to compounds of formula (I) wherein $R^1$ is hydroxy-methyl- (i.e. —$CH_2$—OH).

In an embodiment, the present invention is directed to compounds of formula (I) wherein $R^2$ is selected from the group consisting of hydrogen, halogen, hydroxy, $C_{1-4}$alkyl, —($C_{1-4}$alkyl)-OH, $C_{1-4}$alkoxy, cyano substituted $C_{1-2}$alkoxy, $C_{2-4}$alkenyl-oxy-, benzyloxy- and carboxy. In another embodiment, the present invention is directed to compounds of formula (I) wherein $R^2$ is selected from the group consisting of hydrogen, halogen, hydroxy, $C_{1-2}$alkyl, —($C_{1-4}$alkyl)-OH, $C_{1-2}$alkoxy, cyano substituted $C_{1-2}$alkoxy, $C_{2-3}$alkenyl-oxy-, benzyloxy- and carboxy.

In another embodiment, the present invention is directed to compounds of formula (I) wherein $R^2$ is selected from the group consisting of hydrogen, chloro, fluoro, hydroxy, methyl, hydroxy-methyl-, methoxy, tri-deutero-methoxy, cyano-methoxy-, ethoxy, propen-2-yl-oxy, benzyloxy and carboxy. In another embodiment, the present invention is directed to compounds of formula (I) wherein $R^2$ is selected from the group consisting of hydrogen, chloro, fluoro, hydroxy, hydroxy-methyl-, methoxy, tri-deutero-methoxy, cyano-methoxy-, ethoxy, propen-2-yl-oxy, benzyloxy and carboxy.

In another embodiment, the present invention is directed to compounds of formula (I) wherein $R^2$ is selected from the group consisting of hydrogen, hydroxy, methyl, methoxy, benzyloxy and tri-deutero-methoxy. In another embodiment, the present invention is directed to compounds of formula (I) wherein $R^2$ is selected from the group consisting of hydrogen, fluoro, hydroxy, methyl, hydroxy-methyl-, methoxy, tri-deutero-methoxy and ethoxy. In another embodiment, the present invention is directed to compounds of formula (I) wherein $R^2$ is selected from the group consisting of hydrogen, hydroxy, methyl, hydroxy-methyl-, methoxy, ethoxy and tri-deutero-methoxy. In another embodiment, the present invention is directed to compounds of formula (I) wherein $R^2$ is selected from the group consisting of hydrogen, hydroxy, methoxy and ethoxy. In another embodiment, the present invention is directed to compounds of formula (I) wherein $R^2$ is selected from the group consisting of hydroxy, methoxy and ethoxy.

In another embodiment, the present invention is directed to compounds of formula (I) wherein $R^2$ is selected from the group consisting of hydroxy and methoxy.

In an embodiment, the present invention is directed to compounds of formula (I) wherein $R^3$ is selected from the group consisting of hydrogen, halogen, $C_{1-4}$alkyl and $C_{2-4}$alkenyl. In another embodiment, the present invention is directed to compounds of formula (I) wherein $R^3$ is selected from the group consisting of hydrogen, halogen, $C_{1-2}$alkyl and $C_{2-3}$alkenyl.

In another embodiment, the present invention is directed to compounds of formula (I) wherein $R^3$ is selected from the group consisting of hydrogen, fluoro, methyl and n-propen-2-yl. In another embodiment, the present invention is directed to compounds of formula (I) wherein $R^3$ is selected from the group consisting of hydrogen and methyl. In another embodiment, the present invention is directed to compounds of formula (I) wherein $R^3$ is hydrogen;

In an embodiment, the present invention is directed to compounds of formula (I) wherein $R^4$ is selected from the group consisting of hydrogen, halogen, hydroxy, cyano, $C_{1-4}$alkyl, fluorinated $C_{1-2}$alkyl, $C_{1-4}$alkoxy, fluorinated $C_{1-2}$alkoxy, and $C_{3-6}$cycloalkyl. In another embodiment, the present invention is directed to compounds of formula (I) wherein $R^4$ is selected from the group consisting of hydrogen, halogen, hydroxy, $C_{1-2}$alkyl, fluorinated $C_{1-2}$alkyl, $C_{1-4}$alkoxy, fluorinated $C_{1-2}$alkoxy, cyano and $C_{3-6}$cycloalkyl;

In another embodiment, the present invention is directed to compounds of formula (I) wherein $R^4$ is selected from the group consisting of hydrogen, chloro, fluoro, hydroxy, methyl, ethyl, trifluoromethyl, methoxy, ethoxy, isopropyloxy, trifluoromethoxy, cyano and cyclopropyl. In another embodiment, the present invention is directed to compounds of formula (I) wherein $R^4$ is selected from the group consisting of hydrogen, chloro, fluoro, methyl, ethyl, trifluoromethyl, methoxy, ethoxy, isopropyloxy, trifluoromethoxy, cyano and cyclopropyl.

In another embodiment, the present invention is directed to compounds of formula (I) wherein $R^4$ is selected from the group consisting of hydroxy, chloro, methyl, ethyl, methoxy and ethoxy. In another embodiment, the present invention is directed to compounds of formula (I) wherein $R^4$ is selected from the group consisting of chloro, methyl, ethyl, methoxy and ethoxy. In another embodiment, the present invention is directed to compounds of formula (I) wherein $R^4$ is selected from the group consisting of hydroxy, chloro, methyl, ethyl, methoxy, and cyclopropyl. In another embodiment, the present invention is directed to compounds of formula (I) wherein $R^4$ is selected from the group consisting of chloro, methyl, ethyl and methoxy.

In another embodiment, the present invention is directed to compounds of formula (I) wherein $R^4$ is methoxy.

In certain embodiments, the present invention is directed to compounds of formula (I) wherein the

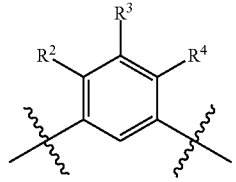

is selected from the group consisting of

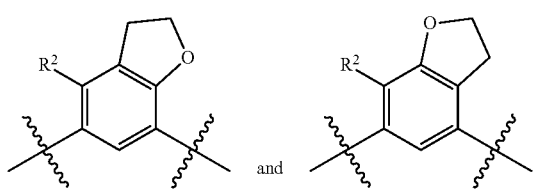

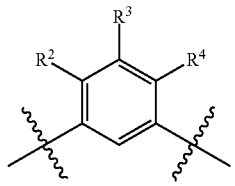

(such that —R²-R³— is selected from the group consisting of —O—CH₂—CH₂— and —CH₂—CH₂—O; and —R³-R⁴— is selected from the group consisting of —CH₂—CH₂—O— and —O—CH₂—CH₂—, respectively); and wherein the 2,3-dihydrofuranyl portion of the structure is optionally substituted as herein defined.

In certain embodiments, the present invention is directed to compounds of formula (I) wherein the

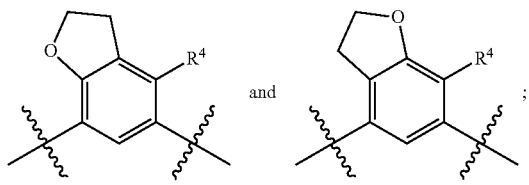

is selected from the group consisting of

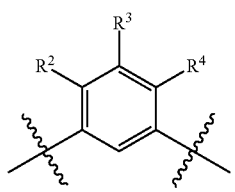

and wherein the 2,3-dihydrofuranyl portion of the structure is optionally substituted as herein defined. In certain embodiments, the present invention is directed to compounds of formula (I) wherein the is selected from the group consisting of

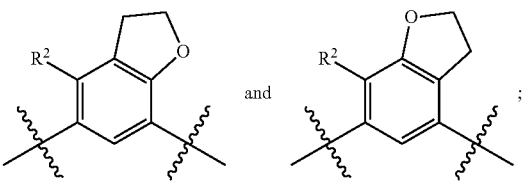

and wherein the 2,3-dihydrofuranyl portion of the structure is optionally substituted as herein defined.

In certain embodiments, the present invention is directed to compounds of formula (I) wherein the

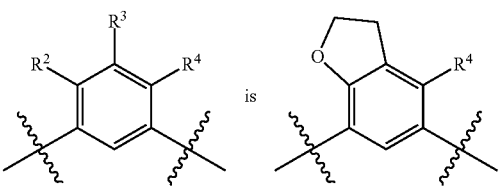

(such that —R²-R³— is —O—CH₂—CH₂—); and wherein the 2,3-dihydrofuranyl portion of the structure is optionally substituted as herein defined. In certain embodiments, the present invention is directed to compounds of formula (I) wherein the

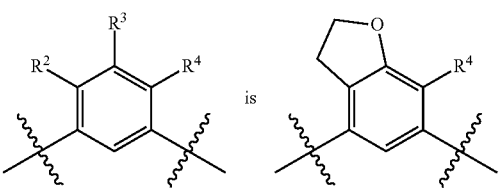

(such that —R²-R³— is —CH₂—CH₂—O—); and wherein the 2,3-dihydrofuranyl portion of the structure is optionally substituted as herein defined. In certain embodiments, the present invention is directed to compounds of formula (I) wherein the

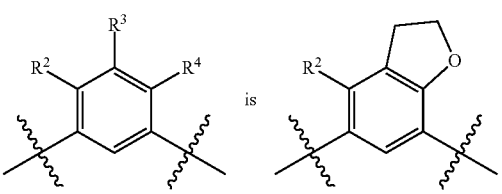

such that —R³-R⁴— is —CH₂—CH₂—O—); and wherein the 2,3-dihydrofuranyl portion of the structure is optionally substituted as herein defined. In certain embodiments, the present invention is directed to compounds of formula (I) wherein the

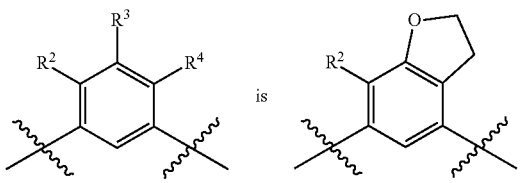

(such that —R³-R⁴— is —O—CH₂—CH₂—); and wherein the 2,3-dihydrofuranyl portion of the structure is optionally substituted as herein defined.

In an embodiment, the present invention is directed to compounds of formula (I) wherein R² and R³ or R³ and R⁴ are taken together with the carbon atoms to which they are bound to form a ring structure selected from the group consisting of 2,3-dihydrofuranyl and 3,4-dihydro-2H-pyranyl; wherein the 2,3-dihydrofuranyl is optionally substituted as herein defined.

In an embodiment, the present invention is directed to compounds of formula (I) wherein R² and R³ or R³ and R⁴ are taken together with the carbon atoms to which they are bound to form 2,3-dihydro-furanyl; wherein the 2,3-dihydro-furanyl is optionally substituted with one to three substituent independently selected from the group consisting of methyl, ethyl, hydroxy-methyl- and hydroxy-ethyl-. In another embodiment, the present invention is directed to compounds of formula (I) wherein R² and R³ or R³ and R⁴ are taken together with the carbon atoms to which they are bound to form 2,3-dihydro-furanyl; wherein the 2,3-dihydro-furanyl, is optionally substituted with one to three substituent independently selected from the group consisting of methyl, hydroxy-methyl- and hydroxy-ethyl-.

In another embodiment, the present invention is directed to compounds of formula (I) wherein, R² and R³ or R³ and R⁴ are taken together with the carbon atoms to which they are bound to form a ring structure selected from the group consisting of 2,3-dihydro-furanyl, 3-hydroxy-methyl-2,3-dihydro-furanyl, 3-hydroxy-ethyl-2,3-dihydro-furanyl, 3-hydroxy-methyl-2,2-dimethyl-2,3-dihydro-furanyl, 3-methyl-2,3-dihydro-furanyl and 3-methyl-3-hydroxymethyl-2,3-dihydro-furanyl.

In another embodiment, the present invention is directed to compounds of formula (I) wherein alternatively, R² and R³ or R³ and R⁴ are taken together with the carbon atoms to which they are bound to form 2,3-dihydro-furanyl.

In an embodiment, the present invention is directed to compounds of formula (I) wherein R² and R³ are taken together with the carbon atoms to which they are bound to form 2,3-dihydro-furanyl, wherein the 2,3-furanyl is optionally substituted as herein defined. In another embodiment, the present invention is directed to compounds of formula (I) wherein R² and R³ are taken together with the carbon atoms to which they are bound to form 2,3-dihydro-furanyl.

In an embodiment, the present invention is directed to compounds of formula (I) wherein R³ and R⁴ are taken together with the carbon atoms to which they are bound to form 2,3-dihydro-furanyl, wherein the 2,3-dihydro-furanyl is optionally substituted as herein defined.

In another embodiment, the present invention is directed to compounds of formula (I) wherein R³ and R⁴ are taken together with the carbon atoms to which they are bound to form a ring structure selected from the group consisting of 2,3-dihydro-furanyl, 3-hydroxy-2,2-dimethyl-2,3-dihydro-furanyl, 3-hydroxymethyl-2,3-dihydro-furanyl, 3-hydroxy-ethyl-2,3-dihydro-furanyl, 3-methyl-3-hydroxymethyl-2,3-dihydro-furanyl and 3-methyl-2,3-dihydro-furanyl.

In another embodiment, the present invention is directed to compounds of formula (I) wherein R³ and R⁴ are taken together with the carbon atoms to which they are bound to form 2,3-dihydro-furanyl.

In an embodiment, the present invention is directed to compounds of formula (I) wherein R⁵ and R⁶ are the same and are hydrogen. In another embodiment, the present invention is directed to compounds of formula (I) wherein R⁵ and R⁶ are the same and are selected from the group consisting of hydrogen and deuterium.

In another embodiment, the present invention is directed to compounds of formula (I) wherein Ⓐ is selected from the group consisting of $C_{5-12}$cycloalkyl, $C_{5-12}$cycloalkenyl, phenyl, heteroaryl and heterocyclyl; wherein the phenyl, heteroaryl or heterocyclyl is optionally substituted with one to two substituent independently selected from the group consisting of halogen, hydroxy, oxo, $C_{1-4}$alkyl, $C_{1-4}$alkoxy, fluorinated $C_{1-2}$alkoxy, cyano, 2,5-dimethyl-thien-3-yl, 5-methyl-thiazol-2-yl and —C(O)—R¹¹; and wherein R¹¹ is selected from the group consisting of $C_{1-4}$alkyl, $C_{1-4}$alkoxy, $C_{3-6}$cycloalkyl, azetidin-1-yl, pyrrolidin-1-yl, piperidin-1-yl, piperazin-1-yl, morpholin-4-yl and thiazol-2-yl. In another embodiment, the present invention is directed to compounds of formula (I) wherein Ⓐ is selected from the group consisting of $C_{5-12}$cycloalkyl, $C_{5-12}$cycloalkenyl, phenyl, heteroaryl and heterocyclyl; wherein the phenyl is optionally substituted with one substituent independently selected from the group consisting of halogen, $C_{1-2}$alkyl, $C_{1-2}$alkoxy and fluorinated $C_{1-2}$alkoxy; wherein the heteroaryl or heterocyclyl is optionally substituted with one to two substituents independently selected from the group consisting of halogen, $C_{1-2}$alkyl, oxo, cyano, 2,5-dimethyl-thien-3-yl, 5-methyl-thiazol-2-yl and —C(O)—R¹¹; and wherein R¹¹ is selected from the group consisting of $C_{1-2}$alkyl, $C_{1-2}$alkoxy, $C_{3-6}$cycloalkyl, pyrrolidin-1-yl, morpholin-4-yl and thiazol-2-yl.

In another embodiment, the present invention is directed to compounds of formula (I) wherein Ⓐ is selected from the group consisting of 4-chloro-phenyl, 4-ethyl-phenyl, 4-methoxy-phenyl, 4-ethoxy-phenyl, 4-(fluoro-methoxy)-phenyl, chroman-6-yl, benzothien-2-yl, 3,4-dihydro-2H-quinolin-7-yl, 1-methyl-3,4-dihydro-2H-quinolin-7-yl, benzo[b][1,4]oxazin-7-yl-3-one, 6,7-dihydrobenzo[b]thiophen-2-yl-4-one, 2,2-difluoro-benzo[d][1,3]dioxol-5-yl, 2,3-dihydro-benzo[b][1,4]dioxin-6-yl, 2,3-dihydrobenzo[b][1,4]oxathiin-6-yl, bicyclo[4.2.0]octa-1 (6),2,4-trien-3-yl, 6,7-dihydro-5H-thieno[3,2-b]pyran-2-yl, 5,6-dihydro-7H-thieno[3,2-b]pyran-2-yl-7-one, 5-(5-methyl-thiazol-2-yl)-6,7-dihydrothieno[3,2-c]pyridin-2-yl, 5-(2,5-dimethyl-thien-3-yl)-6,7-dihydrothieno[3,2-c]pyridin-2-yl, 5-methyl-carbonyl-6,7-dihydrothieno[3,2-c]pyridin-2-yl, 5-methoxy-carbonyl-6,7-dihydrothieno[3,2-c]pyridin-2-yl, 5-ethoxy-carbonyl-6,7-dihydrothieno[3,2-c]pyridin-2-yl, 5-cyano-6,7-dihydrothieno[3,2-c]pyridin-2-yl, 5-(cyclopentyl-carbonyl)-6,7-dihydrothieno[3,2-c]pyridin-2-yl, 5-(pyrrolidin-1-yl-carbonyl)-6,7-dihydrothieno[3,2-c]pyridin-2-yl, 5-(morpholin-4-yl-carbonyl)-6,7-dihydrothieno[3,2-c]pyridin-2-yl, 5-(thiazol-2-yl-carbonyl)-6,7-dihydrothieno[3,2-c]pyridin-2-yl, 3,3-dideutero-2,3-dihydrobenzo[b][1,4]dioxin-6-yl and 2,2,3,3-tetra-deutero-2,3-dihydrobenzo[b][1,4]dioxin-6-yl.

In another embodiment, the present invention is directed to compounds of formula (I) wherein Ⓐ is selected from the group consisting of chroman-6-yl, benzothien-2-yl, 6,7-dihydrobenzo[b]thiophen-2-yl-4-one, 2,2-difluoro-benzo[d]

[1,3]dioxol-5-yl, 2,3-dihydro-benzo[b][1,4]dioxin-6-yl, bicyclo[4.2.0]octa-1(6),2,4-trien-3-yl, 6,7-dihydro-5H-thieno[3,2-b]pyran-2-yl, 5,6-dihydro-7H-thieno[3,2-b]pyran-2-yl-7-one, 5-(5-methyl-thiazol-2-yl)-6,7-dihydrothieno[3,2-c]pyridin-2-yl, 5-(2,5-dimethyl-thien-3-yl)-6,7-dihydrothieno[3,2-c]pyridin-2-yl, 5-methyl-carbonyl-6,7-dihydrothieno[3,2-c]pyridin-2-yl, 5-methoxy-carbonyl-6,7-dihydrothieno[3,2-c]pyridin-2-yl, 5-ethoxy-carbonyl-6,7-dihydrothieno[3,2-c]pyridin-2-yl, 5-cyano-6,7-dihydrothieno[3,2-c]pyridin-2-yl, 5-(cyclopentyl-carbonyl)-6,7-dihydrothieno[3,2-c]pyridin-2-yl, 5-(pyrrolidin-1-yl-carbonyl)-6,7-dihydrothieno[3,2-c]pyridin-2-yl, 5-(morpholin-4-yl-carbonyl)-6,7-dihydrothieno[3,2-c]pyridin-2-yl, 5-(thiazol-2-yl-carbonyl)-6,7-dihydrothieno[3,2-c]pyridin-2-yl and 2,2,3,3-tetra-deutero-2,3-dihydrobenzo[b][1,4]dioxin-6-yl. In another embodiment, the present invention is directed to compounds of formula (I) wherein Ⓐ is selected from the group consisting of benzothien-2-yl, chroman-6-yl, 2,3-dihydro-benzo[b][1,4]dioxin-6-yl, 2,3-dihydro-benzo[b][1,4]oxathiin-6-yl, bicyclo[4.2.0]octa-1 (6),2,4-trien-3-yl, 3,3-dideutero-2,3-dihydro-benzo[b][1,4]dioxin-6-yl and 2,2,3,3-tetradeutero-2,3-dihydro-benzo[b][1,4]dioxin-6-yl. In another embodiment, the present invention is directed to compounds of formula (I) wherein Ⓐ is selected from the group consisting of 4-ethyl-phenyl, 4-ethoxy-phenyl, 4-(fluoro-methoxy)-phenyl, benzothien-2-yl, chroman-6-yl, 2,3-dihydro-benzo[b][1,4]dioxin-6-yl, 3,4-dihydro-quiunolin-7-yl, 1-methyl-3,4-dihydro-quinolin-7-yl, benzo[b][1,4]oxazin-7-yl-3-one, 2,3-dihydro-benzo[b][1,4]oxathiin-6-yl, 5-(pyrrolidin-1-yl-carbonyl)-6,7-dihydro-thieno[3,2-c]pyridin-2-yl and 2,2,3,3-tetradeutero-2,3-dihydro-benzo[b][1,4]dioxin-6-yl.

In another embodiment, the present invention is directed to compounds of formula (I) wherein Ⓐ is selected from the group consisting of 4-ethyl-phenyl, 4-ethoxy-phenyl, 4-(fluoro-methoxy)-phenyl, chroman-6-yl, benzothien-2-yl, 3,4-dihydro-2H-quinolin-7-yl, 1-methyl-3,4-dihydro-2H-quinolin-7-yl, 6,7-dihydrobenzo[b]thiophen-2-yl-4-one, 2,3-dihydro-benzo[b][1,4]dioxin-6-yl, 2,3-dihydrobenzo[b][1,4]oxathiin-6-yl, bicyclo[4.2.0]octa-1 (6),2,4-trien-3-yl, 5,6-dihydro-7H-thieno[3,2-b]pyran-2-yl-7-one, 5-(5-methyl-thiazol-2-yl)-6,7-dihydrothieno[3,2-c]pyridin-2-yl, 5-methoxy-carbonyl-6,7-dihydrothieno[3,2-c]pyridin-2-yl, 5-ethoxy-carbonyl-6,7-dihydrothieno[3,2-c]pyridin-2-yl, 5-cyano-6,7-dihydrothieno[3,2-c]pyridin-2-yl, 5-(cyclopentyl-carbonyl)-6,7-dihydrothieno[3,2-c]pyridin-2-yl, 5-(pyrrolidin-1-yl-carbonyl)-6,7-dihydrothieno[3,2-c]pyridin-2-yl, 5-(thiazol-2-yl-carbonyl)-6,7-dihydrothieno[3,2-c]pyridin-2-yl, 3,3-dideutero-2,3-dihydrobenzo[b][1,4]dioxin-6-yl and 2,2,3,3-tetra-deutero-2,3-dihydrobenzo[b][1,4]dioxin-6-yl. In another embodiment, the present invention is directed to compounds of formula (I) wherein Ⓐ is selected from the group consisting of 4-ethyl-phenyl, 4-ethoxy-phenyl, 4-(fluoro-methoxy)-phenyl, benzothien-2-yl, 3,4-dihydro-2H-quinolin-7-yl, 2,3-dihydro-benzo[b][1,4]dioxin-6-yl, 2,3-dihydrobenzo[b][1,4]oxathiin-6-yl, bicyclo[4.2.0]octa-1 (6),2,4-trien-3-yl, 5,6-dihydro-7H-thieno[3,2-b]pyran-2-yl-7-one, 5-cyano-6,7-dihydrothieno[3,2-c]pyridin-2-yl and 2,2,3,3-tetra-deutero-2,3-dihydrobenzo[b][1,4]dioxin-6-yl. In another embodiment, the present invention is directed to compounds of formula (I) wherein Ⓐ is selected from the group consisting of 4-ethyl-phenyl, 4-ethoxy-phenyl, benzothien-2-yl, 2,3-dihydro-benzo[b][1,4]dioxin-6-yl, bicyclo[4.2.0]octa-1 (6),2,4-trien-3-yl and 5-cyano-6,7-dihydrothieno[3,2-c]pyridin-2-yl. In another embodiment, the present invention is directed to compounds of formula (I) wherein Ⓐ is selected from the group consisting of 5-cyano-6,7-dihydro-thieno[3,2-c]pyridin-2-yl, bicyclo[4.2.0]octa-1(6),2,4-trien-3-yl and 2,3-dihydrobenzo[b][1,4]dioxin-6-yl.

In another embodiment, the present invention is directed to compounds of formula (I) wherein Ⓐ is selected from the group consisting of $C_{5-12}$cycloalkyl, $C_{5-12}$cycloalkenyl, heteroaryl and heterocyclyl; wherein the phenyl, heteroaryl or heterocyclyl is optionally substituted as herein defined. In another embodiment, the present invention is directed to compounds of formula (I) wherein Ⓐ is selected from the group consisting of heteroaryl and heterocyclyl; wherein the heteroaryl or heterocyclyl is optionally substituted as herein defined. In another embodiment, the present invention is directed to compounds of formula (I) wherein Ⓐ is selected from the group consisting of $C_{5-12}$cycloalkyl and $C_{5-12}$cycloalkenyl.

In another embodiment, the present invention is directed to compounds of formula (I) wherein Ⓐ is selected from the group consisting of 2,3-dihydro-benzo[b][1,4]-dioxin-6-yl and 2,2,3,3-tetradeutero- of 2,3-dihydro-benzo[b][1,4]-dioxin-6-yl.

In an embodiment, the present invention is directed to a compound of formula (I) selected from the group consisting of (2S,3R,4R,5S,6R)-2-(7-((2,3-dihydrobenzo[b][1,4]dioxin-6-yl)methyl)-4-methoxy-2,3-dihydrobenzofuran-5-yl)-5-fluoro-6-(hydroxymethyl)tetrahydro-2H-pyran-3,4-diol (Compound #65);

(2S,3R,4R,5S,6R)-2-[5-(2,3-dihydro-1,4-benzodioxin-6-ylmethyl)-4-methoxy-2,3-dihydrobenzofuran-7-yl]-5-fluoro-6-(hydroxymethyl)tetrahydropyran-3,4-diol (Compound #101);

(2S,3R,4R,5S,6R)-2-(7-((2,3-dihydrobenzo[b][1,4]dioxin-6-yl)methyl)-4-hydroxy-2,3-dihydrobenzofuran-5-yl)-5-fluoro-6-(hydroxymethyl)tetrahydro-2H-pyran-3,4-diol (Compound #61);

(2S,3R,4R,5S,6R)-5-fluoro-6-(hydroxymethyl)-2-[4-methoxy-7-[(2,2,3,3-tetradeuterio-1,4-benzodioxin-6-yl)methyl]-2,3-dihydrobenzofuran-5-yl]tetrahydropyran-3,4-diol (Compound #172);

(2S,3R,4R,5S,6R)-2-[7-[dideuterio(2,3-dihydro-1,4-benzodioxin-6-yl)methyl]-4-methoxy-2,3-dihydrobenzofuran-5-yl]-5-fluoro-6-(hydroxymethyl)tetrahydropyran-3,4-diol (Compound #163);

and isotopologues and pharmaceutically acceptable salts thereof.

In an embodiment, the present invention is directed to compounds of formula (I) wherein Ⓐ is other than phenyl. In another embodiment, the present invention is directed to compounds of formula (I) wherein Ⓐ is other than thienyl or pyridyl. In another embodiment, the present invention is directed to compounds of formula (I) wherein Ⓐ is other than benzothien-2-yl. In another embodiment, the present invention is directed to compounds of formula (I) wherein Ⓐ is other than thienyl or pyridyl. In another embodiment, the present invention is directed to compounds of formula (I) wherein Ⓐ is other than phenyl, thienyl or pyridyl.

In another embodiment, the present invention is directed to compounds of formula (I) wherein Ⓐ is other than phenyl, thienyl, furyl, pyridyl, pyrrolyl, imidazolyl, thioimidazolyl, oxazolyl, pyrimidinyl, pyrrolidinyl, naphthyl, benzofuryl, benzothienyl, benzothiazolyl, benzopyrazolyl, benzoxazolyl, indolyl or quinolinyl.

In an embodiment, the present invention is directed to compounds of formula (I) wherein when Ⓐ is phenyl, then then $R^2$ and $R^3$ or $R^3$ and $R^4$ are taken together with the carbon atoms to which they are bound to form a ring structure selected from the group consisting of 2,3-dihydrofuranyl and 3,4-dihydro-2H-pyranyl. In another embodiment, the present invention is directed to compounds of formula (I) wherein when Ⓐ is thien-2-yl or pyridyl, then $R^2$ and $R^3$ or $R^3$ and $R^4$ are taken together with the carbon atoms to which they are bound to form a ring structure selected from the group consisting of 2,3-dihydrofuranyl and 3,4-dihydro-2H-pyranyl. In another embodiment, the present invention is directed to compounds of formula (I) wherein when Ⓐ is benzothien-2-yl, then $R^2$ and $R^3$ or $R^3$ and $R^4$ are taken together with the carbon atoms to which they are bound to form a ring structure selected from the group consisting of 2,3-dihydrofuranyl and 3,4-dihydro-2H-pyranyl. In another embodiment, the present invention is directed to compounds of formula (I) wherein when Ⓐ is thienyl, pyridyl or benzothien-2-yl, then $R^2$ and $R^3$ or $R^3$ and $R^4$ are taken together with the carbon atoms to which they are bound to form a ring structure selected from the group consisting of 2,3-dihydrofuranyl and 3,4-dihydro-2H-pyranyl. In another embodiment, the present invention is directed to compounds of formula (I) wherein when Ⓐ is phenyl, thienyl, pyridyl or benzothien-2-yl, then $R^2$ and $R^3$ or $R^3$ and $R^4$ are taken together with the carbon atoms to which they are bound to form a ring structure selected from the group consisting of 2,3-dihydrofuranyl and 3,4-dihydro-2H-pyranyl.

In another embodiment, the present invention is directed to compounds of formula (I) wherein $R^1$ is hydroxy-methyl-, $R^2$ is hydrogen, $R^3$ is hydrogen, $R^4$ is hydrogen or chloro, $R^5$ is hydrogen, $R^6$ is hydrogen and Ⓐ is other than benzothien-2-yl. In another embodiment, the present invention is directed to compounds of formula (I) wherein $R^1$ is hydroxy-methyl-, $R^2$ is hydrogen, $R^3$ is hydrogen, $R^4$ is chloro, $R^5$ is hydrogen, $R^6$ is hydrogen and Ⓐ is other than benzothien-2-yl.

In another embodiment, the present invention is directed to compounds of formula (I) wherein $R^1$ is hydroxy-methyl-, $R^2$ is hydrogen, $R^3$ is hydrogen, $R^4$ is hydrogen or chloro, $R^5$ is hydrogen, $R^6$ is hydrogen and Ⓐ is other than benzothien-2-yl, thien-2-yl or indol-3-yl. In another embodiment, the present invention is directed to compounds of formula (I) wherein $R^1$ is hydroxy-methyl-, $R^2$ is hydrogen, $R^3$ is hydrogen, $R^4$ is chloro, $R^5$ is hydrogen, $R^6$ is hydrogen and Ⓐ is other than benzothien-2-yl, thien-2-yl or indol-3-yl.

In another embodiment, the present invention is directed to compounds of formula (I) wherein when Ⓐ is phenyl, thienyl, furyl, pyridyl, pyrrolyl, imidazolyl, thioimidazolyl, oxazolyl, pyrimidinyl, pyrrolidinyl, naphthyl, benzofuryl, benzothienyl, benzothiazolyl, benzopyrazolyl, benzoxazolyl, indolyl or quinolinyl then $R^2$ and $R^3$ or $R^3$ and $R^4$ are taken together with the carbon atoms to which they are bound to form a ring structure selected from the group consisting of 2,3-dihydrofuranyl and 3,4-dihydro-2H-pyranyl.

Additional embodiments of the present invention, include those wherein the substituents selected for one or more of the variables defined herein (i.e. $R^1$, $R^2$, $R^3$, $R^4$, $R^5$, $R^6$, Ⓐ, etc.) are independently selected to be any individual substituent or any subset of substituents selected from the complete list as defined herein. Additional embodiments of the present invention, include those wherein the substituents selected for one or more of the variables defined herein (i.e. $R^1$, $R^2$, $R^3$, $R^4$, $R^5$, $R^6$, Ⓐ, etc.) are independently selected to correspond to any of the embodiments as defined herein.

In another embodiment of the present invention is any single compound or subset of compounds selected from the representative compounds listed in Tables 1 to 3 below.

Representative compounds of the present invention are as listed in Table 1 to 3 below. Unless otherwise noted, wherein a stereogenic center is present in the listed compound, the compound was prepared as a mixture of stereo-configurations. Where a stereogenic center is present, the S*- and R* designations are intended to indicate that the exact stereo-configuration of the center has not been determined.

TABLE 1

Representative Compounds Formula (I)

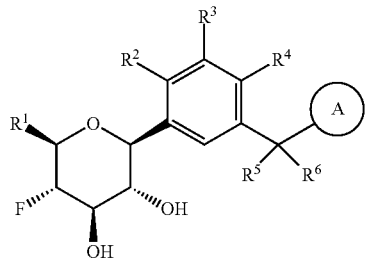

| ID No. | $R^1$ | $R^2$ | $R^3$ | $R^4$ | $R^5$ | $R^6$ | Ⓐ |
|---|---|---|---|---|---|---|---|
| 2 | CH₂—OH | hydroxy | H | methoxy | H | H | benzothien-2-yl |
| 4 | CH₂—OH | hydroxy | H | methyl | H | H | benzothien-2-yl |
| 7 | CH₂—OH | hydroxy | H | chloro | H | H | benzothien-2-yl |
| 9 | CH₂—OCH₃ | hydroxy | H | methoxy | H | H | benzothien-2-yl |
| 10 | CH₃ | hydroxy | H | methoxy | H | H | benzothien-2-yl |
| 11 | CH₂F | hydroxy | H | methoxy | H | H | benzothien-2-yl |
| 12 | CH₂—OH | methoxy | H | methoxy- | H | H | benzothien-2-yl |
| 13 | CH₂—OH | hydroxy | methyl | methyl | H | H | benzothien-2-yl |
| 14 | CH₂—OH | hydroxy | methyl | methoxy | H | H | benzothien-2-yl |
| 15 | CH₂—OH | methoxy | methyl | methoxy | H | H | benzothien-2-yl |
| 16 | CH₃ | hydroxy | H | methyl | H | H | benzothien-2-yl |
| 18 | CH₂—OH | methoxy | H | methyl | H | H | benzothien-2-yl |
| 19 | CH₂—OCH₃ | hydroxy | H | methyl | H | H | benzothien-2-yl |
| 20 | CH₂F | hydroxy | H | methyl | H | H | benzothien-2-yl |
| 21 | CH₂—OH | chloro | H | methoxy | H | H | benzothien-2-yl |
| 22 | CH₂—CN | hydroxy | H | methoxy | H | H | benzothien-2-yl |
| 23 | CH₂—CN | hydroxy | H | methyl | H | H | benzothien-2-yl |
| 24 | CH₂—NH₂ | hydroxy | H | methyl | H | H | benzothien-2-yl |
| 26 | CH₂—CN | chloro | H | methoxy | H | H | benzothien-2-yl |
| 28 | CH₂—NH₂ | hydroxy | H | methoxy | H | H | benzothien-2-yl |
| 29 | CH₂—OH | hydroxy | H | cyclopropyl | H | H | benzothien-2-yl |
| 30 | CH₂—OH | hydroxy | H | ethoxy | H | H | benzothien-2-yl |
| 31 | CH₂—OH | hydroxy | H | ethyl | H | H | benzothien-2-yl |
| 32 | CH₂—OH | hydroxy | H | iso-propyl-oxy | H | H | benzothien-2-yl |
| 33 | CH₂—OH | hydroxy | H | cyano | H | H | benzothien-2-yl |
| 34 | CH₂—OH | hydroxy-methyl- | H | methoxy | H | H | benzothien-2-yl |

TABLE 1-continued

Representative Compounds Formula (I)

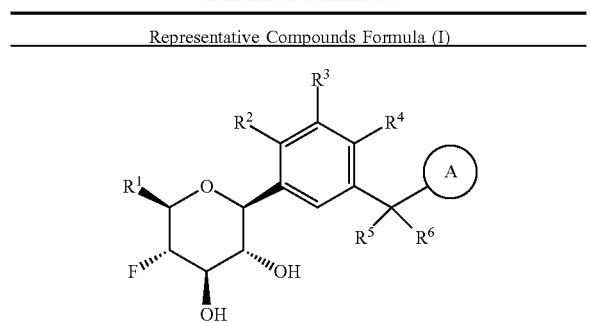
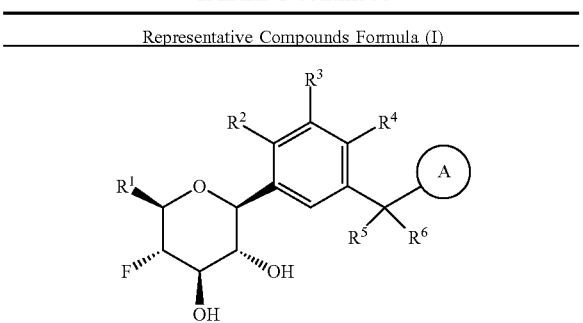

| ID No. | R¹ | R² | R³ | R⁴ | R⁵ | R⁶ | A |
|---|---|---|---|---|---|---|---|
| 35 | CH₂—OH | methoxy | H | chloro | H | H | benzothien-2-yl |
| 36 | CH₂—OH | hydroxy | H | fluoro | H | H | benzothien-2-yl |
| 37 | CH(R*—OH)CH₃ | hydroxy | H | methyl | H | H | benzothien-2-yl |
| 38 | CH(S*—OH)CH₃ | hydroxy | H | methyl | H | H | benzothien-2-yl |
| 39 | C(OH)(CH₃)₂ | hydroxy | H | methyl | H | H | benzothien-2-yl |
| 40 | CH₂—OH | carboxy | H | methoxy | H | H | benzothien-2-yl |
| 41 | CH₂—OH | hydroxy | H | trifluoromethyl | H | H | benzothien-2-yl |
| 42 | CH₂—OH | hydroxymethyl- | H | methyl | H | H | benzothien-2-yl |
| 43 | 1-OH—cycloprop-1-yl | hydroxy | H | methyl | H | H | benzothien-2-yl |
| 44 | C(O)OH | hydroxy | H | methyl | H | H | benzothien-2-yl |
| 46 | 1-OH—cycloprop-1-yl | hydroxy | H | methoxy | H | H | benzothien-2-yl |
| 47 | CH₂—OH | benzyloxy | H | methoxy | H | H | benzothien-2-yl |
| 48 | C(OH)(CH₃)₂ | hydroxy | H | methoxy | H | H | benzothien-2-yl |
| 49 | CH₂—OH | propen-2-yl-oxy | H | methoxy | H | H | benzothien-2-yl |
| 50 | CH₂—OH | hydroxy | H | trifluoromethoxy | H | H | benzothien-2-yl |
| 51 | C(O)OH | hydroxy | H | methoxy | H | H | benzothien-2-yl |
| 52 | C(R*—OH)CH₃ | hydroxy | H | methoxy | H | H | benzothien-2-yl |
| 53 | C(S*—OH)CH₃ | hydroxy | H | methoxy | H | H | benzothien-2-yl |
| 55 | CH₂—OH | H | H | methoxy | H | H | 6,7-dihydro-5H-thieno[3,2-b]pyran-2-yl |
| 57 | C(OH)(CH₃)₂ | hydroxy | H | ethyl | H | H | benzothien-2-yl |
| 64 | CH₂—OH | hydroxy | H | methyl | H | H | 5-ethoxy-carbonyl-6,7-dihydrothieno[3,2-c]pyridin-2-yl |
| 66 | CH₂—OH | hydroxy | H | methyl | H | H | 5-(pyrrolidin-1-yl-carbonyl)-6,7-dihydrothieno[3,2-c]pyridin-2-yl |
| 67 | CH₂—OH | hydroxy | H | methyl | H | H | 5-(morpholin-4-yl-carbonyl)-6,7-dihydrothieno[3,2-c]pyridin-2-yl |
| 69 | CH₂—OH | methoxy | H | methyl | H | H | 5-(morpholin-4-yl-carbonyl)-6,7-dihydrothieno[3,2-c]pyridin-2-yl |
| 71 | C(R*—OH)CH₃ | cyano-methoxy- | H | methoxy | H | H | benzothien-2-yl |
| 72 | C(R*—OH)CH₃ | methoxy | H | methoxy | H | H | benzothien-2-yl |
| 73 | CH₂—OH | hydroxy | H | chloro | H | H | 5-methoxy-carbonyl-6,7-dihydrothieno[3,2-c]pyridin-2-yl |
| 74 | CH₂—OH | hydroxy | H | chloro | H | H | 5-methyl-carbonyl-6,7-dihydrothieno[3,2-c]pyridin-2-yl |
| 76 | CH₂—OH | methoxy | H | chloro | H | H | 5-methoxy-carbonyl-6,7-dihydrothieno[3,2-c]pyridin-2-yl |
| 77 | CH₂—OH | methoxy | H | chloro | H | H | 5-methyl-carbonyl-6,7-dihydrothieno[3,2-c]pyridin-2-yl |
| 78 | CH₂—OH | H | H | methyl | H | H | 5-(pyrrolidin-1-yl-carbonyl)-6,7-dihydrothieno[3,2-c]pyridin-2-yl |
| 79 | CH₂—OH | hydroxy | H | methoxy | H | H | 5-methyl-carbonyl-6,7-dihydrothieno[3,2-c]pyridin-2-yl |
| 80 | CH₂—OH | H | H | chloro | H | H | 5-methoxy-carbonyl-6,7-dihydrothieno[3,2-c]pyridin-2-yl |
| 81 | CH₂—OH | methoxy | H | methyl | H | H | 5-(pyrrolidin-1-yl-carbonyl)-6,7-dihydrothieno[3,2-c]pyridin-2-yl |
| 82 | CH₂—OH | methoxy | H | methoxy | H | H | 5-methyl-carbonyl-6,7-dihydrothieno[3,2-c]pyridin-2-yl |
| 83 | CH₂—OH | methoxy | H | methoxy | H | H | 5-methoxy-carbonyl-6,7-dihydrothieno[3,2-c]pyridin-2-yl |
| 84 | CH₂—OH | hydroxy | H | methyl | H | H | 5-(thiazol-2-yl-carbonyl)-6,7-dihydrothieno[3,2-c]pyridin-2-yl |
| 86 | CH₂—OH | hydroxy | H | methyl | H | H | 5-(cyclopentyl-carbonyl)-6,7-dihydrothieno[3,2-c]pyridin-2-yl |

TABLE 1-continued

Representative Compounds Formula (I)

| ID No. | R¹ | R² | R³ | R⁴ | R⁵ | R⁶ | A |
|---|---|---|---|---|---|---|---|
| 87 | CH₂—OH | H | H | methyl | H | H | 5-(cyclopentyl-carbonyl)-6,7-dihydrothieno[3,2-c]pyridin-2-yl |
| 90 | CH₂—OH | H | n-propen-2-yl | me-thoxy | H | H | benzothien-2-yl |
| 91 | CH₂—OH | methoxy | H | methyl | H | H | 5-(cyclopentyl-carbonyl)-6,7-dihydrothieno[3,2-c]pyridin-2-yl |
| 92 | CH₂—OH | H | H | methyl | H | H | 5-cyano-6,7-dihydrothieno[3,2-c]pyridin-2-yl |
| 96 | CH₂—OH | methoxy | H | chloro | H | H | 5-(pyrrolidin-1-yl-carbonyl)-6,7-dihydrothieno[3,2-c]pyridin-2-yl |
| 99 | CH₂—OH | methoxy | H | chloro | H | H | 5-cyano-6,7-dihydrothieno[3,2-c]pyridin-2-yl |
| 100 | CH₂—OH | hydroxy | H | me-thoxy | H | H | 5-cyano-6,7-dihydrothieno[3,2-c]pyridin-2-yl |
| 103 | CH₂—OH | hydroxy | H | methyl | H | H | 5-cyano-6,7-dihydrothieno[3,2-c]pyridin-2-yl |
| 104 | CH₂—OH | methoxy | H | me-thoxy | H | H | 5-cyano-6,7-dihydrothieno[3,2-c]pyridin-2-yl |
| 106 | CH₂—OH | methoxy | H | chloro | H | H | 5-(thiazol-2-yl-carbonyl)-6,7-dihydrothieno[3,2-c]pyridin-2-yl |
| 109 | CH₂—OH | H | H | methyl | H | H | 5-(thiazol-2-yl-carbonyl)-6,7-dihydrothieno[3,2-c]pyridin-2-yl |
| 110 | CH₂—OH | methoxy | H | methyl | H | H | 5-cyano-6,7-dihydrothieno[3,2-c]pyridin-2-yl |
| 111 | CH₂—OH | hydroxy | H | methyl | H | H | 5-(5-methyl-thiazol-2-yl)-6,7-dihydrothieno[3,2-c]pyridin-2-yl |
| 112 | CH₂—OH | methoxy | H | methyl | H | H | 5-(thiazol-2-yl-carbonyl)-6,7-dihydrothieno[3,2-c]pyridin-2-yl |
| 113 | CH₂—OH | H | H | methyl | H | H | 5-(5-methyl-thiazol-2-yl)-6,7-dihydrothieno[3,2-c]pyridin-2-yl |
| 114 | CH₂—OH | hydroxy | H | chloro | H | H | 5-cyano-6,7-dihydrothieno[3,2-c]pyridin-2-yl |
| 115 | CH₂—OH | methoxy | H | ethyl | H | H | 5-cyano-6,7-dihydrothieno[3,2-c]pyridin-2-yl |
| 116 | CH₂—OH | H | H | methyl | H | H | 6,7-dihydrobenzo[b]thiophen-2-yl-4-one |
| 117 | CH₂—OH | hydroxy | H | methyl | H | H | 5-(5-methyl-thiazol-2-yl)-6,7-dihydrothieno[3,2-c]pyridin-2-yl |
| 118 | CH₂—OH | hydroxy | H | ethyl | H | H | 5-cyano-6,7-dihydrothieno[3,2-c]pyridin-2-yl |
| 119 | CH₂—OH | hydroxy | H | methyl | H | H | 6,7-dihydrobenzo[b]thiophen-2-yl-4-one |
| 120 | CH₂—OH | H | H | me-thoxy | H | H | 5-cyano-6,7-dihydrothieno[3,2-c]pyridin-2-yl |
| 121 | CH₂—OH | H | H | chloro | H | H | 5-cyano-6,7-dihydrothieno[3,2-c]pyridin-2-yl |
| 122 | CH₂—OH | H | H | methyl | H | H | 5-(5-methyl-thiazol-2-yl)-6,7-dihydrothieno[3,2-c]pyridin-2-yl |
| 123 | CH₂—OH | methoxy | H | methyl | H | H | 5-(5-methyl-thiazol-2-yl)-6,7-dihydrothieno[3,2-c]pyridin-2-yl |
| 129 | CH₂—OH | hydroxy | H | methyl | H | H | 5,6-dihydro-7H-thieno[3,2-b]pyran-2-yl-7-one |
| 138 | CH₂—OH | H | H | methyl | H | H | 5-(2,5-dimethyl-thien-3-yl)-6,7-dihydrothieno[3,2-c]pyridin-2-yl |
| 156 | CH₂—OH | H | H | ethyl | D | D | 2,3-dihydro-benzo[b][1,4]dioxin-6-yl |
| 157 | CH₂—OH | H | H | ethyl | D | D | 2,3-dihydro-benzo[b][1,4]dioxin-6-yl |
| 158 | CH₂—OH | H | H | ethyl | H | H | 2,2-difluoro-benzo[b][1,3]dioxol-5-yl |
| 159 | CH₂—OH | H | H | ethyl | H | H | 2,2-difluoro-benzo[b][1,3]dioxol-5-yl |
| 165 | CH₂—OH | fluoro | H | me-thoxy | D | D | 2,3-dihydro-benzo[b][1,4]dioxin-6-yl |
| 166 | CH₂—OH | H | H | chloro | D | D | 2,3-dihydro-benzo[b][1,4]dioxin-6-yl |
| 167 | CH₂—OH | H | H | methyl | D | D | 2,3-dihydro-benzo[b][1,4]dioxin-6-yl |
| 169 | CH₂—OH | H | H | ethyl | D | D | chroman-6-yl |

TABLE 1-continued

Representative Compounds Formula (I)

| ID No. | R¹ | R² | R³ | R⁴ | R⁵ | R⁶ | A |
|---|---|---|---|---|---|---|---|
| 171 | CH₂—OH | H | H | methoxy | D | D | chroman-6-yl |
| 173 | CH₂—OH | H | H | methoxy | H | H | 2,2,3,3-tetradeutero-2,3-dihydrobenzo[b][1,4]dioxin-6-yl |
| 175 | CH₂—OH | H | H | ethyl | H | H | 2,2,3,3-tetradeutero-2,3-dihydrobenzo[b][1,4]dioxin-6-yl |
| 176 | CH₂—OH | H | H | ethyl | D | D | 2,2,3,3-tetradeutero-2,3-dihydrobenzo[b][1,4]dioxin-6-yl |
| 178 | CH₂—OH | H | fluoro | methoxy | H | H | 2,2,3,3-tetradeutero-2,3-dihydrobenzo[b][1,4]dioxin-6-yl |
| 182 | CH₂—OH | OCD₃ | H | ethyl | H | H | 2,3-dihydro-benzo[b][1,4]dioxin-6-yl |

TABLE 2

Representative Compounds of Formula (I) wherein R² and R³ are taken together to form a ring structure

| ID No. | R¹ | —R²—R³— together | R⁴ | R⁵ | R⁶ | A |
|---|---|---|---|---|---|---|
| 68 | CH₂—OH | —O—CH₂—CH₂— | methyl | H | H | benzothien-2-yl |
| 98 | CH₂—OH | —O—CH₂—CH₂ | hydroxy | H | H | 2,3-dihydro-benzo[b][1,4]dioxin-6-yl |
| 101 | CH₂—OH | —O—CH₂—CH₂ | methoxy | H | H | 2,3-dihydro-benzo[b][1,4]dioxin-6-yl |
| 102 | CH₂—OH | —O—CH₂—CH₂ | ethoxy | H | H | 2,3-dihydro-benzo[b][1,4]dioxin-6-yl |
| 125 | CH₂—OH | —O—CH₂—CH₂ | chloro | H | H | chroman-6-yl |
| 126 | CH₂—OH | —O—CH₂—CH₂ | methoxy | H | H | chroman-6-yl |

TABLE 2-continued

Representative Compounds of Formula (I) wherein R² and R³ are taken together to form a ring structure

| ID No. | R¹ | —R²—R³— together | R⁴ | R⁵ | R⁶ | A |
|---|---|---|---|---|---|---|
| 127 | CH₂—OH | —O—CH₂—CH₂ | chloro | H | H | 2,3-dihydrobenzo[b][1,4]oxathiin-6-yl |
| 128 | CH₂—OH | —O—CH₂—CH₂ | methoxy | H | H | 2,3-dihydrobenzo[b][1,4]oxathiin-6-yl |
| 130 | CH₂—OH | —O—CH₂—CH₂ | methyl | H | H | chroman-6-yl |
| 132 | CH₂—OH | —O—CH₂—CH₂ | methyl | H | H | 2,3-dihydrobenzo[b][1,4]oxathiin-6-yl |
| 152 | CH₂—OH | —O—CH₂—CH₂ | methoxy | H | H | bicyclo[4.2.0]octa-1(6),2,4-trien-3-yl |
| 154 | CH₂—OH | —CH₂—CH₂—O | chloro | H | H | 2,3-dihydro-benzo[b][1,4]dioxin-6-yl |
| 179 | CH₂—OH | —O—CH₂—CH₂ | ethyl | H | H | 2,2,3,3-tetradeutero-2,3-dihydrobenzo[b][1,4]dioxin-6-yl |
| 180 | CH₂—OH | —O—CH₂—CH₂ | ethyl | H | H | 3,3-dideutero-2,3-dihydrobenzo[b][1,4]dioxin-6-yl |

TABLE 3

Representative Compounds of Formula (I) wherein R³ and R⁴ are taken together to form a ring structure

| ID No. | R¹ | R² | —R³—R⁴— together | R⁵ | R⁶ | A |
|---|---|---|---|---|---|---|
| 54 | CH₂—OH | H | —CH₂—CH₂—O— | H | H | 2,3-dihydro-benzo[b][1,4]dioxin-6-yl |
| 56 | CH₂—OH | H | —CH₂—CH₂—O— | H | H | chroman-6-yl |
| 58 | CH₂—OH | benzyloxy | —CH₂—CH₂—O— | H | H | benzothien-2-yl |
| 59 | CH₂—OH | hydroxy | —CH₂—CH₂—O— | H | H | benzothien-2-yl |
| 60 | CH₂—OH | benzyloxy | —CH₂—CH₂—O— | H | H | 2,3-dihydro-benzo[b][1,4]dioxin-6-yl |
| 61 | CH₂—OH | hydroxy | —CH₂—CH₂—O— | H | H | 2,3-dihydro-benzo[b][1,4]dioxin-6-yl |
| 62 | CH₂—OH | hydroxy | —CH₂—CH₂—O— | H | H | 4-ethyl-phenyl |

TABLE 3-continued

Representative Compounds of Formula (I)
wherein R³ and R⁴ are taken together to form a ring structure

| ID No. | R¹ | R² | —R³—R⁴— together | R⁵ | R⁶ | Ⓐ |
|---|---|---|---|---|---|---|
| 63 | CH₂OH | hydroxy | —CH₂—CH₂—O— | H | H | 4-ethoxy-phenyl |
| 65 | CH₂OH | methoxy | —CH₂—CH₂—O— | H | H | 2,3-dihydro-benzo[b][1,4]dioxin-6-yl |
| 70 | CH₂OH | H | —CH₂—CH₂—O— | H | H | 5-(pyrrolidin-1-yl-carbonyl)-6,7-dihydrothieno[3,2-c]pyridin-2-yl |
| 75 | CH₂OH | H | —CH(CH₂OH)—CH₂—O— | H | H | 2,3-dihydro-benzo[b][1,4]dioxin-6-yl |
| 85 | CH₂OH | H | —CH(CH₂OH)—C(CH₃)₂—O— | H | H | 2,3-dihydro-benzo[b][1,4]dioxin-6-yl |
| 88 | CH₂OH | H | —C(CH₂OH)(CH₃)—CH₂—O— | H | H | 2,3-dihydro-benzo[b][1,4]dioxin-6-yl |
| 89 | CH₂OH | H | —CH₂—CH₂—O— | H | H | 3,4-dihydro-2H-quinolin-7-yl |
| 93 | CH₂OH | H | —CH(CH₂CH₂OH)—CH₂—O— | H | H | 2,3-dihydro-benzo[b][1,4]dioxin-6-yl |
| 94 | CH₂OH | H | —CH₂—CH₂—O | H | H | 1-methyl-3,4-dihydro-2H-quinolin-7-yl |
| 95 | CH₂OH | H | —CH(CH₃)—CH₂—O— | H | H | 2,3-dihydro-benzo[b][1,4]dioxin-6-yl |
| 97 | CH₂OH | H | —CH₂—CH₂—O— | H | H | benzo[b][1,4]oxazin-7-yl-3-one |
| 105 | CH₂OH | methoxy | —CH₂—CH₂—O— | H | H | 3,4-dihydro-2H-quinolin-7-yl |
| 107 | CH₂OH | methoxy | —CH₂—CH₂—O— | H | H | 2,3-dihydrobenzo[b][1,4]oxathiin-6-yl |
| 108 | CH₂OH | methoxy | —CH₂—CH₂—O— | H | H | 1-methyl-3,4-dihydro-2H-quinolin-7-yl |
| 124 | CH₂OH | H | —CH₂—CH₂—O— | H | H | 2,3-dihydrobenzo[b][1,4]oxathiin-6-yl |
| 131 | CH₂OH | methyl | —CH₂—CH₂—O— | H | H | 2,3-dihydrobenzo[b][1,4]oxathiin-6-yl |
| 133 | CH₂OH | H | —CH₂—CH₂—O— | H | H | 4-(fluoro-methoxy)-phenyl |
| 134 | CH₂OH | H | —CH₂—CH₂—O— | H | H | 4-ethyl-phenyl |
| 135 | CH₂OH | methoxy | —CH₂—CH₂—O— | H | H | 4-ethyl-phenyl |
| 142 | CH₂OH | methoxy | —CH₂—CH₂—O— | H | H | 4-(fluoro-methoxy)-phenyl |
| 153 | CH₂OH | H | —O—CH₂—CH₂— | H | H | 2,3-dihydro-benzo[b][1,4]dioxin-6-yl |
| 160 | CH₂OH | OCD₃ | —CH₂—CH₂—O— | H | H | 2,3-dihydro-benzo[b][1,4]dioxin-6-yl |
| 161 | CH₂OH | OCD₃ | —CH₂—CH₂—O— | D | D | 2,3-dihydro-benzo[b][1,4]dioxin-6-yl |
| 163 | CH₂OH | methoxy | —CH₂—CH₂—O— | D | D | 2,3-dihydro-benzo[b][1,4]dioxin-6-yl |
| 172 | CH₂OH | methoxy | —CH₂—CH₂—O— | H | H | 2,2,3,3-tetra-deutero-2,3-dihydrobenzo[b][1,4]dioxin-6-yl |
| 181 | CH₂OH | H | —O—CH₂—CH₂— | H | H | 2,2,3,3-tetra-deutero-2,3-dihydrobenzo[b][1,4]dioxin-6-yl |

The present invention is further directed to compounds of formula (V-S)

(V-S)

wherein $A^1$, $A^2$ and $A^3$ are as herein defined. The present invention is further directed to a process for the preparation of compounds of formula (V-S) as described in more detail herein. The compounds of formula (V-S) are useful as intermediates in the synthesis of pharmaceutically active compounds, including but not limited to the compounds of formula (I) of the present invention.

In certain embodiments of the present invention, $A^1$, $A^2$ and $A^3$ are each an independently selected from the group consisting of $C_{1-4}$alkyl.

In certain embodiments of the present invention $A^1$, $A^2$ and $A^3$ are each an independently selected from the group consisting of $C_{1-4}$alkyl, phenyl and 3,5-di(trifluoromethyl)phenyl. In certain embodiments of the present invention, $A^1$, $A^2$ and $A^3$ are each an independently selected from the group consisting of $C_{1-4}$alkyl. In certain embodiments of the present invention $A^1$, $A^2$ and $A^3$ are each an independently selected from the group consisting of $C_{1-4}$alkyl, $C_{3-6}$cycloalkyl and bicyclo[2.2.1]heptan-2-yl.

In certain embodiments, the present invention is directed to any one or more compounds of formula (V-S), wherein
$A^1$ is methyl, $A^2$ is methyl and $A^3$ is t-butyl; or
$A^1$ is methyl, $A^2$ is methyl and $A^3$ is 2,3,3-trimethylbutan-2-yl; or
$A^1$ is methyl, $A^2$ is methyl and $A^3$ is isopropyl; or
$A^1$ is methyl, $A^2$ is methyl and $A^3$ is cyclohexyl; or
$A^1$ is methyl, $A^2$ is methyl and $A^3$ is bicyclo[2.2.1]heptan-2-yl; or
$A^1$ is methyl, $A^2$ is methyl and $A^3$ is phenyl; or
$A^1$ is methyl, $A^2$ is methyl and $A^3$ is 3,5-di(trifluoromethyl)phenyl; or
$A^1$ is t-butyl, $A^2$ is phenyl and $A^3$ is phenyl.

In certain embodiment of the present invention, the compound of formula (V-S) is (3R,4R,5R,6R)-3,4-bis((tert-butyldimethylsilyl)oxy)-6-(((tert-butyldimethylsilyl)oxy)methyl)-5-fluorotetrahydro-2H-pyran-2-one, wherein $A^1$ is t-butyl, $A^2$ is methyl and $A^3$ is methyl.

Definitions

As used herein, "halogen" shall mean chlorine, bromine, fluorine and iodine. Preferably, the halogen is selected from the group consisting of chlorine and fluorine, more preferably fluorine.

As used herein, unless otherwise noted, the term "acyl" shall mean a group of the formula —C(O)R, wherein R is alkyl, optionally substituted aryl, and the like. Suitable examples include, but are not limited to acetyl, propanoyl, isopropanoyl, benzoyl, 4-methylbenzoyl, 4-methoxybenzoyl, dichloroacetyl, trichloroacetyl, methoxyacetyl, phenoxyacetyl, p-chlorophenoxyacetyl, phenylacetyl, pivaloyl and the like.

As used herein, the term "$C_{X-Y}$alkyl" wherein X and Y are integers, whether used alone or as part of a substituent group, include straight and branched chains containing between X and Y carbon atoms. For example, $C_{1-4}$alkyl radicals include straight and branched chains of between 1 and 4 carbon atoms, including methyl, ethyl, propyl, isopropyl, butyl, isobutyl, sec-butyl and t-butyl.

As used herein, unless otherwise noted, the terms "fluorinated $C_{X-Y}$alkyl" and "fluoro substituted $C_{X-Y}$alkyl" shall mean any $C_{X-Y}$alkyl group as defined above substituted with at least one fluorine atom, preferably one to three fluorine atoms. In an example, "fluorinated $C_{1-4}$alkyl" include, but are not limited, to —CH$_2$F, —CF$_2$H, —CF$_3$, —CH$_2$—CF$_3$, —CF$_2$—CF$_2$—CF$_2$—CF$_3$, and the like.

As used herein, unless otherwise noted, the term "hydroxy substituted $C_{X-Y}$alkyl" shall mean any $C_{X-Y}$alkyl group as defined above substituted with at least one hydroxy, preferably one to two hydroxy groups, wherein the hydroxy group(s) may be bound to any carbon atom of the $C_{X-Y}$alkyl, preferably, the hydroxy group(s) are bound to the terminal carbon atom. In an example, "hydroxy substituted $C_{1-4}$alkyl" include, but are not limited, to —CH$_2$OH, —CH$_2$—CH$_2$OH, —CH(OH)—CH$_3$, —CH(OH)—CH$_2$OH, —CH$_2$—CH$_2$—CH$_2$OH, —CH(OH)—CH$_2$—CH$_3$, —CH(OH)(CH$_3$)$_2$, and the like.

As used herein, unless otherwise noted, "$C_{1-4}$alkoxy" shall denote an oxygen ether radical of the above described straight or branched chain alkyl groups containing one to four carbon atoms. For example, methoxy, ethoxy, n-propoxy, isopropoxy, sec-butoxy, t-butoxy, and the like.

As used herein, unless otherwise noted, the terms "fluorinated $C_{X-Y}$alkoxy" and "fluoro substituted $C_{X-Y}$alkoxy", shall mean any $C_{X-Y}$alkoxy group as defined above substituted with at least one fluorine atom, preferably one to three fluorine atoms. In an example, "fluorinated $C_{1-4}$alkoxy" include, but are not limited, —OCH$_2$F, —OCF$_2$H, —OCF$_3$, —OCH$_2$—CF$_3$, —OCF$_2$—CF$_2$—CF$_2$—CF$_3$, and the like.

As used herein, unless otherwise noted, the term "cyano substituted $C_{X-Y}$alkoxy" shall mean any $C_{X-Y}$alkoxy group as defined above substituted with one cyano group, wherein the cyano group may be bound to any carbon atom of the $C_{X-Y}$alkoxy, preferably, the cyano group are bound to the terminal carbon atom. In an example, "cyano substituted $C_{1-4}$alkoxy" include, but are not limited, to —O—CH$_2$CN, —O—CH$_2$—CH$_2$CN, —O—CH(CN)—CH$_3$, —O—CH(CN)—CH$_2$OH, —O—CH$_2$—CH$_2$—CH$_2$CN, —O—CH(CN)—CH$_2$—CH$_3$, —O—CH(CN)(CH$_3$)$_2$, and the like.

As used herein, unless otherwise noted, the term "$C_{X-Y}$cycloalkyl", wherein X and Y are integers, shall mean any stable X- to Y-membered monocyclic, bicyclic, polycyclic or bridges saturated ring system, preferably a monocyclic or bicyclic saturated ring system. For example, the term "$C_{3-12}$cycloalkyl" includes, but is not limited to cyclopropyl, cyclobutyl, cyclopentyl, cyclohexyl, cycloheptyl, cyclooctyl, cyclononyl, cyclodecyl, and the like.

As used herein, unless otherwise noted, the term "$C_{X-Y}$cycloalkenyl", wherein X and Y are integers, shall mean any stable X- to Y-membered monocyclic, bicyclic, polycyclic or bridged, preferably a monocyclic or bicyclic, ring system containing at least one, preferably one to three, unsaturated double bonds. For example, the term "$C_{6-10}$cycloalkenyl" includes, but is not limited to cyclohexenyl, bicyclo[4.2.0]octa-1 (6),2,4-trien-3-yl, and the like.

As used herein, unless otherwise noted, "heteroaryl" shall denote any five or six membered monocyclic aromatic ring structure containing at least one heteroatom selected from the group consisting of O, N and S, optionally containing one to three additional heteroatoms independently selected from the group consisting of O, N and S; or a nine or ten membered bicyclic aromatic ring structure containing at least one heteroatom selected from the group consisting of O, N and S, optionally containing one to four additional heteroatoms independently selected from the group consisting of O, N and S. The heteroaryl group may be attached at any heteroatom or carbon atom of the ring such that the result is a stable structure.

Examples of suitable heteroaryl groups include, but are not limited to, pyrrolyl, furyl, thienyl, oxazolyl, imidazolyl, purazolyl, isoxazolyl, isothiazolyl, triazolyl, thiadiazolyl, pyridyl, pyridazinyl, pyrimidinyl, pyrazinyl, pyranyl, furazanyl, indolizinyl, indolyl, isoindolinyl, indazolyl, benzofuryl, benzothienyl, benzimidazolyl, benzthiazolyl, purinyl, quinolizinyl, quinolinyl, isoquinolinyl, isothiazolyl, cinnolinyl, phthalazinyl, quinazolinyl, quinoxalinyl, naphthyridinyl, pteridinyl, and the like.

As used herein, the term "heterocycloalkyl" shall denote any five to seven membered monocyclic, saturated or partially unsaturated ring structure containing at least one heteroatom selected from the group consisting of O, N and S, optionally containing one to three additional heteroatoms independently selected from the group consisting of O, N and S; or an eight to ten membered saturated, partially unsaturated, partially aromatic or benzo-fused bicyclic ring system containing at least one heteroatom selected from the group consisting of O, N and S, optionally containing one to four additional heteroatoms independently selected from the group consisting of O, N and S. The heterocycloalkyl group may be attached at any heteroatom or carbon atom of the ring such that the result is a stable structure.

Examples of suitable heterocycloalkyl groups include, but are not limited to, pyrrolinyl, pyrrolidinyl, dioxalanyl, imidazolinyl, imidazolidinyl, pyrazolinyl, pyrazolidinyl, piperidinyl, dioxanyl, morpholinyl, dithianyl, thiomorpholinyl, piperazinyl, trithianyl, indolinyl, chromenyl, 3,4-methylenedioxyphenyl, 2,3-dihydrobenzofuryl, and the like.

When a particular group is "substituted" (e.g. alkyl, alkoxy, cycloalkyl, etc.), that group may have one or more substituents, preferably from one to five substituents, more preferably from one to three substituents, most preferably from one to two substituents, independently selected from the list of substituents.

With reference to substituents, the term "independently" means that when more than one of such substituents is possible, such substituents may be the same or different from each other.

As used herein, the notation "*" shall denote the presence of a stereogenic center.

Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention. Preferably, wherein the compound is present as an enantiomer, the enantiomer is present at an enantiomeric excess of greater than or equal to about 80%, more preferably, at an enantiomeric excess of greater than or equal to about 90%, more preferably still, at an enantiomeric excess of greater than or equal to about 95%, more preferably still, at an enantiomeric excess of greater than or equal to about 98%, most preferably, at an enantiomeric excess of greater than or equal to about 99%. Similarly, wherein the compound is present as a diastereomer, the diastereomer is present at an diastereomeric excess of greater than or equal to about 80%, more preferably, at an diastereomeric excess of greater than or equal to about 90%, more preferably still, at an diastereomeric excess of greater than or equal to about 95%, more preferably still, at an diastereomeric excess of greater than or equal to about 98%, most preferably, at an diastereomeric excess of greater than or equal to about 99%.

Furthermore, some of the crystalline forms for the compounds of the present invention may exist as polymorphs and as such are intended to be included in the present invention. In addition, some of the compounds of the present invention may form solvates with water (i.e., hydrates) or common organic solvents, and such solvates are also intended to be encompassed within the scope of this invention.

As used herein, unless otherwise noted, the term "isotopologues" shall mean molecules that differ only in their isotopic composition. More particularly, an isotopologue of a molecule differs from the parent molecule in that it contains at least one atom which is an isotope (i.e. has a different number of neutrons from its parent atom).

For example, isotopologues of water include, but are not limited to, "light water" (HOH or $H_2O$), "semi-heavy water" with the deuterium isotope in equal proportion to protium (HDO or $^1H^2HO$), "heavy water" with two deuterium isotopes of hydrogen per molecule ($D_2O$ or $^2H_2O$), "super-heavy water" or tritiated water ($T_2O$ or $^3H_2O$), where the hydrogen atoms are replaced with tritium ($^3H$) isotopes, two heavy-oxygen water isotopologues ($H_2^{18}O$ and $H_2^{17}O$) and isotopologues where the hydrogen and oxygen atoms may each independently be replaced by isotopes, for example the doubly labeled water isotopologue $D_2^{18}O$.

It is intended that within the scope of the present invention, any one or more element(s), in particular when mentioned in relation to a compound of formula (I), shall comprise all isotopes and isotopic mixtures of said element(s), either naturally occurring or synthetically produced, either with natural abundance or in an isotopically enriched form. For example, a reference to hydrogen includes within its scope $^1H$, $^2H$ (D), and $^3H$ (T). Similarly, references to carbon and oxygen include within their scope respectively $^{12}C$, $^{13}C$ and $^{14}C$ and $^{16}O$ and $^{18}O$. The isotopes may be radioactive or non-radioactive. Radiolabelled compounds of formula (I) may comprise one or more radioactive isotope(s) selected from the group of $^3H$, $^{11}C$, $^{18}F$, $^{122}I$, $^{123}I$, $^{125}I$, $^{131}I$, $^{75}Br$, $^{76}Br$, $^{77}Br$ and $^{82}Br$. Preferably, the radioactive isotope is selected from the group of $^3H$, $^{11}C$ and $^{18}F$.

In certain embodiments, the present invention is directed to compounds of formula (I) wherein $R^2$ is $OCD_3$. In certain embodiments, the present invention is directed to compounds of formula (I) wherein the $R^5$ and $R^6$ groups are the same and are both deuterium (D). In certain embodiments, the present invention is directed to compounds of formula (I) wherein Ⓐ is 2,2,3,3-tetradeutero-dihydrobenzo[b][1,4]dioxin-6-yl.

In certain embodiments, the present invention is directed to compounds of formula (I) wherein any $C_{1-4}$alkyl or $C_{1-4}$alkoxy substituent is deuterated (i.e. wherein one or more hydrogen atoms on the substituent group are replaced with a deuterium atom (D), preferably one to three hydrogen atoms are each replaced with a deuterium atom), for example —$CD_3$, —$CH_2CD_3$, —$OCD_3$, and the like.

Under standard nomenclature used throughout this disclosure, the terminal portion of the designated side chain is described first, followed by the adjacent functionality toward the point of attachment. Thus, for example, a "phenyl$C_1$-$C_6$alkylaminocarbonyl$C_1$-$C_6$alkyl" substituent refers to a group of the formula

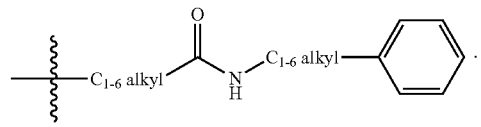

One skilled in the art will recognize that when $R^2$ and $R^3$ or $R^3$ and $R^4$ are taken together with the carbon atoms to which they are bound to form 2,3-dihydrofuranyl or 3,4-dihydro-2H-pyranyl, said 2,3-dihydrofuranyl or 3,4-dihydro-2H-pyranyl ring structure is one ring of a bicyclic ring structure. More particularly, when $R^2$ and $R^3$ or $R^3$ and $R^4$ are taken together with the phenyl ring to which they are bound (through the carbon atoms to which they are bound), the resulting structure is a partially unsaturated, benzo-fused bicyclic ring structure. Thus, for example, when $R^2$ and $R^3$ are taken together with the carbon atoms to which they are bound to form 2,3-dihydrofuranyl, a group of the following structure, with numbering order as indicated

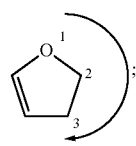

then the resulting bicyclic structure (where $R^2$ and $R^3$ are taken together with the phenyl to which they are bound, through the carbon atoms to which they are bound) is 2,3-dihydrobenzofuranyl, a group of the following structure, with numbering order as indicated:

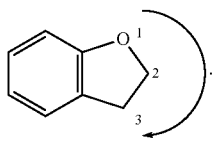

One skilled in the art will further recognize that when $R^2$ and $R^3$ or $R^3$ and $R^4$ are taken together with the phenyl ring to which they are bound (through the carbon atoms to which they are bound) to form the corresponding benzo-fused bicyclic ring structure, said benzo-fused ring structure may exist as either of two orientations.

For example, when $R^2$ and $R^3$ are taken together with the phenyl ring to which they are bound (through the carbon atoms to which they are bound) to form the corresponding 2,3-dihydrobenzofuranyl, then the 2,3-dihydrobenzofuranyl may be incorporated into the compound of formula (I) in either of two orientations, more particularly as the corresponding structure (R1)

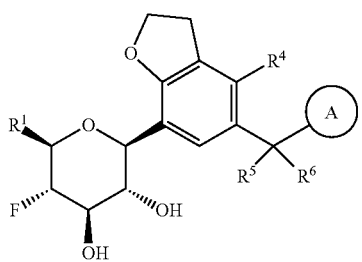

(R1)

or the corresponding structure (R2)

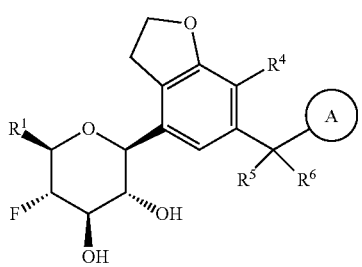

(R2)

One skilled in the art will further recognize that the orientation of the compound of formula (I) can be identified by its drawn structure (for example as shown at the head of the Examples which follow hereinafter), or by the chemical name which identifies the binding orientation of the 2,3-dihydro-benzofuranyl or isochromanyl ring structure within the complete compound of formula (I).

Abbreviations used in the specification, particularly the Schemes and Examples, are as follows:
18-Crown-6=1,4,7,10,13,16-hexaoxacyclooctadecane
AcCl=Acyl chloride
AcOH or HOAc=Acetic acid
ARB=Angiotensin receptor blockers
CAN=Acetonitrile
AMG=Alpha-Methyl Glucopyranoside
aq.=aqueous
BAIB=Bis-acetoxyiodobenzene
$BF_3.Et_2O$=Boron trifluoride diethyl etherate
BnBr=Benzylbromide
Boc=tert-Butoxycarbonyl
$Boc_2O$=Boc anhydride (Di-tert-butyl dicarbonate)
$Bu_4NCl$=Tetrabutylammonium chloride
n-$Bu_4NF$ Tetra-n-butylammonium fluoride
n-BuLi=n-Butyl lithium
sec-BuLi=sec-Butyl lithium
t-BuLi=tert-Butyl lithium
n-$Bu_4NI$=Tetra-n-butylammonium iodide
t-BuOH=tert-Butanol
t-BuONa or NaOt-Bu=Sodium tert-butoxide
conc.=concentrated
$[CpRu(CH_3CN)_3]PF_6$=Pentamethylcyclopentadienyltris (acetonitrile)ruthenium(II) hexafluorophosphate
DABCO=1,4-Diazabicyclo[2.2.2]octane
DAST=Diethylaminosulfur trifluoride
DBU=1,8-Diazabicyclo[5.4.0]undec-7-ene
DCC=N,N'-Dicyclohexylcarbodiimide
DCM=Dichloromethane
Dess-Martin Reagent or Dess-Martin Periodinane=1,1,1-Triacetoxy-1,1-dihydro-1,2-benziodoxol-3(1H)-one
DEXOX-FLKUOR®=Bis(2-methoxyethyl)aminosulfur trifluoride
DIBAL or DIBAL-H=Diisobutylaluminium hydride
DIPEA or DIEA=Diisopropylethylamine
DMF=N,N-Dimethylformamide
DMPU-HF=1,3-Dimethyl-3,4,5,6-tetrahydro-2(1H)-pyrimidinone—Hydrogen fluoride Complex
DMSO=Dimethylsulfoxide
EDCI=1-Ethyl-3-(3-dimetylaminopropyl)carbodiimide
$Et_2O$=Diethyl Ether
$Et_3N$ or TEA=Triethylamine
$Et_3NHPF_6$=Triethylammonium hexafluorophosphate
$Et_3SiD$=Mono-deuterated Triethylsilane
$Et_3SiH$=Triethylsilane
EtOAc or EA=Ethyl acetate
EtOH=Ethanol
GCMS=Gas chromatography-mass spectrometry
HATU=O-(7-Azabenzotriazol-1-yl)-N,N,N",N"-Tetramethyl Uronium Hexafluorophosphate
HDL=High density lipoprotein
HEPES=4-(2-Hydroxyethyl)-1-Piperizine Ethane Sulfonic Acid
HOBT=1-Hydroxybenzotriazole
HMPA=Hexamethylphosphoramide
HPLC=High Pressure Liquid Chromatography
$HRuCl(PPh_3)_3$=Chlorohydridotris(triphenylphosphine)ruthenium (II) complex
IDDM=Insulin-dependent Diabetes Mellitus
IFG=Impaired fasting glucose
IGT=Impaired glucose tolerance
$[Ir(Ph2MeP)2(cod)]*PF^{6-}$=(1,5-Cyclooctadiene)(pyridine)(tricyclohexylphosphine)-iridium(I) hexafluorophosphate
IRS=Insulin resistance syndrome
Jones reagent=solution of chromium trioxide or sodium dichromate in diluted sulfuric acid
LAH=Lithium aluminum hydride
LC-MS or LCMS=Liquid chromatography-mass spectrometry
Me=Methyl (i.e. —$CH_3$)
MeCN=Acetonitrile
MeI=Methyl iodide
MeOH=Methanol
$MeSO_3H$=Methanesulfonic acid Mesyl or Ms=Methylsulfonyl
MOM=Methoxy methyl
MsCl=Mesyl chloride
MTBE=Methyl t-butyl ether
NAFLD=Non-alcoholic fatty liver disease
NASH=Non-alcoholic steatohepatitis,
NaOMe=Sodium methoxide
NaOEt=Sodium Ethoxide
NBS=N-Bromosuccinimide
NIS=N-Iodosuccinimide
NIDDM=Non-insulin-dependent Diabetes Mellitus
NMO=N-Methylmorpholine-N-oxide
NMR=Nuclear magnetic resonance
OMe=Methoxy
OTf=Trifluoromethanesulfonate (triflate)
PCC=Pyridinium chlorochromate
$Pd_2Cl_2(PhCN)_2$=Bis(benzonitrile)palladium chloride
$Pd(OAc)_2$=Palladium acetate
$Pd(PPh_3)_4$=Tetrakistriphenylphosphine palladium (0)
PE=Petroleum ether
PHENOFLUOR™=1,3-Bis(2,6-diisopropylphenyl)-2,2-difluoro-2,3-dihydro-1H-imidazole
$PhI(OAc)_2$=(Diacetoxyiodo)benzene
$(Ph_3P)_2CpRuCl$=Bis(triphenylphosphine)cyclopentadienyl ruthium chloride
$(PPh_3)_3RhCl$=Chloridotris(triphenylphosposphane)rhodium (I) (Wilkinson's catalyst)
i-PrOH or IPA=Isopropanol
iPrMg.LiCl=Isopropyl magnesium chloride/Lithium chloride complex
PyFluor=2-Pyridinesulfonyl Fluoride
RAS=Renin-angiotensin system
$Rh_2$—$(S$-$DOSP)_4$=Tetrakis[(R)-(+)—N-(p-dodecylphenylsulfonyl)prolinato]dirhodium(II)
SELECTFLUO®=1-Chloromethyl-4-fluoro-1,4-diazoniabicyclo[2.2.2]octane bis(tetrafluoroborate
SGLT=Sodium glucose transport
SGLT1=Sodium glucose transport-1
SGLT2=Sodium glucose transport-2
TBAI=Tetrabutylammonium iodide
TBDMS=tert-Butyldimethylsilyl
TBDMSCl=tert-Butyldimethylsilyl chloride
TBDMSOTf or tert-$BuMe_2SiOTf$=tert-Butyldimethylsilyl trifluoromethanesulfonate
TBDPS=tert-Butyl-diphenyl-silyl
TBDPSCl=tert-Butyl-diphenyl-silyl chloride
TEA=Triethylamine
TEMPO=$(CH_3)_4$-piperidoxyl (also known as (2,2,6,6-tetramethylpiperidin-1-yl)oxidany))
TFA=Trifluoroacetic Acid
THF=Tetrahydrofuran
THP=Tetrahydropyran
TLC=Thin Layer Chromatography
TMS=Trimethylsilyl
TMEDA=Tetramethylethylenediamine
TMSCl=Trimethylsilyl chloride
Tosyl or Ts=p-Toluenesulfonyl
TrCl=Triphenylmethyl chloride or trityl chloride
TsCl=Tosyl chloride
TsOH or p-TsOH=p-Toluenesulfonic acid
Tris HCl or Tris-Cl or Tris=Tris[hydroxymethyl]aminomethyl hydrochloride buffer
XTALFLUOR-E®=(Diethylamino)difluorosulfonium tetrafluoroborate
XTALFLUOR-M®=(Difluoro(morpholino)sulfonium tetrafluoroborate As used herein, unless otherwise noted, the term "isolated form" shall mean that the compound is present in a form which is separate from any solid mixture with another compound(s), solvent system or biological environment. In an embodiment of the present invention, the compound of formula (I) is present in an isolated form.

As used herein, unless otherwise noted, the term "substantially pure form" shall mean that the mole percent of impurities in the isolated compound is less than about 5 mole percent, preferably less than about 2 mole percent, more preferably, less than about 0.5 mole percent, most preferably, less than about 0.1 mole percent. In an embodiment of the present invention, the compound of formula (I) is present as a substantially pure form.

As used herein, unless otherwise noted, the term "substantially free of a corresponding salt form(s)" when used to described the compound of formula (I) shall mean that mole percent of the corresponding salt form(s) in the isolated base of formula (I) is less than about 5 mole percent, preferably less than about 2 mole percent, more preferably, less than about 0.5 mole percent, most preferably less than about 0.1 mole percent. In an embodiment of the present invention, the compound of formula (I) is present in a form which is substantially free of corresponding salt form(s).

As used herein, unless otherwise noted, the terms "treating", "treatment" and the like, shall include the management and care of a subject or patient (preferably mammal, more preferably human) for the purpose of combating a disease, condition, or disorder and includes the administration of a compound of the present invention to prevent the onset of the symptoms or complications, alleviate the symptoms or complications, slow the progression of the disease or disorder, or eliminate the disease, condition, or disorder.

As used herein, unless otherwise noted, the term "prevention" shall include (a) reduction in the frequency of one or more symptoms; (b) reduction in the severity of one or more symptoms; (c) the delay or avoidance of the development of additional symptoms; and/or (d) delay or avoidance of the development of the disorder or condition.

One skilled in the art will recognize that wherein the present invention is directed to methods of prevention, a subject in need of thereof (i.e. a subject in need of prevention) shall include any subject or patient (preferably a mammal, more preferably a human) who has experienced or exhibited at least one symptom of the disorder, disease or condition to be prevented. Further, a subject in need thereof may additionally be a subject (preferably a mammal, more preferably a human) who has not exhibited any symptoms of the disorder, disease or condition to be prevented, but who has been deemed by a physician, clinician or other medical profession to be at risk of developing said disorder, disease or condition. For example, the subject may be deemed at risk of developing a disorder, disease or condition (and therefore in need of prevention or preventive treatment) as a consequence of the subject's medical history, including, but not limited to, family history, pre-disposition, co-existing (co-morbid) disorders or conditions, genetic testing, and the like.

The term "subject" as used herein, refers to an animal, preferably a mammal, most preferably a human, who has been the object of treatment, observation or experiment. Preferably, the subject has experienced and/or exhibited at least one symptom of the disease or disorder to be treated and/or prevented.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated.

As used herein, the term "composition" is intended to encompass a product comprising the specified ingredients in the specified amounts, as well as any product which results, directly or indirectly, from combinations of the specified ingredients in the specified amounts.

As more extensively provided in this written description, terms such as "reacting" and "reacted" are used herein in reference to a chemical entity that is any one of: (a) the actually recited form of such chemical entity, and (b) any of the forms of such chemical entity in the medium in which the compound is being considered when named.

One skilled in the art will recognize that, where not otherwise specified, the reaction step(s) is performed under suitable conditions, according to known methods, to provide the desired product. One skilled in the art will further recognize that, in the specification and claims as presented herein, wherein a reagent or reagent class/type (e.g. base, solvent, etc.) is recited in more than one step of a process, the individual reagents are independently selected for each reaction step and may be the same of different from each other. For example wherein two steps of a process recite an organic or inorganic base as a reagent, the organic or inorganic base selected for the first step may be the same or different than the organic or inorganic base of the second step. Further, one skilled in the art will recognize that wherein a reaction step of the present invention may be carried out in a variety of solvents or solvent systems, said reaction step may also be carried out in a mixture of the suitable solvents or solvent systems.

One skilled in the art will recognize that wherein a reaction step of the present invention may be carried out in a variety of solvents or solvent systems, said reaction step may also be carried out in a mixture of the suitable solvents or solvent systems.

One skilled in the art will further recognize that the reaction or process step(s) as herein described are allowed to proceed for a sufficient period of time until the reaction is complete, as determined by any method known to one skilled in the art, for example, chromatography (e.g. HPLC). In this context a "completed reaction or process step" shall mean that the reaction mixture contains a significantly diminished amount of the starting material(s)/reagent(s) and a significantly reduced amount of the desired product(s), as compared to the amounts of each present at the beginning of the reaction.

To provide a more concise description, some of the quantitative expressions given herein are not qualified with the term "about". It is understood that whether the term "about" is used explicitly or not, every quantity given herein is meant to refer to the actual given value, and it is also meant to refer to the approximation to such given value that would reasonably be inferred based on the ordinary skill in the art, including approximations due to the experimental and/or measurement conditions for such given value.

To provide a more concise description, some of the quantitative expressions herein are recited as a range from about amount X to about amount Y. It is understood that wherein a range is recited, the range is not limited to the recited upper and lower bounds, but rather includes the full range from about amount X through about amount Y, or any amount or range therein.

Examples of suitable solvents, bases, reaction temperatures, and other reaction parameters and components are provided in the detailed descriptions which follow herein.

One skilled in the art will recognize that the listing of said examples is not intended, and should not be construed, as limiting in any way the invention set forth in the claims which follow thereafter.

As used herein, unless otherwise noted, the term "aprotic solvent" shall mean any solvent that does not yield a proton. Suitable examples include, but are not limited to DMF, 1,4-dioxane, THF, acetonitrile, pyridine, dichloroethane, dichloromethane, MTBE, toluene, acetone, and the like.

As used herein, unless otherwise noted, the term "leaving group" shall mean a charged or uncharged atom or group which departs during a substitution or displacement reaction. Suitable examples include, but are not limited to, Br, Cl, I, mesylate, tosylate, and the like.

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

As used herein, unless otherwise noted, the term "nitrogen protecting group" shall mean a group which may be attached to a nitrogen atom to protect said nitrogen atom from participating in a reaction and which may be readily removed following the reaction. Suitable nitrogen protecting groups include, but are not limited to carbamates—groups of the formula —C(O)O—R wherein R is for example methyl, ethyl, t-butyl, benzyl, phenylethyl, $CH_2$=CH—$CH_2$—, and the like; amides—groups of the formula —C(O)—R' wherein R' is for example methyl, phenyl, trifluoromethyl, and the like; N-sulfonyl derivatives—groups of the formula —$SO_2$—R" wherein R" is for example tolyl, phenyl, trifluoromethyl, 2,2,5,7,8-pentamethylchroman-6-yl-, 2,3,6-trimethyl-4-methoxybenzene, and the like. Other suitable nitrogen protecting groups may be found in texts such as T. W. Greene & P. G. M. Wuts, *Protective Groups in Organic Synthesis*, John Wiley & Sons, 1991.

As used herein, unless otherwise noted, the term "oxygen protecting group" shall mean a group which may be attached to an oxygen atom to protect said oxygen atom from participating in a reaction and which may be readily removed following the reaction. Suitable oxygen protecting groups include, but are not limited to, acetyl, benzoyl, t-butyl-dimethylsilyl, trimethylsilyl (TMS), MOM, THP, and the like. Other suitable oxygen protecting groups may be found in texts such as T. W. Greene & P. G. M. Wuts, *Protective Groups in Organic Synthesis*, John Wiley & Sons, 1991.

Where the processes for the preparation of the compounds according to the invention give rise to mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-D-tartaric acid and/or (+)-di-p-toluoyl-L-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

Additionally, chiral HPLC against a standard may be used to determine percent enantiomeric excess (% ee). The enantiomeric excess may be calculated as follows

[(Rmoles−Smoles)/(Rmoles+Smoles)]×100% where Rmoles and Smoles are the R and S mole fractions in the mixture such that Rmoles+Smoles=1. The enantiomeric excess may alternatively be calculated from the specific rotations of the desired enantiomer and the prepared mixture as follows:

ee=([α-obs]/[α-max])×100.

The present invention includes within its scope prodrugs of the compounds of this invention. In general, such prodrugs will be functional derivatives of the compounds which are readily convertible in vivo into the required compound. Thus, in the methods of treatment of the present invention, the term "administering" shall encompass the treatment of the various disorders described with the compound specifically disclosed or with a compound which may not be specifically disclosed, but which converts in vivo to the specified compound in vivo after administration to the patient. Conventional procedures for the selection and preparation of suitable prodrug derivatives are described, for example, in "Design of Prodrugs", ed. H. Bundgaard, Elsevier, 1985.

For use in medicine, the salts of the compounds of this invention refer to non-toxic "pharmaceutically acceptable salts." Other salts may, however, be useful in the preparation of compounds according to this invention or of their pharmaceutically acceptable salts. Suitable pharmaceutically acceptable salts of the compounds include acid addition salts which may, for example, be formed by mixing a solution of the compound with a solution of a pharmaceutically acceptable acid such as hydrochloric acid, sulfuric acid, fumaric acid, maleic acid, succinic acid, acetic acid, benzoic acid, citric acid, tartaric acid, carbonic acid or phosphoric acid. Furthermore, where the compounds of the invention carry an acidic moiety, suitable pharmaceutically acceptable salts thereof may include alkali metal salts, e.g., sodium or potassium salts; alkaline earth metal salts, e.g., calcium or magnesium salts; and salts formed with suitable organic ligands, e.g., quaternary ammonium salts. Thus, representative pharmaceutically acceptable salts include, but are not limited to, the following: acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate.

Representative acids which may be used in the preparation of pharmaceutically acceptable salts include, but are not limited to, the following: acids including acetic acid, 2,2-dichloroacetic acid, acylated amino acids, adipic acid, alginic acid, ascorbic acid, L-aspartic acid, benzenesulfonic acid, benzoic acid, 4-acetamidobenzoic acid, (+)-camphoric acid, camphorsulfonic acid, (+)-(1S)-camphor-10-sulfonic acid, capric acid, caproic acid, caprylic acid, cinnamic acid, citric acid, cyclamic acid, dodecylsulfuric acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucoronic acid, L-glutamic acid, α-oxo-glutaric acid, glycolic acid, hipuric acid, hydrobromic acid, hydrochloric acid, (+)-L-lactic acid, (±)-DL-lactic acid, lactobionic acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinc acid, nitric acid, oleic acid, orotic acid, oxalic acid, palmitic acid, pamoic acid, phosphoric acid, L-pyroglutamic acid, salicylic acid, 4-amino-salicylic acid, sebaic acid, stearic acid, succinic acid, sulfuric acid, tannic acid, (+)-L-tartaric acid, thiocyanic acid, p-toluenesulfonic acid and undecylenic acid.

Representative bases which may be used in the preparation of pharmaceutically acceptable salts include, but are not limited to, the following: bases including ammonia, L-arginine, benethamine, benzathine, calcium hydroxide, choline, deanol, diethanolamine, diethylamine, 2-(diethylamino)-ethanol, ethanolamine, ethylenediamine, N-methyl-glucamine, hydrabamine, 1H-imidazole, L-lysine, magnesium hydroxide, 4-(2-hydroxyethyl)-morpholine, piperazine, potassium hydroxide, 1-(2-hydroxyethyl)-pyrrolidine, secondary amine, sodium hydroxide, triethanolamine, tromethamine and zinc hydroxide.

Compounds of formula (I) of the present invention may be synthesized according to the general synthesis schemes described below. The preparation of the various starting materials used in the synthesis schemes which follow hereinafter is well within the skill of persons versed in the art.

Compounds of formula (I) wherein $R^1$ is hydroxy-methyl- (i.e. —CH$_2$OH) may be prepared as described in Scheme 1, below.

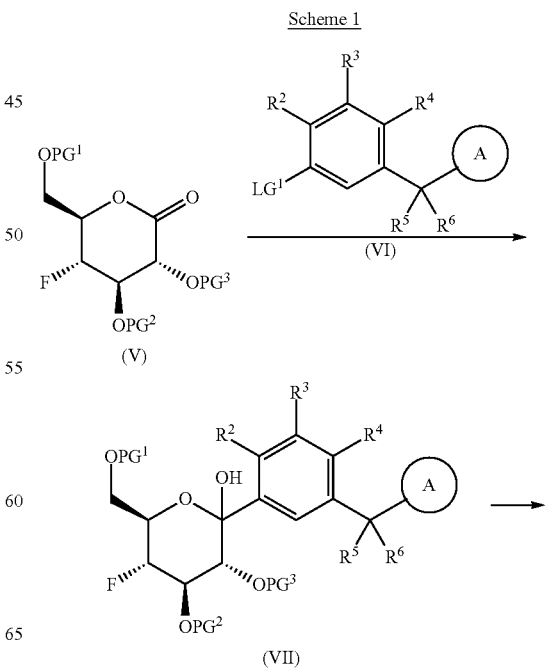

Scheme 1

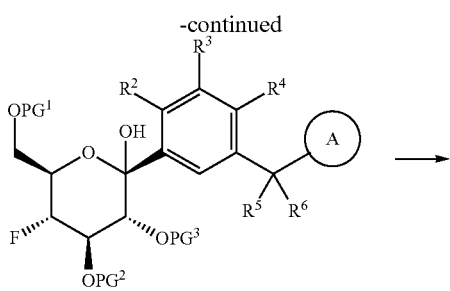

(VIII)

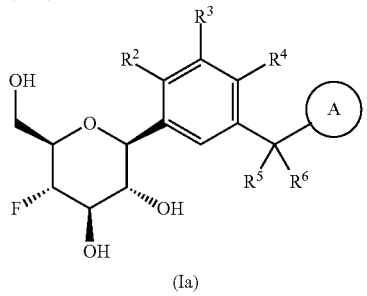

(Ia)

Accordingly, a suitably substituted compound of formula (V) wherein $PG^1$, $PG^2$ and $PG^3$ are each an independently selected oxygen protecting group such as benzyl, trimethylsilyl (TMS), t-butyl-dimethyl-silyl (TBDMS), t-butyl-diphenyl-silyl (TBDPS), and the like, is reacted with a suitably substituted and optionally protected compound of formula (VI), wherein $LG^1$ is a suitably selected leaving group such as Br, Cl, I, mesylate, tosylate, trifluoromethanesulfonyl, and the like;

in the presence of a suitably selected organolithium or Grignard reagent such as n-BuLi, s-BuLi, i-PrMgCl.LiCl, and the like; in a suitably selected organic solvent such as THF, TMEDA (tetramethylethylenediamine), HMPA (hexamethylphosphoramide), and the like; at a temperature less than about room temperature, preferably at about −78° C.; to yield the corresponding compound of formula (VII).

The compound of formula (VII) is reacted with a suitably selected reducing agent such as a mixture of $Et_3SiH$ and $BF_3.Et_2O$, $Et_3SiH$ and TFA, and the like; in a suitably selected organic solvent such as DCM, a mixture of DCM and acetonitrile, $CHCl_3$, and the like; to yield the corresponding compound of formula (VIII).

The compound of formula (VIII) is de-protected (in one or more steps), according to known methods, to remove the $PG^1$, $PG^2$ and $PG^3$ groups, and if present, any protecting groups introduced through the compound of formula (VI); to yield the corresponding compound of formula (Ia).

For example, wherein one or more of $PG^1$, $PG^2$ and/or $PG^3$ are benzyl, said group(s) may be removed by reacting with a $BCl_3$ in the presence of 1,2,3,4,5-pentamethylbenzene, in an organic solvent such as DCM, at about −78° C.; or by reacting with hydrogen in the presence of Pd/C, in an organic solvent such as MeOH; or reacting with hydrogen, in the presence of $Pd(OH)_2/C$, in a mixture of organic solvents such as ethyl acetate and methanol. In another example, wherein one or more of $PG^1$, $PG^2$ and/or $PG^3$ are a suitably selected silyl group such as trimethylsilyl (TMS), t-butyl-dimethyl-silyl (TBDMS), t-butyl-diphenyl-silyl (TBDPS), and the like, said group(s) may be removed by reacting with a suitably selected reagent or mixture of reagents such as n-$Bu_4NF$, HF-pyridine, KF, $Bu_4NCl$/KF.$H_2O$, and the like; wherein the reaction with HF, $NH_4F$—HF, $Bu_4NCl$/KF.$H_2O$, and the like is in a suitably selected organic solvent such as THF, 18-crown-6, methanol, acetonitrile, cyclohexane, and the like.

Compounds of formula (I) wherein $R^1$ is hydroxy-methyl- (i.e. —$CH_2$—OH) and wherein $R^5$ and $R^6$ are each hydrogen may alternatively be prepared as described in Scheme 2, below.

Scheme 2

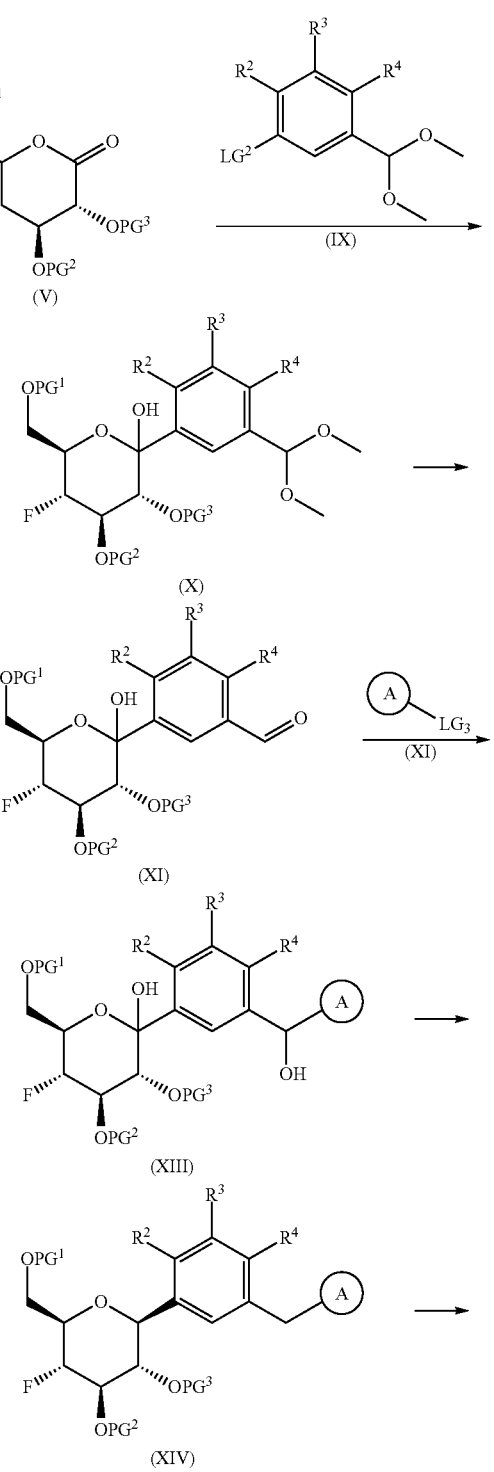

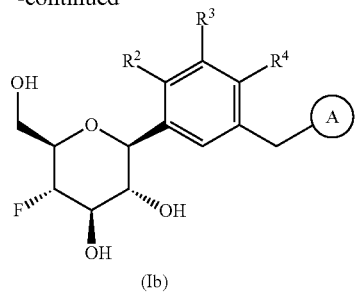

(Ib)

Scheme 3

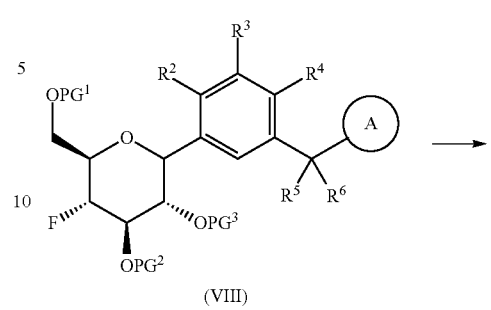

(VIII)

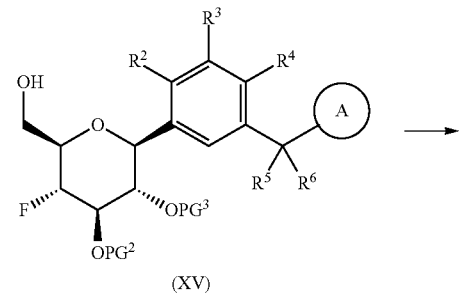

(XV)

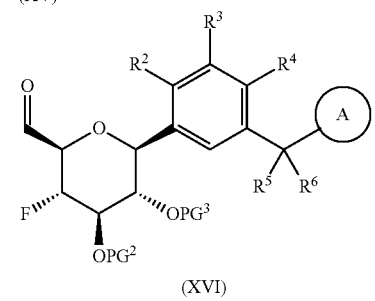

(XVI)

Accordingly, a suitably substituted compound of formula (V), for example a compound of formula (V) wherein PG¹, PG² an PG³ are each benzyl, is reacted with a suitably substituted compound of formula (IX), wherein LG² is a suitably selected leaving group such as Br, I, mesylate, tosylate, trifluoromethanesulfonyl, and the like, a known compound or compound prepared by known methods, in the presence of a suitably selected organolithium or Grignard reagent such as n-BuLi, s-BuLi, i-PrMgCl.LiCl, and the like; in a suitably selected organic solvent such as THF, diethyl ether, HMPA, and the like; at a temperature less than about room temperature, preferably at about −78° C.; to yield the corresponding compound of formula (X).

The compound of formula (X) is reacted with a suitably selected acid such as HCl, diluted $H_2SO_4$, TFA, and the like; in a suitably selected organic solvent such as THF, diethyl ether, MeOH, and the like; to yield the corresponding compound of formula (XI).

The compound of formula (XI) is reacted with a suitably substituted, and optionally protected, compound of formula (XII), wherein LG³ is a suitably selected leaving group such as Br, I, mesylate, tosylate, trifluoromethanesulfonyl, and the like, a known compound or compound prepared by known methods; in the presence of a suitably selected organolithium reagent such as n-BuLi, s-BuLi, t-BuLi, and the like; in a suitably selected organic solvent such as THF, diethyl ether, 2-methyltetrahydrofuran, and the like; at a temperature less than about room temperature, preferably at about −78° C.; to yield the corresponding compound of formula (XIII).

The compound of formula (XIII) is reacted with a suitably selected reducing agent such as a mixture of $Et_3SiH$ and $BF_3.Et_2O$, $Et_3SiH$ and TFA, and the like; in a suitably selected organic solvent such as DCM, a mixture of DCM and acetonitrile, $CHCl_3$, THF, and the like; to yield the corresponding compound of formula (XIV).

The compound of formula (XIV) is de-protected according to known methods, or according to methods as described herein; to yield the corresponding compound of formula (Ib).

Compounds of formula (I) wherein $R^1$ is selected from the group consisting of —$C_{1-4}$alkyl, hydroxy substituted $C_{1-4}$alkyl (including —CH(OH)CH₃, —C(OH)(CH₃)₂), —CH₂—F, —CH₂—CN, —CH₂—NH₂, —CH₂—O-(methyl or ethyl), —$C_{3-6}$cycloalkyl, —$C_{3-6}$cycloalkyl-OH, —C(O)OH and —C(O)O—($C_{1-4}$alkyl), may be prepared from the corresponding compound of formula (XV) or compound of formula (XVI), which compounds may be prepared as described in Scheme 3 below.

Accordingly, a suitably substituted compound (VIII) is selectively deprotected according to known methods, to yield the corresponding compound of formula (XV). For example, wherein PG¹ benzyl, the compound of formula (VIII) is selectively deprotected under hydrogen atmosphere in the presence of catalyst such as 5% Pd on carbon, 10% Pd/C, 20% of $Pd(OH)_2$, and the like, to yield the corresponding compound of formula (XV).

The compound of formula (XV) is then optionally reacted with a suitably selected oxidizing agent such as Dess-Martin reagent, DMSO/oxalyl chloride, PCC, and the like; in a suitably selected organic solvent such as 1,2-dichloroethane, chloroform, dichloromethyl (DCM), and the like; to yield the corresponding compound of formula (XVI) (wherein the hydroxymethyl (i.e. —CH₂OH) group is converted to the corresponding aldehyde (i.e —CH=O) group.

Compounds of formula (I) wherein $R^1$ is hydroxy substituted $C_{1-4}$alkyl may be prepared by reacting a suitably substituted compound of formula (XVI) with a suitably selected $C_{1-4}$alkylmagnesium bromide or $C_{1-4}$alkyllithium, a known compound or compound prepared by known methods, in a suitably selected organic solvent such as THF, 2-methyl tetrahydrofuran (2-Me-THF), diethyl ether, and the like; to yield the corresponding compound wherein the aldehyde group is converted to the corresponding hydroxy-substituted $C_{1-4}$alkyl group; and then de-protecting said compound as described herein, to remove the PG² and PG³ groups; to yield the compound of formula (I) wherein $R^1$ is hydroxy substituted $C_{1-4}$alkyl.

One skilled in the art will recognize that compounds of formula (I) wherein $R^1$ is hydroxy substituted $C_{3-6}$cycloalkyl, may be similarly prepared by substituting a suitably selected $C_{3-6}$cycloalkyl magnesium bromide for the $C_{1-4}$alkylmagnesium bromide, and reacting as described in the paragraph above.

Compounds of formula (I) wherein $R^1$ is $C_{1-4}$alkyl may be similarly prepared by reacting a suitably substituted compound of formula (XVI) with a suitably selected $C_{1-4}$alkylmagnesium bromide or $C_{1-4}$alkyllithium, a known compound or compound prepared by known methods, in a suitably selected organic solvent such as THF, 2-methyl tetrahydrofuran (2-Me-THF), diethyl ether, and the like; to yield the corresponding compound wherein the aldehyde group is converted to the corresponding hydroxy-substituted $C_{1-4}$alkyl group; reacting said hydroxy-substituted $C_{1-4}$alkyl substituted compound with for example, $BF_3.Et_2O$ and $Et_3SiH$ in a solvent such as DCM; to yield the corresponding compound wherein the hydroxy-substituted $C_{1-4}$alkyl group is converted to the corresponding $C_{1-4}$alkyl; and then de-protecting said $C_{1-4}$alkyl substituted compound as described herein, to remove the $PG^2$ and $PG^3$ groups; to yield the compound of formula (I) wherein $R^1$ is $C_{1-4}$alkyl.

One skilled in the art will recognize that compounds of formula (I) wherein $R^1$ is $C_{3-6}$cycloalkyl, may be similarly prepared by substituting a suitably selected $C_{3-6}$cycloalkyl magnesium bromide for the $C_{1-4}$alkylmagnesium bromide, and reacting as described in the paragraph above.

Compounds of formula (I) wherein $R^1$ is —$CH_2F$ may be prepared by reacting a suitably substituted compound of formula (XV) with a suitably selected fluorinating agent such as DAST, DEXOX-FLUOR®, and the like, in a suitably selected organic solvent such as DCM, chloroform, and the like; to yield the corresponding compound wherein the $R^1$ group (i.e the —$CH_2OH$ substituent group) is monofluorinated (i.e. converted to the corresponding —$CH_2F$ group); and then de-protecting said compound to remove the $PG^2$ and $PG^3$; to yield the corresponding compound of formula (I), where $R^1$ is $CH_2F$.

Compounds of formula (I) wherein $R^1$ is —$CH_2$—CN may be prepared by reacting a suitably substituted compound of formula (XV) with a suitably selected sulfonating agent such as MsCl, TsCl, and the like; in the presence of a suitably selected base such as $Et_3N$, DIPEA, pyridine, and the like, to yield the corresponding compound wherein $R^1$ group (i.e the —$CH_2OH$ substituent group) is converted to the corresponding mesylate or tosylate; said mesylate or tosylate substituted compound is then further reacted with for example, KCN, NaCN, and the like; in a suitably selected organic solvent such as DMF, DMSO, and the like; to the corresponding compound wherein the mesylate or tosylate group is converted to cyanomethyl (i.e. —$CH_2CN$); which compound is then de-protected as described herein, to remove the $PG^2$ and $PG^3$; to yield the corresponding compound of formula (I), where $R^1$ is $CH_2CN$.

Alternatively, the mesylate or tosylate substituted compound may be reacted with for example, $NaN_3$ in DMF or DMSO; to yield the corresponding compound wherein the mesylate or tosylate group is converted to azidomethyl— (i.e. —$CH_2N_3$); which compound is then reduced and de-protected (to remove the $PG^2$ and $PG^3$ groups) in one pot by reacting with $H_2$ gas in the presence of catalyst such as 5% Pd/C, 10% Pd/C, 20% $Pd(OH)_2$, and the like; to yield the corresponding compound of formula (I) where $R^1$ is $CH_2NH_2$.

Compounds of formula (I) wherein $R^1$ is —$CH_2$—$OCH_3$ or —$CH_2$—$OCH_2CH_3$ may be prepared by reacting a suitably substituted compound of formula (XV) with a suitably selected sulfonating agent such as MsCl, TsCl, and the like; in the presence of a suitably selected base such as $Et_3N$, DIPEA, pyridine, and the like, to yield the corresponding compound wherein $R^1$ group (i.e the —$CH_2OH$ substituent group) is converted to the corresponding mesylate or tosylate; said mesylate or tosylate substituted compound is then further reacted with $NaOCH_3$ or $NaOCH_2CH_3$, in a suitably selected organic solvent such as THF, DMF, and the like; to yield the corresponding compound wherein the mesylate or tosylate is converted to the corresponding —$CH_2$—$OCH_3$ or —$CH_2$—$OCH_2CH_3$ group, respectively; which compound is then de-protected as described herein, to remove the $PG^2$ and $PG^3$; to yield the corresponding compound of formula (I), where $R^1$ is —$CH_2$—$OCH_3$ or —$CH_2$—$OCH_2CH_3$ group.

Compounds of formula (I) wherein $R^1$ is —C(O)OH may be prepared by reacting a suitably substituted compound of formula (XV) with a suitably selected oxidizing agent such as $CrO_3/H_2SO_4$, $KMnO_4$, $PhI(OAc)_2$ [(diacetoxyiodo)benzene or bis-acetoxyiodobenzene (BAIB)]/$(CH_3)_4$-piperidoxyl (TEMPO), and the like, in a suitably selected solvent such as acetone, a mixture of ACN/water, and the like; to yield the corresponding compound wherein the $R^1$ group (i.e the —$CH_2OH$ substituent group) is converted to the corresponding carboxylic acid group (i.e —C(O)OH). Said carboxylic acid substituted compound is then de-protected as described herein, to remove the $PG^2$ and $PG^3$; to yield the corresponding compound of formula (I), where $R^1$ is —C(O)OH.

Compounds of formula (I) wherein $R^1$ is —C(O)O—($C_{1-4}$alkyl) may be prepared by reacting a suitably substituted compound of formula (XV) with a suitably selected oxidizing agent such as $CrO_3/H_2SO_4$, $KMnO_4$, $PhI(OAc)_2$ [(diacetoxyiodo)benzene or bis-acetoxyiodobenzene (BAIB)]/$(CH_3)_4$-piperidoxyl (TEMPO), and the like, in a suitably selected solvent such as acetone, a mixture of ACN/water, and the like; to yield the corresponding compound wherein the $R^1$ group (i.e the —$CH_2OH$ substituent group) is converted to the corresponding carboxylic acid group (i.e —C(O)OH). Said carboxylic acid substituted compound is then reacted with a suitably selected $C_{1-4}$alkyl alcohol, in the presence of a suitably selected coupling agent such as DCC, EDCl/HOBt, and the like; in a suitably selected organic solvent such as DCM, THF, DMF, and the like; to yield the corresponding compound wherein the carboxylic acid group (i.e. —C(O)OH) is functionalized to the corresponding $C_{1-4}$alkyl ester group (i.e. —C(O)O—($C_{1-4}$alkyl) group); and then said $C_{1-4}$alkyl ester substituted compound is de-protected as described herein, to remove the $PG^2$ and $PG^3$; to yield the corresponding compound of formula (I), where $R^1$ is —C(O)O—($C_{1-4}$alkyl).

One skilled in the art will recognize that compounds of formula (VI)

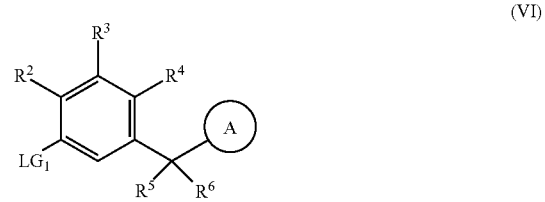

are known compounds or compounds which may be prepared by known methods or compounds which may be prepared according to the methods as described in the Schemes and Examples herein.

Compounds of formula (I) wherein $R^2$, $R^3$ and $R^4$ are each independently a substituent group may be prepared as described in Scheme 4, below.

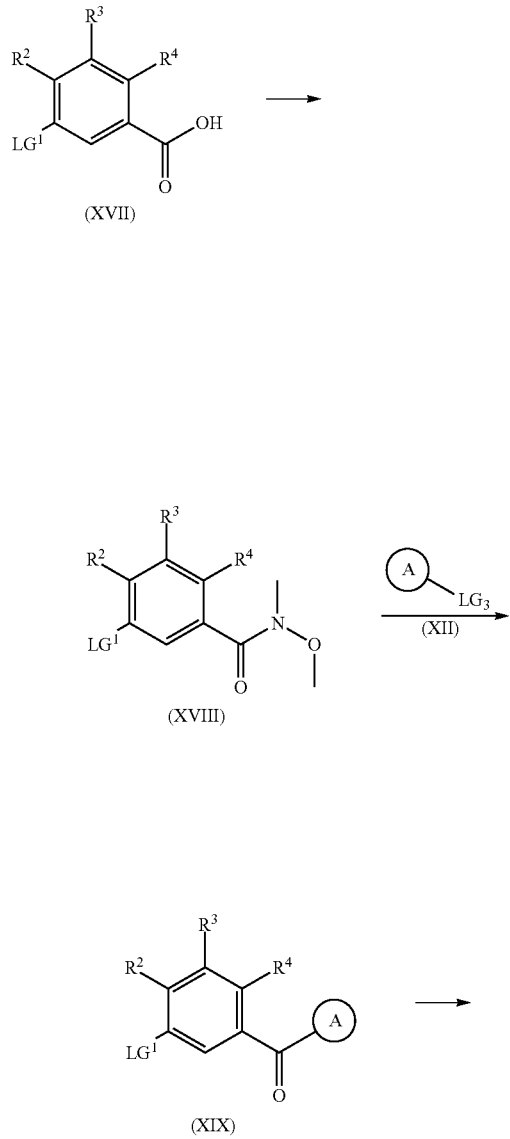

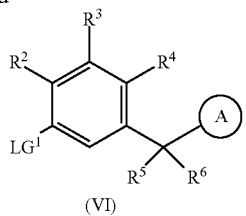

Accordingly, a suitably substituted compound of formula (XVII), a known compound or compound prepared by known methods, is reacted with for example, a suitably selected coupling reagent such as HATU, EDCl/HOBt, and the like; in the presence of a suitably selected base such as $Et_3N$, DIPEA, and the like; in a suitably selected organic solvent such as DCM, DMF, and the like;

to yield the corresponding compound of formula (XVIII) wherein the carboxylic acid substituent group on the compound of formula (XVII) is converted to a Weinreb amide.

The compound of formula (XVIII) is pre-treated (and admixed with) a suitably selected base such as n-BuLi, t-BuLi, sec-BuLi and the like; in a suitably selected organic solvent such as THF, diethyl ether, and the like; at a temperature in the range of from about −78° C. to about 20° C., preferably at a temperature of about −78° C.; and then immediately reacted with a suitably substituted compound of formula (XII), wherein $LG^3$ is a suitably selected leaving group such as Br, I, and the like; a known compound or compound prepared by known methods, to yield the corresponding compound of formula (XIX).

The compound of formula (XIX) is reacted with a suitably selected reducing agent such as triethylsilane, LAH, and the like; in the presence of suitably selected Lewis acid such as $BF_3 \cdot Et_2O$, TFA, $AlCl_3$, and the like; in a suitably selected organic solvent such as DCM, diethyl ether, and the like; to yield the corresponding compound of formula compound formula (VI), wherein $R^5$ and $R^6$ are each hydrogen.

Alternatively, the compound of formula (XIX) is reacted with a suitably selected reducing agent such as deuterium-substituted triethylsilane (triethylsilane-$d_4$), deuterium-substituted LAH, and the like; in the presence of suitably selected Lewis acid such as $BF_3 \cdot Et_2O$, TFA, $AlCl_3$, and the like; in a suitably selected organic solvent such as DCM, diethyl ether, and the like; to yield the corresponding compound of formula (VI), wherein $R^5$ and $R^6$ are each deuterium.

Compounds of formula (I) wherein $R^2$ and $R^3$ or $R^3$ and $R^4$ are taken together with the carbon atoms to which they are bound to form a ring structure as herein defined may be prepared as described in Scheme 5, below.

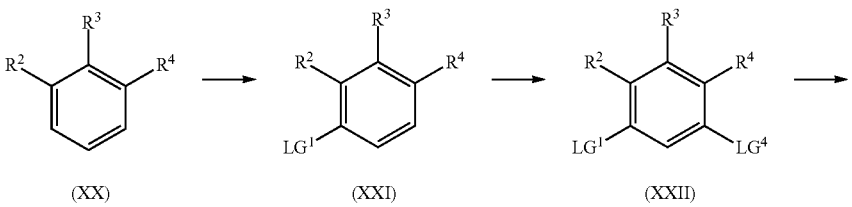

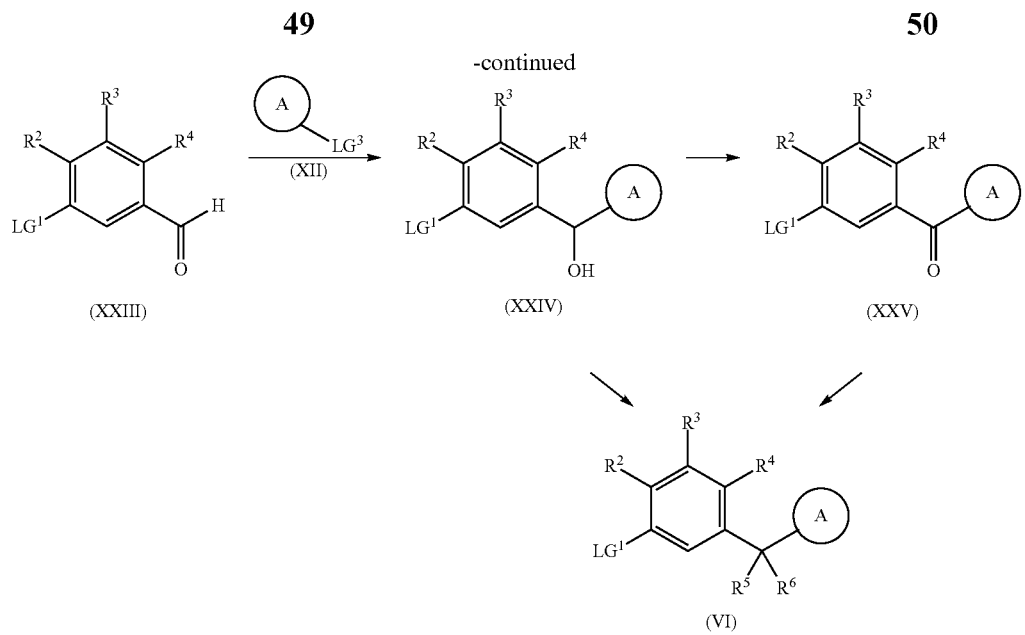

Accordingly, a suitably substituted compound of formula (XX), a known compound or compound prepared by known methods, is reacted with a first suitably selected brominating reagent such as $Br_2$, NBS, and the like; in a suitably selected organic solvent such as DCM, THF, $CH_3CN$, and the like; to yield the corresponding compound of formula (XXI) wherein $LG^1$ is bromine.

The compound of formula (XXI) is reacted with a second suitably selected iodinating reagent such as $I_2$, NIS, and the like; in a suitably selected organic solvent such as DCM, THF, $CH_3CN$ and the like; to yield the corresponding compound of formula (XXII) wherein $LG^1$ is bromine and wherein $LG^4$ is iodine.

The compound of formula (XXII) is reacted with a suitably selected organolithium or Grignard reagent such as n-BuLi, s-BuLi, i-PrMgCl.LiCl, and the like; and the resulting intermediate (which is not isolated) is then immediately reacted with DMF; to yield the compound of formula (XXIII).

The compound of formula (XII) wherein $LG^3$ is a suitably selected leaving group such as Br, Cl, I, and the like; a known compound or compound prepared by known methods; in a suitably selected organic solvent such as THF, diethyl ether, and the like; at a temperature in the range of from about −78° C. to about 20° C., preferably at about −78° C.; is pre-treated (and admixed with) a suitably selected base such as n-BuLi, t-BuLi, sec-BuLi and the like; and then immediately reacted with a suitably substituted compound of formula (XXIII), to yield the corresponding compound of formula of (XXIV).

The compound of formula (XXIV) is reacted with a suitably selected reducing agent such as triethylsilane, LAH, and the like; in the presence of suitably selected Lewis acid such as $BF_3.Et_2O$, TFA, $AlC_3$, and the like; in a suitably selected organic solvent such as DCM, diethyl ether, and the like; to yield compound formula (VI), wherein $R^5$ and $R^6$ are each H.

Alternatively, the compound of formula (XXIV) is reacted with a suitably selected oxidizing reagent such as PCC, $MnO_2$, Dess-Martin reagent, and the like; in a suitably selected organic solvent such as DCM, 1,2-dicholorethane, DMSO and the like; to yield the compound of formula (XXV).

The compound of formula (XXV) is reacted with a suitably selected reducing agent such as deuterium-substituted triethylsilane (triethylsilane-d4), deuterium-substituted LAH, and the like; in the presence of suitably selected Lewis acid such as $BF_3.Et_2O$, $AlCl_3$, and the like; in a suitably selected organic solvent such as DCM, diethyl ether, and the like; to yield compound formula (VI), wherein $R^5$ and $R^6$ are each deuterium.

In certain embodiments, the present invention is directed to compounds of formula (V-S), and a method for the preparation of the compounds of formula (V-S).

The compound of formula (V-S), for example, compounds of formula (V-S) wherein $A^1$ is t-butyl, $A^2$ is methyl and $A^3$ is methyl, may be prepared as described in Scheme A, below.

Scheme A

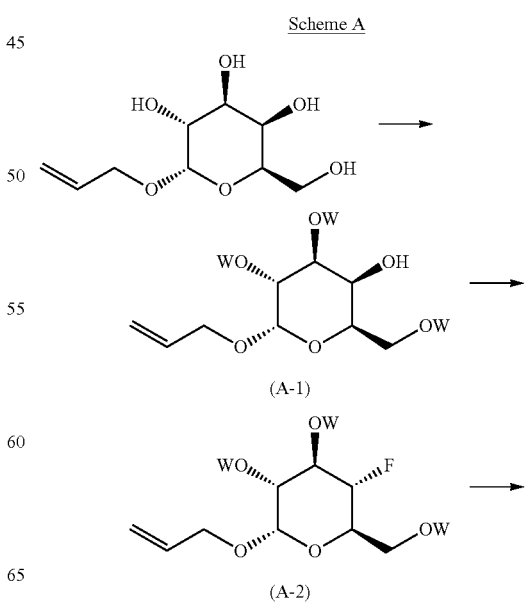

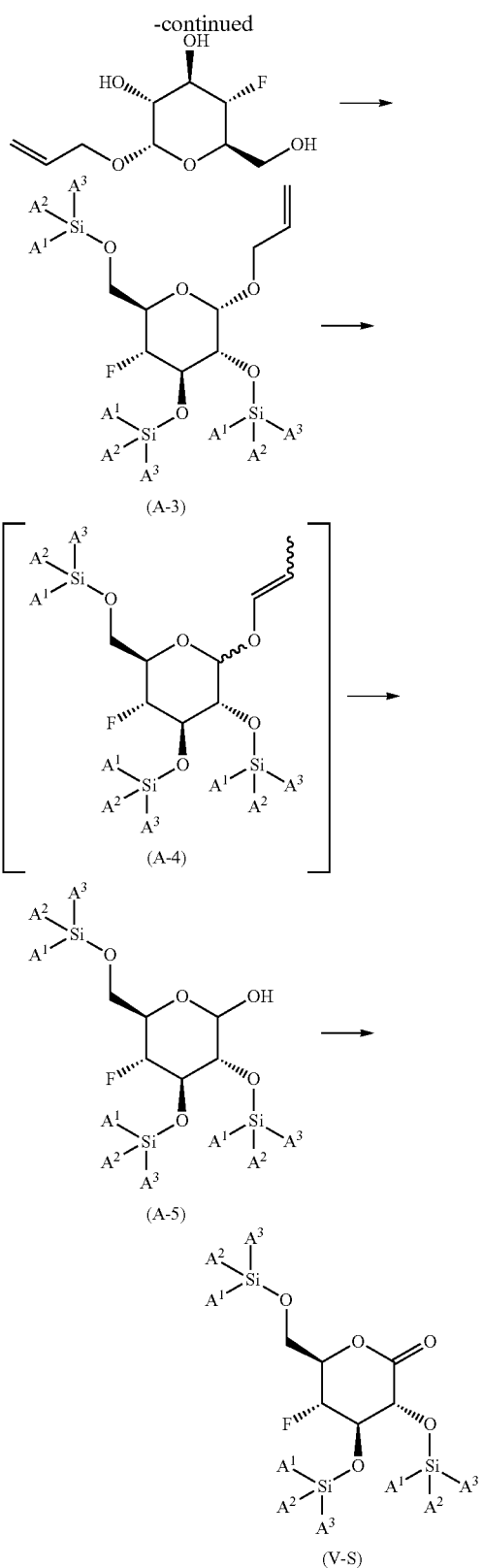

limited to acetyl chloride, acetic anhydride, propanoyl chloride, isopropanoyl chloride, pivaloyl chloride, trichloroacetyl chloride, benzoyl chloride, 4-methoxy benzoyl chloride, benzoyl anhydride, 4-methyl-benzoyl chloride, and the like, wherein the acylating agent is preferably present in an amount in the range of from about 1 to about 3.9 molar equivalents (relative to the moles of the starting material), more preferably about 3 to about 3.5 molar equivalents, more preferably, between about 3 and about 3.25 molar equivalents, for example, about 3.1 molar equivalents;

in the presence of an inorganic or organic base, preferably a base which is soluble in the reaction solvent, more preferably an organic base such as pyridine, DIPEA, $Et_3N$, and the like; wherein the inorganic or organic base is preferably present in an amount in the range of from about 1 to about 20 molar equivalents, preferably in an amount in the range of from about 2 to about 10 molar equivalents, more preferably in an amount in the range of from about 2 to about 6 molar equivalents, more preferably in an amount in the range of from about 3 to about 4 molar equivalents, for example, about 3.1 molar equivalents;

neat, when in the presence of an organic base or when in the presence of an inorganic base, in a suitably selected organic solvent such as DCM, 1,2-dichloroethane, chlorobenzene, fluorobenzene, THF, 2-methyl-THF, toluene, di-n-butyl ether, ethyl acetate, acetone, and the like; at a temperature in the range of from about −50° C. to about room temperature, preferably at about −35° C. to about 20° C. (preferably at a temperature in the range of from about −35° C. to about 0° C.); to yield the corresponding compound of formula (A-1), wherein W is the corresponding acyl group, preferably —C(O)-methyl, —C(O)— ethyl, —C(O)-benzyl, more preferably —C(O)-benzyl (benzoyl).

Preferably, the acyl chloride is added a mixture comprising the (2S,3R,4S,5R,6R)-2-(allyloxy)-6-(hydroxymethyl)tetrahydro-2H-pyran-3,4,5-triol and the base. Preferably, the acyl chloride is added to the mixture at a rate which maintains the internal temperature of the reaction mixture below 0° C.

The compound of (A-1) is reacted with a suitably selected fluorinating agent such as DAST, DEXOX-FLUOR® (Bis(2-methoxyethyl)aminosulfur trifluoride available from Sigma-Aldrich), SELECTFLUOR® (1-Chloromethyl-4-fluoro-1,4-diazoniabicyclo[2.2.2]octane bis(tetrafluoroborate) available from Sigma-Aldrich), XTALFLUOR-E® ((Diethylamino)difluorosulfonium tetrafluoroborate available from Sigma-Aldrich), XTALFLUOR-M® ((Difluoro(morpholino)sulfonium tetrafluoroborate available from Sigma-Aldrich), PyFluor (2-Pyridinesulfonyl Fluoride available from Sigma-Aldrich), 4-tert-butyl-2,6-dimethylphenylsulfur trifluoride, AlkylFluor (available from Sigma-Aldrich), N-fluorobenzenesulfonimide, DMPU-HF Complex (HF 65% w/w), 1-fluoropyridinium triflate, 1-fluoro-2,4,6-trimethylpyridinium tetrafluoroborate, 1-fluoro-4-hydroxy-1,4-diazoniabicyclo[2,2,2]octane bis(tetrafluoroborate) on aluminum oxide, fluoro-N,N,N',N'-tetramethylformamidinium hexafluorophosphate, hydrogen fluoride pyridine (pyridine ~30%, hydrogen fluoride ~70%), PHENOFLUOR™ solution (0.1 M in toluene), and the like, preferably DAST; wherein the fluorinating agent is preferably present in an amount in the range of from about 2 to about 10 molar equivalents, (relative to the molar amount of (2S,3R,4S,5S,6R)-2-(allyloxy)-6-((benzoyloxy)methyl)-5-hydroxytetrahydro-2H-pyran-3,4-diyl dibenzoate) more preferably in an amount in the range of from about 3 to about 7 molar equivalents, for example, about 6 molar equivalents;

Accordingly, (2S,3R,4S,5R,6R)-2-(allyloxy)-6-(hydroxymethyl)tetrahydro-2H-pyran-3,4,5-triol, a known compound or compound prepared by known methods, is reacted with a suitably selected acylating agent such as an acyl chloride, acyl anhydride, and the like, including, but not in a suitably selected organic solvent or mixture of organic solvents such as DCM, CHCl$_3$, Et$_2$O, and the like; at a temperature in the range of from about −50° C. to about room temperature, preferably at about −40° C. to about 20° C.; to yield the corresponding compound of formula (A-2).

Preferably the fluorinating agent is added to the mixture comprising the compound of formula (A-1), at a rate which maintains the internal temperature of the reaction mixture between 0° C. and room temperature (depending on the fluorinating agent as would be readily recognized by those skilled in the art).

The compound of formula (A-2) is de-protected according to known methods, to remove the acyl groups. For example, the compound of formula (A-2) is reacted with a suitably selected base such as NaOCH$_3$, NaOCH$_2$CH$_3$, NaOH, KOH, and the like; wherein the base is preferably present in an amount in the range of from about 0.1 to about 3 molar equivalents, (relative to the molar amount of the compound of formula (A-2)), more preferably in an amount in the range of from about 0.4 to about 2 molar equivalents, for example, about 0.5 molar equivalents; in a suitably selected organic solvent or mixture of organic solvents such as methanol, ethanol, i-PrOH, MeOH/THF, 2-methyl-THF, and the like; to yield (2S,3R,4R,5S,6R)-2-(allyloxy)-5-fluoro-6-(hydroxymethyl)tetrahydro-2H-pyran-3,4-diol.

The (2S,3R,4R,5S,6R)-2-(allyloxy)-5-fluoro-6-(hydroxymethyl)tetrahydro-2H-pyran-3,4-diol is reacted with a suitably selected trialkyl silyl reagent such as TBDMSOTf, TBDMSCl, triethylsilyl chloride, triisopropylsilyl chloride, TBDPSCl, diethylisopropylsilyl chloride, isopropyldimethylsilyl chloride, a known compound; wherein the trialkyl silyl reagent is preferably present in an amount in the range of from about 1 to about 10 molar equivalents, (relative to the molar amount of 2S,3R,4R,5S,6R)-2-(allyloxy)-5-fluoro-6-(hydroxymethyl)tetrahydro-2H-pyran-3,4-diol), more preferably in an amount in the range of from about 3 to about 10 molar equivalents, more preferably in an amount in the range of from about 5 to about 10 molar equivalents, for example, about 8 molar equivalents;

in the presence of a suitably selected organic base such as 2,6-lutidine, 1H-imidazole, TEA, DIPEA, pyridine, and the like; wherein the organic base is preferably present in an amount in the range of from about 1 to about 15 molar equivalents, (relative to the molar amount of 2S,3R,4R,5S,6R)-2-(allyloxy)-5-fluoro-6-(hydroxymethyl)tetrahydro-2H-pyran-3,4-diol) more preferably in an amount in the range of from about 3 to about 15 molar equivalents, more preferably in an amount in the range of from about 10 to about 15 molar equivalents, for example, about 12 molar equivalents; in a suitably selected organic solvent or mixture of organic solvents such as DCM, 1,2-dichloroethane, DMF, dimethylacetamide, THF, acetonitrile, and the like; at a temperature in the range of about 0° C. to about 50° C., preferably at about room temperature; to yield the corresponding compound of formula (A-3) wherein A$^1$, A$^2$ and A$^3$ are the corresponding alkyl groups (from the trialkyl silyl reagent).

The compound of formula (A-3) is reacted with a suitably selected O-allyl isomerization catalyst such as (PPh$_3$)$_3$RhCl, CpRu(CH$_3$CN)$_3$]PF$_6$ (tris(acetonitrile)cyclopentadienylruthenium hexafluorophosphate), [{Ru(η$^3$:η$^3$-C$_{10}$H$_{16}$)Cl(μ-Cl)}$_2$], Fe(CO)$_5$, HRuCl(PPh$_3$)$_3$(chlorohydridotris(triphenylphosphine)ruthenium (II) complex) [Ir(Ph$_2$MeP)$_2$(cod)]$^+$PF$_6^-$, (Ph$_3$P)$_2$CpRuCl, PdCl$_2$(PhCN)$_2$, and the like; wherein the O-allyl isomerization catalyst is present in a catalytic amount, for example in an amount in the range of from about 1 mole % to about 15 mole %, for example, about 10%; in the presence of a suitably selected organic base such as DABCO, DBU, Et$_3$NHPF$_6$ (triethylammonium hexafluorophosphate), and the like; wherein the organic base is preferably present in an amount in the range of from about 1 to about 3 molar equivalents, (relative to the molar amount of the compound of formula (A-3)), more preferably in an amount in the range of from about 1.5 to about 2.5 molar equivalents, for example, about 2 molar equivalents;

in a suitably selected organic solvent or mixture of water and a water miscible organic solvent such as ethanol/water, i-PrOH/water, THF/water, and the like; at a temperature of in the range of from about 75° C. to about 105° C., preferably at about reflux temperature; to yield the corresponding compound of formula (A-4), wherein the compound of formula (A-4) is preferably not isolated. (One skilled in the art will recognize that in this reaction step, the allyl group on the compound of formula (A-3) is isomerized to the corresponding vinyl group on the compound of formula (A-4)).

The compound of formula (A-4) is reacted with a suitably selected co-oxidant such as NMO, NaHSO$_3$, benzoquinone, and the like; wherein the oxidizing agent is preferably present in an amount in the range of from about 1 to about 5 molar equivalents, (relative to the molar amount of the compound of formula (A-3)), more preferably in an amount in the range of form about 1 to about 2.5 molar equivalents, more preferably in an amount in the range of from about 1 to about 2 molar equivalents, for example, about 1.5 molar equivalents; in the presence of a suitably selected oxidizing reagent such as OsO$_4$, KMnO$_4$, NaIO$_4$, and the like; wherein the oxidizing reagent is preferably present in a catalytic amount, for example, in an amount in the range of from about 1 mole % to about 20%, more preferably in an amount in the range of from about 1 mole % to about 10 mole %, for example, about 5%; in a suitably selected organic solvent or mixture of water and a water miscible organic solvent such as acetone/water, t-BuOH/water, acetone/t-BuOH/water, CH$_3$CN/water, DMSO/water, and the like; at a temperature in the range of from about 0° C. to about 50° C., preferably at a temperature in the range of from about 15° C. to about 40° C., more preferably at about 30° C.; to yield the corresponding compound of formula (A-5).

The compound of formula (A-5) is reacted with a suitably selected oxidizing agent; to yield the corresponding compound of formula (V-S). In an example, the compound of formula (A-5) is reacted under SWERN oxidation conditions, e.g. with a suitably selected reagent such as acetic anhydride, trifluoromethyl acetic anhydride, oxalyl chloride, cyanuric chloride, pyridine-sulfur trioxide, and the like; wherein the reagent is preferably present in an amount in the range of from about 2 to about 50 molar equivalents, (relative to the molar amount of the compound of formula (A-5)) for example, about 25 molar equivalents; in DMSO; at a temperature in the range of from about −60° C. to about 30° C.; to yield the corresponding compound of formula (V-S). Alternatively, the compound of formula (A-5) is reacted with a suitably selected oxidizing agent such as Dess-Martin periodinane, pyridinium chlorochromate (preferably in DCM), and the like; in a suitably selected organic solvent such as DCM, 1,2-dichloroethane, and the like; to yield the corresponding compound of formula (V-S). Alternatively, the compound of formula (A-5) is reacted with a suitably selected oxidizing agent/organic solvent combination such as Jones reagent in acetone, NaClO$_2$/TEMPO in DCM or AgCO$_3$ in benzene, and the like; to yield the corresponding compound of formula (V-S).

The compound of formula (V-S) is preferably isolated (from the DMSO) and/or purified (e.g. by column chromatography or recrystallization) according to known methods, as would be readily recognized by those skilled in the art.

Pharmaceutical Compositions

The present invention further comprises pharmaceutical compositions containing one or more compounds of formula (I) with a pharmaceutically acceptable carrier. Pharmaceutical compositions containing one or more of the compounds of the invention described herein as the active ingredient can be prepared by intimately mixing the compound or compounds with a pharmaceutical carrier according to conventional pharmaceutical compounding techniques. The carrier may take a wide variety of forms depending upon the desired route of administration (e.g., oral, parenteral). Thus for liquid oral preparations such as suspensions, elixirs and solutions, suitable carriers and additives include water, glycols, oils, alcohols, flavoring agents, preservatives, stabilizers, coloring agents and the like; for solid oral preparations, such as powders, capsules and tablets, suitable carriers and additives include starches, sugars, diluents, granulating agents, lubricants, binders, disintegrating agents and the like. Solid oral preparations may also be coated with substances such as sugars or be enteric-coated so as to modulate major site of absorption. For parenteral administration, the carrier will usually consist of sterile water and other ingredients may be added to increase solubility or preservation. Injectable suspensions or solutions may also be prepared utilizing aqueous carriers along with appropriate additives.

To prepare the pharmaceutical compositions of this invention, one or more compounds of the present invention as the active ingredient is intimately admixed with a pharmaceutical carrier according to conventional pharmaceutical compounding techniques, which carrier may take a wide variety of forms depending of the form of preparation desired for administration, e.g., oral or parenteral such as intramuscular. In preparing the compositions in oral dosage form, any of the usual pharmaceutical media may be employed. Thus, for liquid oral preparations, such as for example, suspensions, elixirs and solutions, suitable carriers and additives include water, glycols, oils, alcohols, flavoring agents, preservatives, coloring agents and the like; for solid oral preparations such as, for example, powders, capsules, caplets, gelcaps and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carriers are obviously employed. If desired, tablets may be sugar coated or enteric coated by standard techniques. For parenterals, the carrier will usually comprise sterile water, through other ingredients, for example, for purposes such as aiding solubility or for preservation, may be included. Injectable suspensions may also be prepared, in which case appropriate liquid carriers, suspending agents and the like may be employed. The pharmaceutical compositions herein will contain, per dosage unit, e.g., tablet, capsule, powder, injection, teaspoonful and the like, an amount of the active ingredient necessary to deliver an effective dose as described above. The pharmaceutical compositions herein will contain, per unit dosage unit, e.g., tablet, capsule, powder, injection, suppository, teaspoonful and the like, of from about 0.01 mg to about 1000 mg or any amount or range therein, and may be given at a dosage of from about 0.05 mg/day to about 300 mg/day, or any amount or range therein, preferably from about 0.1 mg/day to about 100 mg/day, or any amount or range therein, preferably from about 1 mg/day to about 50 mg/day, or any amount or range therein. The dosages, however, may be varied depending upon the requirement of the patients, the severity of the condition being treated and the compound being employed. The use of either daily administration or post-periodic dosing may be employed.

Preferably these compositions are in unit dosage forms from such as tablets, pills, capsules, powders, granules, sterile parenteral solutions or suspensions, metered aerosol or liquid sprays, drops, ampoules, autoinjector devices or suppositories; for oral parenteral, intranasal, sublingual or rectal administration, or for administration by inhalation or insufflation. Alternatively, the composition may be presented in a form suitable for once-weekly or once-monthly administration; for example, an insoluble salt of the active compound, such as the decanoate salt, may be adapted to provide a depot preparation for intramuscular injection. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective dosage forms such as tablets, pills and capsules. This solid preformulation composition is then subdivided into unit dosage forms of the type described above containing from about 0.01 mg to about 1,000 mg, or any amount or range therein, of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of material can be used for such enteric layers or coatings, such materials including a number of polymeric acids with such materials as shellac, cetyl alcohol and cellulose acetate.

The liquid forms in which the novel compositions of the present invention may be incorporated for administration orally or by injection include, aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions, include synthetic and natural gums such as tragacanth, acacia, alginate, dextran, sodium carboxymethylcellulose, methylcellulose, polyvinyl-pyrrolidone or gelatin.

The method of treating disorders mediated by SGLT activity, preferably dual SGLT1 and SGLT2 activity, described in the present invention may also be carried out using a pharmaceutical composition comprising any of the compounds as defined herein and a pharmaceutically acceptable carrier. The pharmaceutical composition may contain between about 0.01 mg and about 1000 mg of the compound, or any amount or range therein, preferably from about 0.05 mg to about 300 mg of the compound, or any amount or range therein, more preferably from about 0.1 mg to about 100 mg of the compound, or any amount or range therein, more preferably from about 0.1 mg to about 50 mg of the compound, or any amount or range therein; and may be constituted into any form suitable for the mode of administration selected. Carriers include necessary and inert pharmaceutical excipients, including, but not limited to, binders, suspending agents, lubricants, flavorants, sweeteners, preservatives, dyes, and coatings. Compositions suitable for oral administration include solid forms, such as pills, tablets, caplets, capsules (each including immediate release, timed release and sustained release formulations), granules, and powders, and liquid forms, such as solutions, syrups, elixers, emulsions, and suspensions. Forms useful for parenteral administration include sterile solutions, emulsions and suspensions.

Advantageously, compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal skin patches well known to those of ordinary skill in that art. To be administered in the form of a transdermal delivery system, the dosage administration will, of course, be continuous rather than intermittent throughout the dosage regimen.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders; lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The liquid forms in suitably flavored suspending or dispersing agents such as the synthetic and natural gums, for example, tragacanth, acacia, methylcellulose and the like. For parenteral administration, sterile suspensions and solutions are desired. Isotonic preparations which generally contain suitable preservatives are employed when intravenous administration is desired.

To prepare a pharmaceutical composition of the present invention, a compound of formula (I) as the active ingredient is intimately admixed with a pharmaceutical carrier according to conventional pharmaceutical compounding techniques, which carrier may take a wide variety of forms depending of the form of preparation desired for administration (e.g. oral or parenteral). Suitable pharmaceutically acceptable carriers are well known in the art. Descriptions of some of these pharmaceutically acceptable carriers may be found in *The Handbook of Pharmaceutical Excipients*, published by the American Pharmaceutical Association and the Pharmaceutical Society of Great Britain.

Methods of formulating pharmaceutical compositions have been described in numerous publications such as *Pharmaceutical Dosage Forms: Tablets, Second Edition, Revised and Expanded*, Volumes 1-3, edited by Lieberman et al; *Pharmaceutical Dosage Forms: Parenteral Medications*, Volumes 1-2, edited by Avis et al; and *Pharmaceutical Dosage Forms: Disperse Systems*, Volumes 1-2, edited by Lieberman et al; published by Marcel Dekker, Inc.

Compounds of this invention may be administered in any of the foregoing compositions and according to dosage regimens established in the art whenever treatment of disorders mediated by SGLT activity, preferably dual SGLT1 and SGLT2 activity, is required.

The daily dosage of the products may be varied over a wide range from about 0.01 mg to about 1,000 mg per adult human per day, or any amount or range therein. For oral administration, the compositions are preferably provided in the form of tablets containing, 0.01, 0.05, 0.1, 0.5, 1.0, 2.5, 5.0, 10.0, 15.0, 25.0, 50.0, 100, 150, 200, 250 and 500 milligrams of the active ingredient for the symptomatic adjustment of the dosage to the patient to be treated. An effective amount of the drug may be ordinarily supplied at a dosage level of from about 0.005 mg/kg to about 10 mg/kg of body weight per day, or any amount or range therein. Preferably, the range is from about 0.01 to about 5.0 mg/kg of body weight per day, or any amount or range therein, more preferably, from about 0.1 to about 1.0 mg/kg of body weight per day, or any amount or range therein, more preferably, from about 0.1 to about 0.5 mg/kg of body weight per day, or any amount or range therein. The compounds may be administered on a regimen of 1 to 4 times per day.

Optimal dosages to be administered may be readily determined by those skilled in the art, and will vary with the particular compound used, the mode of administration, the strength of the preparation, the mode of administration, and the advancement of the disease condition. In addition, factors associated with the particular patient being treated, including patient age, weight, diet and time of administration, will result in the need to adjust dosages.

One skilled in the art will recognize that, both in vivo and in vitro trials using suitable, known and generally accepted cell and/or animal models are predictive of the ability of a test compound to treat or prevent a given disorder.

One skilled in the art will further recognize that human clinical trails including first-in-human, dose ranging and efficacy trials, in healthy patients and/or those suffering from a given disorder, may be completed according to methods well known in the clinical and medical arts.

The following Examples are set forth to aid in the understanding of the invention, and are not intended and should not be construed to limit in any way the invention set forth in the claims which follow thereafter.

In the Examples which follow, some synthesis products are listed as having been isolated as a residue. It will be understood by one of ordinary skill in the art that the term "residue" does not limit the physical state in which the product was isolated and may include, for example, a solid, an oil, a foam, a gum, a syrup, and the like.

Intermediate Synthesis Example A (3R,4R,5R,6R)-3,4-bis((tert-butyldimethylsilyl)oxy)-6-(((tert-butyldimethylsilyl)oxy)methyl)-5-fluorotetrahydro-2H-pyran-2-one

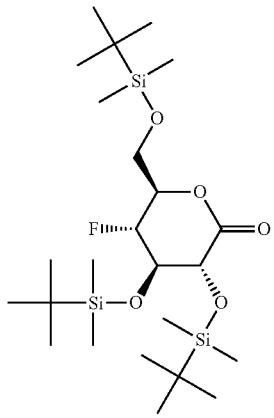 [SMILES: CC(C)(C)[Si](C)(C)OC[C@H]1OC(=O)[C@H](O[Si](C)(C)C(C)(C)C)[C@@H](O[Si](C)(C)C(C)(C)C)[C@@H]1F]

Step 1: (2S,3R,4S,5S,6R)-2-(allyloxy)-6-((benzoyloxy)methyl)-5-hydroxytetrahydro-2H-pyran-3,4-diyl dibenzoate To a solution of allyl alpha-D-galactopyranoside (5 g, 22.1 mmol) in dry pyridine (80 ml) at −35° C.~−30° C. was added benzoyl chloride (8.17 ml, 70.4 mmol) dropwise with stirring. The reaction mixture was stirred at that temperature for 20 min, then warmed to room temperature and stirred at room temperature for 8 h. The reaction mixture was then added dropwise to an aqueous sodium bicarbonate solution (200 ml) at 0° C. The resulting mixture was extracted with EtOAc three times (150 ml each time). The combined organic extracts were washed with 1N HCl twice, then washed once with brine, dried over Na$_2$SO$_4$, and concentrated under reduced pressure to yield a light orange oil. The isolated material was divided into two portions and each portion was dissolved in 6 ml of DCM and loaded onto an 80 g column—chromatography on silica gel (EtOAc/heptanes: 0>>>20%>>>30%) to yield a white solid. $^1$H NMR (CHLOROFORM-d) δ: 8.07 (s, 1H), 8.04-8.06 (m, 1H), 7.97-8.02 (m, 4H), 7.56-7.62 (m, 1H), 7.49-7.55 (m, 2H), 7.43-7.48 (m, 2H), 7.35-7.42 (m, 4H), 5.77 (d, J=3.0 Hz, 2H), 5.72 (d, J=3.5 Hz, 1H), 5.12 (dd, J=10.6, 1.5 Hz, 1H), 4.62-4.75 (m, 1H), 4.51-4.62 (m, 1H), 4.36-4.47 (m, 2H), 4.21-4.31 (m, 1H), 3.99-4.16 (m, 1H). LC/MS m/z (M+Na)$^+$ 554.8.

Step 2: (2S,3R,4R,5R,6R)-2-(allyloxy)-6-((benzoyloxy)methyl)-5-fluorotetrahydro-2H-pyran-3,4-diyl Dibenzoate To a solution of (2S,3R,4S,5S,6R)-2-(allyloxy)-6-((benzoyloxy)methyl)-5-hydroxytetrahydro-2H-pyran-3,4-diyl dibenzoate (1.47 g, 2.76 mmol) anhydrous DCM (15 mL) at −40° C. was added neat DAST (diethylaminosulfur trifluoride) (2.03 ml, 16.56 mmol) dropwise, and the resulting mixture was stirred at that temperature for 30 min, then warmed to room temperature and stirred for 20 h. The resulting mixture was slowly added to a dry-ice cooled MeOH (80 ml) and the resulting mixture was stirred for 10 min, concentrated and the residue was loaded onto a 40 g column and purified by flash column chromatography (EtOAc/heptanes: 0>>>5%>>>15%) to yield a white foam. $^1$H NMR (CHLOROFORM-d) δ: 8.06-8.17 (m, 2H), 7.93-8.04 (m, 4H), 7.57-7.66 (m, 1H), 7.46-7.57 (m, 4H), 7.39 (td, J=7.6, 1.5 Hz, 4H), 6.08-6.24 (m, 1H), 5.76-5.95 (m, 1H), 5.10-5.35 (m, 4H), 4.66-4.89 (m, 2H), 4.56-4.65 (m, 1H), 4.33-4.44 (m, 1H), 4.22-4.33 (m, 1H), 4.03-4.14 (m, 1H).

Step 3: (2S,3R,4R,5S,6R)-2-(allyloxy)-5-fluoro-6-(hydroxymethyl)tetrahydro-2H-pyran-3,4-diol To a suspension of (2S,3R,4R,5R,6R)-2-(allyloxy)-6-((benzoyloxy)methyl)-5-fluorotetrahydro-2H-pyran-3,4-diyl dibenzoate (3.4 g, 6.36 mmol) in anhydrous MeOH (100 ml) was added 25% NaOMe in MeOH (0.5 mL) dropwise and the resulting mixture was stirred at room temperature for 16 h. The base was neutralized with Dowex 50WX8 (H$^+$) ion-exchange resin, filtered and the filtrate was concentrated and the residue was purified by flash column chromatography on silica gel (12 g column, EtOAc) to yield a white foam (initially a colorless syrup). $^1$H NMR (METHANOL-d$_4$) δ: 5.97 (ddt, J=16.9, 11.1, 5.5 Hz, 1H), 5.35 (dd, J=17.2, 1.5 Hz, 1H), 5.19 (dd, J=10.4, 1.3 Hz, 1H), 4.82-4.87 (m, 1H), 3.99-4.35 (m, 4H), 3.89 (dt, J=16.4, 9.0 Hz, 1H), 3.63-3.81 (m, 3H), 3.43 (dd, J=9.9, 3.8 Hz, 1H).

Step 4: (((2S,3R,4R,5R,6R)-2-(allyloxy)-6-(((tert-butyldimethylsilyl)oxy)methyl)-5-fluorotetrahydro-2H-pyran-3,4-diyl)bis(oxy))bis(tert-butyldimethylsilane)

To a cooled (0° C.) mixture of (2S,3R,4R,5S,6R)-2-(allyloxy)-5-fluoro-6-(hydroxymethyl)tetrahydro-2H-pyran-3,4-diol (519.8 mg, 2.339 mol) and 2,6-lutidine (3.3 ml, 28.1 mmol) in anhydrous dichloromethane (10 ml) was added tert-BuMe$_2$SiOTf (4.4 ml, 18.7 mmol). The reaction mixture was warmed to room temperature and stirred for 10 min, then kept stirring at 40° C. for 2 days, allowed to cool, and then diluted with DCM (70 ml). The reaction mixture was washed with aq. NaHCO$_3$, dried with Na$_2$SO$_4$, and concentrated under reduced pressure to yield a light brown oil, which was purified by flash column chromatography on silica gel (EtOAc/heptanes: 0>>>5%) to yield a colorless oil. $^1$H NMR (CHLOROFORM-d) δ: 5.85 (br d, J=5.1 Hz, 1H), 5.21 (dd, J=17.2, 1.5 Hz, 1H), 5.11 (d, J=10.1 Hz, 1H), 4.70 (t, J=3.3 Hz, 1H), 3.85-4.19 (m, 4H), 3.74-3.82 (m, 1H), 3.62-3.73 (m, 2H), 3.44 (dd, J=9.1, 3.5 Hz, 1H), 0.74-0.88 (m, 18H), −0.05-0.07 (m, 18H).

Step 5: (3R,4R,5R,6R)-3,4-bis((tert-butyldimethylsilyl)oxy)-6-(((tert-butyldimethylsilyl)oxy)methyl)-5-fluorotetrahydro-2H-pyran-2-ol

[(Ph$_3$P)$_3$RhCl] (195.1 mg, 0.211 mmol) and DABCO (481.6 mg, 4.29 mmol) were added to a 50 ml round-bottle flask under argon. To the flask was then added a EtOH/H$_2$O (10:1 v/v) solution of (((2S,3R,4R,5R,6R)-2-(allyloxy)-6-(((tert-butyldimethylsilyl)oxy)methyl)-5-fluorotetrahydro-2H-pyran-3,4-diyl)bis(oxy))bis(tert-butyldimethylsilane) (22 ml, 1617 mg, 2.86 mmol) and the resulting mixture was heated under reflux for 16 h (overnight), then diluted with DCM (80 ml) and washed with saturated aqueous NaHCO$_3$ (20 ml) and brine (15 ml). The solvents were removed under reduced pressure. The resulting residue was dissolved in acetone/H$_2$O (10:1 v/v, 22 ml). NMO (415 mg, 3.44 mmol)

and OsO₄ (220 uL, 4% solution in water) were added and the reaction was monitored by TLC (starting material: top spot, Rf ~0.85/Eluent: EtOAc/heptane: 1/8 v/v; desired product: Rf ~0.25/eluent: EtOAc/heptane: 1/8 v/v, for this scale, reaction time: 5 h). The reaction mixture was concentrated under reduced pressure and the residue was diluted with DCM (80 ml) and washed with saturated aqueous NaHCO₃ (20 ml) and brine (15 ml). The organic layer was dried with Na₂SO₄ and the solvent was removed under reduced pressure. The residue was purified by flash column chromatography on silica gel (EtOAc/heptane: 0>>>5%>>>10%) to yield a colorless syrup. ¹H NMR (CHLOROFORM-d) δ: 5.03-5.17 (m, 1H), 4.15-4.39 (m, 1H), 3.73-4.03 (m, 4H), 3.54 (dd, J=8.6, 3.5 Hz, 1H), 2.93 (br s, 1H), 0.83-0.97 (m, 18H), 0.06-0.18 (m, 18H). LC/MS m/z (M+Na)⁺: 547.05.

Step 6: (3R,4R,5R,6R)-3,4-bis((tert-butyldimethylsilyl)oxy)-6-(((tert-butyldimethylsilyl)oxy)methyl)-5-fluorotetrahydro-2H-pyran-2-one (3R,4R,5R,6R)-3,4-bis((tert-butyldimethylsilyl)oxy)-6-(((tert-butyldimethylsilyl)oxy)methyl)-5-fluorotetrahydro-2H-pyran-2-ol (856.1 mg, 1.63 mmol) was dissolved in DMSO (4.3 ml) and stirred at room temperature for 10 min. To the resulting solution was then added acetic anhydride (3 ml) dropwise at room temperature. The mixture was stirred at room temperature for 24 h, diluted with EtOAc, washed with ice-water and aq. NaHCO₃ solution, dried with Na₂SO₄. The resulting residue was purified by flash column chromatography on silica gel (40 g column, EtOAc/heptane: 0>>>5%) to yield a colorless syrup, which was solidified in vacuo to yield the title compound as a white crystal.

¹H NMR (CHLOROFORM-d) δ: 4.54-4.69 (m, 1H), 4.51-4.54 (m, 1H), 3.88-4.00 (m, 2H), 3.79-3.86 (m, 1H), 3.68-3.76 (m, 1H), 0.74-0.82 (m, 18H), −0.08-0.05 (m, 18H).

Intermediate Synthesis Example B (3R,4R,5R,6R)-3,4-bis(benzyloxy)-6-((benzyloxy)methyl)-5-fluorotetrahydro-2H-pyran-2-one

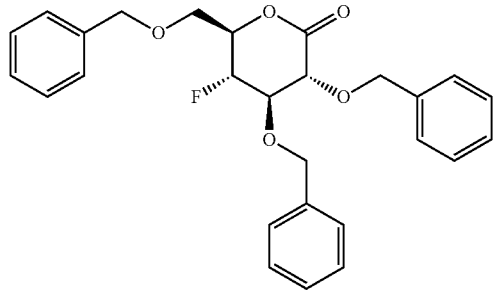 [SMILES: O=C1O[C@H](COCc2ccccc2)[C@@H](F)[C@H](OCc2ccccc2)[C@H]1OCc1ccccc1]

Step 1: (3R,4R,5R,6R)-6-(acetoxymethyl)-5-fluorotetrahydro-2H-pyran-2,3,4-triyl Triacetate To a mixture of (3R,4R,5S,6R)-5-fluoro-6-(hydroxymethyl)tetrahydro-2H-pyran-2,3,4-triol (3.00 g, 16.5 mmol) and sodium acetate (1.90 g, 23.1 mmol) was added acetic anhydride (90 mL) and the suspension was heated at 100° C. and stirred at this temperature for 2 h, then cooled to room temperature and stirred at room temperature for 6 h. Evaporation of the mixture yielded a residue which was crystallized in methanol to yield a white solid. ¹H NMR (CHLOROFORM-d) δ: 5.67-5.79 (m, 1H), 5.30-5.47 (m, 1H), 5.01-5.16 (m, 1H), 4.39 (br s, 2H), 4.21-4.32 (m, 1H), 3.82-3.93 (m, 1H), 2.10-2.16 (m, 9H), 2.05 (s, 3H).

Step 2: (2R,3R,4R,5R,6R)-6-(acetoxymethyl)-2-bromo-5-fluorotetrahydro-2H-pyran-3,4-diyl Diacetate A mixture of 1,2,3,6-tetra-O-acetyl-4-deoxy-4-fluoro-alpha-D-galactopyranoside (3.52 g, 10.1 mmol) in a solution of 33% HBr-HOAc was stirred at room temperature for 3 h. The mixture was concentrated under reduced pressure to yield an oily product, which was used for the next step reaction without further purification. ¹H NMR (CHLOROFORM-d) δ: 6.42-6.65 (m, 1H), 5.56-5.82 (m, 1H), 4.70-4.86 (m, 1H), 4.26-4.68 (m, 4H), 2.09-2.18 (m, 9H).

Step 3: (2S,3R,4R,5R,6R)-6-(acetoxymethyl)-5-fluoro-2-(p-tolylthio)tetrahydro-2H-pyran-3,4-diyl Diacetate A mixture of 2,3,6-tri-O-acetyl-α-D-glucopyranosylbromide (3.73 g, 10.1 mmol based) and Et₃N (5.6 ml, 40.2 mmol) were dissolved in dichloromethane (100 mL). Thereafter p-thiocresol (2.55 g, 20.1 mmol) was added and the reaction mixture was stirred at room temperature for 16 h. The solid was filtered, then washed with dichloromethane three times. The filtrate was concentrated under reduced pressure and the resulting residue was purified by flash column chromatography on silica gel (40 g COMBIFLAS® column, EtOAc/heptane: 0>>>5%>>>30%) to yield a white solid. ¹H NMR (CHLOROFORM-d) δ: 7.33-7.44 (m, 2H), 7.05-7.19 (m, 2H), 5.25-5.42 (m, 1H), 4.83-4.93 (m, 1H), 4.61-4.71 (m, 1H), 4.31-4.55 (m, 2H), 4.19-4.28 (m, 1H), 3.67-3.83 (m, 1H), 2.35 (s, 3H), 2.05-2.15 (m, 9H). LC/MS: m/z (M+Na): 436.80.

Step 4: (2S,3R,4R,5S,6R)-5-fluoro-6-(hydroxymethyl)-2-(p-tolylthio)tetrahydro-2H-pyran-3,4-diol (2S,3R,4R,5R,6R)-6-(acetoxymethyl)-5-fluoro-2-(p-tolylthio)tetrahydro-2H-pyran-3,4-diyl diacetate (1.90 g, 4.58 mmol) was suspended in anhydrous MeOH (60 mL). Sodium methoxide (25% methanol solution, 10 drops) was added and the resulting mixture was stirred at room temperature for 16 h. The base was neutralized with Dowex 50WX8 (H+) ion-exchange resin, the resulting suspension was filtered, and the filtrate was concentrated to yield a white crystalline solid. ¹H NMR (METHANOL-d₄) δ: 7.46 (brd, J=8.1 Hz, 2H), 7.13 (s, 2H), 4.51-4.61 (m, 1H), 4.06-4.36 (m, 1H), 3.75-3.88 (m, 1H), 3.60-3.73 (m, 2H), 3.48 (td, J=4.7, 2.3 Hz, 1H), 3.22 (t, J=9.3 Hz, 1H), 2.30 (s, 3H). LC/MS: m/z (M+Na)⁺: 310.8.

Step 5: (2S,3R,4R,5R,6R)-3,4-bis(benzyloxy)-6-((benzyloxy)methyl)-5-fluoro-2-(p-tolylthio)tetrahydro-2H-pyran To a mixture of (2S,3R,4R,5S,6R)-5-fluoro-6-(hydroxymethyl)-2-(p-tolylthio)tetrahydro-2H-pyran-3,4-diol (1.27 g, 4.41 mmol), sodium hydride (1.06 g, 26.4 mmol) and n-Bu₄NI (tetrabutylammonium iodide) (1.63 g, 4.41 mmol) was added anhydrous DMF (55 mL) under argon atmosphere at 0° C. and the resulting mixture was stirred at that temperature for 20 min. Neat benzyl bromide (2.5 mL)

was then added dropwise and the reaction mixture was allowed to warm to room temperature, then kept stirring for 16 h. The resulting mixture was diluted with dichloromethane and aq. NH$_4$Cl. The water layer was extracted with dichloromethane twice and the combined organic extracts were washed with brine, then dried with Na$_2$SO$_4$, filtered and concentrated under reduced pressure to yield an oily product, which was purified by flash column chromatography on silica gel (120 g COMBIFLASH® column, EtOAc/heptane: 0>>>5%) to yield a white solid. $^1$H NMR (CHLOROFORM-d) δ: 7.46 (d, J=8.1 Hz, 2H), 7.26-7.44 (m, 15H), 7.03 (d, J=8.1 Hz, 2H), 4.82-4.93 (m, 2H), 4.77 (s, 2H), 4.40-4.67 (m, 4H), 3.67-3.90 (m, 3H), 3.55-3.65 (m, 1H), 3.44 (s, 1H), 2.30 (s, 3H).

Step 6: (3R,4R,5R,6R)-3,4-bis(benzyloxy)-6-((benzyloxy)methyl)-5-fluorotetrahydro-2H-pyran-2-ol To a solution of (2S,3R,4R,5R,6R)-3,4-bis(benzyloxy)-6-((benzyloxy)methyl)-5-fluoro-2-(p-tolylthio)tetrahydro-2H-pyran (2390 mg, 4.28 mmol) in acetone-H$_2$O (9:1, 40 ml) was added NBS (1.52 g, 8.56 mmol) and the mixture was stirred at room temperature. After completion as measured by TLC analysis), the reaction mixture was evaporated to dryness, diluted with Na$_2$SO$_3$, and extracted with EtOAc. The organic layer was washed with brine, dried with Na$_2$SO$_4$ and concentrated to yield a colorless oil which was further purified by flash column chromatography on silica gel (80 g AnaLogix column, EtOAc/heptane: 0>>>10%>>>35%) to yield a syrup.

Step 7: (3R,4R,5R,6R)-3,4-bis(benzyloxy)-6-((benzyloxy)methyl)-5-fluorotetrahydro-2H-pyran-2-one (3R,4R,5R,6R)-3,4-bis(benzyloxy)-6-((benzyloxy)methyl)-5-fluorotetrahydro-2H-pyran-2-ol (1.50 g, 3.32 mmol) was dissolved in DMSO (8.7 ml) and stirred at 0° C. for 10 min. To the resulting solution was added acetic anhydride (6 ml) at 0° C. under argon atmosphere. The mixture was then stirred at room temperature for 16 h. Ice-water was added and the resulting mixture was extracted with ethyl acetate. The organic layer was washed with cold water twice and then dried with Na$_2$SO$_4$. The filtrate was concentrated and the residue was purified by flash column chromatography on silica gel (40 g COMBIFLASH® column, EtOAc/heptane: 0>>>5%>>>15%) to yield the title compound as a white solid.
$^1$H NMR (CHLOROFORM-d) δ: 7.28-7.41 (m, 15H), 4.92 (s, 2H), 4.50-4.75 (m, 6H), 4.11-4.21 (m, 1H), 3.91-4.07 (m, 1H), 3.69-3.85 (m, 2H). LC/MS: m/z (M+Na)$^+$: 472.95.

Synthesis Example 1: Compound #9

(2S,3R,4R,5S,6R)-2-[5-(1-benzothiophen-2-ylmethyl)-2-hydroxy-4-methoxyphenyl]-5-fluoro-6-(methoxymethyl)oxane-3,4-diol

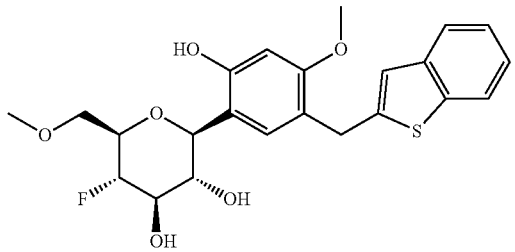 [SMILES: COC[C@H]1O[C@@H](c2cc(Cc3cc4ccccc4s3)c(OC)cc2O)[C@H](O)[C@@H](O)[C@@H]1F]

To a mixture of (3R,4S,5R,6R)-6-(hydroxymethyl)tetrahydro-2H-pyran-2,3,4,5-tetraol (50 g, 277.54 mmol, 1.00 equiv) in DMF (500 mL) with (dimethoxymethyl)benzene (50 mL, 1.10 equiv) was added TsOH (800 mg, 4.65 mmol, 0.20 equiv) and the reaction was stirred for 3 h at 60° C. Sodium bicarbonate was added, the resulting mixture was concentration and then extracted with DCM thrice. The combined extracts were washed with brine and dried over Na$_2$SO$_4$. The resulting residue was concentrated and purified by chromatography on silica gel (10:1 DCM/MeOH) to yield (4aR,7R,8R,8aR)-2-phenylhexahydropyrano[3,2-d][1,3]dioxine-6,7,8-triol as yellow oil.

To a mixture of (4aR,7R,8R,8aR)-2-phenylhexahydropyrano[3,2-d][1,3]dioxine-6,7,8-triol (80 g, 298.22 mmol, 1.00 equiv) in DMF (1000 mL) was added NaH (72 g, 1.80 mol, 6.00 equiv) in portions and the mixture stirred for 30 min at 0° C. To the resulting solution was then added BnBr (304.5 g, 1.78 mol, 6.00 equiv) dropwise at 0° C., and the reaction was stirred for overnight at room temperature. MeOH was added to quench the reaction at 0° C., and the resulting mixture was then diluted with water (2000 mL), and extracted with ethyl acetate thrice. The combined extracts were washed with brine and dried over Na$_2$SO$_4$, The mixture was then concentrated and purified by chromatography on silica gel (10:1 PE/EA) to yield (4aR,7R,8S,8aS)-6,7,8-tris(benzyloxy)-2-phenylhexahydropyrano[3,2-d][1,3]dioxine as white solid. MS (ES) m/z: 556 [M+NH$_4$]$^+$ To a mixture of (4aR,7R,8S,8aS)-6,7,8-tris(benzyloxy)-2-phenylhexahydropyrano[3,2-d][1,3]dioxine (9 g, 16.71 mmol, 1.00 equiv) in 1,4-dioxane (90 mL) was added 3N HCl (90 mL), and the reaction was stirred for 4 h at 100° C. Water was added and the mixture was extracted with DCM thrice. The combined extracts were washed with water, brine and dried over Na$_2$SO$_4$, The mixture was then concentrated and purified by chromatography on silica gel (10:1 DCM/MeOH) to yield (3R,4S,5S,6R)-3,4-bis(benzyloxy)-6-(hydroxymethyl)tetrahydro-2H-pyran-2,5-diol as yellow solid. MS (ES) m/z: 383 [M+Na]$^+$ To a mixture of (3R,4S,5S,6R)-3,4-bis(benzyloxy)-6-(hydroxymethyl)tetrahydro-2H-pyran-2,5-diol (2.45 g, 6.80 mmol, 1.00 equiv) in DCM (20 mL) was added NIS (3 g, 13.45 mmol, 2.00 equiv) and TBAI (750 mg, 2.03 mmol, 0.30 equiv), and the reaction was stirred for overnight at 25° C. NaHSO$_3$/H$_2$O was added and the mixture was extracted with DCM thrice. The combined extracts were washed with brine and dried over Na$_2$SO$_4$, The mixture was then concentrated and purified by chromatography on silica gel (10:1 DCM/MeOH) to yield (3R,4S,5S,6R)-3,4-bis(benzyloxy)-5-hydroxy-6-(hydroxymethyl)tetrahydro-2H-pyran-2-one as yellow solid. MS (ES) m/z: 376 [M+NH$_4$]$^+$ To a mixture of (3R,4S,5S,6R)-3,4-bis(benzyloxy)-5-hydroxy-6-(hydroxymethyl)tetrahydro-2H-pyran-2-one (6.8 g, 18.97 mmol, 1.00 equiv) in THF (40 mL) with NMM (N-methylmorpholine) (6.7 g, 66.24 mmol, 3.50 equiv) was added TMSCl (trimethylsilyl chloride) (6.15 g, 56.61 mmol, 3.00 equiv) dropwise at 0° C., and the reaction was stirred for overnight at 30° C. Water was added and the mixture was extracted with ethyl acetate thrice. The combined extracts were washed with NaH$_2$PO$_4$/H$_2$O, brine and dried over Na$_2$SO$_4$, then concentration and purified by chromatography on silica gel (10:1 PE/EA) to yield (3R,4R,5S,6R)-3,4-bis(benzyloxy)-5-((trimethylsilyl)oxy)-6-(((trimethylsilyl)oxy)methyl)tetrahydro-2H-pyran-2-one as light yellow oil.

To a mixture of 2-(4-(benzyloxy)-5-bromo-2-methoxybenzyl)benzo[b]thiophene (4.26 g, 9.70 mmol, 1.10 equiv) in tetrahydrofuran (50 mL) was added n-BuLi (4.2 mL, 1.15 equiv) dropwise at −78° C. and the mixture was stirred for 25 min. to the mixture was then added (3R,4R,5S,6R)-3,4-bis(benzyloxy)-5-((trimethylsilyl)oxy)-6-(((trimethylsilyl)oxy)methyl)tetrahydro-2H-pyran-2-one (4.44 g, 8.83 mmol, 1.00 equiv) in tetrahydrofuran (10 mL) dropwise at −78° C. The solution was stirred at −78° C. for 1.5 h, and then MeSO$_3$H (1.3 mL, 20 mmol) in MeOH (20 mL) was added, the reaction was stirred overnight at room temperature. H$_2$O was added and the mixture was extracted with EtOAc thrice. The combined extracts were washed with brine and dried over Na$_2$SO$_4$. The mixture was then concentrated and purified by chromatography on silica gel (1:1 PE/EA) gave 4.5 g (69.6%) of (2R,3S,4S,5R)-6-(5-(benzo[b]thiophen-2-ylmethyl)-2-(benzyloxy)-4-methoxyphenyl)-4,5-bis(benzyloxy)-2-(hydroxymethyl)-6-methoxytetrahydro-2H-pyran-3-ol as yellow oil. MS (ES) m/z: 701 [M-OMe]$^+$ To a mixture of (2R,3S,4S,5R)-6-(5-(benzo[b]thiophen-2-ylmethyl)-2-(benzyloxy)-4-methoxyphenyl)-4,5-bis(benzyloxy)-2-(hydroxymethyl)-6-methoxytetrahydro-2H-pyran-3-ol (6.5 g, 8.87 mmol, 1.00 equiv) in dichloromethane (50 mL) with Et$_3$SiH (2.1 g, 18.06 mmol, 2.00 equiv) was added BF$_3$.Et$_2$O (1.9 g, 13.38 mmol, 1.50 equiv) at 0° C. The reaction was stirred for 2 h at 0° C. Sodium bicarbonate/H$_2$O was added and the mixture was extracted with dichloromethane thrice. The combined extracts were washed with brine and dried over Na$_2$SO$_4$. The mixture was then concentrated and purified by chromatography on silica gel (1:1 PE/EA) gave 4.6 g (73.9%) of (2R,3S,4S,5S,6S)-6-(5-(benzo[b]thiophen-2-ylmethyl)-2-(benzyloxy)-4-methoxyphenyl)-4,5-bis(benzyloxy)-2-(hydroxymethyl)tetrahydro-2H-pyran-3-ol as yellow oil. MS (ES) m/z: 720 [M+NH$_4$]$^+$ To a mixture of (2R,3S,4S,5S,6S)-6-(5-(benzo[b]thiophen-2-ylmethyl)-2-(benzyloxy)-4-methoxyphenyl)-4,5-bis(benzyloxy)-2-(hydroxymethyl)tetrahydro-2H-pyran-3-ol (2.3 g, 3.27 mmol, 1.00 equiv) in pyridine (20 mL) was added TrCl (triphenylmethyl chloride)(1.1 g, 3.96 mmol, 1.20 equiv). The reaction was stirred for overnight at 90° C. The mixture was then concentrated to remove the pyridine. H$_2$O was added and the mixture was extracted with ethyl acetate thrice. The combined extracts were washed with brine and dried over Na$_2$SO$_4$. The mixture was then concentrated and purified by chromatography on silica gel (3:1 PE/EA) to yield (2R,3S,4S,5S,6S)-6-(5-(benzo[b]thiophen-2-ylmethyl)-2-(benzyloxy)-4-methoxyphenyl)-4,5-bis(benzyloxy)-2-((trityloxy)methyl)tetrahydro-2H-pyran-3-ol as yellow solid.

To a mixture of (2R,3S,4S,5S,6S)-6-(5-(benzo[b]thiophen-2-ylmethyl)-2-(benzyloxy)-4-methoxyphenyl)-4,5-bis(benzyloxy)-2-((trityloxy)methyl)tetrahydro-2H-pyran-3-ol (200 mg, 0.21 mmol, 1.00 equiv) in dichloromethane (5 mL) was added a solution of DAST (100 mg, 0.62 mmol, 3.00 equiv) in DCM (0.5 ml) dropwise at −30° C. The reaction was stirred for 3 h at room temperature. Sodium bicarbonate/H$_2$O was added and the mixture was extracted with dichloromethane thrice. The combined extracts were washed with brine and dried over Na$_2$SO$_4$. The mixture was then concentrated and purified by chromatography on silica gel (5:1 PE/EA) to yield (2S,3S,4R,5R,6R)-2-(5-(benzo[b]thiophen-2-ylmethyl)-2-(benzyloxy)-4-methoxyphenyl)-3,4-bis(benzyloxy)-5-fluoro-6-((trityloxy)methyl)tetrahydro-2H-pyran as colorless oil. MS (ES) m/z: 964 [M+NH$_4$]$^+$ To a mixture of (2S,3S,4R,5R,6R)-2-(5-(benzo[b]thiophen-2-ylmethyl)-2-(benzyloxy)-4-methoxyphenyl)-3,4-bis(benzyloxy)-5-fluoro-6-((trityloxy)methyl)tetrahydro-2H-pyran (168 mg, 0.177 mmol, 1.00 equiv) in dichloromethane/MeOH (5/5 mL) was added AcCl (acetyl chloride) (0.1 ml). The reaction was stirred for 2 h at room temperature. Sodium bicarbonate/H$_2$O was added and the mixture was extracted with dichloromethane thrice. The combined extracts were washed with brine and dried over Na$_2$SO$_4$. The mixture was then concentrated and purified by chromatography on silica gel (2:1 PE/EA) to yield ((2R,3R,4R,5S,6S)-6-(5-(benzo[b]thiophen-2-ylmethyl)-2-(benzyloxy)-4-methoxyphenyl)-4,5-bis(benzyloxy)-3-fluorotetrahydro-2H-pyran-2-yl)methanol as light yellow oil. MS (ES) m/z: 722 [M+NH$_4$]$^+$ To a mixture of ((2R,3R,4R,5S,6S)-6-(5-(benzo[b]thiophen-2-ylmethyl)-2-(benzyloxy)-4-methoxyphenyl)-4,5-bis(benzyloxy)-3-fluorotetrahydro-2H-pyran-2-yl)methanol (100 mg, 0.14 mmol, 1.00 equiv) in DMF (5 mL) with KOH (25 mg, 0.45 mmol, 3.00 equiv) was added CH$_3$I (60 mg, 0.42 mmol, 3.00 equiv). The reaction was stirred for 5 h at room temperature. H$_2$O was added and the mixture was extracted with EA thrice. The combined extracts were washed with brine and dried over Na$_2$SO$_4$. The mixture was then concentrated and purified by chromatography on silica gel (2:1 PE/EA) to yield (2S,3S,4R,5R,6R)-2-(5-(benzo[b]thiophen-2-ylmethyl)-2-(benzyloxy)-4-methoxyphenyl)-3,4-bis(benzyloxy)-5-fluoro-6-(methoxymethyl)tetrahydro-2H-pyran as a yellow oil.

To a mixture of (2S,3S,4R,5R,6R)-2-(5-(benzo[b]thiophen-2-ylmethyl)-2-(benzyloxy)-4-methoxyphenyl)-3,4-bis(benzyloxy)-5-fluoro-6-(methoxymethyl)tetrahydro-2H-pyran (100 mg, 0.14 mmol, 1.00 equiv) in dichloromethane (5 mL) with 1,2,3,4,5-pentamethylbenzene (200 mg, 1.35 mmol, 9.65 equiv) was added BCl$_3$ (2 mL, 14.3 equiv, 1 N) at −78° C. The reaction was stirred at −78° C. for 1 h. Methanol (2 mL) was added and the resulting mixture concentrated, the residue purified by chromatography on Prep-HPLC (0%-45% CH$_3$CN/H$_2$O) to yield (2S,3R,4R,5S,6R)-2-(5-(benzo[b]thiophen-2-ylmethyl)-2-hydroxy-4-methoxyphenyl)-5-fluoro-6-(methoxymethyl)tetrahydro-2H-pyran-3,4-diol as a white solid.

$^1$H NMR (300 MHz, Methanol-d$_4$) δ: 7.72 (d, J=7.8 Hz, 1H), 7.64 (d, J=7.2 Hz, 1H), 7.18-7.42 (m, 3H), 7.00 (s, 1H), 6.50 (s, 1H), 4.59 (d, J=9.6 Hz, 1H), 4.45 (t, J=18 Hz, 0.5H), 4.28 (t, J=18 Hz, 0.5H), 4.13 (s, 2H), 3.83 (s, 3H), 3.54-3.80 (m, 5H), 3.34 (s, 3H). MS (ES) m/z: 471[M+Na]$^+$ Synthesis Example 2: Compound #11

(2S,3R,4R,5S,6R)-2-[5-(1-benzothiophen-2-ylmethyl)-2-hydroxy-4-methoxyphenyl]-5-fluoro-6-(fluoromethyl)oxane-3,4-diol

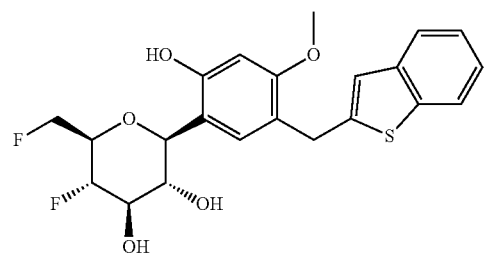 [SMILES: COc1cc(O)c([C@@H]2O[C@H](CF)[C@@H](F)[C@H](O)[C@H]2O)cc1Cc1cc2ccccc2s1]

To a mixture of ((2R,3R,4R,5S,6S)-6-(5-(benzo[b]thiophen-2-ylmethyl)-2-(benzyloxy)-4-methoxyphenyl)-4,5-bis(benzyloxy)-3-fluorotetrahydro-2H-pyran-2-yl)methanol (100 mg, 0.14 mmol, 1.00 equiv) in dichloromethane (5 mL) was added a solution of DAST (68.6 mg, 0.43 mmol, 3.00 equiv) in DCM (0.5 ml) dropwise at −30° C. The reaction was stirred for 3 h at room temperature. Sodium bicarbonate/H$_2$O was added and the mixture was extracted with dichloromethane thrice. The combined extracts were washed with brine and dried over Na$_2$SO$_4$, The mixture was then concentrated and purified by chromatography on silica gel (5:1 PE/EA) to yield 1-((2S,3S,4R,5S,6R)-2-(5-(benzo[b]thiophen-2-ylmethyl)-2-(benzyloxy)-4-methoxyphenyl)-4-(benzyloxy)-5-fluoro-6-(fluoromethyl)tetrahydro-2H-pyran-3-yl)-1I3-oxaspiro[2.5]octa-3(8),4,6-triene as yellow oil.

To a mixture of 1-((2S,3S,4R,5S,6R)-2-(5-(benzo[b]thiophen-2-ylmethyl)-2-(benzyloxy)-4-methoxyphenyl)-4-(benzyloxy)-5-fluoro-6-(fluoromethyl)tetrahydro-2H-pyran-3-yl)-1I3-oxaspiro[2.5]octa-3(8),4,6-triene (100 mg, 0.14 mmol, 1.00 equiv) in dichloromethane (5 mL) with 1,2,3,4,5-pentamethylbenzene (200 mg, 1.35 mmol, 9.65 equiv) was added BCl$_3$ (2 mL, 14.3 equiv, 1 N) at −78° C. The reaction was stirred at −78° C. for 1 h. Methanol (2 mL) was added. The resulting mixture was concentrated and purified by chromatography on Prep-HPLC (0%-45% CH$_3$CN/H$_2$O) to yield (2S,3R,4R,5S,6R)-2-(5-(benzo[b]thiophen-2-ylmethyl)-2-hydroxy-4-methoxyphenyl)-5-fluoro-6-(fluoromethyl)tetrahydro-2H-pyran-3,4-diol as a white solid.

$^1$H NMR (300 MHz, Methanol-d$_4$) δ: 7.72 (d, J=7.8 Hz, 1H), 7.64 (d, J=7.8 Hz, 1H), 7.19-7.30 (m, 3H), 7.00 (s, 1H), 6.51 (s, 1H), 4.71 (s, 1H), 4.65 (d, J=9.6 Hz, 1H), 4.55 (s, 1H), 4.50 (t, J=18.6 Hz, 0.5H), 4.33 (t, J=18.3 Hz, 0.5H), 4.14 (d, J=5.4 Hz, 2H), 3.83-3.73 (m, 5H), 3.59-3.65 (m, 1H). MS (ES) m/z: 459 [M+Na]$^+$.

Synthesis Example 3: Compound #2

(2S,3R,4R,5S,6R)-2-(5-(benzo[b]thiophen-2-ylmethyl)-2-hydroxy-4-methoxyphenyl)-5-fluoro-6-(hydroxymethyl)tetrahydro-2H-pyran-3,4-diol

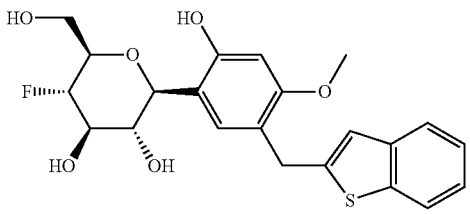 [SMILES: COc1cc(O)c([C@@H]2O[C@H](CO)[C@@H](F)[C@H](O)[C@H]2O)cc1Cc1cc2ccccc2s1]

Into a 500-mL round-bottom flask, was placed a solution of 2,4-dihydroxybenzaldehyde (25 g, 181.00 mmol, 1.00 equiv) in dry CH$_3$CN (200 mL), sodium bicarbonate (20 g, 238.08 mmol, 1.30 equiv) and KI (3 g, 18.10 mmol, 0.10 equiv) at room temperature under an nitrogen atmosphere. The mixture was slowly warmed to 60° C., followed by addition of (chloromethyl)benzene (27.5 g, 217.25 mmol, 1.20 equiv). The resulting solution was heated to reflux for 16 h, cooled and the solids were filtered out. The resulting mixture was concentrated under vacuum. The mixture was washed by 2×100 ml PE:EA (1:20) to yield 4-(benzyloxy)-2-hydroxybenzaldehyde as a yellow solid.

Into a 250-mL round-bottom flask, was placed a solution of 4-(benzyloxy)-2-hydroxybenzaldehyde (12.7 g, 55.64 mmol, 1.00 equiv) in MeOH (150 mL). This was followed by the addition of pyridine perbromide hydrobromide (18.6 g, 58.49 mmol, 1.05 equiv) in several batches at 0° C. The resulting solution was stirred overnight at 25° C., monitored by TLC (EA:PE=1:5), and the reaction terminated by addition of water (50 mL). The MeOH was removed under vacuum. The resulting solution was diluted with water (200 mL). The resulting solution was extracted with ethyl acetate (3×100 mL) and the organic layers were combined. The resulting mixture was washed with 1N HCl (1×100 mL) and water (1×100 mL). The resulting mixture was washed with brine (1×100 mL). The mixture was dried over anhydrous sodium sulfate and concentrated under vacuum. The residue was washed by 2×50 ml PE:EA=1:20 to yield 4-(benzyloxy)-5-bromo-2-hydroxybenzaldehyde as a yellow solid.

Into a 500-mL round-bottom flask, was placed a solution of 4-(benzyloxy)-5-bromo-2-hydroxybenzaldehyde (13 g, 42.33 mmol, 1.00 equiv) in N,N-dimethylformamide (100 mL), KOH (2.855 g, 50.89 mmol, 1.20 equiv), iodomethane (18.1 g, 127.52 mmol, 3.00 equiv). The resulting solution was stirred 3-4 h at room temperature. The reaction was then quenched by the addition of water (200 mL). The resulting solution was extracted with ethyl acetate (2×100 mL) and the organic layers combine d. The resulting mixture was washed with water (1×200 mL) and brine (1×100 mL), dried over anhydrous sodium sulfate and concentrated under vacuum. The residue was washed by 2×50 ml PE:EA=1:10 to yield 4-(benzyloxy)-5-bromo-2-methoxybenzaldehyde as a yellow solid.

Into a 500-mL 3-necked round-bottom flask purged and maintained with an inert atmosphere of nitrogen, was placed a solution of 1-benzothiophene (6 g, 44.71 mmol, 1.10 equiv) in tetrahydrofuran (100 mL). This was followed by the addition of (2.5M in hexane) butyllithium (18.7 mL, 1.15 equiv) dropwise with stirring at −78° C. The resulting mixture was stirred 20 min at −78° C. To the mixture was then added a solution of 4-(benzyloxy)-5-bromo-2-methoxybenzaldehyde (13 g, 40.48 mmol, 1.00 equiv) in tetrahydrofuran (30 mL) dropwise with stirring at −78° C. The resulting solution was stirred at −78° C. for 1 h. The reaction was then quenched by the addition of NH$_4$Cl/H$_2$O (100 mL), extracted with ethyl acetate (3×100 mL). The combined organic layer was washed with brine (2×100 mL), dried over anhydrous sodium sulfate, and concentrated under vacuum to yield 1-benzothiophen-2-yl[4-(benzyloxy)-5-bromo-2-methoxyphenyl]methanol as a yellow oil.

Into a 500-mL round-bottom flask, was placed a solution of 1-benzothiophen-2-yl[4-(benzyloxy)-5-bromo-2-methoxyphenyl]methanol (19 g) in dichloromethane (200 mL), triethylsilane (9.5 g, 82.54 mmol), trifluoroacetic acid (9.5 g, 83.32 mmol) was added into at 0° C. The resulting solution was stirred for 2 h at room temperature. The reaction mixture was then quenched by the addition of NaHCO$_3$/H$_2$O (100 mL) and the aqueous layer was extracted with DCM (2×100 mL) and the combined organic layer was washed with brine (1×100 mL), dried over anhydrous sodium sulfate, and concentrated under vacuum. The residue was washed by 2×50 ml PE:EA=1:20 to yield 2-[[4-(benzyloxy)-5-bromo-2-methoxyphenyl]methyl]-1-benzothiophene as a yellow solid.

To a mixture of 2-[[4-(benzyloxy)-5-bromo-2-methylphenyl]methyl]-1-benzothiophene (245.4 mg, 0.58 mmol, 1.00 equiv) in THF (3 mL) was added n-BuLi (2.5 M in hexane, 0.233 mL, 1.00 equiv) dropwise at −78° C. The reaction was stirred for 30 min at −78° C. To this was added a solution of the compound prepared in Intermediate Synthesis Example B (261 mg, 0.58 mmol, 1.00 equiv) in THF (2 mL) dropwise at −78° C. The reaction was stirred for 2 h at −78° C. NH$_4$Cl/H$_2$O was added and the mixture was extracted with EtOAc thrice. The combined extracts were washed with brine and dried over Na$_2$SO$_4$. The mixture was then concentrated and purified by chromatography on silica gel (5:1 PE/EA) to yield (3R,4R,5R,6R)-2-(5-(benzo[b]thiophen-2- ylmethyl)-2-(benzyloxy)-4-methoxyphenyl)-3,4-bis(benzyloxy)-6-((benzyloxy)methyl)-5-fluorotetrahydro-2H-pyran-2-ol as yellow oil.

To a mixture of (3R,4R,5R,6R)-2-(5-(benzo[b]thiophen-2-ylmethyl)-2-(benzyloxy)-4-methoxyphenyl)-3,4-bis(benzyloxy)-6-((benzyloxy)methyl)-5-fluorotetrahydro-2H-pyran-2-ol (348 mg, 0.58 mmol, 1.00 equiv) in DCM/CH$_3$CN (3/3 mL) with Et$_3$SiH (202.3 mg, 1.74 mmol, 3.00 equiv) was added BF$_3$.Et$_2$O (165.1 mg, 1.16 mmol, 2.00 equiv) dropwise at 0° C. The reaction was stirred for 2 h at 0° C. Sodium bicarbonate was added and the mixture was extracted with DCM thrice. The combined extracts were washed with brine and dried over Na$_2$SO$_4$. The mixture was then concentrated and purified by chromatography on silica gel (10:1 PE/EA) to yield (2S,3S,4R,5R,6R)-2-(5-(benzo[b]thiophen-2-ylmethyl)-2-(benzyloxy)-4-methoxyphenyl)-3,4-bis(benzyloxy)-6-((benzyloxy)methyl)-5-fluorotetrahydro-2H-pyran as a yellow oil.

To a mixture of (2S,3S,4R,5R,6R)-2-(5-(benzo[b]thiophen-2-ylmethyl)-2-(benzyloxy)-4-methoxyphenyl)-3,4-bis(benzyloxy)-6-((benzyloxy)methyl)-5-fluorotetrahydro-2H-pyran (327 mg, 0.41 mmol, 1.00 equiv) in dichloromethane (5 mL) with 1,2,3,4,5-pentamethylbenzene (551 mg, 3.72 mmol, 9.08 equiv) was added BCl$_3$ (5.5 mL, 13.3 equiv, 1 N) with stirring at −78° C. The reaction was stirred at −78° C. for 1 h. Methanol was added. The reaction mixture was The mixture was then concentrated and purified by chromatography on silica gel (10:1 DCM/MeOH) to yield (2S,3R,4R,5S,6R)-2-(5-(benzo[b]thiophen-2-ylmethyl)-2-hydroxy-4-methoxyphenyl)-5-fluoro-6-(hydroxymethyl)tetrahydro-2H-pyran-3,4-diol as white solid.

$^1$H NMR (300 MHz, Methanol-d$_4$) δ: 7.70 (d, J=7.80 Hz, 1H), 7.62 (d, J=9.0 Hz, 1H), 7.23 (m, 3H), 6.98 (s, 1H), 6.50 (s, 1H), 4.57 (d, J=9.6 Hz, 1H), 4.36 (dt, J=51.3 and 9.6 Hz, 1H), 4.12 (s, 2H), 3.57-3.85 (m, 8H). MS (ES) m/z: 457.0 [M+Na]$^+$.

Synthesis Example 4: Compound #16

(2S,3R,4R,5S,6R)-2-(5-(benzo[b]thiophen-2-ylmethyl)-2-hydroxy-4-methylphenyl)-5-fluoro-6-methyl-tetrahydro-2H-pyran-3,4-diol

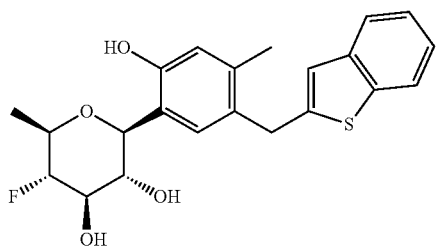 [SMILES: Cc1cc(O)c([C@@H]2O[C@H](C)[C@@H](F)[C@H](O)[C@H]2O)cc1Cc1cc2ccccc2s1]

To a mixture of (3R,4R,5S,6R)-5-fluoro-6-(hydroxymethyl)tetrahydro-2H-pyran-2,3,4-triol (10 g, 54.90 mmol, 1.00 equiv) in acetic anhydride (200 mL) was added NaOAc (5.68 g, 69.27 mmol, 1.26 equiv) at room temperature. The reaction was stirred for 3 h at 160° C. The mixture was then concentrated. Ethyl acetate/brine was added and the mixture was extracted with EtOAc thrice. The combined extracts were washed with brine and dried over Na$_2$SO$_4$. The mixture was then concentrated and purified by chromatography on silica gel (2:1 PE/EA) to yield (2S,3R,4R,5R,6R)-6-(acetoxymethyl)-5-fluorotetrahydro-2H-pyran-2,3,4-triyl triacetate as a white solid.

To a solution of HBr/HAc (40 mL) was added (2S,3R,4R,5R,6R)-6-(acetoxymethyl)-5-fluorotetrahydro-2H-pyran-2,3,4-triyl triacetate (3.17 g, 9.05 mmol, 1.00 equiv). The reaction was stirred at room temperature for 1 h. H$_2$O was added and the mixture was extracted with EtOAc thrice. The combined extracts were washed with brine and dried over Na$_2$SO$_4$. The mixture was then concentrated and purified by chromatography on silica gel (2:1 PE/EA) to yield (2R,3R,4R,5R,6R)-6-(acetoxymethyl)-2-bromo-5-fluorotetrahydro-2H-pyran-3,4-diyl diacetate as a yellow oil.

To a mixture of (2R,3R,4R,5R,6R)-6-(acetoxymethyl)-2-bromo-5-fluorotetrahydro-2H-pyran-3,4-diyl diacetate (12.5 g, 33.68 mmol, 1.00 equiv) in DMF (120 mL) with K$_2$CO$_3$ (13.9 g, 100.57 mmol, 3.00 equiv) was added 4-methylbenzene-1-thiol (8.35 g, 67.23 mmol, 2.00 equiv) at room temperature. The reaction was stirred at room temperature for 1 h. H$_2$O was added and and the mixture was extracted with EtOAc thrice. The combined extracts were washed with brine and dried over Na$_2$SO$_4$, The mixture was then concentrated and purified by chromatography on silica gel (5:1 PE/EA) to yield (2S,3R,4R,5R,6R)-6-(acetoxymethyl)-5-fluoro-2-(p-tolylthio)tetrahydro-2H-pyran-3,4-diyl diacetate as a brown solid. MS (ES) m/z: 437 [M+Na]$^+$.

To a mixture of (2S,3R,4R,5R,6R)-6-(acetoxymethyl)-5-fluoro-2-(p-tolylthio)tetrahydro-2H-pyran-3,4-diyl diacetate (3.2 g, 7.72 mmol, 1.00 equiv) in MeOH (30 mL) was added NaOMe (cat.) at room temperature. The reaction was stirred for overnight at room temperature. Dowex 50wx 8-200 ion-exchange resin was added and the mixture was filtrated. The filtrate was concentrated to yield (2S,3R,4R,5S,6R)-5-fluoro-6-(hydroxymethyl)-2-(p-tolylthio)tetrahydro-2H-pyran-3,4-diol as a yellow solid. $^1$H NMR (300 MHz, CDCl$_3$) b 7.42 (d, J=8.1 Hz, 2H), 7.16 (d, J=8.1 Hz, 2H), 4.52 (d, J=9.6 Hz, 1H), 4.45 (t, J=18.3 Hz, 0.5H), 4.28 (t, J=18.6 Hz, 0.5H), 3.73-3.96 (m, 3H), 3.49-3.58 (m, 1H), 3.28-3.39 (m, 1H), 2.35 (s, 3H). MS (ES) m/z: 311 [M+Na]$^+$.

To a mixture of (2S,3R,4R,5S,6R)-5-fluoro-6-(hydroxymethyl)-2-(p-tolylthio)tetrahydro-2H-pyran-3,4-diol (200 mg, 0.690 mmol, 1.00 equiv) in pyridine (2 mL) was added TsCl (4-toluenesulfonyl chloride) (158.3 mg, 0.83 mmol, 1.20 equiv) at room temperature. The reaction was stirred for overnight at room temperature. After concentrated, ethyl acetate was added and the mixture was washed with 1N HCl, brine and dried over Na$_2$SO$_4$. The mixture was The mixture was then concentrated and purified by chromatography on silica gel (20:1 DCM/MeOH) to yield ((2R,3S,4R,5R,6S)-3-fluoro-4,5-dihydroxy-6-(p-tolylthio)tetrahydro-2H-pyran-2-yl)methyl 4-methylbenzenesulfonate as a yellow oil.

To a mixture of ((2R,3S,4R,5R,6S)-3-fluoro-4,5-dihydroxy-6-(p-tolylthio)tetrahydro-2H-pyran-2-yl)methyl 4-methylbenzenesulfonate (470 mg, 1.06 mmol, 1.00 equiv) in tetrahydrofuran (10 mL) was added LiAlH$_4$ (121.3 mg, 3.20 mmol, 3.00 equiv). The reaction was heated to reflux for 1 h. Water/ice was added. The mixture was The mixture was then concentrated and purified by chromatography on silica gel (1:1 PE/EA) to yield (2S,3R,4R,5S,6R)-5-fluoro-6-methyl-2-(p-tolylthio)tetrahydro-2H-pyran-3,4-diol as a yellow oil.

To a mixture of (2S,3R,4R,5S,6R)-5-fluoro-6-methyl-2-(p-tolylthio)tetrahydro-2H-pyran-3,4-diol (270 mg, 0.99 mmol, 1.00 equiv) in DMF (5 mL) with BnBr (1.02 g, 5.96 mmol, 6.00 equiv) was added NaH (160 mg, 4.00 mmol, 4.00 equiv, 60% purity). The reaction was stirred for overnight at room temperature. Ice water was added and the mixture was extracted with EtOAc twice. The combined extracts were washed with brine and dried over Na$_2$SO$_4$. The mixture was then concentrated and purified by chromatography on silica gel (10:1 PE/EA) to yield (2S,3R,4R,5R,6R)-3,4-bis(benzyloxy)-5-fluoro-6-methyl-2-(p-tolylthio)tetrahydro-2H-pyran as a yellow oil.

To a mixture of (2S,3R,4R,5R,6R)-3,4-bis(benzyloxy)-5-fluoro-6-methyl-2-(p-tolylthio)tetrahydro-2H-pyran (343 mg, 0.76 mmol, 1.00 equiv) in acetone/H$_2$O (5/0.5 mL) was added NBS (405.2 mg, 2.28 mmol, 3.00 equiv) at room temperature. The reaction was stirred at room temperature for 2 h. Ice water was added and the mixture was extracted with EtOAc thrice. The combined extracts were washed with brine and dried over Na$_2$SO$_4$. The mixture was then concentrated and purified by chromatography on silica gel (5:1 PE/EA) to yield (3R,4R,5R,6R)-3,4-bis(benzyloxy)-5-fluoro-6-methyltetrahydro-2H-pyran-2-ol as a yellow oil.

To a mixture of (3R,4R,5R,6R)-3,4-bis(benzyloxy)-5-fluoro-6-methyltetrahydro-2H-pyran-2-ol (240 mg, 0.69 mmol, 1.00 equiv) in DMSO (5 mL) was added acetic anhydride (2 mL) dropwise at room temperature. The reaction was stirred for overnight at room temperature. Ice water was added and the mixture was extracted with EtOAc thrice. The combined extracts were washed with brine and dried over Na$_2$SO$_4$. The mixture was then concentrated and purified by chromatography on silica gel (10:1 PE/EA) to yield (3R,4R,5R,6R)-3,4-bis(benzyloxy)-5-fluoro-6-methyltetrahydro-2H-pyran-2-one as a yellow oil.

To a mixture of 2-[[4-(benzyloxy)-5-bromo-2-methylphenyl]methyl]-1-benzothiophene (245.4 mg, 0.58 mmol, 1.00 equiv) in THF (3 mL) was added n-BuLi (2.5 M in hexane, 0.233 mL, 1.00 equiv) dropwise at −78° C. The reaction was stirred for 30 min at −78° C. To this was added a solution of (3R,4R,5R,6R)-3,4-bis(benzyloxy)-5-fluoro-6-methyltetrahydro-2H-pyran-2-one (200 mg, 0.58 mmol, 1.00 equiv) in THF (2 mL) dropwise at −78° C. The reaction was stirred for 2 h at −78° C. NH$_4$Cl/H$_2$O was added and the mixture was extracted with EtOAc thrice. The combined extracts were washed with brine and dried over Na$_2$SO$_4$. The mixture was then concentrated and purified by chromatography on silica gel (5:1 PE/EA) to yield (3R,4R,5R,6R)-2-(5-(benzo[b]thiophen-2-ylmethyl)-2-(benzyloxy)-4-methylphenyl)-3,4-bis(benzyloxy)-5-fluoro-6-methyltetrahydro-2H-pyran-2-ol as a yellow oil.

To a mixture of (3R,4R,5R,6R)-2-(5-(benzo[b]thiophen-2-ylmethyl)-2-(benzyloxy)-4-methylphenyl)-3,4-bis(benzyloxy)-5-fluoro-6-methyltetrahydro-2H-pyran-2-ol (400 mg, 0.58 mmol, 1.00 equiv) in DCM/CH$_3$CN (3/3 mL) with Et$_3$SiH (202.3 mg, 1.74 mmol, 3.00 equiv) was added BF$_3$.Et$_2$O (165.1 mg, 1.16 mmol, 2.00 equiv) dropwise at 0° C. The reaction was stirred for 2 h at 0° C. Sodium bicarbonate was added and the mixture was extracted with DCM thrice. The combined extracts were washed with brine and dried over Na$_2$SO$_4$. The mixture was then concentrated and purified by chromatography on silica gel (10:1 PE/EA) to yield (2S,3S,4R,5R,6R)-2-(5-(benzo[b]thiophen-2-ylmethyl)-2-(benzyloxy)-4-methylphenyl)-3,4-bis(benzyloxy)-5-fluoro-6-methyltetrahydro-2H-pyran as a yellow oil.

To a mixture of (2S,3S,4R,5R,6R)-2-(5-(benzo[b]thiophen-2-ylmethyl)-2-(benzyloxy)-4-methyl phenyl)-3,4-bis(benzyloxy)-5-fluoro-6-methyltetrahydro-2H-pyran (100 mg, 0.15 mmol, 1.00 equiv) in dichloromethane (5 mL) with 1,2,3,4,5-pentamethylbenzene (200 mg, 1.35 mmol, 9.08 equiv) was added BCl$_3$ (2 mL, 13.3 equiv, 1 N) with stirring at −78° C. The reaction was stirred at −78° C. for 1 h. Methanol was added. The mixture was then concentrated and purified by chromatography on silica gel (10:1 DCM/MeOH) to yield (2S,3R,4R,5S,6R)-2-(5-(benzo[b]thiophen-2-ylmethyl)-2-hydroxy-4-methylphenyl)-5-fluoro-6-methyltetrahydro-2H-pyran-3,4-diol as a white solid.

$^1$H-NMR: (400 MHz, CD$_3$OD) δ: 7.72 (d, J=7.6 Hz, 1H), 7.62 (d, J=8.0 Hz, 1H), 7.20-7.29 (m, 3H), 6.91 (s, 1H), 6.69 (s, 1H), 4.60 (d, J=9.2 Hz, 1H), 4.15 (s, 2H), 4.07 (t, J=8.8 Hz, 0.5H), 3.93 (t, J=8.8 Hz, 0.5H), 3.62-3.73 (m, 3H), 2.23 (s, 3H), 1.33 (d, J=6.0 Hz, 3H). MS (ES) m/z: 425 [M+Na]$^+$.

Synthesis Example 5: Compound #20

(2S,3R,4R,5S,6R)-2-(5-(benzo[b]thiophen-2-ylmethyl)-2-hydroxy-4-methylphenyl)-5-fluoro-6-(fluoromethyl)-tetrahydro-2H-pyran-3,4-diol

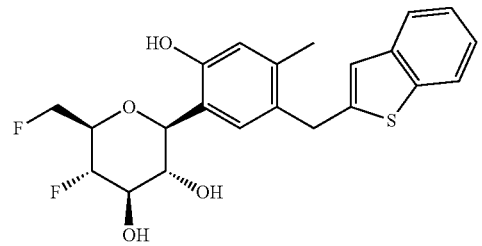 [SMILES: Cc1cc(O)c([C@@H]2O[C@H](CF)[C@@H](F)[C@H](O)[C@H]2O)cc1Cc1cc2ccccc2s1]

To a mixture of (2S,3R,4S,5R,6R)-2-(allyloxy)-6-(hydroxymethyl)tetrahydro-2H-pyran-3,4,5-triol (28.9 g, 131.23 mmol, 1.00 equiv) in pyridine (450 mL) was added benzyl chloride (58.9 g, 419.01 mmol, 3.20 equiv) dropwise at −30° C. The reaction was stirred for 7 h at 25° C. Ice water was added and the mixture was extracted with ethyl acetate thrice. The combined extracts were washed with 1N HCl, brine and dried over Na$_2$SO$_4$. The mixture was then concentrated and purified by chromatography on silica gel (2:1 PE/EA) to yield (2S,3R,4S,5S,6R)-2-(allyloxy)-6-((benzoyloxy)methyl)-5-hydroxytetrahydro-2H-pyran-3,4-diyl dibenzoate as a colorless oil. MS (ES) m/z: 555 [M+Na]$^+$.

To a mixture of (2S,3R,4S,5S,6R)-2-(allyloxy)-6-((benzoyloxy)methyl)-5-hydroxytetrahydro-2H-pyran-3,4-diyl dibenzoate (29.5 g, 55.40 mmol, 1.00 equiv) in dichloromethane (400 mL) was added DAST [(diethylamino)sulfur trifluoride] (24.5 g, 110.86 mmol, 2.00 equiv) dropwise at −30° C. The reaction was stirred for 3.5 h at room temperature. NaHCO$_3$/H$_2$O was added and the mixture was extracted with DCM thrice. The combined extracts were washed with brine and dried over Na$_2$SO$_4$. The mixture was then concentrated and purified by chromatography on silica gel (5:1 PE/EA) to yield (2S,3R,4R,5R,6R)-2-(allyloxy)-6-((benzoyloxy)methyl)-5-fluorotetrahydro-2H-pyran-3,4-diyl dibenzoate as a light yellow oil. MS (ES) m/z: 557 [M+Na]$^+$.

To a mixture of (2S,3R,4R,5R,6R)-2-(allyloxy)-6-((benzoyloxy)methyl)-5-fluorotetrahydro-2H-pyran-3,4-diyl dibenzoate (21 g, 39.29 mmol, 1.00 equiv) in methanol (300 mL) was added MeONa (212 mg, 3.929 mmol, 0.1 equiv). The reaction was stirred for overnight at room temperature. Amberlight IR-120 (H$^+$) was added and the mixture was filtered. The mixture was then concentrated and purified by chromatography on silica gel (5:1 PE/EA) to yield (2S,3R,4R,5S,6R)-2-(allyloxy)-5-fluoro-6-(hydroxymethyl)tetrahydro-2H-pyran-3,4-diol as a light yellow oil. MS (ES) m/z: 245 [M+Na]$^+$.

To a mixture of (2S,3R,4R,5S,6R)-2-(allyloxy)-5-fluoro-6-(hydroxymethyl)tetrahydro-2H-pyran-3,4-diol (12 g, 54.00 mmol, 1.00 equiv) in DMF (200 mL) with imidazole (11 g, 161.58 mmol, 3.00 equiv) was added TBDPSCl (tert-butyldiphenylsilyl chloride) (22.2 g, 1.50 equiv). The reaction was stirred for 3 h at 20° C. Ice water was added and the mixture was extracted with EA thrice. The combined extracts were washed with brine and dried over $Na_2SO_4$. The mixture was then concentrated and purified by chromatography on silica gel (1:1 PE/EA) to yield (2S,3R,4R,5S,6R)-2-(allyloxy)-6-(((tert-butyldiphenylsilyl)oxy)methyl)-5-fluorotetrahydro-2H-pyran-3,4-diol as a colorless oil.

To a mixture of (2S,3R,4R,5S,6R)-2-(allyloxy)-6-(((tert-butyldiphenylsilyl)oxy)methyl)-5-fluorotetrahydro-2H-pyran-3,4-diol (6.2 g, 13.46 mmol, 1.00 equiv) in DMF (60 mL) with BnBr (benzyl bromide) (9.2 g, 53.79 mmol, 4.00 equiv) was added sodium hydride (1.3 g, 54.17 mmol, 4.00 equiv, 60% purity) at 0° C. The reaction was stirred for 10 h at room temperature. Ice water was added and the mixture was extracted with EA thrice. The combined extracts were washed with brine and dried over $Na_2SO_4$. The mixture was then concentrated and purified by chromatography on silica gel (20:1 PE/EA) to yield (((2R,3R,4R,5R,6S)-6-(allyloxy)-4,5-bis(benzyloxy)-3-fluorotetrahydro-2H-pyran-2-yl)methoxy)(tert-butyl)diphenylsilane as a yellow oil. MS (ES) m/z: 663 [M+Na]$^+$.

To a mixture of (((2R,3R,4R,5R,6S)-6-(allyloxy)-4,5-bis(benzyloxy)-3-fluorotetrahydro-2H-pyran-2-yl)methoxy)(tert-butyl)diphenylsilane (5.8 g, 9.05 mmol, 1.00 equiv) in THF (60 mL) with $ZnCl_2$ (3 g, 22.01 mmol, 2.50 equiv) and $Bu_3SnH$ (10.5 g, 4.00 equiv) was added $Pd(PPh_3)_4$ (2.6 g, 2.25 mmol, 0.25 equiv). The reaction was stirred for 3 h at room temperature. Ice water was added and the mixture was extracted with EA thrice. The combined extracts were washed with brine and dried over $Na_2SO_4$. The mixture was then concentrated and purified by chromatography on silica gel (4:1 PE/EA) to yield (3R,4R,5R,6R)-3,4-bis(benzyloxy)-6-(((tert-butyldiphenylsilyl)oxy)methyl)-5-fluorotetrahydro-2H-pyran-2-ol as a yellow oil. MS (ES) m/z: 623 [M+Na]$^+$.

To a mixture of (3R,4R,5R,6R)-3,4-bis(benzyloxy)-6-(((tert-butyldiphenylsilyl)oxy)methyl)-5-fluorotetrahydro-2H-pyran-2-ol (4.62 g, 7.70 mmol, 1.00 equiv) in DMSO (100 mL) was added acetic anhydride (50 mL) at room temperature. The reaction was stirred for 5 h at room temperature. Ice water was added and the mixture was extracted with EA thrice. The combined extracts were washed with $H_2O$, brine and dried over $Na_2SO_4$. The mixture was then concentrated and purified by chromatography on silica gel (4:1 PE/EA) to yield (3R,4R,5R,6R)-3,4-bis(benzyloxy)-6-(((tert-butyldiphenylsilyl)oxy)methyl)-5-fluorotetrahydro-2H-pyran-2-one as a yellow oil. MS (ES) m/z: 621 [M+Na]$^+$.

To a mixture of 2-(4-(benzyloxy)-5-bromo-2-methylbenzyl)benzo[b]thiophene (780 mg, 1.84 mmol, 1.10 equiv) in THF (15 mL) was added n-BuLi (2.5 M in hexane, 0.74 mL, 1.10 equiv) dropwise at −78° C. The reaction was stirred for 30 min at −78° C. To the mixture was then added a solution of (3R,4R,5R,6R)-3,4-bis(benzyloxy)-6-(((tert-butyldiphenylsilyl)oxy)methyl)-5-fluorotetrahydro-2H-pyran-2-one (1 g, 1.67 mmol, 1.00 equiv) in THF (10 mL) dropwise at −78° C. The reaction was stirred for 2 h at −78° C. $NH_4Cl/H_2O$ was added and the mixture was extracted with EtOAc thrice. The combined extracts were washed with brine and dried over $Na_2SO_4$. The mixture was then concentrated and purified by chromatography on silica gel (20:1 PE/EA) to yield (3R,4R,5R,6R)-2-(5-(benzo[b]thiophen-2-ylmethyl)-2-(benzyloxy)-4-methylphenyl)-3,4-bis(benzyloxy)-6-(((tert-butyldiphenylsilyl)oxy)methyl)-5-fluorotetrahydro-2H-pyran-2-ol as a yellow oil.

To a mixture of (3R,4R,5R,6R)-2-(5-(benzo[b]thiophen-2-ylmethyl)-2-(benzyloxy)-4-methylphenyl)-3,4-bis(benzyloxy)-6-(((tert-butyldiphenylsilyl)oxy)methyl)-5-fluorotetrahydro-2H-pyran-2-ol (700 mg, 0.74 mmol, 1.00 equiv) in $DCM/CH_3CN$ (5/5 mL) with $Et_3SiH$ (260 mg, 2.24 mmol, 3.00 equiv) was added $BF_3.Et_2O$ (289 mg, 2.22 mmol, 3.00 equiv) dropwise at 0° C. The reaction was stirred for 1 h at 0° C. Sodium bicarbonate was added and the mixture was extracted with DCM thrice. The combined extracts were washed with brine and dried over $Na_2SO_4$. The mixture was then concentrated and purified by chromatography on silica gel (10:1 PE/EA) to yield ((2R,3R,4R,5S,6S)-6-(5-(benzo[b]thiophen-2-ylmethyl)-2-(benzyloxy)-4-methylphenyl)-4,5-bis(benzyloxy)-3-fluorotetrahydro-2H-pyran-2-yl)methanol as a colorless oil.

To a mixture of ((2R,3R,4R,5S,6S)-6-(5-(benzo[b]thiophen-2-ylmethyl)-2-(benzyloxy)-4-methylphenyl)-4,5-bis(benzyloxy)-3-fluorotetrahydro-2H-pyran-2-yl)methanol (70 mg, 0.100 mmol, 1.00 equiv) in dichloromethane (5 mL) was added DAST (50 mg, 0.310 mmol, 3.00 equiv) dropwise at −20° C. The reaction was stirred at room temperature for 3 h. Sodium bicarbonate was added and the mixture was extracted with DCM twice. The combined extracts were washed with brine and dried over $Na_2SO_4$. The mixture was then concentrated and purified by chromatography on silica gel (5:1 PE/EA) to yield (2S,3S,4R,5S,6R)-2-(5-(benzo[b]thiophen-2-ylmethyl)-2-(benzyloxy)-4-methylphenyl)-3,4-bis(benzyloxy)-5-fluoro-6-(fluoromethyl)tetrahydro-2H-pyran as a yellow oil. MS (ES) m/z: 713 [M+Na]$^+$.

To a mixture of (2S,3S,4R,5S,6R)-2-(5-(benzo[b]thiophen-2-ylmethyl)-2-(benzyloxy)-4-methylphenyl)-3,4-bis(benzyloxy)-5-fluoro-6-(fluoromethyl)tetrahydro-2H-pyran (20 mg, 0.030 mmol, 1.00 equiv) in dichloromethane (2 mL) with 1,2,3,4,5-pentamethylbenzene (40 mg, 0.270 mmol, 9.32 equiv) was added $BCl_3$ (0.4 mL, 0.400 mmol, 13.3 equiv) dropwise at −78° C. The reaction was stirred for 1 h at −78° C. Methanol was added. The resulting mixture was concentrated and purified by Pre-HPLC (33%-48% $CH_3CN/H_2O$) to yield (2S,3R,4R,5S,6R)-2-(5-(benzo[b]thiophen-2-ylmethyl)-2-hydroxy-4-methyl phenyl)-5-fluoro-6-(fluoromethyl)tetrahydro-2H-pyran-3,4-diol as a white solid.

$^1$H NMR (400 MHz, $CD_3OD$) δ: 7.73 (d, J=7.6 Hz, 1H), 7.63 (d, J=8.0 Hz, 1H), 7.20-7.29 (m, 3H), 6.92 (s, 1H), 6.70 (s, 1H), 4.61-4.70 (m, 3H), 4.45 (t, J=9.6 Hz, 0.5H), 4.33 (t, J=9.6 Hz, 0.5H), 4.17 (s, 2H), 3.76-3.85 (m, 2H), 3.64 (t, J=9.2 Hz, 1H), 2.23 (s, 3H). MS (ES) m/z: 443 [M+Na]$^+$.

Synthesis Example 6: Compound #92

2-(5-((2S,3R,4R,5S,6R)-5-fluoro-3,4-dihydroxy-6-(hydroxymethyl)-tetrahydro-2H-pyran-2-yl)-2-methyl benzyl)-6,7-dihydrothieno[3,2-c]pyridine-5 (4H)-carbonitrile

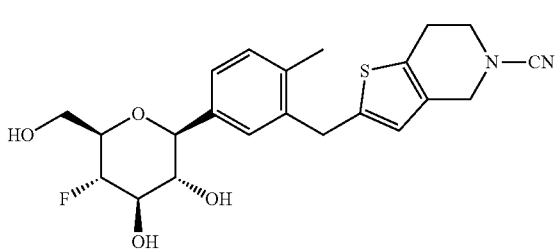 [SMILES: Cc1ccc([C@@H]2O[C@H](CO)[C@@H](F)[C@H](O)[C@H]2O)cc1Cc1cc2c(s1)CCN(C#N)C2]

To a mixture of 2-(5-((2S,3S,4R,5R,6R)-3,4-bis(benzyloxy)-6-((benzyloxy)methyl)-5-fluorotetrahydro-2H-pyran-2-yl)-2-methylbenzyl)-4,5,6,7-tetrahydrothieno[3,2-c]pyridine (110 mg, 0.16 mmol, 1.00 equiv) in methanol (3 mL) with potassium carbonate (69.3 mg, 0.50 mmol, 3.10 equiv) was added BrCN (cyanogen bromide) (86 mg, 0.81 mmol, 5.00 equiv), and the reaction was stirred for 4 h at 20° C. Water was added and the mixture was extracted with EA thrice. The combined extracts were washed with brine and dried over $Na_2SO_4$. The mixture was then concentrated and purified by chromatography on silica gel (30:1 PE/EA) to yield 2-(5-((2S,3S,4R,5R,6R)-3,4-bis(benzyloxy)-6-((benzyloxy)methyl)-5-fluorotetrahydro-2H-pyran-2-yl)-2-methylbenzyl)-6,7-dihydrothieno[3,2-c]pyridine-5(4H)-carbonitrile as a light brown oil. MS (ES) m/z: 703.3[M+H]$^+$ To a mixture of 2-(5-((2S,3S,4R,5R,6R)-3,4-bis(benzyloxy)-6-((benzyloxy)methyl)-5-fluorotetrahydro-2H-pyran-2-yl)-2-methylbenzyl)-6,7-dihydrothieno[3,2-c]pyridine-5(4H)-carbonitrile (65 mg, 0.09 mmol, 1.00 equiv) in dichloromethane (3 mL) with 1,2,3,4,5-pentamethylbenzene (130 mg, 0.88 mmol, 9.50 equiv) was added $BCl_3$ (1.3 mL, 1.30 mmol, 14.10 equiv, 1 M in DCM) at −78° C. The reaction was stirred at −78° C. for 1 h. Methanol (2 mL) was added. The mixture was then concentrated and purified by chromatography on Prep-HPLC (0%-45% $CH_3CN/H_2O$) to yield 2-(5-((2S,3R,4R,5S,6R)-5-fluoro-3,4-dihydroxy-6-(hydroxymethyl)tetrahydro-2H-pyran-2-yl)-2-methylbenzyl)-6,7-dihydrothieno[3,2-c]pyridine-5(4H)-carbonitriles as a white solid.

1H NMR (300 MHz, Methanol-d4) δ: 7.20-7.31 (m, 2H), 7.15 (d, J=7.7 Hz, 1H), 6.41 (s, 1H), 4.45 (t, J=9.3 Hz, 0.5H), 4.28 (t, J=9.3 Hz, 0.5H), 4.25 (s, 2H), 4.14 (d, J=9.5 Hz, 1H), 4.08 (s, 2H), 3.78-3.91 (m, 1H), 3.68-3.78 (m, 2H), 3.35-3.64 (m, 4H), 2.88 (t, J=5.6 Hz, 2H), 2.27 (s, 3H). MS (ES) m/z: 431.0[M−H]$^-$.

Synthesis Example 7: Compound #103

2-(5-((2S,3R,4R,5S,6R)-5-fluoro-3,4-dihydroxy-6-(hydroxymethyl)-tetrahydro-2H-pyran-2-yl)-4-hydroxy-2-methylbenzyl)-6,7-dihydrothieno[3,2-c]pyridine-5(4H)-carbonitrile

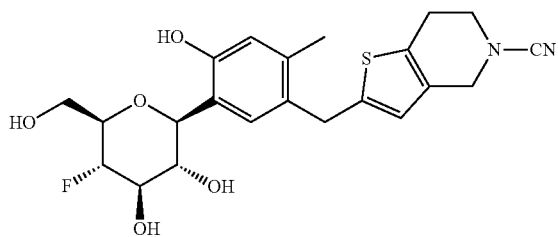 [SMILES: Cc1cc(O)c([C@@H]2O[C@H](CO)[C@@H](F)[C@H](O)[C@H]2O)cc1Cc1cc2c(s1)CCN(C#N)C2]

To a mixture of 1-(benzyloxy)-2-bromo-4-(dimethoxymethyl)-5-methylbenzene (856 mg, 2.44 mmol, 1.10 equiv) in tetrahydrofuran (25 mL) was added n-BuLi (2.5M in hexane, 1.06 mL, 2.66 mmol, 1.20 equiv) dropwise at −78° C., the mixture was stirred for 30 mins at −78° C. After that, (3R,4R,5R,6R)-3,4-bis(benzyloxy)-6-(benzyloxymethyl)-5-fluoro-tetrahydropyran-2-one (1 g, 2.22 mmol, 1.00 equiv) in tetrahydrofuran (3 mL) was added. The reaction was stirred at −78° C. for 2 h. $NH_4Cl/H_2O$ was added and the mixture was extracted with EtOAc thrice. The combined extracts were washed with brine and dried over $Na_2SO_4$. The mixture was then concentrated to yield (3R,4R,5R,6R)-3,4-bis(benzyloxy)-2-(2-(benzyloxy)-5-(dimethoxymethyl)-4-methylphenyl)-6-((benzyloxy)methyl)-5-fluorotetrahydro-2H-pyran-2-ol as a yellow oil.

To a mixture of (3R,4R,5R,6R)-3,4-bis(benzyloxy)-2-(2-(benzyloxy)-5-(dimethoxymethyl)-4-methylphenyl)-6-((benzyloxy)methyl)-5-fluorotetrahydro-2H-pyran-2-ol (1.8 g, 2.49 mmol, 1.00 equiv) in tetrahydrofuran (10 mL) was added HCl (1 N, 30 mL). The reaction was stirred at room temperature for 2 h. The mixture was extracted with EtOAc thrice. The combined extracts were washed with brine and dried over $Na_2SO_4$. The mixture was then concentrated and purified by chromatography on silica gel (4:1 PE/EA) to yield 4-(benzyloxy)-5-((3R,4R,5R,6R)-3,4-bis(benzyloxy)-6-((benzyloxy)methyl)-5-fluoro-2-hydroxytetrahydro-2H-pyran-2-yl)-2-methylbenzaldehyde as a yellow oil. MS (ES) m/z: 694.2[M+NH$_4$]$^+$ To a mixture of tert-butyl 2-bromo-4H,5H,6H,7H-thieno[3,2-c]pyridine-5-carboxylate (1.62 g, 5.09 mmol, 3.00 equiv) in tetrahydrofuran (16 mL) was added n-BuLi (2.5M in hexane, 2.03 mL, 5.09 mmol, 3.00 equiv) dropwise at −78° C., and the mixture was stirred for 25 mins at −78° C. 4-(Benzyloxy)-5-((3R,4R,5R,6R)-3,4-bis(benzyloxy)-6-((benzyloxy)methyl)-5-fluoro-2-hydroxytetrahydro-2H-pyran-2-yl)-2-methylbenzaldehyde (1.15 g, 1.70 mmol, 1.00 equiv) in tetrahydrofuran (4 mL) was then added to the solution. The reaction was stirred for 2 h at −78° C. $NH_4Cl/H_2O$ was added and the mixture was extracted with EtOAc thrice. The combined extracts were washed with brine and dried over $Na_2SO_4$. The mixture was then concentrated and purified by chromatography on silica gel (3:1 PE/EA) to yield tert-butyl 2-((4-(benzyloxy)-5-((3R,4R,5R,6R)-3,4-bis(benzyloxy)-6-((benzyloxy)methyl)-5-fluoro-2-hydroxytetrahydro-2H-pyran-2-yl)-2-methylphenyl)(hydroxy)methyl)-6,7-dihydrothieno[3,2-c]pyridine-5(4H)-carboxylate as a yellow oil.

To a mixture of tert-butyl 2-((4-(benzyloxy)-5-((3R,4R,5R,6R)-3,4-bis(benzyloxy)-6-((benzyloxy)methyl)-5-fluoro-2-hydroxytetrahydro-2H-pyran-2-yl)-2-methylphenyl)(hydroxy)methyl)-6,7-dihydrothieno[3,2-c]pyridine-5(4H)-carboxylate (1.25 g, 1.36 mmol, 1.00 equiv) in dichloromethane (12 mL) with $Et_3SiH$ (634 mg, 5.45 mmol, 4.00 equiv) was added $BF_3.Et_2O$ (775 mg, 5.45 mmol, 4.00 equiv) dropwise at 0° C. The reaction was stirred at 0° C. for 1 h. Sodium bicarbonate/$H_2O$ was added and the mixture was extracted with dichloromethane thrice. The combined extracts were washed with brine and dried over $Na_2SO_4$. The mixture was then concentrated and purified by chromatography on silica gel (11:1 DCM/MeOH) to yield 2-(4-(benzyloxy)-5-((2S,3S,4R,5R,6R)-3,4-bis(benzyloxy)-6-((benzyloxy)methyl)-5-fluorotetrahydro-2H-pyran-2-yl)-2-methylbenzyl)-4,5,6,7-tetrahydrothieno[3,2-c]pyridine as a yellow oil.

To a mixture 2-(4-(benzyloxy)-5-((2S,3S,4R,5R,6R)-3,4-bis(benzyloxy)-6-((benzyloxy)methyl)-5-fluorotetrahydro-2H-pyran-2-yl)-2-methylbenzyl)-4,5,6,7-tetrahydrothieno[3,2-c]pyridine (150 mg, 0.19 mmol, 1.00 equiv) in MeOH (5 mL) with $K_2CO_3$ (79.5 mg, 0.58 mmol, 3.00 equiv) was added BrCN (101 mg, 0.95 mmol, 5.00 equiv). The reaction was stirred at room temperature for 4 h. Water (0.1 mL) was added to quench the reaction. The mixture was then concentrated and purified by chromatography on silica gel (78:22 PE/EtOAc) to yield 2-(4-(benzyloxy)-5-((2S,3S,4R,5R,6R)-3,4-bis(benzyloxy)-6-((benzyloxy)methyl)-5-fluorotetrahydro-2H-pyran-2-yl)-2-methylbenzyl)-6,7-dihydrothieno[3,2-c]pyridine-5(4H)-carbonitrile as a yellow oil.

To a mixture of 2-(4-(benzyloxy)-5-((2S,3S,4R,5R,6R)-3,4-bis(benzyloxy)-6-((benzyloxy)methyl)-5-fluorotetrahydro-2H-pyran-2-yl)-2-methylbenzyl)-6,7-dihydrothieno[3,2-c]pyridine-5(4H)-carbonitrile (130 mg, 0.16 mmol, 1.00 equiv) in dichloromethane (5 mL) with 1,2,3,4,5-pentamethylbenzene (238 mg, 1.61 mmol, 10.00 equiv) was added BCl$_3$ (1M in DCM, 2.60 mL, 2.60 mmol, 16.20 equiv) dropwise at −78° C. The reaction was stirred for 30 min at −78° C. Methanol (3 mL) was added to quench the reaction. The mixture was then concentrated and purified by chromatography on a C18 reversed column ACN/H$_2$O (5%-40%) to yield 2-(5-((2S,3R,4R,5S,6R)-5-fluoro-3,4-dihydroxy-6-(hydroxymethyl)tetrahydro-2H-pyran-2-yl)-4-hydroxy-2-methyl benzyl)-6,7-dihydrothieno[3,2-c]pyridine-5(4H)-carbonitrile as a white solid.

$^1$H-NMR (400 MHz, CD$_3$OD) δ: 7.17 (s, 1H), 6.65 (s, 1H), 6.38 (s, 1H), 4.56 (d, J=9.7 Hz, 1H), 4.46 (t, J=9.3 Hz, 0.5H), 4.29 (t, J=9.3 Hz, 0.5H), 4.25 (s, 2H), 3.99 (s, 2H), 3.69-3.86 (m, 3H), 3.56-3.64 (m, 2H), 3.49 (t, J=5.7 Hz, 2H), 2.87 (t, J=5.8 Hz, 2H), 2.18 (s, 3H); MS (ES) m/z: 447.1[M−H]$^-$

Synthesis Example 8: Compound #110

2-(5-((2S,3R,4R,5S,6R)-5-fluoro-3,4-dihydroxy-6-(hydroxymethyl)-tetrahydro-2H-pyran-2-yl)-4-methoxy-2-methylbenzyl)-6,7-dihydrothieno[3,2-c]pyridine-5(4H)-carbonitrile

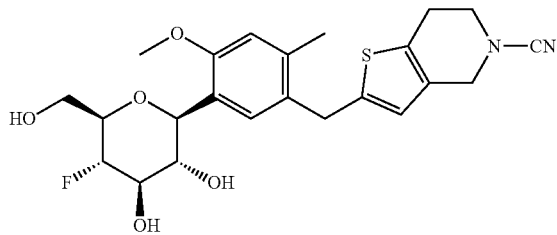 [SMILES: COc1cc(C)c(Cc2cc3c(s2)CCN(C#N)C3)cc1[C@@H]1O[C@H](CO)[C@@H](F)[C@H](O)[C@H]1O]

To a mixture of 2-(5-((2S,3R,4R,5S,6R)-5-fluoro-3,4-dihydroxy-6-(hydroxymethyl)tetrahydro-2H-pyran-2-yl)-4-hydroxy-2-methylbenzyl)-6,7-dihydrothieno[3,2-c]pyridine-5(4H)-carbonitrile, prepared as in Synthesis Example 7 above (20 mg, 0.04 mmol, 1.00 equiv) in N,N-dimethylformamide (1.5 mL) with K$_2$CO$_3$ (18.5 mg, 0.13 mmol, 3.00 equiv) was added CH$_3$I (25.3 mg, 0.17 mmol, 4.00 equiv). The reaction was stirred at room temperature for 2 h. The resulting mixture was purified by chromatography on a C18 reversed column ACN/H$_2$O (5%-40%) to yield 2-(5-((2S,3R,4R,5S,6R)-5-fluoro-3,4-dihydroxy-6-(hydroxymethyl)tetrahydro-2H-pyran-2-yl)-4-methoxy-2-methylbenzyl)-6,7-dihydrothieno[3,2-c]pyridine-5(4H)-carbonitrile as a white solid.

$^1$H-NMR (400 MHz, CD$_3$OD) δ: 7.14 (s, 1H), 6.70 (s, 1H), 6.28 (s, 1H), 4.57 (d, J=9.8 Hz, 1H), 4.30 (t, J=9.3 Hz, 0.5H), 4.17 (t, J=9.3 Hz, 0.5H), 4.14 (s, 2H), 3.92 (s, 2H), 3.56-3.74 (m, 6H), 3.43-3.51 (m, 2H), 3.39 (t, J=5.7 Hz, 2H), 2.77 (t, J=5.8 Hz, 2H), 2.17 (s, 3H); MS (ES) m/z: 461.1[M−H]$^-$

Synthesis Example 9: Compound #86

Cyclopentyl(2-(5-((2S,3R,4R,5S,6R)-5-fluoro-3,4-dihydroxy-6-(hydroxymethyl)-tetrahydro-2H-pyran-2-yl)-4-hydroxy-2-methylbenzyl)-6,7-dihydrothieno[3,2-c]pyridin-5(4H)-yl)methanone

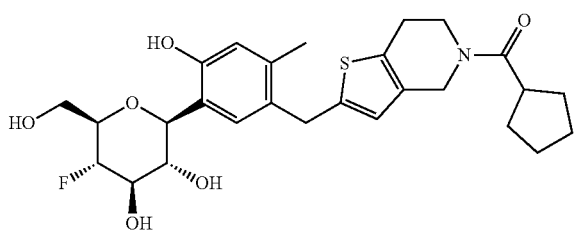 [SMILES: Cc1cc(O)c([C@@H]2O[C@H](CO)[C@@H](F)[C@H](O)[C@H]2O)cc1Cc1cc2c(s1)CCN(C(=O)C1CCCC1)C2]

To a mixture of 2-(4-(benzyloxy)-5-((2S,3S,4R,5R,6R)-3,4-bis(benzyloxy)-6-((benzyloxy)methyl)-5-fluorotetrahydro-2H-pyran-2-yl)-2-methylbenzyl)-4,5,6,7-tetrahydrothieno[3,2-c]pyridine (110 mg, 0.14 mmol, 1.00 equiv) in dichloromethane (5 mL) with triethylamine (71 mg, 0.70 mmol, 5.00 equiv) was added cyclopentanecarbonyl chloride (47 mg, 0.35 mmol, 2.53 equiv) dropwise at 0° C. The reaction was stirred at room temperature for 2 h. The mixture was then concentrated and purified by chromatography on silica gel (1:1 PE/EA) to yield (2-(4-(benzyloxy)-5-((2S,3S,4R,5R,6R)-3,4-bis(benzyloxy)-6-((benzyloxy)methyl)-5-fluorotetrahydro-2H-pyran-2-yl)-2-methylbenzyl)-6,7-dihydrothieno[3,2-c]pyridin-5(4H)-yl)(cyclopentyl)methanone as a light yellow oil.

To a mixture of (2-(4-(benzyloxy)-5-((2S,3S,4R,5R,6R)-3,4-bis(benzyloxy)-6-((benzyloxy)methyl)-5-fluorotetrahydro-2H-pyran-2-yl)-2-methylbenzyl)-6,7-dihydrothieno[3,2-c]pyridin-5(4H)-yl)(cyclopentyl)methanone (85 mg, 0.10 mmol, 1.00 equiv) in dichloromethane (5 mL) with 1,2,3,4,5-pentamethylbenzene (170 mg, 1.15 mmol, 11.87 equiv) was added BCl$_3$ (1.7 mL, 1.70 mmol, 17.58 equiv) dropwise at −78° C. The reaction was stirred for 1 h at −78° C. Methanol was added. The mixture was then concentrated and purified by chromatography on C18 (5%-40% CH$_3$CN/H$_2$O) to yield cyclopentyl(2-(5-((2S,3R,4R,5S,6R)-5-fluoro-3,4-dihydroxy-6-(hydroxymethyl)tetrahydro-2H-pyran-2-yl)-4-hydroxy-2-methylbenzyl)-6,7-dihydrothieno[3,2-c]pyridin-5(4H)-yl)methanone as a white solid.

$^1$H NMR (300 MHz, CD$_3$OD) δ: 7.17 (s, 1H), 6.65 (s, 1H), 6.41 (d, J=5.1 Hz, 1H), 4.50-4.59 (m, 3H), 4.46 (t, J=9.0 Hz, 0.5H), 4.29 (t, J=9.0 Hz, 0.5H), 3.99 (s, 2H), 3.83-3.87 (m, 3H), 3.71-3.79 (m, 2H), 3.55-3.65 (m, 2H), 3.04-3.14 (m, 1H), 2.73-2.82 (m, 2H), 2.19 (s, 3H), 1.58-1.96 (m, 8H); MS (ES) m/z: 520.1 [M+H]$^+$.

Synthesis Example 10: Compound #84

(2-(5-((2S,3R,4R,5S,6R)-5-fluoro-3,4-dihydroxy-6-(hydroxymethyl)-tetrahydro-2H-pyran-2-yl)-4-hydroxy-2-methylbenzyl)-6,7-dihydrothieno[3,2-c]pyridin-5(4H)-yl)(thiazol-2-yl)methanone

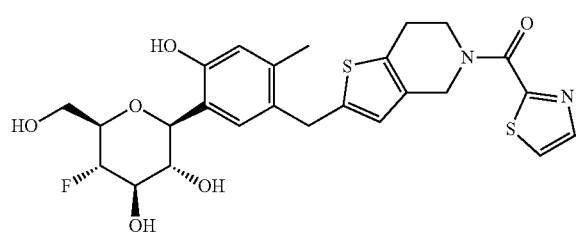 [SMILES: Cc1cc(O)c([C@@H]2O[C@H](CO)[C@@H](F)[C@H](O)[C@H]2O)cc1Cc1cc2c(s1)CCN(C(=O)c1nccs1)C2]

To a mixture of 2-(4-(benzyloxy)-5-((2S,3S,4R,5R,6R)-3,4-bis(benzyloxy)-6-((benzyloxy)methyl)-5-fluorotetrahydro-2H-pyran-2-yl)-2-methylbenzyl)-4,5,6,7-tetrahydrothieno[3,2-c]pyridine (100 mg, 0.13 mmol, 1.00 equiv) in dichloromethane (3 mL) with triethylamine (52 mg, 0.51 mmol, 4.03 equiv) was added 1,3-thiazole-2-carbonyl chloride (37.5 mg, 0.25 mmol, 1.99 equiv) dropwise at 0° C. The reaction was stirred for 2 h at room temperature. The mixture was then concentrated and purified by chromatography on silica gel (1:1 PE/EA) to yield (2-(4-(benzyloxy)-5-((2S,3S,4R,5R,6R)-3,4-bis(benzyloxy)-6-((benzyloxy)methyl)-5-fluorotetrahydro-2H-pyran-2-yl)-2-methylbenzyl)-6,7-dihydrothieno[3,2-c]pyridin-5(4H)-yl)(thiazol-2-yl)methanone as a light yellow oil.

To a mixture of (2-(4-(benzyloxy)-5-((2S,3S,4R,5R,6R)-3,4-bis(benzyloxy)-6-((benzyloxy)methyl)-5-fluorotetrahydro-2H-pyran-2-yl)-2-methylbenzyl)-6,7-dihydrothieno[3,2-c]pyridin-5(4H)-yl)(thiazol-2-yl)methanone (25 mg, 0.03 mmol, 1.00 equiv) in dichloromethane (3 mL) with 1,2,3,4,5-pentamethylbenzene (50 mg, 0.34 mmol, 12.08 equiv) was added $BCl_3$ (0.5 mL, 0.50 mmol, 17.88 equiv) dropwise at −78° C. The reaction was stirred for 1 h at −78° C. Methanol was added. The mixture was then concentrated and purified by chromatography on C18 (5%-40% $CH_3CN/H_2O$) to yield (2-(5-((2S,3R,4R,5S,6R)-5-fluoro-3,4-dihydroxy-6-(hydroxymethyl)tetrahydro-2H-pyran-2-yl)-4-hydroxy-2-m ethylbenzyl)-6,7-dihydrothieno[3,2-c]pyridin-5(4H)-yl)(thiazol-2-yl)methanone as a white solid.

$^1$H NMR (300 MHz, $CD_3OD$) δ: 7.98 (s, 1H), 7.83 (s, 1H), 7.20 (s, 1H), 6.66 (s, 1H), 6.42 (d, J=26.1 Hz, 1H), 5.27 (s, 1H), 4.68 (s, 1H), 4.46-4.60 (m, 3H), 4.46 (t, J=9.0 Hz, 0.5H), 4.29 (t, J=9.9 Hz, 0.5H), 3.99-4.07 (m, 2H), 3.68-3.78 (m, 3H), 3.54-3.66 (m, 2H), 2.85-2.94 (m, 2H), 2.20 (s, 3H); MS (ES) m/z: 535.1 [M+H]$^+$.

Synthesis Example 11: Compound #66

(2-(5-((2S,3R,4R,5S,6R)-5-fluoro-3,4-dihydroxy-6-(hydroxymethyl)tetrahydro-2H-pyran-2-yl)-4-hydroxy-2-methylbenzyl)-6,7-dihydrothieno[3,2-c]pyridin-5(4H)-yl)(pyrrolidin-1-yl)methanone

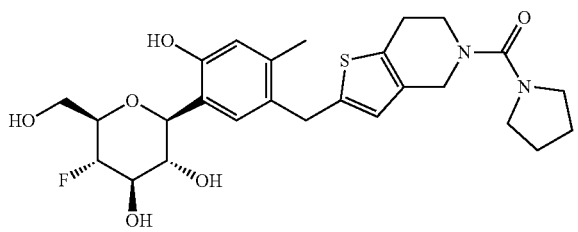 [SMILES: Cc1cc(O)c([C@@H]2O[C@H](CO)[C@@H](F)[C@H](O)[C@H]2O)cc1Cc1cc2c(s1)CCN(C(=O)N1CCCC1)C2]

To a mixture of 2-(4-(benzyloxy)-5-((2S,3S,4R,5R,6R)-3,4-bis(benzyloxy)-6-((benzyloxy)methyl)-5-fluorotetrahydro-2H-pyran-2-yl)-2-methylbenzyl)-4,5,6,7-tetrahydrothieno[3,2-c]pyridine (90 mg, 0.11 mmol, 1.00 equiv) in dichloromethane (3 mL) with triethylamine (34.8 mg, 0.34 mmol, 3.00 equiv) was added pyrrolidine-1-carbonyl chloride (23 mg, 0.17 mmol, 1.50 equiv) dropwise at 0° C. The reaction was stirred for 2 h at room temperature. The mixture was then concentrated and purified by chromatography on silica gel (1:1 PE/EA) to yield (2-(4-(benzyloxy)-5-((2S,3S,4R,5R,6R)-3,4-bis(benzyloxy)-6-((benzyloxy)methyl)-5-fluorotetrahydro-2H-pyran-2-yl)-2-methylbenzyl)-6,7-dihydrothieno[3,2-c]pyridin-5(4H)-yl)(pyrrolidin-1-yl)methanone as a colorless oil. MS (ES) m/z: 881.4 [M+H]$^+$.

To a mixture of (2-(4-(benzyloxy)-5-((2S,3S,4R,5R,6R)-3,4-bis(benzyloxy)-6-((benzyloxy)methyl)-5-fluorotetrahydro-2H-pyran-2-yl)-2-methylbenzyl)-6,7-dihydrothieno[3,2-c]pyridin-5(4H)-yl)(pyrrolidin-1-yl)methanone (60 mg, 0.07 mmol, 1.00 equiv) in dichloromethane (5 mL) with 1,2,3,4,5-pentamethylbenzene (120 mg, 0.81 mmol, 11.89 equiv) was added $BCl_3$ (1.2 mL, 1.20 mmol, 17.6 equiv) dropwise at −78° C. The reaction was stirred for 1 h at −78° C. Methanol was added. The mixture was then concentrated and purified by chromatography on C18 (½ $CH_3CN/H_2O$) to yield (2-(5-((2S,3R,4R,5S,6R)-5-fluoro-3,4-dihydroxy-6-(hydroxymethyl)tetrahydro-2H-pyran-2-yl)-4-hydroxy-2-methylbenzyl)-6,7-dihydrothieno[3,2-c]pyridin-5(4H)-yl)(pyrrolidin-1-yl)methanone as a white solid.

$^1$H NMR (300 MHz, $CD_3OD$) δ: 7.17 (s, 1H), 6.65 (s, 1H), 6.36 (s, 1H), 4.58 (d, J=9.6 Hz, 1H), 4.46 (t, J=9.2 Hz, 0.5H), 4.29 (t, J=9.2 Hz, 0.5H), 4.24 (s, 2H), 3.96 (s, 2H), 3.65-3.87 (m, 3H), 3.53-3.62 (m, 4H), 3.38-3.42 (m, 4H), 2.80 (t, J=5.3 Hz, 2H), 2.20 (s, 3H), 1.83-1.86 (m, 4H); MS (ES) m/z: 521.1 [M+H]$^+$.

Synthesis Example 12: Compound #109

(2-(5-((2S,3R,4R,5S,6R)-5-fluoro-3,4-dihydroxy-6-(hydroxymethyl)-tetrahydro-2H-pyran-2-yl)-2-methyl benzyl)-6,7-dihydrothieno[3,2-c]pyridin-5(4H)-yl)(thiazol-2-yl)methanone

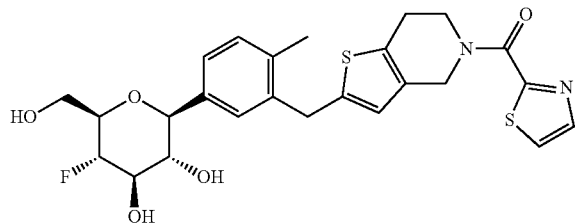 [SMILES: Cc1ccc([C@@H]2O[C@H](CO)[C@@H](F)[C@H](O)[C@H]2O)cc1Cc1cc2c(s1)CCN(C(=O)c1nccs1)C2]

To a mixture of 2-bromo-4H,5H,6H,7H-thieno[3,2-c]pyridine-5-carboxylate (2.0 g, 6.28 mmol, 1.00 equiv) in tetrahydrofuran (25 mL) was added n-BuLi (2.64 mL, 6.60 mmol, 1.05 equiv, 2.5 M in hexane) dropwise at −78° C. The reaction was stirred for 20 min at −78° C. Then the solution of 5-bromo-2-methylbenzaldehyde (1.38 g, 6.93 mmol, 1.10 equiv) in THF (1.0 mL) was added at −78° C. The reaction was stirred at −78° C. for 2 h. NH$_4$Cl/H$_2$O was added and the mixture was extracted with EtOAc thrice. The combined extracts were washed with brine and dried over Na$_2$SO$_4$. The mixture was then concentrated and purified by chromatography on silica gel (80:1 PE/EA) to yield tert-butyl 2-((5-bromo-2-methylphenyl)(hydroxy)methyl)-6,7-dihydrothieno[3,2-c]pyridine-5(4H)-carboxylate as a light yellow solid.

To a mixture of tert-butyl 2-((5-bromo-2-methylphenyl)(hydroxy)methyl)-6,7-dihydrothieno[3,2-c]pyridine-5(4H)-carboxylate (2.56 g, 5.84 mmol, 1.00 equiv) and triethylsilane (1.36 g, 11.70 mmol, 2.00 equiv) in dichloromethane (60 mL) was added trifluoroacetic acid (1.0 g, 8.77 mmol, 1.50 equiv) at 0° C., and the reaction mixture stirred for 3 h at 0° C. Sodium bicarbonate was added and the mixture was extracted with DCM thrice. The combined extracts were washed with brine and dried over Na$_2$SO$_4$. The mixture was then concentrated and purified by chromatography on silica gel (20:1 PE/EA) gave 800 mg (32%) of tert-butyl 2-(5-bromo-2-methylbenzyl)-6,7-dihydrothieno[3,2-c]pyridine-5(4H)-carboxylate as a light yellow solid. MS (ES) m/z: 422.0 [M+H]$^+$.

To a mixture of tert-butyl 2-(5-bromo-2-methylbenzyl)-6,7-dihydrothieno[3,2-c]pyridine-5(4H)-carboxylate (420 mg, 0.99 mmol, 1.00 equiv) in tetrahydrofuran (5 mL) was added dropwise n-BuLi (0.44 mL, 1.10 mmol, 1.10 equiv, 2.5 M in hexane) at −78° C. The mixture was stirred for 20 min at the same temperature. Then a solution of (3R,4R,5R,6R)-3,4-bis(benzyloxy)-6-[(benzyloxy)methyl]-5-fluorooxan-2-one (493 mg, 1.09 mmol, 1.10 equiv) in THF (1.5 mL) was added dropwise at −78° C. The reaction was stirred at −78° C. for 2 h, NH$_4$Cl/H$_2$O was added and the mixture was extracted with EtOAc thrice. The combined extracts were washed with brine and dried over Na$_2$SO$_4$. The mixture was then concentrated and purified by chromatography on silica gel (30:1 PE/EA) gave 703 mg (89%) of tert-butyl 2-(5-((3R,4R,5R,6R)-3,4-bis(benzyloxy)-6-((benzyloxy)methyl)-5-fluoro-2-hydroxytetrahydro-2H-pyran-2-yl)-2-methylbenzyl)-6,7-dihydrothieno[3,2-c]pyridine-5(4H)-carboxylate as a light brown oil.

To a mixture of tert-butyl 2-(5-((3R,4R,5R,6R)-3,4-bis(benzyloxy)-6-((benzyloxy)methyl)-5-fluoro-2-hydroxytetrahydro-2H-pyran-2-yl)-2-methylbenzyl)-6,7-dihydrothieno[3,2-c]pyridine-5(4H)-carboxylate (703 mg, 0.89 mmol, 1.00 equiv) and Et$_3$SiH (513.5 mg, 4.42 mmol, 5.00 equiv) in dichloromethane (20 mL) was added BF$_3$.Et$_2$O (628.6 mg, 5.00 equiv) dropwise at 0° C. The reaction was stirred for 3 h at 0° C. Sodium bicarbonate was added and the mixture was extracted with DCM thrice. The combined extracts were washed with brine and dried over Na$_2$SO$_4$. The mixture was then concentrated and purified by chromatography on silica gel (3:1 PE/EA) gave 300 mg (50%) of 2-(5-((2S,3S,4R,5R,6R)-3,4-bis(benzyloxy)-6-((benzyloxy)methyl)-5-fluorotetrahydro-2H-pyran-2-yl)-2-methylbenzyl)-4,5,6,7-tetrahydrothieno[3,2-c]pyridine as a light brown oil. MS (ES) m/z: 678.3 [M+H]$^+$.

To a mixture of 2-(5-((2S,3S,4R,5R,6R)-3,4-bis(benzyloxy)-6-((benzyloxy)methyl)-5-fluorotetrahydro-2H-pyran-2-yl)-2-methylbenzyl)-4,5,6,7-tetrahydrothieno[3,2-c]pyridine (70 mg, 0.10 mmol, 1.00 equiv) in tetrahydrofuran (1.5 mL) with pyridine (24.5 mg, 0.31 mmol, 3.00 equiv) was added 1,3-thiazole-2-carbonyl chloride (30.5 mg, 0.21 mmol, 2.00 equiv) at 0° C. The reaction was stirred for 3 h at 25° C. NH$_4$Cl/H$_2$O was added and the mixture was extracted with EtOAc thrice. The combined extracts were washed with brine and dried over Na$_2$SO$_4$. The mixture was then concentrated and purified by chromatography on silica gel (20:1 PE/EA) gave 60 mg (74%) of (2-(5-((2S,3S,4R,5R,6R)-3,4-bis(benzyloxy)-6-((benzyloxy)methyl)-5-fluorotetrahydro-2H-pyran-2-yl)-2-methylbenzyl)-6,7-dihydrothieno[3,2-c]pyridin-5(4H)-yl)(thiazol-2-yl)methanone as a light brown oil. MS (ES) m/z: 830.2 [M+H+ACN]$^+$.

To a mixture of (2-(5-((2S,3S,4R,5R,6R)-3,4-bis(benzyloxy)-6-((benzyloxy)methyl)-5-fluorotetrahydro-2H-pyran-2-yl)-2-methylbenzyl)-6,7-dihydrothieno[3,2-c]pyridin-5(4H)-yl)(thiazol-2-yl)methanone (70 mg, 0.09 mmol, 1.00 equiv) and 1,2,3,4,5-pentamethylbenzene (140 mg, 0.94 mmol, 10.60 equiv) in dichloromethane (3 mL) was added BCl$_3$ (1 M in DCM, 1.4 mL, 1.40 mmol, 15.70 equiv) dropwise at −78° C. The reaction was stirred for 50 min at −78° C. Methanol was added. The mixture was then concentrated and purified by chromatography on C18 column (MeCN/H$_2$O 40:60) to yield (2-(5-((2S,3R,4R,5S,6R)-5-fluoro-3,4-dihydroxy-6-(hydroxymethyl)tetrahydro-2H-pyran-2-yl)-2-methylbenzyl)-6,7-dihydrothieno[3,2-c]pyridin-5(4H)-yl)(thiazol-2-yl)methanone as a white solid.

$^1$H NMR (400 MHz, Methanol-d4) δ: 7.87 (d, J=3.2 Hz, 1H), 7.73 (t, J=3.5 Hz, 1H), 7.09-7.21 (m, 2H), 7.04 (dd, J=8.2, 3.5 Hz, 1H), 6.34 (d, J=37.0 Hz, 1H), 5.17 (s, 1H), 4.58 (s, 1H), 4.41 (t, J=5.7 Hz, 1H), 4.32 (t, J=9.6 Hz, 0.5H), 4.17 (t, J=9.6 Hz, 0.5H), 3.90-4.10 (m, 4H), 3.74 (d, J=12.2 Hz, 1H), 3.44-3.69 (m, 3H), 3.31 (dd, J=10.7, 8.0 Hz, 1H), 2.75-2.88 (m, 2H), 2.17 (d, J=7.6 Hz, 3H). MS (ES) m/z: 519.1 [M+H]$^+$.

Synthesis Example 13: Compound #112

(2-(5-((2S,3R,4R,5S,6R)-5-fluoro-3,4-dihydroxy-6-(hydroxymethyl)-tetrahydro-2H-pyran-2-yl)-4-methoxy-2-methylbenzyl)-6,7-dihydrothieno[3,2-c]pyridin-5(4H)-yl)(thiazol-2-yl)methanone

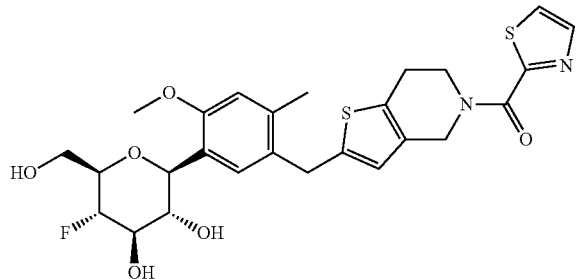 [SMILES: COc1cc(C)c(Cc2cc3c(s2)CCN(C(=O)c2nccs2)C3)cc1[C@@H]1O[C@H](CO)[C@@H](F)[C@H](O)[C@H]1O]

To a mixture of (2-(5-((2S,3R,4R,5S,6R)-5-fluoro-3,4-dihydroxy-6-(hydroxymethyl)tetrahydro-2H-pyran-2-yl)-4-hydroxy-2-methylbenzyl)-6,7-dihydrothieno[3,2-c]pyridin-5(4H)-yl)(thiazol-2-yl)methanone, prepared as in Synthesis Example 12 above (10 mg, 0.02 mmol, 1.00 equiv) in N,N-dimethylformamide (1.5 mL) with $K_2CO_3$ (7.8 mg, 0.06 mmol, 3.00 equiv) was added $CH_3I$ (10.6 mg, 0.07 mmol, 4.00 equiv). The reaction mixture was stirred at room temperature for 2 h. The resulting mixture was then purified by chromatography on a C18 reversed column ($ACN/H_2O$ 40:60) to yield (2-(5-((2S,3R,4R,5S,6R)-5-fluoro-3,4-dihydroxy-6-(hydroxymethyl)tetrahydro-2H-pyran-2-yl)-4-methoxy-2-methylbenzyl)-6,7-dihydrothieno[3,2-c]pyridin-5(4H)-yl)(thiazol-2-yl)methanone as a white solid.

$^1$H-NMR (400 MHz, $CD_3OD$) δ: 7.96 (d, J=3.2 Hz, 1H), 7.82 (d, J=3.5 Hz, 1H), 7.24 (d, J=7.7 Hz, 1H), 6.80 (s, 1H), 6.40 (d, J=35.7 Hz, 1H), 5.25 (s, 1H), 4.67 (d, J=7.0 Hz, 2H), 4.50 (t, J=5.7 Hz, 1H), 4.40 (t, J=10.3 Hz, 0.5H), 4.26 (t, J=10.3 Hz, 0.5H), 4.02 (s, 3H), 3.80 (s, 4H), 3.63-3.79 (m, 2H), 3.58 (d, J=17.5 Hz, 2H), 2.89 (d, J=18.9 Hz, 2H), 2.26 (d, J=7.5 Hz, 3H); MS (ES) m/z: 547.0[M–H]$^-$

Synthesis Example 14: Compound #61

(2S,3R,4R,5S,6R)-2-(7-((2,3-dihydrobenzo[b][1,4]dioxin-6-yl)methyl)-4-hydroxy-2,3-dihydrobenzofuran-5-yl)-5-fluoro-6-(hydroxymethyl)tetrahydro-2H-pyran-3,4-diol

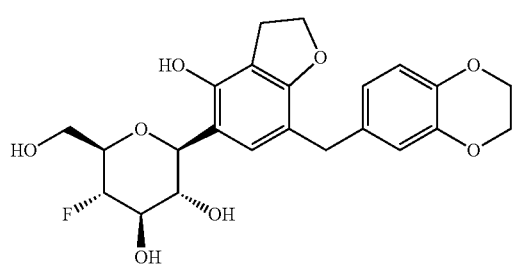 [SMILES: OC[C@H]1O[C@@H](c2cc(Cc3ccc4c(c3)OCCO4)c3c(c2O)CCO3)[C@H](O)[C@@H](O)[C@@H]1F]

Step 1: 5-Bromo-2,3-dihydrobenzofuran-4-ol 2,3-dihydrobenzofuran-4-ol (3000 mg, 20.93 mmol) was dissolved in methanol (100 mL), then cooled to –40° C. To the mixture was then added pyridine tribromide in portions (7.44 g, 20.9 mmol). The resulting mixture was stirred at –40° C. for ½ h, then warmed to room temperature and stirred at room temperature for 16 h. The solvent was removed under reduced pressure. The residue was partitioned between EtOAc and 1N HCl aqueous solution. The combined EtOAc extracts were dried over $Na_2SO_4$, filtered, concentrated. The residue was purified by flash column chromatography on silica gel (80 g, EtOAc/heptane: 0>>>10%) to yield 5-bromo-2,3-dihydrobenzofuran-4-ol as a white solid. $^1$H NMR (CHLOROFORM-d) δ: 7.17 (d, J=8.6 Hz, 1H), 6.32 (d, J=8.6 Hz, 1H), 5.48-5.63 (m, 1H), 4.61 (t, J=8.8 Hz, 2H), 3.21 (t, J=8.8 Hz, 2H).

Step 2: 5-Bromo-7-iodo-2,3-dihydrobenzofuran-4-ol

To 5-bromo-2,3-dihydrobenzofuran-4-ol (689 mg, 3.20 mmol) in 30 ml of acetonitrile was added NIS (N-iodosuccinimide) (757 mg, 3.36 mmol) and the reaction mixture was stirred at room temperature for 2 h. The mixture was concentrated and the residue was purified by flash column chromatography on silica gel (EtOAc/heptane: 0>>>5%>>>20%) to yield 5-bromo-7-iodo-2,3-dihydrobenzofuran-4-ol as a white solid. $^1$H NMR (CHLOROFORM-d) δ: 7.51 (s, 1H), 5.52 (s, 1H), 4.70 (t, J=8.8 Hz, 2H), 3.34 (t, J=8.8 Hz, 2H).

Step 3: 4-(Benzyloxy)-5-bromo-7-iodo-2,3-dihydrobenzofuran

A 250 ml round bottom flask was charged with 5-bromo-7-iodo-2,3-dihydrobenzofuran-4-ol (1.10 g, 3.23 mmol) and $K_2CO_3$. To the mixture was then added acetone (30 mL). The resulting mixture was stirred at room temperature for 5 min, then benzyl bromide (0.46 ml, 3.87 mmol) was added and the resulting mixture was stirred at 50° C. for 3 h. The solvent was removed under reduced pressure and the residue was purified by flash column chromatography on silica gel (EtOAc/heptane: 0>>>10%) to yield 4-(benzyloxy)-5-bromo-7-iodo-2,3-dihydrobenzofuran as a white solid. $^1$H NMR (CHLOROFORM-d) δ: 7.65 (s, 1H), 7.33-7.47 (m, 5H), 5.04 (s, 2H), 4.58 (t, J=8.6 Hz, 2H), 3.18 (t, J=8.8 Hz, 2H). LC/MS: m/z (M+Na)$^+$452.9.

Step 4: (4-(Benzyloxy)-5-bromo-2,3-dihydrobenzofuran-7-yl)(2,3-dihydrobenzo[b][1,4]dioxin-6-yl)methanol To a solution of 4-(benzyloxy)-5-bromo-7-iodo-2,3-dihydrobenzofuran (1.40 g, 3.25 mmol) in anhydrous THF (4 mL) was added i-PrMgCl.LiCl (2.50 ml, 1.3 M) at –78° C. under argon and the resulting mixture was stirred at –40° C. for 40 min. Then a pre-cooled solution of 2,3-dihydrobenzo[b][1,4]dioxine-6-carbaldehyde (559.8 mg, 3.41 mmol) in THF (3 ml) was added to the above mixture dropwise, and the resulting mixture was stirred at –78° C. for 1 h. The resulting mixture was quenched with aqueous $NH_4Cl$ solution, extracted with EtOAc three times. The combined organic extracts were washed with brine, dried over $Na_2SO_4$, filtered, and concentrated. The residue was purified by flash column chromatography on silica gel (EtOAc/heptane: 0>>>10%>>>40%) to yield (4-(benzyloxy)-5-bromo-2,3-dihydrobenzofuran-7-yl)(2,3-dihydrobenzo[b][1,4]dioxin-6-yl)methanol as a white solid. $^1$H NMR (CHLOROFORM-d) δ: 7.43-7.48 (m, 2H), 7.31-7.41 (m, 3H), 7.29 (s, 1H), 6.77-6.96 (m, 3H), 5.76 (d, J=4.5 Hz, 1H), 5.02 (s, 2H), 4.53 (t, J=8.8 Hz, 2H), 4.23 (s, 4H), 3.07 (t, J=8.6 Hz, 2H), 2.68 (d, J=5.1 Hz, 1H). LC/MS: m/z (MH$^+$-18): 451.0.

Step 5: 6-((4-(Benzyloxy)-5-bromo-2,3-dihydrobenzofuran-7-yl)methyl)-2,3-dihydrobenzo[b][1,4]dioxine A 100 ml round bottom flask was charged with (4-(benzyloxy)-5-bromo-2,3-dihydrobenzofuran-7-yl)(2,3-dihydrobenzo[b][1,4]dioxin-6-yl)methanol (1.07 g, 2.28 mmol) and DCM (30 mL) was added. To the mixture was added triethylsilane (1.09 ml, 6.84 mmol) at 0° C., followed by the addition of BF$_3$.Et$_2$O (0.43 ml, 3.42 mmol)). The reaction mixture was kept stirring at 0° C. for ½ h. Saturated aqueous NaHCO$_3$ was added and the mixture was stirred at 0° C. for 20 min, and concentrated. The residue was extracted with dichloromethane three times and the combined organic extracts were washed with brine, dried over Na$_2$SO$_4$, filtered and concentrated. The residue was purified by flash column chromatography on silica gel (EtOAc/heptane: 0>>>20%) to yield 6-((4-(benzyloxy)-5-bromo-2,3-dihydrobenzofuran-7-yl)methyl)-2,3-dihydrobenzo[b][1,4]dioxine as colorless syrup. $^1$H NMR (CHLOROFORM-d) δ: 7.43-7.50 (m, 2H), 7.30-7.42 (m, 3H), 7.07 (s, 1H), 6.76-6.82 (m, 1H), 6.66-6.73 (m, 2H), 5.00 (s, 2H), 4.52 (t, J=8.6 Hz, 2H), 4.23 (s, 4H), 3.72 (s, 2H), 3.10 (t, J=8.6 Hz, 2H). LC/MS: m/z (M+Na)$^+$: 475.05.

Step 6: (3R,4R,5R,6R)-2-(4-(benzyloxy)-7-((2,3-dihydrobenzo[b][1,4]dioxin-6-yl)methyl)-2,3-dihydrobenzofuran-5-yl)-3,4-bis((tert-butyldimethylsilyl)oxy)-6-(((tert-butyldimethylsilyl)oxy)methyl)-5-fluorotetrahydro-2H-pyran-2-ol A 25 ml round bottom flask was charged with 6-((4-(benzyloxy)-5-bromo-2,3-dihydrobenzofuran-7-yl)methyl)-2,3-dihydrobenzo[b][1,4]dioxine (291.6 mg, 0.64 mmol) and evacuated, re-filled with argon, and this process was repeated twice. To the mixture was then added anhydrous THF (2 mL) and the solution was cooled to −78° C. n-BuLi (0.4 ml, 1.6 M in hexanes) was added to the resulting solution and the resulting light orange mixture was stirred at −78° C. for 30 min, then transferred to a cooled solution of (3R,4R,5R,6R)-3,4-bis((tert-butyldimethylsilyl)oxy)-6-(((tert-butyldimethylsilyl)oxy)methyl)-5-fluorotetrahydro-2H-pyran-2-one (336.4 mg, 0.64 mmol) in THF (3 ml) under argon (at −78° C.) via cannula. The reaction mixture was stirred at −78° C. for 1.5 h, quenched with aq. NH$_4$Cl, extracted with EtOAc three times. The combined organic layer was washed with brine, dried with Na$_2$SO$_4$. The inorganic salt was filtered off and the filtrate was concentrated under reduced pressure to yield (3R,4R,5R,6R)-2-(4-(benzyloxy)-7-((2,3-dihydrobenzo[b][1,4]dioxin-6-yl)methyl)-2,3-dihydrobenzofuran-5-yl)-3,4-bis((tert-butyldimethylsilyl)oxy)-6-(((tert-butyldimethylsilyl)oxy)methyl)-5-fluorotetrahydro-2H-pyran-2-ol, which was used for the next step reaction without further purification. LC/MS m/z (M+Na)$^+$: 919.3.

Step 7: (2S,3R,4R,5S,6R)-2-(4-(benzyloxy)-7-((2,3-dihydrobenzo[b][1,4]dioxin-6-yl)methyl)-2,3-dihydrobenzofuran-5-yl)-5-fluoro-6-(hydroxymethyl)tetrahydro-2H-pyran-3,4-diol Et$_3$SiH (0.34 ml, 2.12 mmol) was added in one portion to a stirred solution of (3R,4R,5R,6R)-2-(4-(benzyloxy)-7-((2, 3-dihydrobenzo[b][1,4]dioxin-6-yl)methyl)-2,3-dihydrobenzofuran-5-yl)-3,4-bis((tert-butyldimethylsilyl)oxy)-6-(((tert-butyldimethylsilyl)oxy)methyl)-5-fluorotetrahydro-2H-pyran-2-ol (577 mg, 0.64 mmol) in dry DCM (5 ml)/ACN (5 ml) at 0° C. under an atmosphere of argon. After 3 min, BF$_3$.Et$_2$O (95 µL) was added dropwise to the above solution by syringe. The resulting mixture was stirred at −4° C. (in a diluted brine-ice bath) for 15 min, then another portion of BF$_3$.Et$_2$O (95 µL) was added and the mixture was stirred at −4° C. for 25 min, quenched with saturated NaHCO$_3$ (10 ml). The volatile organic solvent was evaporated under reduced pressure and the residue was extracted with EtOAc three times. The combined extracts were washed with brine, dried with Na$_2$SO$_4$, and concentrated under vacuum to yield a white foam, which was purified by flash column chromatography on silica gel (12 g, EtOAc/heptane: 0>>>10%>>>90%) to yield (2S,3R,4R,5S,6R)-2-(4-(benzyloxy)-7-((2,3-dihydrobenzo[b][1,4]dioxin-6-yl)methyl)-2,3-dihydrobenzofuran-5-yl)-5-fluoro-6-(hydroxymethyl)tetrahydro-2H-pyran-3,4-diol as a white solid. $^1$H NMR (METHANOL-d$_4$) δ: 7.47 (d, J=7.1 Hz, 2H), 7.24-7.42 (m, 3H), 7.01 (s, 1H), 6.62-6.72 (m, 3H), 5.03-5.11 (m, 1H), 4.96-5.02 (m, 1H), 4.48-4.59 (m, 3H), 4.14-4.37 (m, 5H), 3.58-3.77 (m, 6H), 3.40-3.49 (m, 1H), 3.22 (t, J=8.8 Hz, 2H).

Step 8: (2S,3R,4R,5S,6R)-2-(7-((2,3-dihydrobenzo[b][1,4]dioxin-6-yl)methyl)-4-hydroxy-2,3-dihydrobenzofuran-5-yl)-5-fluoro-6-(hydroxymethyl)tetrahydro-2H-pyran-3,4-diol (2S,3R,4R,5S,6R)-2-(4-(benzyloxy)-7-((2,3-dihydrobenzo[b][1,4]dioxin-6-yl)methyl)-2,3-dihydrobenzofuran-5-yl)-5-fluoro-6-(hydroxymethyl)tetrahydro-2H-pyran-3,4-diol (70 mg, 0.13 mmol) was dissolved in EtOAc (8 mL). To the resulting mixture was then added 30% HCl (15 µL) and 20% Pd(OH)$_2$ (70 mg) and the hydrogen bottle was evacuated, re-filled with hydrogen (43 psi), and this process was repeated twice. The mixture was shaken with Parr hydrogenation shaker for 2 h. The catalyst was filtered off and the solvent was evaporated to yield (2S,3R,4R,5S,6R)-2-(7-((2,3-dihydrobenzo[b][1,4]dioxin-6-yl)methyl)-4-hydroxy-2,3-dihydrobenzofuran-5-yl)-5-fluoro-6-(hydroxymethyl)tetrahydro-2H-pyran-3,4-diol as a white solid.
$^1$H NMR (MeOH) δ: 6.88 (s, 1H), 6.60-6.68 (m, 3H), 4.50-4.58 (m, 2H), 4.45-4.50 (m, 1H), 4.26-4.44 (m, 1H), 4.16 (s, 4H), 3.66 (d, J=3.5 Hz, 5H), 3.55 (s, 2H), 3.13 (t, J=8.6 Hz, 2H). LC/MS: m/z (MH$^+$): 449.20.

Synthesis Example 15: Compound #65

(2S,3R,4R,5S,6R)-2-(7-((2,3-dihydrobenzo[b][1,4]dioxin-6-yl)methyl)-4-methoxy-2,3-dihydrobenzofuran-5-yl)-5-fluoro-6-(hydroxymethyl)tetrahydro-2H-pyran-3,4-diol

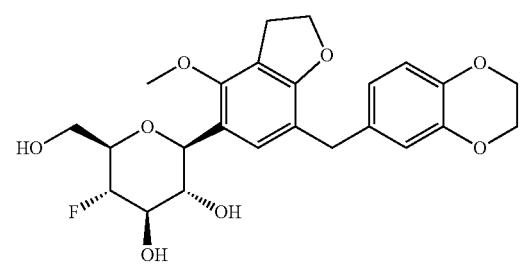 [SMILES: COc1c([C@@H]2O[C@H](CO)[C@@H](F)[C@H](O)[C@H]2O)cc(Cc2ccc3c(c2)OCCO3)c2c1CCO2]

To a 4 ml vial was added (2S,3R,4R,5S,6R)-2-(7-((2,3-dihydrobenzo[b][1,4]dioxin-6-yl)methyl)-4-hydroxy-2,3-dihydrobenzofuran-5-yl)-5-fluoro-6-(hydroxymethyl)tetrahydro-2H-pyran-3,4-diol, prepared as described in Synthesis Example 14 (18.7 mg, 0.042 mmol), K$_2$CO$_3$ (28.8 mg, 0.21 mmol), acetone (1 mL), followed by MeI (26 µL) and the vial was sealed with a TFE cap and the mixture was stirred at room temperature for 16 h. The solid was filtered off and the filtrate was concentrated under reduced pressure. The residue was re-dissolved in MeOH (2 mL) and subjected to Gilson HPLC purification (15 min gradient time, 10%>>>90% ACN, flow rate: 35 ml/min) to yield (2S,3R,4R,5S,6R)-2-(7-((2,3-dihydrobenzo[b][1,4]dioxin-6-yl)methyl)-4-methoxy-2,3-dihydrobenzofuran-5-yl)-5-fluoro-6-(hydroxymethyl)tetrahydro-2H-pyran-3,4-diol as a white solid.

$^1$H NMR (CD$_3$CN): 7.01 (s, 1H), 6.76 (d, J=8.59 Hz, 1H), 6.72 (s, 1H), 6.71 (d, J=8.59 Hz, 1H), 4.58 (t, J=8.59 Hz, 2H), 4.52 (d, J=9.60 Hz, 1H), 4.31 (dt, J=51.03 and 9.09 Hz, 1H), 4.22 (m, 1H), 4.21 (s, 3H), 3.81 (s, 3H), 3.67-3.78 (4H), 3.52-3.63 (3H), 3.31 (t, J=8.59 Hz, 2H). LC/MS: m/z (M+NH$_4$)$^+$: 480.1.

Synthesis Example 16: Compound #75

(2S,3R,4R,5S,6R)-2-(7-((2,3-dihydrobenzo[b][1,4]dioxin-6-yl)methyl)-3-(hydroxymethyl)-2,3-dihydrobenzofuran-5-yl)-5-fluoro-6-(hydroxymethyl)-tetrahydro-2H-pyran-3,4-diol

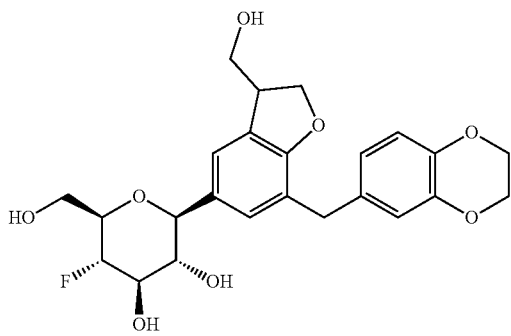 [SMILES: OCC1COc2c(Cc3ccc4c(c3)OCCO4)cc([C@@H]3O[C@H](CO)[C@@H](F)[C@H](O)[C@H]3O)cc21]

To a mixture of 2-(2-hydroxyphenyl)acetic acid (15.0 g, 98.59 mmol, 1.00 equiv) in methanol (200 mL) was added nBu$_4$NBr$_3$ (47.56 g, 98.67 mmol, 1.00 equiv) at 0° C. The reaction was stirred for 16 h at room temperature. NH$_4$Cl/H$_2$O was added and the mixture was extracted with EtOAc thrice. The combined extracts were washed with brine and dried over Na$_2$SO$_4$. The mixture was then concentrated and purified by chromatography on silica gel (5:1 PE/EA) to yield methyl 2-(5-bromo-2-hydroxyphenyl)acetate as a light yellow solid.

To a mixture of methyl 2-(5-bromo-2-hydroxyphenyl)acetate (5.4 g, 22.03 mmol, 1.00 equiv) in CH$_3$CN (100 mL) was added NIS (4.96 g, 22.04 mmol, 1.00 equiv) in portions. The reaction was stirred for 3 h at room temperature. NH$_4$Cl/H$_2$O was added and the mixture was extracted with EtOAc thrice. The combined extracts were washed with sodium bicarbonate and Na$_2$SO$_3$ solution. The mixture was then concentrated and purified by chromatography on silica gel (10:1 PE/EA) to yield methyl 2-(5-bromo-2-hydroxy-3-iodophenyl)acetate as an off-white solid.

To a mixture of methyl 2-(5-bromo-2-hydroxy-3-iodophenyl)acetate (5.5 g, 14.83 mmol, 1.00 equiv) in N,N-dimethylformamide (100 mL) with potassium carbonate (3.07 g, 22.21 mmol, 1.50 equiv) was added MeI (2.52 g, 1.20 equiv) dropwise. The reaction was stirred for 16 h at room temperature. NH$_4$Cl/H$_2$O was added and the mixture was extracted with EtOAc thrice. The combined extracts were washed with brine and dried over Na$_2$SO$_4$. The mixture was then concentrated and purified by chromatography on silica gel (5:1 PE/EA) to yield methyl 2-(5-bromo-3-iodo-2-methoxyphenyl)acetate as a yellow oil.

To a mixture of methyl 2-(5-bromo-3-iodo-2-methoxyphenyl)acetate (5.2 g, 13.51 mmol, 1.00 equiv) in acetonitrile (50 mL) with 4-acetamidobenzene-1-sulfonyl azide (3.9 g, 16.23 mmol, 1.20 equiv) was added DBU (1,8-diazabicyclo[5.4.0]undec-7-ene) (16.25 g, 106.91 mmol, 1.20 equiv), the reaction was stirred for 16 h at room temperature. NH$_4$Cl/H$_2$O was added and the mixture was extracted with EtOAc thrice. The combined extracts were washed with brine and dried over Na$_2$SO$_4$. The mixture was then concentrated and purified by chromatography on silica gel (10:1 PE/EA) to yield methyl 2-(5-bromo-3-iodo-2-methoxyphenyl)-2-diazoacetate as a yellow oil.

To a mixture of Rh$_2$—(S-DOSP)$_4$ (tetrakis[(S)-(−)-N-(p-dodecylphenylsulfonyl)prolinato]dirhodium (II)) (110 mg, 0.01 equiv) in hexane (50 mL) was added methyl 2-(5-bromo-3-iodo-2-methoxyphenyl)-2-diazoacetate (2.4 g, 5.84 mmol, 1.00 equiv) in hexane (10 mL) at 0° C. The reaction was stirred for 1 h at room temperature. NH$_4$Cl/H$_2$O was added and the mixture was extracted with EtOAc thrice. The combined extracts were washed with brine and dried over Na$_2$SO$_4$. The mixture was then concentrated and purified by chromatography on silica gel (5:1 PE/EA) to yield methyl 5-bromo-7-iodo-2,3-dihydrobenzofuran-3-carboxylate as a light yellow solid.

To a mixture of methyl 5-bromo-7-iodo-2,3-dihydrobenzofuran-3-carboxylate (200 mg, 0.52 mmol, 1.00 equiv) in THF (3 mL) was added DIBAL (diisobutylaluminium hydride) (25% in hexane) (890 g, 6.26 mol, 3.00 equiv) at 0° C. The reaction was stirred for 1 h at 0° C. NH$_4$Cl/H$_2$O was added and the mixture was extracted with EtOAc thrice. The combined extracts were washed with brine and dried over Na$_2$SO$_4$. The mixture was then concentrated and purified by chromatography on silica gel (5:1 PE/EA) to yield (5-bromo-7-iodo-2,3-dihydrobenzofuran-3-yl)methanol as a light yellow oil.

To a mixture of (5-bromo-7-iodo-2,3-dihydrobenzofuran-3-yl)methanol (50 mg, 0.14 mmol, 1.00 equiv) in N,N-dimethylformamide (3 mL) was added sodium hydride (11.3 mg, 0.47 mmol, 2.00 equiv). The reaction was stirred for 20 min at room temperature. To the mixture was then added BnBr (48 mg, 0.28 mmol, 2.00 equiv). The reaction was stirred for 3 h at room temperature. NH$_4$Cl/H$_2$O was added and the mixture was extracted with EtOAc thrice. The combined extracts were washed with brine and dried over Na$_2$SO$_4$. The mixture was then concentrated and purified by chromatography on silica gel (5:1 PE/EA) to yield 3-((benzyloxy)methyl)-5-bromo-7-iodo-2,3-dihydrobenzofuran as a yellow solid.

To a mixture of 3-((benzyloxy)methyl)-5-bromo-7-iodo-2,3-dihydrobenzofuran (444 mg, 1.00 mmol, 1.00 equiv) in tetrahydrofuran (5 mL) was added iPrMgCl.LiCl (0.77 mL) at −78° C. To the resulting mixture was then added a solution of 2,3-dihydro-1,4-benzodioxine-6-carbaldehyde (149 mg, 0.91 mmol, 0.91 equiv) in tetrahydrofuran (2 mL) dropwise with stirring at −78° C. The resulting solution was stirred for 2 h at −78° C. NH$_4$Cl/H$_2$O was added and the mixture was extracted with EtOAc thrice. The combined extracts were washed with brine and dried over Na$_2$SO$_4$. The mixture was then concentrated and purified by chromatography on silica gel (5:1 PE/EA) to yield (3-((benzyloxy)methyl)-5-bromo-2,3-dihydrobenzofuran-7-yl)(2,3-dihydrobenzo[b][1,4]dioxin-6-yl)methanol as a colorless oil.

To a mixture of (3-((benzyloxy)methyl)-5-bromo-2,3-dihydrobenzofuran-7-yl)(2,3-dihydrobenzo[b][1,4]dioxin-6-yl)methanol (240 mg, 0.50 mmol, 1.00 equiv) in dichloromethane (5 mL) with Et$_3$SiH (115 mg, 0.99 mmol, 1.99 equiv) was added BF$_3$.Et$_2$O (106 mg, 0.75 mmol, 1.50 equiv) at 0° C. The reaction was stirred for 2 h at 0° C. Sodium bicarbonate/H$_2$O was added and the mixture was extracted with dichloromethane thrice. The combined extracts were washed with brine and dried over Na$_2$SO$_4$. The mixture was then concentrated and purified by chromatography on silica gel (3:1 PE/EA) to yield 6-((3-((benzyloxy)methyl)-5-bromo-2,3-dihydrobenzofuran-7-yl)methyl)-2,3-dihydrobenzo[b][1,4]dioxine as a colorless oil.

To a mixture of 6-((3-((benzyloxy)methyl)-5-bromo-2,3-dihydrobenzofuran-7-yl)methyl)-2,3-dihydrobenzo[b][1,4]dioxine (190 mg, 0.41 mmol, 1.00 equiv) in tetrahydrofuran (4 mL) was added n-BuLi (017 mL, 2.5M/L) dropwise with stirring at −78° C. The mixture was stirred for 30 min. (3R,4R,5R,6R)-3,4-bis(benzyloxy)-6-[(benzyloxy)methyl]-5-fluorooxan-2-one (174 mg, 0.39 mmol, 0.95 equiv) in tetrahydrofuran (2 mL) was then added at −78° C. The reaction was stirred at −78° C. for 2 h. NH$_4$Cl/H$_2$O was added and the mixture was extracted with EtOAc thrice. The combined extracts were washed with brine and dried over Na$_2$SO$_4$. The mixture was then concentrated and purified by chromatography on silica gel (5:1 PE/EA) to yield (3R,4R,5R,6R)-3,4-bis(benzyloxy)-6-((benzyloxy)methyl)-2-(3-((benzyloxy)methyl)-7-((2,3-dihydrobenzo[b][1,4]dioxin-6-yl)methyl)-2,3-dihydrobenzofuran-5-yl)-5-fluorotetrahydro-2H-pyran-2-ol as a colorless oil.

To a mixture of (3R,4R,5R,6R)-3,4-bis(benzyloxy)-6-((benzyloxy)methyl)-2-(3-((benzyloxy)methyl)-7-((2,3-dihydrobenzo[b][1,4]dioxin-6-yl)methyl)-2,3-dihydrobenzofuran-5-yl)-5-fluorotetrahydro-2H-pyran-2-ol (210 mg, 0.25 mmol, 1.00 equiv) in dichloromethane (4 mL) with Et$_3$SiH (58 mg, 0.50 mmol, 1.99 equiv) was added BF$_3$.OEt$_2$ (53 mg, 0.37 mmol, 1.5 equiv) at 0° C. The reaction was stirred for 2 h at 0° C. Sodium bicarbonate/H$_2$O was added and the mixture was extracted with dichloromethane thrice. The combined extracts were washed with brine and dried over Na$_2$SO$_4$. The mixture was then concentrated and purified by chromatography on silica gel (4:1 PE/EA) to yield 6-((3-((benzyloxy)methyl)-5-((2S,3S,4R,5R,6R)-3,4-bis(benzyloxy)-6-((benzyloxy)methyl)-5-fluorotetrahydro-2H-pyran-2-yl)-2,3-dihydrobenzofuran-7-yl)methyl)-2,3-dihydrobenzo[b][1,4]dioxine as a colorless oil.

To a mixture of 6-((3-((benzyloxy)methyl)-5-((2S,3S,4R,5R,6R)-3,4-bis(benzyloxy)-6-((benzyloxy)methyl)-5-fluorotetrahydro-2H-pyran-2-yl)-2,3-dihydrobenzofuran-7-yl)methyl)-2,3-dihydrobenzo[b][1,4]dioxine (100 mg, 0.12 mmol, 1.00 equiv) in methanol (15 mL) was added Palladium carbon (80 mg). H$_2$ was introduced. The reaction was stirred overnight at 40° C. The solids were filtered out. The mixture was then concentrated and purified by chromatography on C18 (10%-40% CH$_3$CN/H$_2$O) to yield (2S,3R,4R,5S,6R)-2-(7-((2,3-dihydrobenzo[b][1,4]dioxin-6-yl)methyl)-3-(hydroxymethyl)-2,3-dihydrobenzofuran-5-yl)-5-fluoro-6-(hydroxymethyl)tetrahydro-2H-pyran-3,4-diol as a white solid.

$^1$H NMR (300 MHz, CD$_3$OD): $^1$H NMR (300 MHz, CD$_3$OD): δ: 7.15 (s, 1H), 6.99 (s, 1H), 6.67 (s, 3H), 4.65-4.59 (m, 2H), 4.42-4.48 (m, 1H), 4.43 (t, J=9.3 Hz, 0.5H), 4.26 (t, J=9.3 Hz, 0.5H), 4.17 (s, 4H), 4.08 (d, J=9.6 Hz, 1H), 3.80-3.55 (m, 9H), 3.43-3.30 (m, 1H). MS (ES) m/z: 480.05 [M+18]$^+$

Synthesis Example 17: Compound #107

(2S,3R,4R,5S,6R)-2-(7-((2,3-dihydrobenzo[b][1,4] oxathiin-6-yl)methyl)-4-methoxy-2,3-dihydrobenzofuran-5-yl)-5-fluoro-6-(hydroxymethyl)-tetrahydro-2H-pyran-3,4-diol

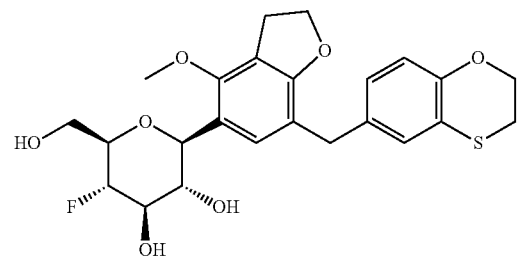 [SMILES: COc1c([C@@H]2O[C@H](CO)[C@@H](F)[C@H](O)[C@H]2O)cc(Cc2ccc3c(c2)SCCO3)c2c1CCO2]

To a mixture of 2,3-dihydrobenzofuran-4-ol (5 g, 36.72 mmol, 1.00 equiv) in MeOH (100 mL) was added pyridine hydrobromide perbromide (12.4 g, 36.81 mmol, 1.00 equiv) at −20° C. The reaction was stirred at −20° C. for 2 h. Ice/H$_2$O was added and the mixture was extracted with EA thrice. The combined extracts were washed with brine and dried over Na$_2$SO$_4$. The mixture was then concentrated and purified by chromatography on silica gel (10:1 PE/EA) to yield 5-bromo-2,3-dihydrobenzofuran-4-ol as a white solid. $^1$H NMR (300 MHz, CDCl$_3$) δ: 7.18 (d, J=8.4 Hz, 1H), 6.32 (d, J=8.4 Hz, 1H), 5.52 (s, 1H), 4.59 (t, J=8.7 Hz, 2H), 3.22 (t, J=8.7 Hz, 2H).

To a mixture of 5-bromo-2,3-dihydrobenzofuran-4-ol (1 g, 4.65 mmol, 1.00 equiv) in dichloromethane (30 mL) with dichloro(methoxy)methane (1.06 g, 9.22 mmol, 1.98 equiv) was added TiCl$_4$ (1.32 g, 6.96 mmol, 1.50 equiv) at 0° C. The reaction was stirred for 1 h at room temperature. Sodium bicarbonate/H$_2$O was added and the mixture was extracted with dichloromethane thrice. The combined extracts were washed with brine and dried over Na$_2$SO$_4$. The mixture was then concentrated and purified by chromatography on silica gel (1:1 PE/EA) to yield 5-bromo-4-hydroxy-2,3-dihydrobenzofuran-7-carbaldehyde as a pink solid. $^1$H NMR (300 MHz, DMSO) δ: 11.08 (s, 1H), 9.85 (s, 1H), 7.62 (s, 1H), 4.72 (t, J=9.0 Hz, 2H), 3.18 (t, J=9.0 Hz, 2H).

To a mixture of 5-bromo-4-hydroxy-2,3-dihydrobenzofuran-7-carbaldehyde (700 mg, 2.88 mmol, 1.00 equiv) in dichloromethane (10 mL) with K$_2$CO$_3$ (799 mg, 5.78 mmol, 2.01 equiv) was added BnBr (541 mg, 3.16 mmol, 1.10 equiv). The reaction was stirred for 1 h at room temperature. Water was added and the mixture was extracted with EA thrice. The combined extracts were washed with brine and dried over Na$_2$SO$_4$. The mixture was then concentrated and purified by chromatography on silica gel (5:1 PE/EA) to yield 4-(benzyloxy)-5-bromo-2,3-dihydrobenzofuran-7-carbaldehyde as a yellow oil. $^1$H NMR (300 MHz, DMSO) δ: 9.94 (s, 1H), 9.84 (s, 1H), 7.71 (s, 1H), 7.50-7.53 (m, 2H), 7.34-7.45 (m, 3H), 5.37 (s, 2H), 4.73 (t, J=9.0 Hz, 2H), 3.51 (t, J=9.0 Hz, 2H).

To a mixture of 6-bromo-2,3-dihydrobenzo[b][1,4]oxathiine (510 mg, 2.21 mmol, 1.10 equiv) in THF (10 mL) was added n-BuLi (0.88 mL, 1.10 equiv, 2.5M) at −78° C. The solution was stirred for 30 min at −78° C. After that was added a solution of 4-(benzyloxy)-5-bromo-2,3-dihydrobenzofuran-7-carbaldehyde (666 mg, 2.00 mmol, 1.00 equiv) in tetrahydrofuran (2 mL) at −78° C. The reaction was stirred for at −78° C. 1 h. NH₄Cl/H₂O was added and the mixture was extracted with EtOAc thrice. The combined extracts were washed with brine and dried over Na₂SO₄. The mixture was then concentrated and purified by chromatography on silica gel (1:1 PE/EA) to yield (4-(benzyloxy)-5-bromo-2,3-dihydrobenzofuran-7-yl)(2,3-dihydrobenzo[b][1,4]oxathiin-6-yl)methanol as a yellow oil. MS (ES) m/z: 467 [M-OH]⁺

To a mixture of (4-(benzyloxy)-5-bromo-2,3-dihydrobenzofuran-7-yl)(2,3-dihydrobenzo[b][1,4]oxathiin-6-yl)methanol (700 mg, 1.44 mmol, 1.00 equiv) in dichloromethane (10 mL) with Et₃SiH (503 mg, 4.33 mmol, 3.00 equiv) was added CF₃COOH (329 mg, 2.89 mmol, 2.00 equiv) at 0° C. The reaction was stirred for 1 h at 0° C. Sodium bicarbonate/H₂O was added and the mixture was extracted with dichloromethane thrice. The combined extracts were washed with brine and dried over Na₂SO₄. The mixture was then concentrated and purified by chromatography on silica gel (5:1 PE/EA) to yield 6-((4-(benzyloxy)-5-bromo-2,3-dihydrobenzofuran-7-yl)methyl)-2,3-dihydrobenzo[b][1,4]oxathiine as a yellow solid. ¹H NMR (300 MHz, CDCl₃) δ: 7.45-7.48 (m, 2H), 7.33-7.40 (m, 3H), 7.06 (s, 1H), 6.81-6.87 (m, 2H), 6.74 (d, J=8.1 Hz, 1H), 5.01 (s, 2H), 4.52 (t, J=8.7 Hz, 2H), 4.37-4.39 (m, 2H), 3.70 (s, 2H), 3.10-3.13 (m, 4H).

To a mixture of 6-((4-(benzyloxy)-5-bromo-2,3-dihydrobenzofuran-7-yl)methyl)-2,3-dihydrobenzo[b][1,4]oxathiine (150 mg, 0.32 mmol, 1.10 equiv) in tetrahydrofuran (2 mL) was added n-BuLi (0.13 mL, 1.10 equiv, 2.5M) at −78° C. The reaction was stirred for 30 min at −78° C. To the resulting mixture was then added a solution of (3R,4R,5R,6R)-3,4-bis(benzyloxy)-6-[(benzyloxy)methyl]-5-fluorooxan-2-one (131 mg, 0.29 mmol, 1.00 equiv) in tetrahydrofuran (1 mL) at −78° C. The reaction was stirred at −78° C. for 1 h. NH₄Cl/H₂O was added and the mixture was extracted with EtOAc thrice. The combined extracts were washed with brine and dried over Na₂SO₄. The mixture was then concentrated and purified by chromatography on silica gel (1:1 PE/EA) to yield (3R,4R,5R,6R)-3,4-bis(benzyloxy)-2-(4-(benzyloxy)-7-((2,3-dihydrobenzo[b][1,4]oxathiin-6-yl)methyl)-2,3-dihydrobenzofuran-5-yl)-6-((benzyloxy)methyl)-5-fluorotetrahydro-2H-pyran-2-ol as a yellow oil. MS (ES) m/z: 823 [M-OH]⁺

To a mixture of (3R,4R,5R,6R)-3,4-bis(benzyloxy)-2-(4-(benzyloxy)-7-((2,3-dihydrobenzo[b][1,4]oxathiin-6-yl)methyl)-2,3-dihydrobenzofuran-5-yl)-6-((benzyloxy)methyl)-5-fluorotetrahydro-2H-pyran-2-ol (160 mg, 0.19 mmol, 1.00 equiv) in dichloromethane (1 mL) with Et₃SiH (45 mg, 0.39 mmol, 2.03 equiv) was added BF₃.Et₂O (27 mg, 0.19 mmol, 1.00 equiv) at 0° C. The reaction was stirred for 1 h at 0° C. Sodium bicarbonate/H₂O was added and the mixture was extracted with dichloromethane thrice. The combined extracts were washed with brine and dried over Na₂SO₄. The mixture was then concentrated and purified by chromatography on silica gel (5:1 PE/EA) to yield 6-((4-(benzyloxy)-5-((2S,3S,4R,5R,6R)-3,4-bis(benzyloxy)-6-((benzyloxy)methyl)-5-fluorotetrahydro-2H-pyran-2-yl)-2,3-dihydrobenzofuran-7-yl)methyl)-2,3-dihydrobenzo[b][1,4]oxathiine as a yellow oil. MS (ES) m/z: 826 [M+H]⁺.

To a mixture of 6-((4-(benzyloxy)-5-((2S,3S,4R,5R,6R)-3,4-bis(benzyloxy)-6-((benzyloxy)methyl)-5-fluorotetrahydro-2H-pyran-2-yl)-2,3-dihydrobenzofuran-7-yl)methyl)-2,3-dihydrobenzo[b][1,4]oxathiine (100 mg, 0.12 mmol, 1.00 equiv) in dichloromethane (5 mL) with 1,2,3,4,5-pentamethylbenzene (100 mg, 0.67 mmol, 5.57 equiv) was added BCl₃ (2 mL, 1 N, 0.002 mmol, 16.7 equiv) at −78° C. The reaction was stirred at −78° C. for 1 h. 5 mL of methanol was added. The mixture was then concentrated and purified by chromatography on a C18 reversed phase column (0%-45% CH₃CN/H₂O) to yield (2S,3R,4R,5S,6R)-2-(7-((2,3-dihydrobenzo[b][1,4]oxathiin-6-yl)methyl)-4-hydroxy-2,3-dihydrobenzofuran-5-yl)-5-fluoro-6-(hydroxymethyl)tetrahydro-2H-pyran-3,4-diol as a white solid. MS (ES) m/z: 466 [M+H]⁺

To a mixture of (2S,3R,4R,5S,6R)-2-(7-((2,3-dihydrobenzo[b][1,4]oxathiin-6-yl)methyl)-4-hydroxy-2,3-dihydrobenzofuran-5-yl)-5-fluoro-6-(hydroxymethyl)tetrahydro-2H-pyran-3,4-diol (10 mg, 0.02 mmol, 1.00 equiv) in N,N-dimethylformamide (2 mL) with potassium carbonate (20 mg, 0.14 mmol, 6.72 equiv) was added CH₃I (20 mg, 0.14 mmol, 6.55 equiv). The reaction was stirred for 1 h at room temperature. The solids were filtered out. The mixture was then concentrated and purified by chromatography on a C18 reversed phase column (0%-45% CH₃CN/H₂O) to yield (2S,3R,4R,5S,6R)-2-(7-((2,3-dihydrobenzo[b][1,4]oxathiin-6-yl)methyl)-4-methoxy-2,3-dihydrobenzofuran-5-yl)-5-fluoro-6-(hydroxymethyl)tetrahydro-2H-pyran-3,4-diol as a white solid.
¹H NMR (300 MHz, CD3OD) δ: 6.99 (s, 1H), 6.80-6.83 (m, 2H), 6.65 (d, J=3.9 Hz, 1H), 4.51-4.57 (m, 3H), 4.23-4.43 (m, 3H), 3.84 (s, 3H), 3.55-3.82 (m, 7H), 3.32-3.34 (m, 1H), 3.28-3.30 (m, 1H), 3.09-3.11 (m, 2H). MS (ES) m/z: 496.1 [M+NH4]+

Synthesis Example 18: Compound #108

(2S,3R,4R,5S,6R)-5-fluoro-6-(hydroxymethyl)-2-(4-methoxy-7-((1-methyl-1,2,3,4-tetrahydroquinolin-7-yl)methyl)-2,3-dihydrobenzofuran-5-yl)-tetrahydro-2H-pyran-3,4-diol

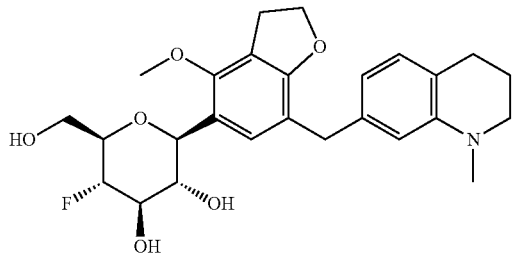 [SMILES: COc1c([C@@H]2O[C@H](CO)[C@@H](F)[C@H](O)[C@H]2O)cc(Cc2ccc3c(c2)N(C)CCC3)c2c1CCO2]

To a mixture of (2S,3R,4R,5S,6R)-5-fluoro-6-(hydroxymethyl)-2-(4-methoxy-7-((1,2,3,4-tetrahydroquinolin-7-yl)methyl)-2,3-dihydrobenzofuran-5-yl)tetrahydro-2H-pyran-3,4-diol, prepared for example, as described in Example 19, below (15 mg, 0.03 mmol, 1.00 equiv) in methanol (1 ml) with HCHO (16.3 mg, 0.16 mmol, 4.99 equiv) was added acetic acid (0.01 mL) and NaBH₃CN (10 mg, 0.16 mmol, 4.87 equiv). The reaction was stirred for 1 h at room temperature. The mixture was then concentrated and purified by chromatography on a C18 (0%-45% CH₃CN/H₂O) reversed phase column to yield (2S,3R,4R,5S,6R)-5-fluoro-6-(hydroxymethyl)-2-(4-methoxy-7-((1-methyl-1,2,3,4-tetrahydroquinolin-7-yl)methyl)-2,3-dihydrobenzofuran-5-yl)tetrahydro-2H-pyran-3,4-diol as a white solid.

¹H NMR (300 MHz, CD₃OD) δ: 7.01 (s, 1H), 6.75-6.77 (m, 1H), 6.54 (s, 1H), 6.38-6.42 (m, 1H), 4.49-4.59 (m, 3H), 4.30-4.43 (m, 0.5H),4.18-4.30 (m, 0.5H), 3.83 (s, 3H), 3.59-3.72 (m, 3H), 3.73-3.78 (m, 7H), 3.27-3.31 (m, 2H), 3.16 (t, J=6.0 Hz, 2H), 2.82 (s, 3H), 2.69 (t, J=6.0 Hz, 2H), 1.94-1.96 (m, 2H). MS (ES) m/z: 474.2 [M+H]⁺.

Synthesis Example 19: Compound #105

(2S,3R,4R,5S,6R)-5-fluoro-6-(hydroxymethyl)-2-(4-methoxy-7-((1,2,3,4-tetrahydroquinolin-7-yl) methyl)-2,3-dihydrobenzofuran-5-yl)-tetrahydro-2H-pyran-3,4-diol

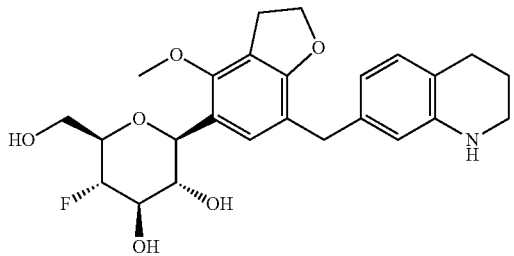 [SMILES: COc1c([C@@H]2O[C@H](CO)[C@@H](F)[C@H](O)[C@H]2O)cc(Cc2ccc3c(c2)NCCC3)c2c1CCO2]

To a mixture of 7-bromo-1,2,3,4-tetrahydroquinoline (2 g, 8.05 mmol, 1.00 equiv) in N,N-dimethylformamide (20 mL) was added sodium hydride (970 mg, 24.25 mmol, 3.01 equiv) at 0° C. The mixture was stirred for 1 h at 0° C. To the resulting mixture was then added 3-bromoprop-1-ene (2.93 g, 24.22 mmol, 3.01 equiv) at 0° C. The reaction was stirred overnight at room temperature. NH₄Cl/H₂O was added and the mixture was extracted with EtOAc thrice. The combined extracts were washed with brine and dried over Na₂SO₄. The mixture was then concentrated and purified by chromatography on silica gel (100:1 PE/EA) to yield 1-allyl-7-bromo-1,2,3,4-tetrahydroquinoline as a colorless oil. ¹H NMR (300 MHz, CDCl₃) b 6.78 (d, J=7.8 Hz, 1H), 6.67 (d, J=7.8 Hz, 1H), 6.65 (s, 1H), 5.76-5.88 (m, 1H), 5.15-5.22 m, 2H), 3.82-3.85 (m, 2H), 3.27 (t, J=5.7 Hz, 2H), 2.67-2.71 (m, 2H), 1.89-1.98 (m, 2H).

To a mixture of 1-allyl-7-bromo-1,2,3,4-tetrahydroquinoline (1.0 g, 3.97 mmol, 1.32 equiv) in tetrahydrofuran (10 mL) was added n-BuLi (1.6 mL, 1.30 equiv, 2.5M) at −78° C. The reaction was stirred for 30 min at −78° C. To the resulting mixture was then added a solution of 4-(benzyloxy)-5-bromo-2,3-dihydro-1-benzofuran-7-carbaldehyde (1.0 g, 3.00 mmol, 1.00 equiv) in tetrahydrofuran (5 mL) at −78° C. The reaction was stirred at −78° C. for 1 h. NH₄Cl/H₂O was added and the mixture was extracted with EtOAc thrice. The combined extracts were washed with brine and dried over Na₂SO₄. The mixture was then concentrated and purified by chromatography on silica gel (1:1 PE/EA) to yield (1-allyl-1,2,3,4-tetrahydroquinolin-7-yl)(4-(benzyloxy)-5-bromo-2,3-dihydrobenzofuran-7-yl)methanol as a yellow oil. MS (ES) m/z: 507[M+H]⁺

To a mixture of (1-allyl-1,2,3,4-tetrahydroquinolin-7-yl)(4-(benzyloxy)-5-bromo-2,3-dihydrobenzofuran-7-yl)methanol (800 mg, 1.58 mmol, 1.00 equiv) in dichloromethane (10 mL) with Et₃SiH (550 mg, 4.73 mmol, 2.99 equiv) was added CF₃COOH (360 mg, 3.16 mmol, 2.00 equiv) at 0° C. The reaction was stirred for 1 h at 0° C. Sodium bicarbonate/H₂O was added and the mixture was extracted with dichloromethane thrice. The combined extracts were washed with brine and dried over Na₂SO₄. The mixture was then concentrated and purified by chromatography on silica gel (5:1 PE/EA) to yield 1-allyl-7-((4-(benzyloxy)-5-bromo-2,3-dihydrobenzofuran-7-yl)methyl)-1,2,3,4-tetrahydroquinoline as a yellow oil. MS (ES) m/z: 491 [M+H]⁺.

To a mixture of 1-allyl-7-((4-(benzyloxy)-5-bromo-2,3-dihydrobenzofuran-7-yl)methyl)-1,2,3,4-tetrahydroquinoline (350 mg, 0.71 mmol, 1.10 equiv) in tetrahydrofuran (3 mL) was added n-BuLi (0.29 mL, 1.10 equiv, 2.5M) at −78° C. The mixture was stirred for 30 min at −78° C. To the resulting mixture was then added a solution of (3R,4R,5R,6R)-3,4-bis(benzyloxy)-6-[(benzyloxy)methyl]-5-fluorooxan-2-one (292 mg, 0.65 mmol, 1.00 equiv) in tetrahydrofuran (1 mL) at −78° C. The reaction was stirred at −78° C. for 1 h. NH₄Cl/H₂O was added and the mixture was extracted with EtOAc thrice. The combined extracts were washed with brine and dried over Na₂SO₄. The mixture was then concentrated and purified by chromatography on silica gel (1:1 PE/EA) to yield (3R,4R,5R,6R)-2-(7-((1-allyl-1,2,3,4-tetrahydroquinolin-7-yl)methyl)-4-(benzyloxy)-2,3-dihydrobenzofuran-5-yl)-3,4-bis(benzyloxy)-6-((benzyloxy)methyl)-5-fluorotetrahydro-2H-pyran-2-ol as a yellow oil. MS (ES) m/z: 863[M+H]⁺

To a mixture of (3R,4R,5R,6R)-2-(7-((1-allyl-1,2,3,4-tetrahydroquinolin-7-yl)methyl)-4-(benzyloxy)-2,3-dihydrobenzofuran-5-yl)-3,4-bis(benzyloxy)-6-((benzyloxy)methyl)-5-fluorotetrahydro-2H-pyran-2-ol (390 mg, 0.45 mmol, 1.00 equiv) in dichloromethane (4 mL) with Et₃SiH (110 mg, 0.95 mmol, 2.09 equiv) was added BE₃.Et₂O (101 mg, 0.71 mmol, 1.57 equiv) at 0° C. The reaction was stirred for 1 h at 0° C. Sodium bicarbonate/H₂O was added and the mixture was extracted with dichloromethane thrice. The combined extracts were washed with brine and dried over Na₂SO₄. The mixture was then concentrated and purified by chromatography on silica gel (5:1 PE/EA) to yield 1-allyl-7-((4-(benzyloxy)-5-((2S,3S,4R,5R,6R)-3,4-bis(benzyloxy)-6-((benzyloxy)methyl)-5-fluorotetrahydro-2H-pyran-2-yl)-2,3-dihydrobenzofuran-7-yl)methyl)-1,2,3,4-tetrahydroquinoline as a yellow oil. MS (ES) m/z: 847[M+H]⁺

To a mixture of 1-allyl-7-((4-(benzyloxy)-5-((2S,3S,4R,5R,6R)-3,4-bis(benzyloxy)-6-((benzyloxy)methyl)-5-fluorotetrahydro-2H-pyran-2-yl)-2,3-dihydrobenzofuran-7-yl)methyl)-1,2,3,4-tetrahydroquinoline (220 mg, 0.26 mmol, 1.00 equiv) in tetrahydrofuran (5 mL) with ZnCl₂ (89 mg, 0.65 mmol, 2.51 equiv) was added Pd(PPh₃)₄(75 mg, 0.06 mmol, 0.25 equiv) and n-Bu₃SnH (305 mg, 1.04 mmol, 4.02 equiv). The reaction was stirred for 2 h at room temperature. NH₄Cl/H₂O was added and the mixture was extracted with EtOAc thrice. The combined extracts were washed with brine and dried over Na₂SO₄. The mixture was then concentrated and purified by chromatography on silica gel (1:1 PE/EA) to yield 7-((4-(benzyloxy)-5-((2S,3S,4R,5R,6R)-3,4-bis(benzyloxy)-6-((benzyloxy)methyl)-5-fluorotetrahydro-2H-pyran-2-yl)-2,3-dihydrobenzofuran-7-yl)methyl)-1,2,3,4-tetrahydroquinoline as a yellow oil. MS (ES) m/z: 807[M+H]⁺

To a mixture of 7-((4-(benzyloxy)-5-((2S,3S,4R,5R,6R)-3,4-bis(benzyloxy)-6-((benzyloxy)methyl)-5-fluorotetrahydro-2H-pyran-2-yl)-2,3-dihydrobenzofuran-7-yl)methyl)-1,2,3,4-tetrahydroquinoline (190 mg, 0.24 mmol, 1.00 equiv) in tetrahydrofuran (10 mL) with triethylamine (120 mg, 1.19 mmol, 5.03 equiv), 4-dimethylaminopyridine (10 mg, 0.08 mmol, 0.35 equiv) was added (Boc)$_2$O (257 mg, 1.18 mmol, 5.00 equiv). The reaction was stirred overnight at 75° C. The mixture was then concentrated and purified by chromatography on silica gel (5:1 PE/EA) to yield tert-butyl 7-((4-(benzyloxy)-5-((2S,3S,4R,5R,6R)-3,4-bis(benzyloxy)-6-((benzyloxy)methyl)-5-fluorotetrahydro-2H-pyran-2-yl)-2,3-dihydrobenzofuran-7-yl)methyl)-3,4-dihydroquinoline-1(2H)-carboxylate as a yellow oil. MS (ES) m/z: 907[M+H]$^+$.

To a mixture of tert-butyl 7-((4-(benzyloxy)-5-((2S,3S,4R,5R,6R)-3,4-bis(benzyloxy)-6-((benzyloxy)methyl)-5-fluorotetrahydro-2H-pyran-2-yl)-2,3-dihydrobenzofuran-7-yl)methyl)-3,4-dihydroquinoline-1 (2H)-carboxylate (120 mg, 0.13 mmol, 1.00 equiv) in MeOH (5 mL) with acetic acid (0.1 mL) was added dry Palladium carbon (120 mg). H$_2$ (g) was introduced. The reaction was stirred overnight at room temperature. The solids were filtered out. The resulting mixture was concentrated to yield tert-butyl 7-((5-((2S,3R,4R,5S,6R)-5-fluoro-3,4-dihydroxy-6-(hydroxymethyl)tetrahydro-2H-pyran-2-yl)-4-hydroxy-2,3-dihydrobenzofuran-7-yl)methyl)-3,4-dihydroquinoline-1 (2H)-carboxylate as a white solid. MS (ES) m/z: 547[M+H]$^+$.

To a mixture of tert-butyl 7-((5-((2S,3R,4R,5S,6R)-5-fluoro-3,4-dihydroxy-6-(hydroxymethyl)tetrahydro-2H-pyran-2-yl)-4-hydroxy-2,3-dihydrobenzofuran-7-yl)methyl)-3,4-dihydroquinoline-1 (2H)-carboxylate (40 mg, 0.07 mmol, 1.00 equiv) in N,N-dimethylformamide (5 mL) with potassium carbonate (102 mg, 0.74 mmol, 10.07 equiv) was added CH$_3$I (105 mg, 0.74 mmol, 10.09 equiv). The reaction was stirred for 2 h at room temperature. The residue was applied chromatograph on a C18 reversed phase column (0%-45% CH$_3$CN/H$_2$O) to yield tert-butyl 7-((5-((2S,3R,4R,5S,6R)-5-fluoro-3,4-dihydroxy-6-(hydroxymethyl)tetrahydro-2H-pyran-2-yl)-4-methoxy-2,3-dihydrobenzofuran-7-yl)methyl)-3,4-dihydroquinoline-1(2H)-carboxylate as a white solid. MS (ES) m/z: 561 [M+H]$^+$.

To a mixture of tert-butyl 7-((5-((2S,3R,4R,5S,6R)-5-fluoro-3,4-dihydroxy-6-(hydroxymethyl)tetrahydro-2H-pyran-2-yl)-4-methoxy-2,3-dihydrobenzofuran-7-yl)methyl)-3,4-dihydroquinoline-1 (2H)-carboxylate (38 mg, 0.07 mmol, 1.00 equiv) in dichloromethane (5 mL) was added hydrogen chloride (in diethyl ether) (0.14 mL, 10.00 equiv). The reaction was stirred for 1 h at room temperature. The mixture was then concentrated and purified by chromatography on a C18 reversed phase column (0%-45% CH$_3$CN/H$_2$O) to yield (2S,3R,4R,5S,6R)-5-fluoro-6-(hydroxymethyl)-2-(4-methoxy-7-((1,2,3,4-tetrahydroquinolin-7-yl)methyl)-2,3-dihydrobenzofuran-5-yl)tetrahydro-2H-pyran-3,4-diol as a white solid.

$^1$H NMR (300 MHz, CD$_3$OD) δ: 6.98 (s, 1H), 6.75 (d, J=7.8 Hz, 1H), 6.45 (d, J=7.8 Hz, 1H), 6.30 (s, 1H), 4.53-4.59 (m, 3H), 4.39 (t, J=8.7 Hz, 0.5H), 4.22 (t, J=8.7 Hz, 0.5H), 3.78-3.83 (m, 3H), 3.73-3.78 (m, 2H), 3.53-3.68 (m, 5H), 3.26-3.33 (m, 2H), 3.17-3.27 (m, 2H), 2.68 (t, J=6.3 Hz, 2H), 1.84-1.88 (m, 2H). MS (ES) m/z: 458.1 [M–H]$^-$.

Synthesis Example 20: Compound #125

(2S,3R,4R,5S,6R)-2-(4-chloro-5-(chroman-6-ylmethyl)-2,3-dihydrobenzofuran-7-yl)-5-fluoro-6-(hydroxymethyl)-tetrahydro-2H-pyran-3,4-diol

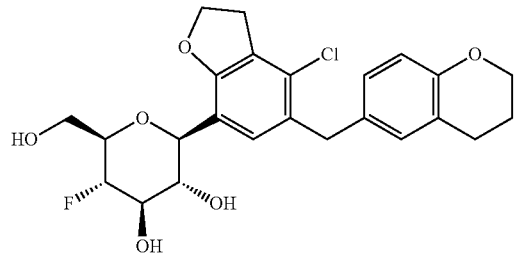 [SMILES: OC[C@H]1O[C@@H](c2cc(Cc3ccc4c(c3)CCCO4)c(Cl)c3c2OCC3)[C@H](O)[C@@H](O)[C@@H]1F]

To a mixture of 2-(2,6-dichlorophenyl)ethan-1-ol (200 g, 1.05 mol, 1.00 equiv) in toluene (3500 mL) was added NaH (52.8 g, 2.20 mol, 1.25 equiv, 60% purity). The mixture was stirred for 20 minutes at 40° C. To the resulting solution was then added CuCl (cuprous chloride) (5.21 g, 52.63 mmol, 0.05 equiv) and ethyl acetate (4.63 g, 52.61 mmol, 0.05 equiv). The reaction was stirred for overnight at reflux. Ice water was added and the mixture was extracted with EtOAc thrice. The combined extracts were washed with brine and dried over Na$_2$SO$_4$. The mixture was then concentrated and purified by chromatography on silica gel (50:1 PE/EA) to yield 4-chloro-2,3-dihydrobenzofuran as a yellow oil.

To a mixture of 4-chloro-2,3-dihydrobenzofuran (36 g, 232.87 mmol, 1.00 equiv) in AcOH (360 mL) was added Br$_2$ (37.3 g, 233.40 mmol, 1.00 equiv) dropwise at 10-15° C. The reaction was stirred for 2 h at 10-15° C. Ice water was added, and the solids were collected by filtration to yield 5-bromo-4-chloro-2,3-dihydrobenzofuran as a white solid.

To a mixture of 5-bromo-4-chloro-2,3-dihydrobenzofuran (48 g, 205.58 mmol, 1.00 equiv) in tetrahydrofuran (1000 mL) was added n-BuLi (2.5M, 91 mL) dropwise at −78° C. The mixture was stirred for 20 minutes. To the resulting solution was then added DMF (64 ml) dropwise at −78° C. The reaction was stirred at −78° C. for 1 h. NH$_4$Cl/H$_2$O was added and the mixture was extracted with EtOAc thrice. The combined extracts were washed with brine and dried over Na$_2$SO$_4$. The mixture was then concentrated and purified by chromatography on silica gel (10:1 PE/EA) to yield 4-chloro-2,3-dihydrobenzofuran-5-carbaldehyde as a yellow solid.

To a mixture of 4-chloro-2,3-dihydrobenzofuran-5-carbaldehyde (26 g, 142.38 mmol, 1.00 equiv) in MeOH (600 mL) was added pyridine hydrobromide perbromide (92 g, 287.50 mmol, 2.00 equiv). The reaction was stirred for overnight at 25° C. Ice water was added and the mixture was extracted with EtOAc thrice. The combined extracts were washed with brine and dried over Na$_2$SO$_4$. The mixture was then concentrated and purified by chromatography on silica gel (10:1 PE/EA) to yield 7-bromo-4-chloro-2,3-dihydrobenzofuran-5-carbaldehyde as a white solid. NMR (300 MHz, CDCl$_3$) δ: 10.25 (s, 1H), 7.98 (s, 1H), 4.88 (t, J=8.9 Hz, 2H), 3.39-3.52 (m, 2H). MS (ES) m/z: 261, 263 [M+H]$^+$ To a mixture of 6-bromo-3,4-dihydro-2H-1-benzopyran (780 mg, 3.66 mmol, 1.20 equiv) in tetrahydrofuran (10 mL) was added n-BuLi (2.5M) (1.59 mL) at −78° C. The mixture was stirred for 30 minutes. To the resulting mixture was then added a solution of 7-bromo-4-chloro-2,3-dihydrobenzofuran-5-carbaldehyde (797 mg, 3.05 mmol, 1.00 equiv) in tetrahydrofuran (1 mL) at −78° C. The reaction was stirred at −78° C. for 1 h. NH$_4$Cl/H$_2$O was added and the mixture was extracted with EtOAc thrice. The combined extracts were washed with brine and dried over Na$_2$SO$_4$. The mixture was then concentrated and purified by chromatography on silica gel (1:1 PE/EA) to yield (7-bromo-4-chloro-2,3-dihydrobenzofuran-5-yl)(chroman-6-yl)methanol as a white solid.

To a mixture of (7-bromo-4-chloro-2,3-dihydrobenzofuran-5-yl)(chroman-6-yl)methanol (510 mg, 1.29 mmol, 1.00 equiv) in dichloromethane (10 mL) with Et$_3$SiH (300 mg, 2.58 mmol, 2.00 equiv) was added CF$_3$COOH (221 mg, 1.94 mmol, 1.50 equiv) dropwise with stirring at 0° C. The reaction was stirred for 1 h at 0° C. Sodium bicarbonate/H$_2$O was added and the mixture was extracted with dichloromethane thrice. The combined extracts were washed with brine and dried over Na$_2$SO$_4$. The mixture was then concentrated and purified by chromatography on silica gel (5:1 PE/EA) to yield 6-((7-bromo-4-chloro-2,3-dihydrobenzofuran-5-yl)methyl)chromane as light yellow oil.

To a mixture of 6-((7-bromo-4-chloro-2,3-dihydrobenzofuran-5-yl)methyl)chromane (230 mg, 0.61 mmol, 1.10 equiv) in tetrahydrofuran (5 mL) was added n-BuLi (2.5M) (0.27 mL) at −78° C. The mixture was stirred for 30 minutes. To the resulting mixture was then added a solution of (3R,4R,5R,6R)-3,4-bis(benzyloxy)-6-[(benzyloxy)methyl]-5-fluorooxan-2-one (249 mg, 0.55 mmol, 1.00 equiv) in tetrahydrofuran (0.5 mL) at −78° C. The reaction was stirred at −78° C. for 1 h. NH$_4$Cl/H$_2$O was added and the mixture was extracted with EtOAc thrice. The combined extracts were washed with brine and dried over Na$_2$SO$_4$. The mixture was then concentrated and purified by chromatography on silica gel (3:1 PE/EA) to yield (3R,4R,5R,6R)-3,4-bis(benzyloxy)-6-((benzyloxy)methyl)-2-(4-chloro-5-(chroman-6-ylmethyl)-2,3-dihydrobenzofuran-7-yl)-5-fluorotetrahydro-2H-pyran-2-ol as a light yellow oil.

To a mixture of (3R,4R,5R,6R)-3,4-bis(benzyloxy)-6-((benzyloxy)methyl)-2-(4-chloro-5-(chroman-6-ylmethyl)-2,3-dihydrobenzofuran-7-yl)-5-fluorotetrahydro-2H-pyran-2-ol (120 mg, 0.16 mmol, 1.00 equiv) in dichloromethane (5 mL) with Et$_3$SiH (37 mg, 0.32 mmol, 1.99 equiv) was added BF$_3$.Et$_2$O (34 mg, 0.24 mmol, 1.50 equiv) at 0° C. The reaction was stirred for 1 h at 0° C. Sodium bicarbonate/H$_2$O was added and the mixture was extracted with dichloromethane thrice. The combined extracts were washed with brine and dried over Na$_2$SO$_4$. The mixture was then concentrated and purified by chromatography on silica gel (5:1 PE/EA) to yield 6-((7-((2S,3S,4R,5R,6R)-3,4-bis(benzyloxy)-6-((benzyloxy)methyl)-5-fluorotetrahydro-2H-pyran-2-yl)-4-chloro-2,3-dihydrobenzofuran-5-yl)methyl)chromane as a light yellow oil.

To a mixture of 6-((7-((2S,3S,4R,5R,6R)-3,4-bis(benzyloxy)-6-((benzyloxy)methyl)-5-fluorotetrahydro-2H-pyran-2-yl)-4-chloro-2,3-dihydrobenzofuran-5-yl)methyl)chromane (50 mg, 0.07 mmol, 1.00 equiv) in methanol (5 mL) was added Pd(OH)$_2$/C (50 mg). H$_2$ was introduced in. The reaction was stirred for 30 min at room temperature. The solids were filtered out. The mixture was then concentrated and purified by chromatography on a C18 reversed phase column (0%-45% CH$_3$CN/H$_2$O) to yield (2S,3R,4R,5S,6R)-2-(4-chloro-5-(chroman-6-ylmethyl)-2,3-dihydrobenzofuran-7-yl)-5-fluoro-6-(hydroxymethyl)tetrahydro-2H-pyran-3,4-diol as a white solid.

$^1$H NMR (300 MHz, CD$_3$OD) δ: 7.10 (s, 1H), 6.85 (d, J=9.9 Hz, 2H), 6.54-6.64 (m, 1H), 4.50-4.58 (m, 0.5H), 4.31-4.40 (m, 1H), 4.19-4.30 (m, 0.5H), 4.08-4.15 (m, 2H), 3.90 (s, 2H), 3.61-3.86 (m, 4H), 3.51-3.58 (m, 1H), 3.24 (t, J=8.8 Hz, 2H), 2.72 (t, J=6.5 Hz, 2H), 1.90-2.01 (m, 2H). MS (ES) m/z: 463.0 [M−H]

Synthesis Example 21: Compound #126

(2S,3R,4R,5S,6R)-2-(5-(chroman-6-ylmethyl)-4-methoxy-2,3-dihydrobenzofuran-7-yl)-5-fluoro-6-(hydroxymethyl)-tetrahydro-2H-pyran-3,4-diol

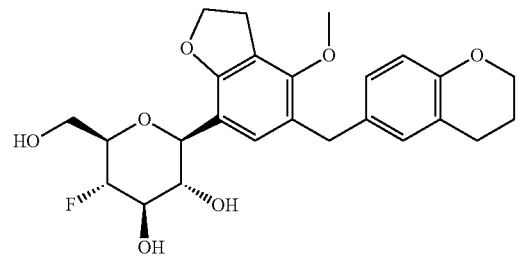 [SMILES: COc1c(Cc2ccc3c(c2)CCCO3)cc([C@@H]2O[C@H](CO)[C@@H](F)[C@H](O)[C@H]2O)c2c1CCO2]

To a mixture of 5-bromo-2,3-dihydrobenzofuran-4-ol (3.5 g, 16.28 mmol, 1.00 equiv) in N,N-dimethylformamide (30 mL) with potassium carbonate (6.74 g, 48.77 mmol, 3.00 equiv) was added CH$_3$I (11.56 g, 81.44 mmol, 5.00 equiv). The reaction was stirred for 1 h at room temperature. NH$_4$Cl/H$_2$O was added and the mixture was extracted with EtOAc thrice. The combined extracts were washed with brine and dried over Na$_2$SO$_4$. The mixture was then concentrated and purified by chromatography on silica gel (3:1 PE/EA) to yield 5-bromo-4-methoxy-2,3-dihydrobenzofuran as a yellow liquid.

To a mixture of 5-bromo-4-methoxy-2,3-dihydrobenzofuran (3.3 g, 14.41 mmol, 1.00 equiv) in tetrahydrofuran (50 mL) was added n-BuLi (5.76 mL, 1.00 equiv, 2.5N) at −78° C. The mixture was stirred for 30 min at −78° C. After that was added N,N-dimethylformamide (2.13 g, 29.14 mmol, 2.02 equiv) at −78° C. The reaction was stirred at −78° C. for 1 h. NH$_4$Cl/H$_2$O was added and the mixture was extracted with EtOAc thrice. The combined extracts were washed with brine and dried over Na$_2$SO$_4$. The mixture was then concentrated and purified by chromatography on silica gel (3:1 PE/EA) to yield 4-methoxy-2,3-dihydrobenzofuran-5-carbaldehyde as a white solid.

To a mixture of 4-methoxy-2,3-dihydrobenzofuran-5-carbaldehyde (2.2 g, 12.35 mmol, 1.00 equiv) in methanol (30 mL) was added Pyridine.Br$_3$ (4.16 g, 12.35 mmol, 1.00 equiv) at 0° C. The reaction was stirred for 2 h at 0° C. The reaction was then quenched by the addition of 30 mL of water. The solids were collected by filtration to yield 7-bromo-4-methoxy-2,3-dihydrobenzofuran-5-carbaldehyde as a white solid. ¹H-NMR: (300 MHz, CDCl₃) δ 10.16 (s, 1H), 7.86 (s, 1H), 4.79 (t, J=9.0 Hz, 2H), 4.00 (s, 3H), 3.51 (t, J=9.0 Hz, 2H).

To a mixture of 6-bromochroman (500 mg, 2.35 mmol, 1.30 equiv) in tetrahydrofuran (10 mL) was added n-BuLi (0.94 mL, 1.30 equiv, 2.5N) at −78° C. The mixture was stirred for 30 min at −78° C. After that was added a solution of 7-bromo-4-methoxy-2,3-dihydrobenzofuran-5-carbaldehyde (465 mg, 1.81 mmol, 1.00 equiv) in tetrahydrofuran (5 mL) at −78° C. The reaction was stirred at −78° C. for 1 h. NH₄Cl/H₂O was added and the mixture was extracted with EtOAc thrice. The combined extracts were washed with brine and dried over Na₂SO₄. The mixture was then concentrated and purified by chromatography on silica gel (3:1 PE/EA) to yield (7-bromo-4-methoxy-2,3-dihydrobenzofuran-5-yl)(chroman-6-yl)methanol as a yellow oil. MS (ES) m/z: 373[M-OH]⁺

To a mixture of (7-bromo-4-methoxy-2,3-dihydrobenzofuran-5-yl)(chroman-6-yl)methanol (600 mg, 1.53 mmol, 1.00 equiv) in dichloromethane (20 mL) with Et₃SiH (356 mg, 3.06 mmol, 2.00 equiv) was added CF₃COOH (263 mg, 2.31 mmol, 1.50 equiv) at 0° C. The reaction was stirred for 1 h at 0° C. Sodium bicarbonate/H₂O was added and the mixture was extracted with dichloromethane thrice. The combined extracts were washed with brine and dried over Na₂SO₄. The mixture was then concentrated and purified by chromatography on silica gel (5:1 PE/EA) to yield 6-((7-bromo-4-methoxy-2,3-dihydrobenzofuran-5-yl)methyl)chromane as a yellow oil. ¹H-NMR: (300 MHz, CDCl₃) δ 10.16 (s, 1H) 6.87-6.90 (m, 1H), 6.82 (s, 1H), 6.69 (d, J=8.4 Hz, 1H), 3.51 (t, J=8.4 Hz, 2H), 4.11-4.16 (m, 2H), 3.74-3.79 (m, 5H), 3.39 (t, J=8.4 Hz, 2H), 2.74 (t, J=8.8 Hz, 2H), 1.96-2.04 (m, 2H).

To a mixture of 6-((7-bromo-4-methoxy-2,3-dihydrobenzofuran-5-yl)methyl)chromane (137 mg, 0.37 mmol, 1.10 equiv) in tetrahydrofuran (2 mL) was added n-BuLi (0.15 mL, 1.10 equiv, 2.5N) at −78° C. The mixture was stirred for 30 min at −78° C. After that was added a solution of (3R,4R,5R,6R)-3,4-bis(benzyloxy)-6-[(benzyloxy)methyl]-5-fluorooxan-2-one (150 mg, 0.33 mmol, 1.00 equiv) in tetrahydrofuran (2 mL) −78° C. The reaction was stirred at −78° C. for 1 h. NH₄Cl/H₂O was added and the mixture was extracted with EtOAc thrice. The combined extracts were washed with brine and dried over Na₂SO₄. The mixture was then concentrated and purified by chromatography on silica gel (1:1 PE/EA) to yield (3R,4R,5R,6R)-3,4-bis(benzyloxy)-6-((benzyloxy)methyl)-2-(5-(chroman-6-ylmethyl)-4-methoxy-2,3-dihydrobenzofuran-7-yl)-5-fluorotetrahydro-2H-pyran-2-ol as a yellow oil. MS (ES) m/z: 747[M+H]⁺

To a mixture of (3R,4R,5R,6R)-3,4-bis(benzyloxy)-6-((benzyloxy)methyl)-2-(5-(chroman-6-ylmethyl)-4-methoxy-2,3-dihydrobenzofuran-7-yl)-5-fluorotetrahydro-2H-pyran-2-ol (160 mg, 0.21 mmol, 1.00 equiv) in dichloromethane (5 mL) with Et₃SiH (50 mg, 0.43 mmol, 2.01 equiv) was added BF₃.Et₂O (46 mg, 0.32 mmol, 1.51 equiv) at 0° C. The reaction was stirred for 1 h at 0° C. Sodium bicarbonate/H₂O was added and the mixture was extracted with dichloromethane thrice. The combined extracts were washed with brine and dried over Na₂SO₄. The mixture was then concentrated and purified by chromatography on silica gel (5:1 PE/EA) to yield 6-((7-((2S,3S,4R,5R,6R)-3,4-bis(benzyloxy)-6-((benzyloxy)methyl)-5-fluorotetrahydro-2H-pyran-2-yl)-4-methoxy-2,3-dihydrobenzofuran-5-yl)methyl)chromane as a yellow oil. MS (ES) m/z: 731 [M+H]⁺

To a mixture of 6-((7-((2S,3S,4R,5R,6R)-3,4-bis(benzyloxy)-6-((benzyloxy)methyl)-5-fluorotetrahydro-2H-pyran-2-yl)-4-methoxy-2,3-dihydrobenzofuran-5-yl)methyl)chromane (100 mg, 0.14 mmol, 1.00 equiv) in EA/MeOH (3:1) (10 mL) was added Pd(OH)₂/C (100 mg, 1.00 equiv) and hydrogen chloride (0.01 mL). H₂ was introduced. The reaction was stirred for 1 h at room temperature. The solids were filtered out. The mixture was then concentrated and purified by chromatography on a C18 reversed phase column (0%-45% CH₃CN/H₂O) to yield (2S,3R,4R,5S,6R)-2-(5-(chroman-6-ylmethyl)-4-methoxy-2,3-dihydrobenzofuran-7-yl)-5-fluoro-6-(hydroxymethyl)tetrahydro-2H-pyran-3,4-diol as a white solid.

¹H NMR (300 MHz, CD₃OD) δ: 7.28 (s, 1H), 6.84-6.87 (m, 2H), 6.56 (d, J=8.1 Hz, 1H), 4.66-4.69 (m, 1H), 4.51-4.63 (m, 3H), 4.08-4.12 (m, 3H), 3.89-3.92 (m, 2H), 3.71-3.80 (m, 4H), 3.68 (s, 3H), 3.53-3.57 (m, 1H), 3.27-3.30 (m, 1H), 2.68-2.73 (m, 2H), 1.90-1.98 (m, 2H). MS (ES) m/z: 459[M-H]⁻

Synthesis Example 22: Compound #128

(2S,3R,4R,5S,6R)-2-(5-((2,3-dihydrobenzo[b][1,4]oxathiin-6-yl)methyl)-4-methoxy-2,3-dihydrobenzofuran-7-yl)-5-fluoro-6-(hydroxymethyl)-tetrahydro-2H-pyran-3,4-diol

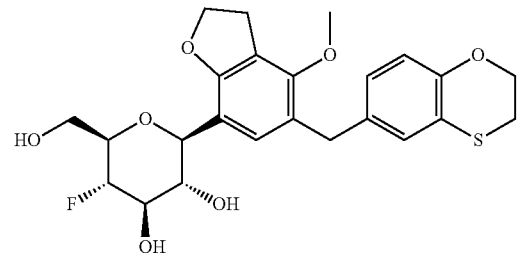 [SMILES: COc1c(Cc2ccc3c(c2)SCCO3)cc([C@@H]2O[C@H](CO)[C@@H](F)[C@H](O)[C@H]2O)c2c1CCO2]

To a mixture of 6-bromo-2,3-dihydro-1,4-benzoxathiine (585 mg, 2.53 mmol, 1.30 equiv) in tetrahydrofuran (10 mL) was added n-BuLi (1.0 mL, 1.30 equiv, 2.5N) at −78° C. The mixture was stirred for 30 min at −78° C. After that was added a solution of 7-bromo-4-methoxy-2,3-dihydrobenzofuran-5-carbaldehyde (500 mg, 1.94 mmol, 1.00 equiv) in tetrahydrofuran (10 mL) at −78° C. The reaction was stirred at −78° C. for 1 h. NH₄Cl/H₂O was added and the mixture was extracted with EtOAc thrice. The combined extracts were washed with brine and dried over Na₂SO₄. The mixture was then concentrated and purified by chromatography on silica gel (2:1 PE/EA) to yield (7-bromo-4-methoxy-2,3-dihydrobenzofuran-5-yl)(2,3-dihydrobenzo[b][1,4]oxathiin-6-yl)methanol as a yellow oil. MS (ES) m/z: 391 [M-OH]⁺

To a mixture of (7-bromo-4-methoxy-2,3-dihydrobenzofuran-5-yl)(2,3-dihydrobenzo[b][1,4]oxathiin-6-yl)methanol (600 mg, 1.47 mmol, 1.00 equiv) in dichloromethane (20 ml) with Et₃SiH (340 mg, 2.92 mmol, 1.99 equiv). was added CF₃COOH (250 mg, 2.19 mmol, 1.50 equiv) at 0° C.

The reaction was stirred for 1 h at 0° C. Sodium bicarbonate/H₂O was added and the mixture was extracted with dichloromethane thrice. The combined extracts were washed with brine and dried over Na₂SO₄. The mixture was then concentrated and purified by chromatography on silica gel (5:1 PE/EA) to yield 6-((7-bromo-4-methoxy-2,3-dihydrobenzofuran-5-yl)methyl)-2,3-dihydrobenzo[b][1,4]oxathiine as a yellow oil. ¹H-NMR: (300 MHz, CD₃OD) δ: 7.01 (s, 1H), 6.71-6.84 (m, 3H), 4.65 (t, J=8.7 Hz, 2H), 4.36-4.39 (m, 2H), 3.75 (s, 5H), 3.40 (t, J=8.7 Hz, 2H), 3.10-3.14 (m, 2H).

To a mixture of 6-((7-bromo-4-methoxy-2,3-dihydrobenzofuran-5-yl)methyl)-2,3-dihydrobenzo[b][1,4]oxathiine (80 mg, 0.20 mmol, 1.09 equiv) in tetrahydrofuran (2 ml) was added n-BuLi (0.08 mL, 1.10 equiv, 2.5N) at −78° C. The mixture was stirred for 30 min at −78° C. After that was added a solution of (3R,4R,5R,6R)-3,4-bis(benzyloxy)-6-[(benzyloxy)methyl]-5-fluorooxan-2-one (84 mg, 0.19 mmol, 1.00 equiv) in tetrahydrofuran (1 ml) at −78° C. NH₄Cl/H₂O was added and the mixture was extracted with EtOAc thrice. The combined extracts were washed with brine and dried over Na₂SO₄. The mixture was then concentrated and purified by chromatography on silica gel (2:1 PE/EA) to yield (3R,4R,5R,6R)-3,4-bis(benzyloxy)-6-((benzyloxy)methyl)-2-(5-((2,3-dihydrobenzo[b][1,4]oxathiin-6-yl)methyl)-4-methoxy-2,3-dihydrobenzofuran-7-yl)-5-fluorotetrahydro-2H-pyran-2-ol as a yellow oil. MS (ES) m/z: 765[M+H]⁺

To a mixture of (3R,4R,5R,6R)-3,4-bis(benzyloxy)-6-((benzyloxy)methyl)-2-(5-((2,3-dihydrobenzo[b][1,4]oxathiin-6-yl)methyl)-4-methoxy-2,3-dihydrobenzofuran-7-yl)-5-fluorotetrahydro-2H-pyran-2-ol (100 mg, 0.13 mmol, 1.00 equiv) in dichloromethane (5 mL) with Et₃SiH (30 mg, 0.26 mmol, 1.97 equiv) was added BF₃.Et₂O (28 mg, 0.20 mmol, 1.51 equiv). The reaction was stirred for 1 h at 0° C. Sodium bicarbonate/H₂O was added and the mixture was extracted with dichloromethane thrice. The combined extracts were washed with brine and dried over Na₂SO₄. The mixture was then concentrated and purified by chromatography on silica gel (5:1 PE/EA) to yield 6-((7-((2S,3S,4R,5R,6R)-3,4-bis(benzyloxy)-6-((benzyloxy)methyl)-5-fluorotetrahydro-2H-pyran-2-yl)-4-methoxy-2,3-dihydrobenzofuran-5-yl)methyl)-2,3-dihydrobenzo[b][1,4]oxathiine as a yellow oil. MS (ES) m/z: 749[M+H]⁺

To a mixture of 6-((7-((2S,3S,4R,5R,6R)-3,4-bis(benzyloxy)-6-((benzyloxy)methyl)-5-fluorotetrahydro-2H-pyran-2-yl)-4-methoxy-2,3-dihydrobenzofuran-5-yl)methyl)-2,3-dihydrobenzo[b][1,4]oxathiine (60 mg, 0.08 mmol, 1.00 equiv) in dichloromethane (10 mL) with 1,2,3,4,5-pentamethylbenzene (60 mg, 0.40 mmol, 5.05 equiv) was added BCl₃ (0.6 mg, 7.50 equiv, 1 N) at −78° C. The reaction was stirred at −78° C. for 1 h. Methanol (2 mL) was added. The mixture was then concentrated and purified by chromatography on Prep-HPLC (0%-45% CH₃CN/H₂O) to yield (2S,3R,4R,5S,6R)-2-(5-((2,3-dihydrobenzo[b][1,4]oxathiin-6-yl)methyl)-4-methoxy-2,3-dihydrobenzofuran-7-yl)-5-fluoro-6-(hydroxymethyl)tetrahydro-2H-pyran-3,4-diol as a white solid.

¹H NMR (300 MHz, CD₃OD): δ: 6.99 (s, 1H), 6.77-6.79 (m, 2H), 6.32-6.66 (m, 1H), 4.51-4.59 (m, 2H), 4.32-4.38 (m, 4H), 3.65-3.83 (m, 9H), 3.53-3.57 (m, 1H), 3.30-3.31 (m, 1H), 3.26-3.30 (m, 1H), 3.12-3.18 (m, 2H). MS (ES) m/z: 477.0 [M−H]⁻

Synthesis Example 23: Compound #161

(2S,3R,4R,5S,6R)-2-(7-((2,3-dihydrobenzo[b][1,4]dioxin-6-yl-)methyl-d2)-4-(methoxy-d3)-2,3-dihydrobenzofuran-5-yl)-5-fluoro-6-(hydroxymethyl)tetrahydro-2H-pyran-3,4-diol

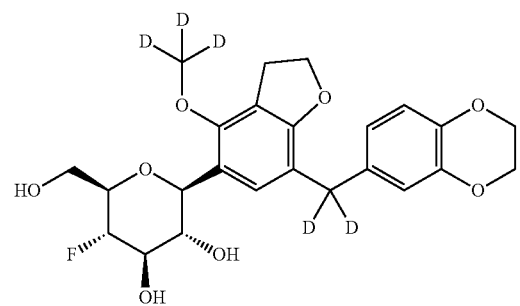 [SMILES: [2H]C([2H])([2H])Oc1c([C@@H]2O[C@H](CO)[C@@H](F)[C@H](O)[C@H]2O)cc(C([2H])([2H])c2ccc3c(c2)OCCO3)c2c1CCO2]

Dess-Martin reagent (943.4 mg, 2.22 mmol) was added to a solution of (4-(benzyloxy)-5-bromo-2,3-dihydrobenzofuran-7-yl)(2,3-dihydrobenzo[b][1,4]dioxin-6-yl)methanol (803 mg, 1.71 mmol) in DCM (20 ml) and the mixture was kept stirring at room temperature for 72 h. The resulting mixture was concentrated and the residue was purified by flash column chromatography on silica gel (40 g, EtOAc/heptane: 0>>>10%) to yield (4-(benzyloxy)-5-bromo-2,3-dihydrobenzofuran-7-yl)(2,3-dihydrobenzo[b][1,4]dioxin-6-yl)methanone as an orange syrup.

To a solution of (4-(benzyloxy)-5-bromo-2,3-dihydrobenzofuran-7-yl)(2,3-dihydrobenzo[b][1,4]dioxin-6-yl)methanone (500 mg, 1.07 mol) in MeOH (5 ml) was added sodium borodeuteride (179.1 mg, 4.28 mmol) in three portions and the mixture was kept stirring at room temperature for 2 h. The resulting mixture was concentrated and diluted with 1N HCl, extracted with EtOAc three times (10 ml each time) and the combined organic extracts were dried over Na₂SO₄, filtered and concentrated. The residue, (4-(benzyloxy)-5-bromo-2,3-dihydrobenzofuran-7-yl)(2,3-dihydrobenzo[b][1,4]dioxin-6-yl)methan-d-ol, was used in the next step without further purification.

To (4-(benzyloxy)-5-bromo-2,3-dihydrobenzofuran-7-yl)(2,3-dihydrobenzo[b][1,4]dioxin-6-yl)methan-d-ol in anhydrous CH₂CO₂ at 0° C. was added Et₃SiD, followed by BF₃.Et₂O and stirred at 0° C. for 1 h, the mixture was quenched with aqueous NaHCO₃, extracted with DCM three times, concentrated and filtered. The filtrate was concentrated and the residue was purified by flash column chromatography on silica gel (12 g, EtOAc/heptane: 0>>>10%) to yield 6-((4-(benzyloxy)-5-bromo-2,3-dihydrobenzofuran-7-yl)methyl-d2)-2,3-dihydrobenzo[b][1,4]dioxine as a colorless syrup.

A 50 round-bottom flask was charged with 6-((4-(benzyloxy)-5-bromo-2,3-dihydrobenzofuran-7-yl)methyl-d2)-2,3-dihydrobenzo[b][1,4]dioxine (254.7 mg, 0.56 mmol) and a magnetic stir bar and the flask was evacuated, re-filled with nitrogen and this process was repeated twice. To the flask was added 4 ml of THF, cooled to −78° C., then n-BuLi (0.35 mL, 1.6 M in hexanes) was added and the mixture was stirred at −78° C. for 35 min. (3R,4R,5R,6R)-3,4-bis((tert-butyldimethylsilyl)oxy)-6-(((tert-butyldimethylsilyl)oxy)methyl)-5-fluorotetrahydro-2H-pyran-2-one in 4 ml of THF was added and the resulting mixture was stirred at −78° C. for 40 min, the reaction mixture quenched with aqueous NH$_4$Cl, extracted with EtOAc three times. The combined organic layer was washed with brine, dried over N$_2$SO$_4$, filtered and the filtrate was concentrated under reduced pressure. The residue was dried in vacuo and re-dissolved in ACN (10 mL) and DCM (10 mL), then cooled to −40° C. To the resulting mixture was then added triethylsilane (0.30 mL), followed by addition of BF$_3$.Et$_2$O (0.16 mL). The reaction was kept stirring at −40° C. for 35 min, then warmed to 0° C. and kept stirring at 0° C. for 1 h. The resulting mixture was quenched with aqueous NaHCO$_3$, extracted with EtOAc three times. The combined organic layer was dried over Na$_2$SO$_4$, filtered and concentrated. The residue was analyzed by LC/MS and then re-dissolved in MeOH (4 ml). The solution was subjected to Gilson HPLC purification (three injections) to yield (2S,3R,4R,5S,6R)-2-(4-(benzyloxy)-7-((2,3-dihydrobenzo[b][1,4]dioxin-6-yl)methyl-d2)-2,3-dihydrobenzofuran-5-yl)-5-fluoro-6-(hydroxymethyl)tetrahydro-2H-pyran-3,4-diol as a white solid. $^1$H NMR (METHANOL-d$_4$) δ: 7.43-7.52 (m, 2H), 7.29-7.39 (m, 3H), 6.99-7.06 (m, 1H), 6.64-6.70 (m, 3H), 4.96-5.11 (m, 2H), 4.46-4.59 (m, 3H), 4.19-4.39 (m, 1H), 4.16 (s, 4H), 3.56-3.78 (m, 4H), 3.40-3.49 (m, 1H), 3.17-3.23 (m, 2H).

To a solution of (2S,3R,4R,5S,6R)-2-(4-(benzyloxy)-7-((2,3-dihydrobenzo[b][1,4]dioxin-6-yl)methyl-d2)-2,3-dihydrobenzofuran-5-yl)-5-fluoro-6-(hydroxymethyl)tetrahydro-2H-pyran-3,4-diol (150 mg, 0.28 mmol) in EtOAc/MeOH (11 ml, 10:1 v/v) was added Pd(OH)$_2$ (30 mg, 20%) and the flask was degassed, filled with hydrogen and this. This process was repeated three times. The mixture was kept stirring at room temperature for 16 h. The catalyst was filtered off and the filtrate was concentrated to yield (2S,3R,4R,5S,6R)-2-(7-((2,3-dihydrobenzo[b][1,4]dioxin-6-yl)methyl-d2)-4-hydroxy-2,3-dihydrobenzofuran-5-yl)-5-fluoro-6-(hydroxymethyl)tetrahydro-2H-pyran-3,4-diol as a white solid.

To a solution of (2S,3R,4R,5S,6R)-2-(7-((2,3-dihydrobenzo[b][1,4]dioxin-6-yl)methyl-d2)-4-hydroxy-2,3-dihydrobenzofuran-5-yl)-5-fluoro-6-(hydroxymethyl)tetrahydro-2H-pyran-3,4-diol (30 mg, 0.067 mmol) in acetone (3 mL) was added K$_2$CO$_3$ (92.5 mg, 0.67 mmol), followed by the addition of CD$_3$I. The resulting mixture was kept stirring at room temperature for 16 h. The solid was filtered and the filtrate was concentrated. The residue was purified by Gilson HPLC to yield (2S,3R,4R,5S,6R)-2-(7-((2,3-dihydrobenzo[b][1,4]dioxin-6-yl)methyl-d2)-4-(methoxy-d3)-2,3-dihydrobenzofuran-5-yl)-5-fluoro-6-(hydroxymethyl)tetrahydro-2H-pyran-3,4-diol as a white solid (18.3 mg, 58.8%).

$^1$H NMR (MeOH) δ: 6.99 (s, 1H), 6.61-6.68 (m, 3H), 4.47-4.62 (m, 3H), 4.19-4.41 (m, 1H), 4.16 (s, 4H), 3.52-3.81 (m, 6H), 3.25-3.29 (m, 1H). LC/MS: m/z (2M+Na): 957.2.

Example 24: Compound #101

(2S,3R,4R,5S,6R)-2-[5-(2,3-dihydro-1,4-benzodioxin-6-ylmethyl)-4-methoxy-2,3-dihydrobenzofuran-7-yl]-5-fluoro-6-(hydroxymethyl)tetrahydropyran-3,4-diol

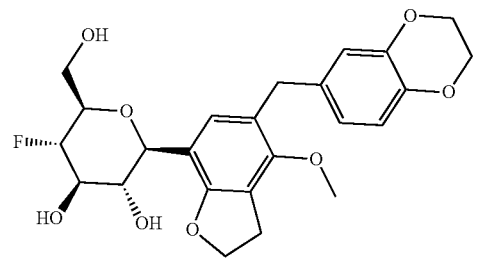 [SMILES: COc1c(Cc2ccc3c(c2)OCCO3)cc([C@@H]2O[C@H](CO)[C@@H](F)[C@H](O)[C@H]2O)c2c1CCO2]

A 2-dram vial was charged with (2S,3R,4R,5S,6R)-2-(5-((2,3-dihydrobenzo[b][1,4]dioxin-6-yl)methyl)-4-hydroxy-2,3-dihydrobenzofuran-7-yl)-5-fluoro-6-(hydroxymethyl)tetrahydro-2H-pyran-3,4-diol (15 mg, 0.033 mmol) and K$_2$CO$_3$ (23 mg, 0.17 mmol). To the mixture was then added acetone (1 ml), followed by addition of CH$_3$I (8 μL), and the reaction mixture was kept stirred at room temperature for 16 h. The resulting mixture was filtered and the filtrate was evaporated to dryness under vacuum. The residue was re-dissolved in methanol (2 ml) and the solution was subjected to Gilson HPLC purification (35 ml/min flow rate, 15 min gradient time, 10%>>>90% ACN) to yield the title compound as a white solid.

$^1$H NMR (MeOH) δ: 6.97 (s, 1H), 6.66 (d, J=8.59 Hz, 1H), 6.62 (d, J=7.58 Hz, 1H), 6.61 (s, 1H), 4.54 (m, 2H), 4.33 (d, J=9.09 Hz, 1H), 4.30 (m, 1H), 4.16 (s, 4H), 3.79 (m, 1H), 3.73 (s, 2H), 3.71 (s, 3H), 3.63-3.70 (3H), 3.53 (m, 1H), 3.31 (m, 2H). LC/MS: m/z (M+NH$_4$)$^+$: 480.3.

Example 25: Compound #163

(2S,3R,4R,5S,6R)-2-[7-[dideuterio(2,3-dihydro-1,4-benzodioxin-6-yl)methyl]-4-methoxy-2,3-dihydrobenzofuran-5-yl]-5-fluoro-6-(hydroxymethyl)tetrahydropyran-3,4-diol

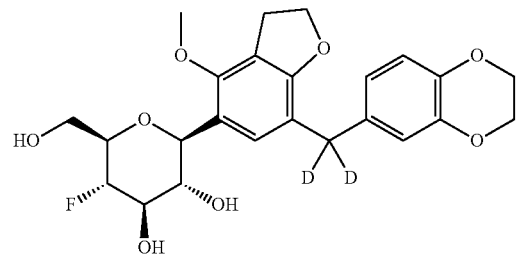 [SMILES: [2H]C([2H])(c1ccc2c(c1)OCCO2)c1cc([C@@H]2O[C@H](CO)[C@@H](F)[C@H](O)[C@H]2O)c(OC)c2c1OCC2]

To a solution of (4-(benzyloxy)-5-bromo-2,3-dihydrobenzofuran-7-yl)(2,3-dihydrobenzo[b][1,4]dioxin-6-yl)methanone (971 mg, 2.08 mmol) in THF (30 mL) was added NaBD$_4$ (434.9 mg, 10.4 mmol), followed by the addition of AlCl$_3$ (831.2 mg, 6.23 mmol). The resulting mixture was then heated at reflux for 16 h. The mixture was quenched with cooled NH$_4$Cl aqueous solution, extracted with EtOAc three times. The combined organic layer was washed with brine, dried over Na$_2$SO$_4$, filtered and concentrated. The residue was purified by flash column chromatography on silica gel (12 g, EtOAc/heptane: 0>>>15%) to yield 5-bromo-7-((2,3-dihydrobenzo[b][1,4]dioxin-6-yl)methyl-d2)-2,3-dihydrobenzofuran-4-ol as a colorless syrup.

To a solution of 5-bromo-7-((2,3-dihydrobenzo[b][1,4]dioxin-6-yl)methyl-d2)-2,3-dihydrobenzofuran-4-ol (467.8 mg, 1.28 mmol) in acetone (6 ml) was added Cs$_2$CO$_3$ (626 mg, 1.92 mmol), followed by the addition of CH$_3$I and the mixture was maintained with stirring at room temperature for 4 h. The resulting solid (precipitate) was filtered off and the filtrate was concentrated. The residue was purified by flash column chromatography on silica gel (12 g, EtOAc/heptane: 0>>>10%>>>20%) to yield 6-((5-bromo-4-methoxy-2,3-dihydrobenzofuran-7-yl)methyl-d2)-2,3-dihydrobenzo[b][1,4]dioxine as a colorless syrup.

A solution of 6-((5-bromo-4-methoxy-2,3-dihydrobenzofuran-7-yl)methyl-d2)-2,3-dihydrobenzo[b][1,4]dioxine (235.5 mg, 0.62 mmol) in anhydrous THF (4 mL) was cooled to −78° C. The vessel was evacuated and re-filled with argon, and this process was repeated twice. To the reaction mixture was added n-BuLi (1.6 M in hexane, 0.39 ml) dropwise and the resulting mixture was stirred at −78° C. under argon for 30 min. A solution of (3R,4R,5R,6R)-3,4-bis((tert-butyldimethylsilyl)oxy)-6-(((tert-butyldimethylsilyl)oxy)methyl)-5-fluorotetrahydro-2H-pyran-2-one (324.7 mg, 0.62 mmol) in THF (4 mL) was then added dropwise and the resulting reaction mixture was maintained stirring at −78° C. under argon for 1 h. The resulting mixture was then quenched with saturated aqueous NH$_4$Cl solution (10 mL), extracted with EtOAc three times (10 mL each time) and the combined extracts were washed with brine and dried with Na$_2$SO$_4$. The resulting insoluble solid (precipitate) was filtered off and the filtrate was concentrated under reduced pressure to yield a residue. The residue was dissolved in acetonitrile (10 mL) and DCM (10 mL) and cooled to −40° C. Triethylsilane (0.17 mL) was added, followed by addition of BF$_3$.Et$_2$O (0.090 mL). The reaction was maintained stirring at −40° C. for 35 min, then warmed to 0° C. and stirred at 0° C. for 1 h. The resulting mixture was quenched with aqueous NaHCO$_3$ and extracted with EtOAc three times. The combined organic layer was dried over Na$_2$SO$_4$, filtered and concentrated. The resulting residue was purified by Gilson HPLC to yield the title compound as a white solid.

$^1$H NMR (MeOH) δ: 6.99 (s, 1H), 6.65 (s, 3H), 4.47-4.61 (m, 3H), 4.30 (dt, J=51.0, 9.1 Hz, 1H), 4.16 (s, 4H), 3.82 (s, 3H), 3.50-3.78 (m, 6H), 3.26 (m, 1H). LC/MS: m/z (M+NH$_4$)$^+$: 482.1.

Example 26: Compound #172

(2S,3R,4R,5S,6R)-5-fluoro-6-(hydroxymethyl)-2-[4-methoxy-7-[(2,2,3,3-tetradeuterio-1,4-benzodioxin-6-yl)methyl]-2,3-dihydrobenzofuran-5-yl]tetrahydro-pyran-3,4-diol

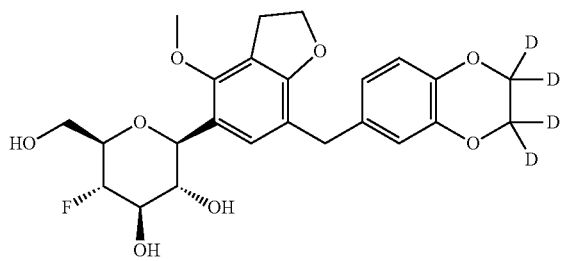 [SMILES: [2H]C1([2H])Oc2ccc(Cc3cc([C@@H]4O[C@H](CO)[C@@H](F)[C@H](O)[C@H]4O)c(OC)c4c3OCC4)cc2OC1([2H])[2H]]

A 50 ml round-bottom flask was charged with 6-bromo-2,2,3,3-tetradeuteriobenzo[b][1,4]dioxine (311 mg, 1.42 mmol) and a magnetic stir bar. The flask was evacuated, re-filled with nitrogen and this process was repeated twice. To the flask was added THF (4 mL) and the reaction mixture was cooled to −78° C. n-BuLi (1.6 M in hexanes, 0.89 mL) was added and the mixture was stirred at −78° C. for 35 min. To the mixture was then added 5-bromo-4-methoxy-2,3-dihydrobenzofuran-7-carbaldehyde (365 mg, 1.42 mmol) in THF (16 mL) and the resulting mixture was stirred at −78° C. for 60 min. The resulting mixture was quenched with aqueous NH$_4$Cl, and extracted with EtOAc three times. The combined organic layer was washed with brine, dried over N$_2$SO$_4$, filtered and the filtrate was concentrated under reduced pressure. The resulting residue was purified by flash column chromatography on silica gel (EtOAc/heptane: 0>>>10%>>>30%) to yield a white foam.

To (4-(benzyloxy)-5-bromo-2,3-dihydrobenzofuran-7-yl)(2,2,3,3-tetradeuteriobenzo[b][1,4]dioxin-6-yl)methan-d-ol in anhydrous CH$_2$Cl$_2$ at 0° C. was added Et$_3$SiH (0.09 ml, 0.54 mmol), followed by BF$_3$.Et$_2$O (0.062 ml, 0.49 mmol) and the mixture was stirred at 0° C. for 1 h. The resulting mixture was then quenched with aqueous NaHCO$_3$, extracted with DCM three times, concentrated and filtered. The filtrate was concentrated and the residue was purified by flash column chromatography on silica gel (12 g, EtOAc/heptane: 0>>>10%) to yield 6-((4-(benzyloxy)-5-bromo-2,3-dihydrobenzofuran-7-yl)methyl)-2,2,3,3-tetradeuteriobenzo[b][1,4]dioxine as a colorless syrup.

A 50 round-bottom flask was charged with 6-((4-(benzyloxy)-5-bromo-2,3-dihydrobenzofuran-7-yl)methyl)-2,2,3,3-tetradeuteriobenzo[b][1,4]dioxine (114.5 mg, 0.3 mmol) and a magnetic stir bar. The flask was evacuated, re-filled with nitrogen and this process was repeated twice. To the flask was then added THF (4 mL), and the reaction mixture was cooled to −78° C. To the reaction mixture was then added n-BuLi (0.19 mL, 1.6 M in hexanes) and the mixture was stirred at −78° C. for 35 min. (3R,4R,5R,6R)-3,4-bis((tert-butyldimethylsilyl)oxy)-6-(((tert-butyldimethylsilyl)oxy)methyl)-5-fluorotetrahydro-2H-pyran-2-one (157 mg, 0.3 mmol) in THF (4 mL) was added and the resulting mixture was stirred at −78° C. for 40 min. The resulting mixture was quenched with aqueous NH$_4$Cl, extracted with EtOAc three times. The combined organic layer was washed with brine, dried over N$_2$SO$_4$, filtered and the filtrate was concentrated under reduced pressure. The residue was dried in vacuo and re-dissolved in ACN (10 mL) and DCM (10 mL), then cooled to −40° C. To the resulting mixture was then added triethylsilane (0.27 mL, 1.7 mmol), followed by addition of BF$_3$.Et$_2$O (0.15 mL, 1.2 mmol). The reaction was maintained stirring at −40° C. for 35 min, then warmed to 0° C. and maintained with stirring at 0° C. for 1 h. The resulting mixture was quenched with aqueous NaHCO$_3$, extracted with EtOAc three times. The combined organic layer was dried over Na$_2$SO$_4$, filtered and concentrated. The residue was analyzed by LC/MS and then re-dissolved in MeOH (4 ml). The solution was subjected to Gilson HPLC purification (three injections) to yield (2S,3R,4R,5S,6R)-2-(4-(benzyloxy)-7-((2,2,3,3-tetradeuterio-1,4-benzodioxin-6-yl)methyl-d2)-2,3-dihydrobenzofuran-5-yl)-5-fluoro-6-(hydroxymethyl)tetrahydro-2H-pyran-3,4-diol as a white solid.

$^1$H NMR (MeOH) δ: 6.98 (s, 1H), 6.65 (s, 3H), 4.48-4.59 (m, 3H), 4.30 (dt, J=51.3, 9.0 Hz, 1H), 3.81 (s, 3H), 3.71-3.80 (m, 2H), 3.69 (s, 2H), 3.62-3.68 (m, 1H), 3.51-3.62 (m, 2H), 3.25-3.28 (m, 1H). LC/MS: m/z (M+NH$_4$): 484.0.

Additional representative compounds of formula (I) were prepared according to the procedures as described in the Examples above, with measured MS and $^1$H NMR as listed in Table 4 below.

TABLE 4

Additional, Prepared, Representative Compounds of Formula (I)

ID No. Name, Measured $^1$H NMR and MS 98 (2S,3R,4R,5S,6R)-2-[5-(2,3-dihydro-1,4-benzodioxin-6-ylmethyl)-4-hydroxy-2,3-dihydrobenzofuran-7-yl]-5-fluoro-6-(hydroxymethyl)tetrahydropyran-3,4-diol
$^1$H NMR (MeOH) δ: 6.86 (s, 1H), 6.65 (s, 3H), 4.47-4.60 (m, 2H), 4.19-4.39 (m, 2H), 4.16 (s, 4H), 3.62-3.83 (m, 6H), 3.47-3.55 (m, 1H), 3.11 (t, J = 8.6 Hz, 2H). LC/MS: m/z (M + Na)$^+$: 471.1.

102 (2S,3R,4R,5S,6R)-2-[5-(2,3-dihydro-1,4-benzodioxin-6-ylmethyl)-4-ethoxy-2,3-dihydrobenzofuran-7-yl]-5-fluoro-6-(hydroxymethyl)tetrahydropyran-3,4-diol
$^1$H NMR (MeOH) δ: 6.98 (s, 1H), 6.66 (d, J = 9.09 Hz, 1H), 6.62 (d, J = 8.59 Hz, 1H), 6.61 (s, 1H), 4.53 (m, 2H), 4.33 (d, J = 9.09 Hz, 1H), 4.30 (m, 1H), 4.16 (s, 4H), 3.87-3.96 (m, 2H), 3.77-3.82 (m, 1H), 3.75 (s, 2H), 3.64-3.72(3 H), 3.53 (m, 1H), 3.26 (t, J = 8.59 Hz, 2H), 1.24 (t, J = 7.07 Hz, 3H). LC/MS: m/z (M + NH$_4$)$^+$: 494.2.

160 (2S,3R,4R,5S,6R)-2-[7-(2,3-dihydro-1,4-benzodioxin-6-ylmethyl)-4-(trideuteriomethoxy)-2,3-dihydrobenzofuran-5-yl]-5-fluoro-6-(hydroxymethyl)tetrahydropyran-3,4-diol
$^1$H NMR (MeOH) δ: 6.98 (s, 1H), 6.62-6.68 (m, 3H), 4.47-4.61 (m, 3H), 4.30 (dt, J = 51.0, 9.1 Hz, 1H), 4.13-4.20 (m, 4H), 3.52-3.82 (m, 8H), 3.28 (m, 1H). LC/MS: m/z (M + NH$_4$)$^+$: 483.1.

Biological Example 1: SGLT1 and SGLT2 Assay

The ability of the compounds of formula (I) of the present invention to treat an SGLT-mediated condition was determined using the following procedures:

SGLT1 and SGLT2 were cloned in form of cDNA from human small intestine (Genbank M24847), and from human kidney (Genbank M95549), respectively. Subsequently, each full cDNA was subcloned into pcDNA with each construct's integrity verified through follow-on sequencing. To generate CHO-K1 cells that stably express human SGLT1 or human SGLT2, CHO-K1 cells were transfected using DMRIE-C reagent (Life Technologies, Gaithersburg, Md.). Transfected cells were then selected in the presence of 500 µg/ml of the Geneticin (G418 Cellgro Catalog No. 30234-Cl)

Individual clones were then characterized using the following cell-based assay for sodium-dependent glucose transport:

Inhibition of SGLT1 and SGLT2 activity was assessed in CHO K1 cells stably expressing either human SGLT1 or SGLT2, using the SGLT specific glucose analog methyl-glucopyranoside (Sigma Catalog No. M-9376). Cells were plated (45,000 cells/well) in white wall 96-well plates (COSTAR, Cat #3903) for 24 hours in growth medium, then a final concentration of 10 mM Na-Butyrate (ALDRICH Cat #30341-0) was added. The cells were incubated for 24 hours. On the day of the assay, cells were rinsed and treated with test compounds (at concentrations of 0.001 µM to 10 µM) in assay buffer (50 mM HEPES, 20 mM Tris base, 5 mM KCl, 1 mM MgCl$_2$, 1 mM CaCl$_2$ and 137 mM NaCl, pH 7.4) for 10 minutes. Cells were then incubated with $^{14}$C-a-methyl-d-glucopyranoside (AMG, Amersham Catalog No. CFB 76), using 0.07 µCi per well in 500 µM AMG final concentration. The cells were incubated for 2 hours at 37° C. with 5% CO$_2$ and washed two times with ice-cold Phosphate Buffer Solution (Cellgro Catalog No. 21030-CV). The cells were then solubilized by adding 60 µl of MICROSCINT™20 and the Na-dependent $^{14}$C-AMG uptake was quantified by measuring radioactivity. Plates were counted in a TopCount (Packard, Meriden, Conn.)

Representative compounds of the present invention were tested according to the procedures as described in Biological Example 1 and 2 above, with results as listed in Table 5, below. Results are reported as the %-inhibition or IC$_{50}$ value. Variability for the functional assay was typically within 20%. The %-inhibition or IC$_{50}$ data were derived from the best curve fit as listed in Table 5, below. When a listed compound was tested more than once, the average is listed in Table 5 below.

TABLE 5

| | SGLT1 and SGLT2 Activity | |
|---|---|---|
| ID No. | SGLT1 IC$_{50}$ (µM) | SGLT2 IC$_{50}$ (µM) |
| 2 | 0.009 | 0.008 |
| 4 | 0.014 | 0.004 |
| 7 | 0.018 | 0.006 |
| 9 | 0.126 | 0.107 |
| 10 | 0.085 | 0.082 |
| 11 | 0.091 | 0.059 |
| 12 | 0.100 | 0.024 |
| 13 | 0.015 | 0.007 |
| 14 | 69.3% @ 0.3 µM | 36.0% @ 0.3 µM |
| 15 | 0.100 | 0.068 |
| 16 | 0.111 | 0.029 |
| 18 | 0.068 | 0.018 |
| 19 | 47.6% @ 0.3 µM | 68.1% @ 0.3 µM |
| 20 | 0.114 | 0.402 |
| 21 | 0.313 | 0.112 |
| 22 | 62.7% @ 0.3 µM | 0.241 |
| 23 | 65.2% @ 0.3 µM | 0.069 |
| 24 | 0.977 | 0.332 |
| 26 | 0.847 | 0.982 |
| 28 | | 50.3% @ 0.3 µM |
| 29 | 0.013 | 0.062 |
| 30 | | 51.0% @ 0.3 µM |
| 31 | 0.009 | 0.019 |
| 32 | | 15.3% @ 0.3 µM |
| 34 | 38.6% @ 0.3 µM | 27.6% @ 0.3 µM |
| 39 | 0.381 | 0.123 |
| 42 | 0.098 | 0.010 |
| 52 | 0.015 | 0.009 |
| 53 | 0.104 | 0.026 |
| 54 | 0.069 | 0.011 |
| 56 | 0.523 | 0.012 |
| 59 | 0.031 | 0.009 |
| 61 | 0.014 | 0.003 |
| 62 | 0.048 | 0.004 |
| 63 | 0.122 | 0.004 |
| 64 | 0.156 | 0.036 |
| 65 | 0.043 | 0.009 |
| 66 | 0.040 | 0.014 |
| 67 | 64.9% @ 0.3 µM | 57.5% @ 0.3 µM |
| 68 | 0.055 | 0.021 |
| 69 | 20.4% @ 0.3 µM | 60.3% @ 0.3 µM |
| 70 | 0.100 | 0.162 |
| 71 | 76.4% @ 0.3 µM | 30.0% @ 0.3 µM |
| 72 | 0.127 | 0.024 |
| 73 | 0.240 | 0.048 |
| 74 | 65.5% @ 0.3 µM | 65.2% @ 0.3 µM |
| 75 | 61.9% @ 0.3 µM | 43.7% @ 0.3 µM |
| 76 | 28.6% @ 0.3 µM | 72.2% @ 0.3 µM |
| 77 | 30.3% @ 0.3 µM | 69.9% @ 0.3 µM |
| 78 | 28.4% @ 0.3 µM | 86.9% @ 0.3 µM |
| 79 | 0.126 | 0.137 |
| 80 | 37.4% @ 0.3 µM | 60.4% @ 0.3 µM |
| 81 | 0.223 | 0.011 |
| 82 | 42.2% @ 0.3 µM | 58.9% @ 0.3 µM |
| 83 | 17.4% @ 0.3 µM | 72.3% @ 0.3 µM |
| 84 | 0.101 | 0.036 |

TABLE 5-continued

SGLT1 and SGLT2 Activity

| ID No. | SGLT1 IC$_{50}$ (µM) | SGLT2 IC$_{50}$ (µM) |
|---|---|---|
| 85 | 37.4% @ 0.3 µM | 10.1% @ 0.3 µM |
| 86 | 0.290 | 0.038 |
| 87 | 48.7% @ 0.3 µM | 59.0% @ 0.3 µM |
| 88 | 42.5% @ 0.3 µM | 44.8% @ 0.3 µM |
| 89 | 0.042 | 0.100 |
| 90 | 30.9% @ 0.3 µM | 54.9% @ 0.3 µM |
| 91 | 31.7% @ 0.3 µM | 65.5% @ 0.3 µM |
| 92 | 29.0% @ 0.3 µM | 76.2% @ 0.3 µM |
| 93 | 33.6% @ 0.3 µM | 42.3% @ 0.3 µM |
| 94 | 32.6% @ 0.3 µM | 19.2% @ 0.3 µM |
| 95 | 45.3% @ 0.3 µM | 62.7% @ 0.3 µM |
| 96 | 29.1% @ 0.3 µM | 18.2% @ 0.3 µM |
| 97 | 31.2% @ 0.3 µM | 67.9% @ 0.3 µM |
| 98 | 30.9% @ 0.3 µM | 26.0% @ 0.3 µM |
| 99 | 28.9% @ 0.3 µM | 83.5% @ 0.3 µM |
| 100 | 0.095 | 0.008 |
| 101 | 0.096 | 0.007 |
| 102 | 27.6% @ 0.3 µM | 40.7% @ 0.3 µM |
| 103 | 0.086 | 0.003 |
| 104 | 32.5% @ 0.3 µM | 81.2% @ 0.3 µM |
| 105 | 0.128 | 0.004 |
| 106 | 29.4% @ 0.3 µM | 82.1% @ 0.3 µM |
| 107 | 0.163 | 0.008 |
| 108 | 0.326 | 0.075 |
| 109 | 39.5% @ 0.3 µM | 72.7 @ 0.3 µM |
| 110 | 1.421 | 0.005 |
| 111 | 0.101 | 0.019 |
| 112 | 0.376 | 0.023 |
| 113 | 21.0% @ 0.3 µM | 53.9% @ 0.3 µM |
| 114 | 0.109 | 0.005 |
| 115 | 35.6% @ 0.3 µM | 79.3% @ 0.3 µM |
| 116 | 11.5% @ 0.3 µM | 78.0% @ 0.3 µM |
| 117 | 44.3% @ 0.3 µM | 69.9% @ 0.3 µM |
| 118 | 0.050 | 0.002 |
| 119 | 0.156 | 0.011 |
| 120 | 6.6% @ 0.3 µM | 54.7% @ 0.3 µM |
| 121 | 20.5% @ 0.3 µM | 79.8% @ 0.3 µM |
| 122 | 31.7% @ 0.3 µM | 63.6% @ 0.3 µM |
| 123 | 1.356 | 0.100 |
| 124 | 0.698 | 0.147 |
| 125 | 0.227 | 0.017 |
| 126 | 21.7% @ 0.3 µM | 16.8% @ 0.3 µM |
| 127 | 63.2% @ 0.3 µM | 78.4% @ 0.3 µM |
| 128 | 0.187 | 0.062 |
| 129 | 0.176 | 0.007 |
| 130 | 44.8% @ 0.3 µM | 81.6% @ 0.3 µM |
| 131 | 0.231 | 0.012 |
| 132 | 0.135 | 0.023 |
| 133 | 0.236 | 0.006 |
| 134 | 0.254 | 0.012 |
| 135 | 0.085 | 0.008 |
| 138 | 37.5% @ 0.3 µM | 46.7% @ 0.3 µM |
| 142 | 59.8% @ 0.3 µM | 85.8% @ 0.3 µM |
| 152 | 0.006 | 0.006 |
| 153 | 0.050 | 0.058 |
| 154 | 0.042 | 0.002 |
| 156 | 0.086 | 0.010 |
| 157 | 47.7% @ 0.3 µM | 61.9% @ 0.3 µM |
| 158 | 2.6% @ 0.3 µM | 18.0% @ 0.3 µM |
| 159 | 6.0% @ 0.3 µM | 0.0% @ 0.3 µM |
| 160 | 0.071 | 0.008 |
| 161 | 0.052 | 0.007 |
| 163 | 0.050 | 0.008 |
| 165 | 0.056 | 0.016 |
| 166 | 0.245 | 0.011 |
| 167 | 37.9% @ 0.3 µM | 80.1% @ 0.3 µM |
| 169 | 37.2% @ 0.3 µM | 72.7% @ 0.3 µM |
| 171 | 27.1% @ 0.3 µM | 69.9% @ 0.3 µM |
| 172 | 0.045 | 0.007 |
| 173 | 0.190 | 0.013 |
| 175 | 0.087 | 0.012 |
| 176 | 68.9% @ 0.3 µM | 56.1% @ 0.3 µM |
| 178 | 42.0% @ 0.3 µM | 70.7% @ 0.3 µM |
| 179 | 0.060 | 0.015 |
| 180 | 0.061 | 0.025 |
| 181 | 67.0% @ 0.3 µM | 85.0% @ 0.3 µM |
| 182 | 0.138 | 0.011 |

Formulation Example 1

Solid, Oral Dosage Form—Prophetic Example

As a specific embodiment of an oral composition, 100 mg of the Compound #61, prepared as in Example 14 is formulated with sufficient finely divided lactose to provide a total amount of 580 to 590 mg to fill a size O hard gel capsule.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

Throughout this application, various publications are cited. The disclosure of these publications is hereby incorporated by reference into this application to describe more fully the state of the art to which this invention pertains.

We claim:

1. A compound of formula (V-S)

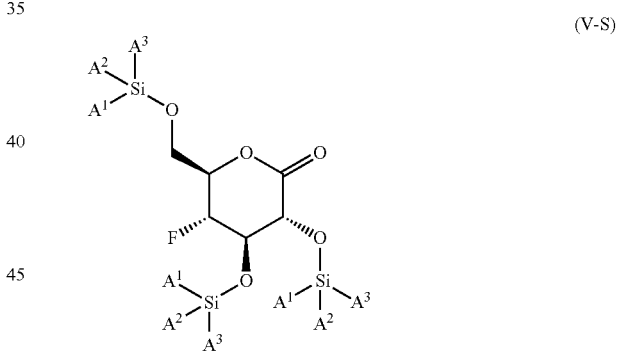

(V-S)

wherein $A^1$, $A^2$ and $A^3$ are each an independently selected from the group consisting of $C_{1-8}$alkyl, $C_{3-6}$cycloalkyl, bicyclo[2.2.1]heptan-2-yl, phenyl and 3,5-di(trifluoromethyl)phenyl.

2. The compound of claim 1, wherein
$A^1$ is methyl, $A^2$ is methyl and $A^3$ is t-butyl; or
$A^1$ is methyl, $A^2$ is methyl and $A^3$ is 2,3,3-trimethylbutan-2-yl; or
$A^1$ is methyl, $A^2$ is methyl and $A^3$ is isopropyl; or
$A^1$ is methyl, $A^2$ is methyl and $A^3$ is cyclohexyl; or
$A^1$ is methyl, $A^2$ is methyl and $A^3$ is bicyclo[2.2.1]heptan-2-yl; or
$A^1$ is methyl, $A^2$ is methyl and $A^3$ is phenyl; or
$A^1$ is methyl, $A^2$ is methyl and $A^3$ is 3,5-di(trifluoromethyl)phenyl; or
$A^1$ is t-butyl, $A^2$ is phenyl and $A^3$ is phenyl.

3. The compound of claim 1, wherein the compound of formula (V-S) is (3R,4R,5R,6R)-3,4-bis((tert-butyldimethylsilyl)oxy)-6-(((tert-butyldimethylsilyl)oxy)methyl)-5-fluorotetrahydro-2H-pyran-2-one.

4. A process for the preparation of a compound of formula (V-S)

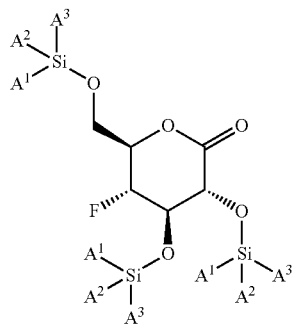
(V-S)

wherein $A^1$, $A^2$ and $A^3$ are each an independently selected from the group consisting of $C_{1-8}$ alkyl, $C_{3-6}$ cycloalkyl, bicyclo[2.2.1]heptan-2-yl, phenyl and 3,5-di(trifluoromethyl)phenyl;

comprising the steps of:

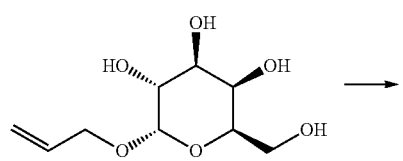

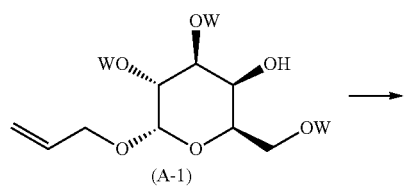
(A-1)

(a) reacting (2S,3R,4S,5R,6R)-2-(allyloxy)-6-(hydroxymethyl)tetrahydro-2H-pyran-3,4,5-triol, with an acylating agent; in the presence of an inorganic or organic base; neat, when in the presence of an organic base or when in the presence of an inorganic base, in an organic solvent; at a temperature in the range of from about −50° C. to room temperature; to yield the corresponding compound of formula (A-1), wherein W is derived from the acylating agent to give the corresponding acyl group, wherein the corresponding acyl group is selected from the group consisting of —C(O)—methyl, —C(O)-ethyl, and —C(O)-benzyl, or is —C(O)-benzyl (benzoyl);

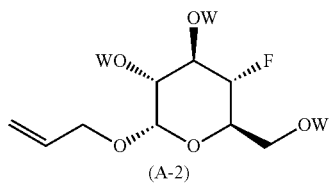
(A-2)

(b) reacting the compound of formula (A-1) with a fluorinating agent; in an organic solvent or mixture of organic solvents; at a temperature ranging from about −50° C. to room temperature; to yield the corresponding compound of formula (A-2);

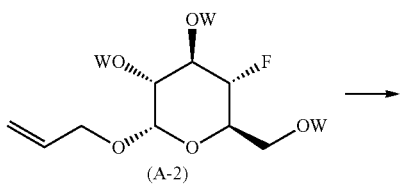
(A-2)

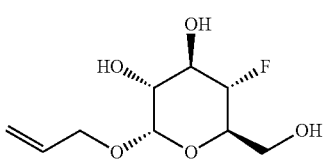

(c) de-protecting the compound of formula (A-2) to yield (2S,3R,4R,5S,6R)-2-(allyloxy)-5-fluoro-6-(hydroxymethyl)tetrahydro-2H-pyran-3,4-diol;

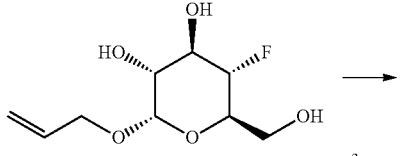

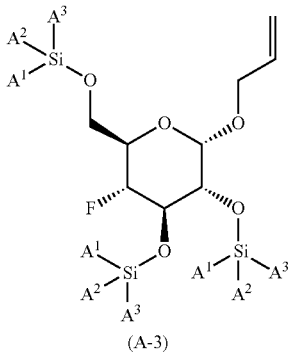
(A-3)

(d) reacting (2S,3R,4R,5S,6R)-2-(allyloxy)-5-fluoro-6-(hydroxymethyl)tetrahydro-2H-pyran-3,4-diol with a silylation reagent; in the presence of an organic base; in an organic solvent or mixture of organic solvents; at a temperature ranging from about 0° C. to about 50° C., to yield the corresponding compound of formula (A-3), wherein $A^1$, $A^2$ and $A^3$ are derived from the silylation reagent and are defined above as in Formula (V-S);

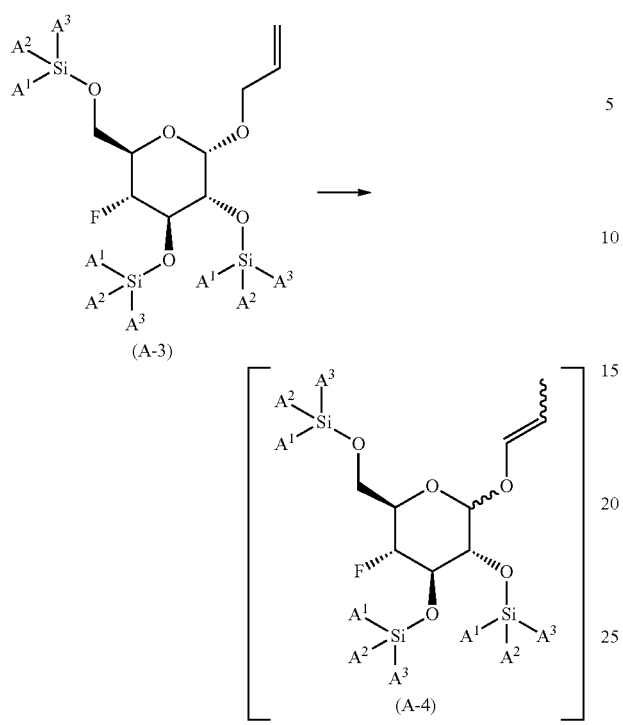

(A-3)

[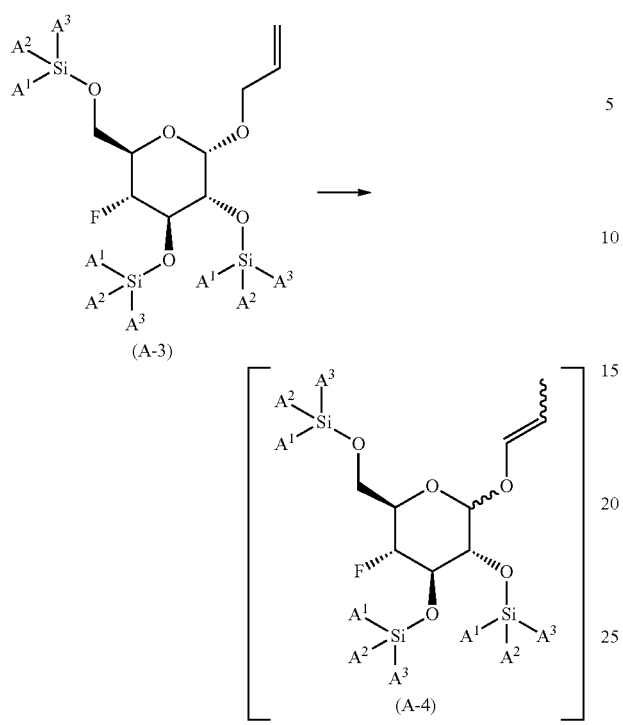]

(A-4)

(e) reacting the compound of formula (A-3) with an allyl isomerization catalyst in an organic solvent or mixture of water and a water miscible organic solvent; at a temperature ranging from about 75° C. to about 105° C., to yield the corresponding compound of formula (A-4), wherein the compound of formula (A-4) is not isolated;

[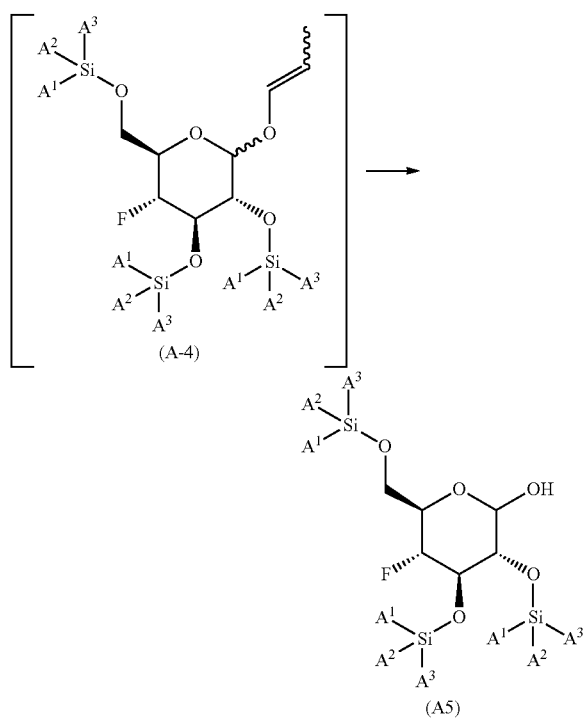]

(A-4)

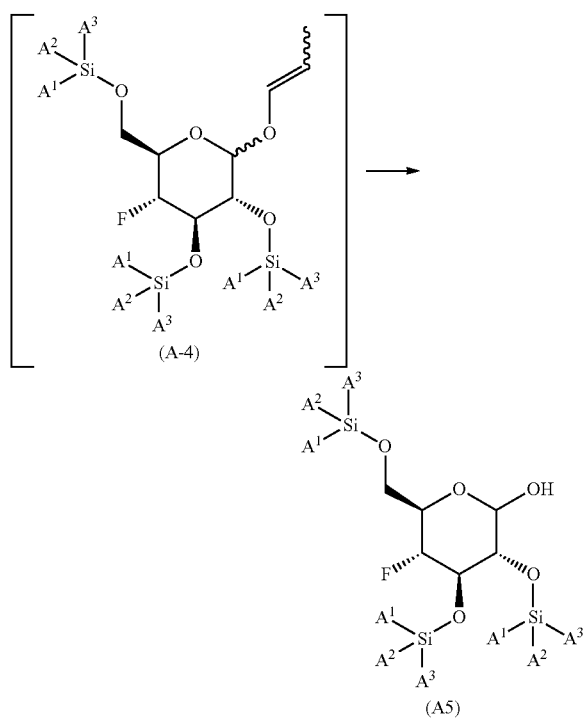

(A5)

(f) reacting the compound of formula (A-4) with a co-oxidant; in the presence of an oxidizing reagent; in an organic solvent or mixture of water and a water miscible organic solvent; at a temperature ranging from about 0° C. to about 50° C.; to yield the corresponding compound o formula (A-5);

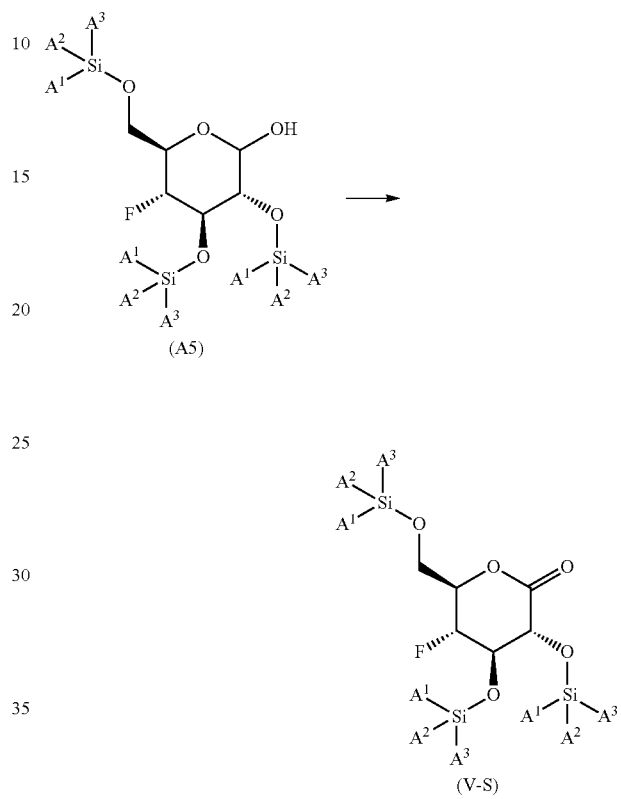

(A5)

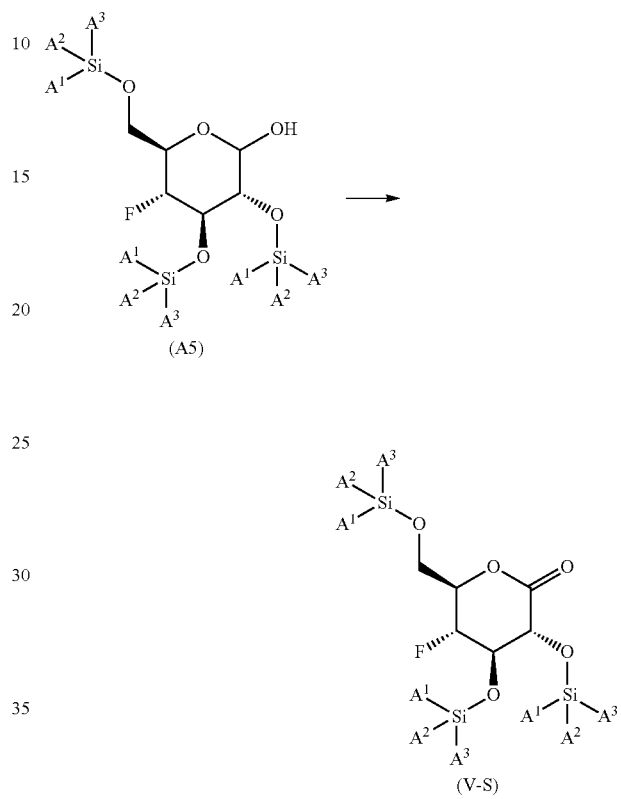

(V-S)

(g) reacting the compound of formula (A-5) under SWERN oxidation conditions; to yield the corresponding compound of formula (V-S).

5. The process of claim 4, wherein $A^1$ is methyl, $A^2$ is methyl and $A^3$ is t-butyl; or $A^1$ is methyl, $A^2$ is methyl and $A^3$ is 2,3,3-trimethylbutan-2-yl; or $A^1$ is methyl, $A^2$ is methyl and $A^3$ is isopropyl; or $A^1$ is methyl, $A^2$ is methyl and $A^3$ is cyclohexyl; or $A^1$ is methyl, $A^2$ is methyl and $A^3$ is bicyclo[2.2.1]heptan-2-yl; or $A^1$ is methyl, $A^2$ is methyl and $A^3$ is phenyl; or $A^1$ is methyl, $A^2$ is methyl and $A^3$ is 3,5-di(trifluoromethyl)phenyl; or $A^1$ is t-butyl, $A^2$ is phenyl and $A^3$ is phenyl.

6. The process of claim 4, wherein the compound of formula (V-S) is (3R,4R,5R,6R)-3,4-bis((tert-butyldimethylsilyl)oxy)-6-(((tert-butyldimethylsilyl)oxy)methyl)-5-fluorotetrahydro-2H-pyran-2-one.

7. A compound prepared according to the process of claim 4.

* * * * *